(12) United States Patent
Crew et al.

(10) Patent No.: US 8,197,848 B2
(45) Date of Patent: *Jun. 12, 2012

(54) PHARMACEUTICAL COMPOSITIONS OF CHOLESTERYL ESTER TRANSFER PROTEIN INHIBITORS

(75) Inventors: Marshall D. Crew, Bend, OR (US); William J. Curatolo, Niantic, CT (US); Dwayne T. Friesen, Bend, OR (US); Michael J. Gumkowski, Old Lyme, CT (US); Douglas A. Lorenz, Bend, OR (US); James A. S. Nightingale, Bend, OR (US); Roger B. Ruggeri, Waterford, CT (US); Ravi M. Shanker, Groton, CT (US)

(73) Assignee: Bend Research, Inc., Bend, OR (US)

( * ) Notice: Subject to any disclaimer, the term of this patent is extended or adjusted under 35 U.S.C. 154(b) by 1406 days.

This patent is subject to a terminal disclaimer.

(21) Appl. No.: 11/799,447

(22) Filed: Apr. 30, 2007

(65) Prior Publication Data
US 2007/0282009 A1    Dec. 6, 2007

Related U.S. Application Data

(63) Continuation of application No. 10/066,091, filed on Feb. 1, 2002, now Pat. No. 7,235,259, which is a continuation-in-part of application No. 09/918,127, filed on Jul. 30, 2001, now Pat. No. 7,115,279.

(60) Provisional application No. 60/223,279, filed on Aug. 3, 2000.

(51) Int. Cl.
A61K 9/14    (2006.01)
A61K 31/135    (2006.01)
A61K 31/47    (2006.01)
A61K 47/32    (2006.01)

(52) U.S. Cl. ..... 424/488; 514/646; 514/313; 514/772.4; 424/489

(58) Field of Classification Search .......... 514/646, 514/313; 424/488
See application file for complete search history.

(56) References Cited

U.S. PATENT DOCUMENTS

| | | | |
|---|---|---|---|
| 4,983,593 A | 1/1991 | Miyajima et al. | 514/110 |
| 5,456,923 A | 10/1995 | Nakamichi et al. | 424/489 |
| 5,714,506 A | 2/1998 | Fisher et al. | 514/352 |
| 5,880,095 A | 3/1999 | Park et al. | 514/12 |
| 5,932,587 A | 8/1999 | Schmeck et al. | 514/278 |
| 5,955,475 A * | 9/1999 | Krape et al. | 514/321 |
| 6,069,148 A | 5/2000 | Schmidt et al. | 514/277 |
| 6,140,342 A | 10/2000 | Goldstein et al. | 514/313 |
| 6,140,343 A | 10/2000 | DeNinno et al. | 514/313 |
| 6,147,090 A | 11/2000 | DeNinno et al. | 514/313 |
| 6,197,786 B1 | 3/2001 | DeNinno et al. | 514/313 |
| 6,246,365 B1 * | 6/2001 | Tokoro | 342/427 |
| 6,310,075 B1 | 10/2001 | DeNinno et al. | 514/313 |
| 2001/0018446 A1 | 8/2001 | Sikorski et al. | 514/357 |
| 2001/0028895 A1 | 10/2001 | Bisgaier et al. | 424/450 |
| 2002/0009494 A1 | 1/2002 | Curatolo et al. | 424/489 |
| 2002/0015731 A1 * | 2/2002 | Appel et al. | 424/473 |
| 2002/0165252 A1 | 11/2002 | Schmidt et al. | 514/311 |
| 2003/0054038 A1 | 3/2003 | Crew et al. | 424/486 |
| 2003/0091643 A1 | 5/2003 | Friesen et al. | 424/486 |

FOREIGN PATENT DOCUMENTS

| | | |
|---|---|---|
| EP | 0299641 | 1/1989 |
| EP | 0344603 | 4/1989 |
| EP | 0580860 | 4/1992 |
| EP | 0796846 | 7/1997 |
| EP | 0801060 | 10/1997 |
| EP | 0818197 | 1/1998 |
| EP | 0818448 | 1/1998 |
| EP | 0901786 | 3/1999 |
| EP | 0992496 | 4/2000 |
| EP | 1020439 | 7/2000 |
| EP | 1027886 | 8/2000 |
| EP | 1160330 | 12/2001 |
| GB | 2305665 | 4/1997 |
| JP | 10287662 | 10/1998 |
| WO | WO 98/35937 * | 8/1998 |
| WO | WO 9839299 | 9/1998 |
| WO | WO 9914174 | 3/1999 |
| WO | WO 9914204 | 3/1999 |
| WO | WO 9914215 | 3/1999 |
| WO | WO 9941237 | 8/1999 |
| WO | WO 0017164 | 3/2000 |
| WO | WO 0018721 | 4/2000 |
| WO | WO 0018723 | 4/2000 |
| WO | WO 0018724 | 4/2000 |
| WO | WO 0072825 | 12/2000 |

OTHER PUBLICATIONS

Chiou et al. ("Pharmaceutical Applications of solid Dispersion Systems," in the Journal of Pharmaceutical Sciences, vol. 60, No. 9, Sep. 1971, pp. 1281-1302).*
Breitenbach ("Melt extrusion: from process to drug delivery technology," in European Journal of Pharmaceutics and Biopharmaceutics, vol. 54, Issue 2, Sep. 2002, pp. 107-117).*
Toyoda et al., Japanese Journal of Pharmacology, vol. 103m, issue 5, May 1994, p. 231-239.
Kitahara et al., Japanese Journal of Pharmacology. vol. 69, issue 2, Oct. 1995, pp. 101-109.
Bisgaler et al., LIPIDS, vol. 29, No. 12, 1994, pp. 811-818. Gordon, Circulation, vol. 79, No. 1, Jan. 1989, pp. 8-15.
U.S. Appl. No. 10/459,808, filed Jun. 10, 2003.
U.S. Appl. No. 10/173,945, filed Jun. 17, 2002.
U.S. Appl. No. 09/495,061, filed Jan. 31, 2000.
U.S. Appl. No. 09/495,059, filed Jan. 31, 2000.

* cited by examiner

Primary Examiner — Blessing Fubara
(74) Attorney, Agent, or Firm — Chernoff, Vilhauer, McClung & Stenzel

(57) ABSTRACT

A pharmaceutical composition comprises a solid amorphous dispersion of a cholesteryl ester transfer protein inhibitor and a concentration-enhancing polymer.

16 Claims, No Drawings

PHARMACEUTICAL COMPOSITIONS OF CHOLESTERYL ESTER TRANSFER PROTEIN INHIBITORS

This application is a continuation of U.S. patent application Ser. No. 10/066,091, filed Feb. 1, 2002, which is a continuation-in-part of U.S. patent application Ser. No. 09/918,127, filed Jul. 30, 2001, which claims the benefit of priority of U.S. provisional patent application No. 60/223,279 filed Aug. 3, 2000.

BACKGROUND OF THE INVENTION

This invention relates to cholesteryl ester transfer protein (CETP) inhibitors, pharmaceutical compositions containing such inhibitors and the use of such inhibitors to elevate certain plasma lipid levels, including high density lipoprotein (HDL)-cholesterol and to lower certain other plasma lipid levels, such as low density lipoprotein (LDL)-cholesterol and triglycerides and accordingly to treat diseases which are affected by low levels of HDL cholesterol and/or high levels of LDL-cholesterol and triglycerides, such as atherosclerosis and cardiovascular diseases in certain mammals (i.e., those which have CETP in their plasma), including humans.

CETP inhibitors, particularly those that have high binding activity, are generally hydrophobic, have extremely low aqueous solubility and have low oral bioavailability when dosed conventionally. Such compounds have generally proven to be difficult to formulate for oral administration such that high bioavailabilities are achieved.

Atherosclerosis and its associated coronary artery disease (CAD) is the leading cause of death in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of this condition has been shown to be strongly correlated with certain plasma lipid levels. While elevated LDL-cholesterol may be the most recognized form of dyslipidemia, it is by no means the only significant lipid associated contributor to CHD. Low HDL-cholesterol is also a known risk factor for CHD (Gordon, D. J., et al.: "High-density Lipoprotein Cholesterol and Cardiovascular Disease," Circulation, (1989), 79: 8-15).

High LDL-cholesterol and triglyceride levels are positively correlated, while high levels of HDL-cholesterol are negatively correlated with the risk for developing cardiovascular diseases. Thus, dyslipidemia is not a unitary risk profile for CHD but may be comprised of one or more lipid aberrations.

Among the many factors controlling plasma levels of these disease dependent principles, cholesteryl ester transfer protein (CETP) activity affects all three. The role of this 70,000 dalton plasma glycoprotein found in a number of animal species, including humans, is to transfer cholesteryl ester and triglyceride between lipoprotein particles, including high density lipoproteins (HDL), low density lipoproteins (LDL), very low density lipoproteins (VLDL), and chylomicrons. The net result of CETP activity is a lowering of HDL cholesterol and an increase in LDL cholesterol. This effect on lipoprotein profile is believed to be pro-atherogenic, especially in subjects whose lipid profile constitutes an increased risk for CHD.

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (±10-12%). As a result, there is a significant unmet medical need for a well-tolerated agent which can significantly elevate plasma HDL levels, thereby reversing or slowing the progression of atherosclerosis.

CETP inhibitors have been developed which inhibit CETP activity, and thus, if present in the blood, should result in higher HDL cholesterol levels and lower LDL cholesterol levels. To be effective, such CETP inhibitors must be absorbed into the blood. Oral dosing of CETP inhibitors is preferred because to be effective such CETP inhibitors must be taken on a regular basis, such as daily. Therefore, it is preferred that patients be able to take CETP inhibitors by oral dosing rather than by injection.

However, it has proven to be difficult to formulate CETP inhibitors for oral administration such that therapeutic blood levels are achieved. CETP inhibitors in general possess a number of characteristics which render them poorly bioavailable when dosed orally in a conventional manner. CETP inhibitors tend to be quite hydrophobic and extremely water insoluble, with solubility in aqueous solution of usually less than about 10 µg/ml and typically less than 1 µg/ml. Often, the aqueous solubility of CETP inhibitors is less than 0.1 µg/ml. Indeed, the solubility of some CETP inhibitors is so low that it is in fact difficult to measure. Accordingly, when CETP inhibitors are dosed orally, concentrations of CETP inhibitor in the aqueous environment of the gastrointestinal tract tend to be extremely low, resulting in poor absorption from the GI tract to blood. The hydrophobicity of CETP inhibitors not only leads to low equilibrium aqueous solubility but also tends to make the drugs poorly wetting and slow to dissolve, further reducing their tendency to dissolve and be absorbed from the gastrointestinal tract. This combination of characteristics has resulted in the bioavailability for orally dosed conventional crystalline or amorphous forms of CETP inhibitors generally to be quite low, often having absolute bioavailabilities of less than 1%.

Various attempts have been made to improve the aqueous concentration of CETP inhibitors, but generally have met with limited success. At the outset, most methods aimed at enhancing aqueous concentration and bioavailability of low-solubility drugs only offer moderate improvements. Such improvements generally lead to enhancements in aqueous concentration on the order of from one to seven fold. In addition, the enhancement may be short-lived, with the drug concentration returning to the equilibrium concentration within 10 to 40 minutes. Such small, short-lived concentration enhancements have led to even lower levels of bioavailability enhancement when tested in vivo via oral administration. Thus, when conventional dosage forms of low-solubility drugs are tested in vivo via oral administration, bioavailability enhancements are typically on the order of 2-fold to 4-fold or less. For CETP inhibitors having low absolute bioavailabilities, such small improvements are insufficient to allow convenient oral dosing of CETP inhibitors; that is, dosage forms having a convenient size and frequency of dosing.

Moreover, some standard methods for improving the concentration of pharmaceuticals in aqueous solution have proven inadequate when applied to CETP inhibitors. For example, even pre-dissolving the CETP inhibitor in a water miscible solvent such as polyethylene glycol followed by delivery as a solution to an aqueous environment of use has failed to raise the aqueous concentration of CETP inhibitor to an acceptable level.

Sikorski, et al., WO 99/14204, and Lee, et al., WO 99/41237, both disclose CETP inhibitors formulated for oral administration using hydroxy propyl methyl celluose in a controlled release dosage form which is characterized as a "dispersion." Both Sikorski and Lee appear to be using the term "dispersion" to mean a controlled release matrix in which drug particles are distributed within a polymer matrix that slowly erodes rather than a solid amorphous dispersion of the type of the present invention. Such controlled release matrix compositions would slow rather than enhance the dissolution and absorption of CETP inhibitor. In any event, both Sikorski and Lee state that CETP inhibitors may be orally dosed by simply dissolving the CETP inhibitor in water without any discussion of the difficulty of dissolving the CETP inhibitors in water. There is no recognition in either Sikorski or Lee of the need to improve the aqueous concentration or bioavailability of CETP inhibitors.

Curatolo et al., EP 0 901 786 A2 disclose solid pharmaceutical dispersions with enhanced bioavailability using spray dried dispersions of a sparingly soluble drug and hydroxy propyl methyl cellulose acetate succinate. However, Curatolo et al. do not disclose the use of CETP inhibitors, or discuss the problems associated with the formulation of CETP inhibitors for oral administration.

Nakamichi et al., U.S. Pat. No. 5,456,923 disclose an extrusion process for producing solid dispersions of sparingly soluble drugs and a variety of polymeric materials, such as hydroxy propyl methyl cellulose acetate succinate. However, Nakamichi et al. does not disclose dispersions containing CETP inhibitors, much less discuss the problems associated with formulating hydrophobic drugs.

Accordingly, there is still a need for developing compositions of CETP inhibitors that may be orally dosed, that improve the aqueous concentration of such drugs, that improve the bioavailability of such drugs relative to compositions of the drugs alone, and that does not adversely affect the ability of the drugs to act therapeutically.

BRIEF SUMMARY OF THE INVENTION

The present invention overcomes the drawbacks of the prior art by providing pharmaceutical compositions comprising a solid amorphous dispersion of a CETP inhibitor and a concentration-enhancing polymer, as well as methods for making the same.

In a first aspect, a method is provided for forming the solid amorphous dispersion by solvent processing. A solution is formed comprising a CETP inhibitor and a concentration-enhancing polymer dissolved in a common solvent. Solvent is then rapidly removed from the solution to form a solid amorphous dispersion of the chloresteryl ester transfer protein inhibitor and the concentration-enhancing polymer.

In another aspect of the invention, a method for forming pharmaceutical compositions by melt extrusion is provided. A CETP inhibitor and a concentration-enhancing polymer are fed to an extruder. The CETP inhibitor and polymer are extruded through the extruder and then rapidly solidified to form a solid amorphous dispersion comprising the chloresteryl ester transfer protein inhibitor and the concentration-enhancing polymer.

In a third aspect of the invention, a method for forming pharmaceutical compositions by melt congealing is provided. A molten mixture comprising a CETP inhibitor and a concentration-enhancing polymer is formed. The mixture is then cooled to form a solid amorphous dispersion comprising the chloresteryl ester transfer protein inhibitor and the concentration-enhancing polymer.

In addition, several compositions are provided comprising chloresteryl ester transfer protein inhibitors and concentration-enhancing polymers. Several different chloresteryl ester transfer protein inhibitors are provided, including (4'S)-5'-(4-fluorophenyl)-6'-[(S)-fluoro[4-(trifluoromethyl)phenyl]methyl]-3',4'-dihydro-7'-(1-methylethyl)-spiro[cyclobutane-1, 2'(1'H)-naphthalen]-4'-ol and (2R)-3-[[3-(4-chloro-3-ethylphenoxy)phenyl][[3-(1,1,2,2-tetrafluoroethoxy) phenyl]methyl]amino]-1,1,1-trifluoro-2-propanol, and pharmaceutically acceptable forms thereof. By "pharmaceutically acceptable forms" thereof is meant any pharmaceutically acceptable derivative or variation, including stereoisomers, stereoisomer mixtures, enantiomers, solvates, hydrates, isomorphs, polymorphs, salt forms and prodrugs.

In another aspect of the invention, several different concentration-enhancing polymers are disclosed. In one aspect of the invention, the concentration-enhancing polymer in the solid amorphous dispersion is carboxymethyl ethyl cellulose. In another aspect of the invention, the concentration-enhancing polymer is a polyoxyethylene-polyoxypropylene copolymer.

As used herein, a "use environment" can be either the in vivo environment of the GI tract of a mammal, particularly a human, or the in vitro environment of a test solution, such as phosphate buffered saline (PBS) or Model Fasted Duodenal (MFD) solution.

The composition may be dosed in a variety of dosage forms, including both immediate release and controlled release dosage forms, the latter including both delayed and sustained release forms. The composition may include blends of polymers, and may further include other excipients that improve the aqueous concentration of the CETP inhibitor.

The various aspects of the present invention each provide one or more of the following advantages. The compositions of the present invention improve the aqueous concentration of CETP inhibitors relative to compositions that are free from concentration-enhancing polymer, by providing aqueous concentration of CETP inhibitors of at least about 10-fold that of control compositions that are free from the concentration-enhancing polymer. Such solubility enhancements are unexpectedly large relative to that typically observed for dispersions of other types of drugs. Accordingly, the compositions of the present invention comprising a CETP inhibitor and concentration-enhancing polymer allow the dose of CETP inhibitor required to obtain adequate efficacy to be reduced.

In fact, compositions of the present invention often exhibit surprisingly large enhancements for some CETP inhibitors, on the order of 50 to 500-fold and in some cases up to a 80,000-fold improvement in concentration relative to that of a control crystalline composition. Such large enhancements are, for some CETP inhibitors, necessary for convenient oral administration. The compositions thus render hydrophobic, substantially insoluble CETP inhibitors therapeutically effective with a convenient dose (mass of drug) for oral administration.

The foregoing and other objectives, features, and advantages of the invention will be more readily understood upon consideration of the following detailed description of the invention.

DETAILED DESCRIPTION OF THE INVENTION

The present invention provides compositions of CETP inhibitors and at least one concentration-enhancing polymer. As discussed above in the Background, CETP inhibitors generally have (1) extremely low solubilities in aqueous solution (i.e., less than about 10 µg/mL) at physiologically relevant pH (e.g., any pH of from 1 through 8) measured at about 22° C.; (2) a relatively hydrophobic nature; and (3) a relatively low bioavailability when orally dosed in the crystalline state. Accordingly, CETP inhibitors require some kind of modification or formulation to enhance their solubility and thereby achieve good bioavailability. Surprisingly, the compositions of the present invention provide unusually large enhancements in aqueous concentration in an environment of use and unusually large enhancements in bioavailability compared with other conventional compositions used to formulate poorly soluble, hydrophobic drugs. The inventors have found that, contrary to conventional wisdom, the compositions provide the greatest enhancements for those drugs which have been thought most difficult to formulate for oral delivery. Specifically, the inventors have found that preparing CETP inhibitors as compositions comprising a solid amorphous dispersion of a CETP inhibitor and concentration-enhancing polymer, and preferably as a homogenous dispersion, improves the aqueous concentration of the CETP inhibitors as well as relative bioavailability. The compositions, CETP inhibitors, suitable polymers, and optional excipients are discussed in more detail as follows.

Compositions of CETP Inhibitors and Concentration-Enhancing Polymer

The present invention finds utility with any low-solubility CETP inhibitor, or any CETP inhibitor which would benefit by improved bioavailability or more rapid absorption. The compositions of the present invention comprise dispersions of a CETP inhibitor and at least one concentration-enhancing polymer. The CETP inhibitor in its pure state may be crystalline or amorphous. Preferably, at least a major portion of the CETP inhibitor in the composition is amorphous. By "amorphous" is meant simply that the CETP inhibitor is in a non-crystalline state. As used herein, the term "a major portion" of the CETP inhibitor means that at least 60% of the CETP inhibitor in the composition is in the amorphous form, rather than the crystalline form. Preferably, the CETP inhibitor in the dispersion is substantially amorphous. As used herein, "substantially amorphous" means that the amount of the CETP inhibitor in crystalline form does not exceed about 25%. More preferably, the CETP inhibitor in the dispersion is "almost completely amorphous" meaning that the amount of CETP inhibitor in the crystalline form does not exceed about 10%. Amounts of crystalline CETP inhibitor may be measured by powder X-ray diffraction, Scanning Electron Microscope (SEM) analysis, differential scanning calorimetry (DSC), or any other standard quantitative measurement.

The composition may contain from about 1 to about 80 wt % CETP inhibitor, depending on the dose of the CETP inhibitor and the effectiveness of the concentration-enhancing polymer. Enhancement of aqueous CETP inhibitor concentrations and relative bioavailability are typically best at low CETP inhibitor levels, typically less than about 25 to 40 wt %. However, due to the practical limit of the dosage form size, higher CETP inhibitor levels are often preferred and in many cases perform well.

The amorphous CETP inhibitor can exist within the solid amorphous dispersion as a pure phase, as a solid solution of CETP inhibitor homogeneously distributed throughout the polymer or any combination of these states or those states that lie intermediate between them. The dispersion is preferably substantially homogeneous so that the amorphous CETP inhibitor is dispersed as homogeneously as possible throughout the polymer. As used herein, "substantially homogeneous" means that the fraction of CETP inhibitor that is present in relatively pure amorphous domains within the solid dispersion is relatively small, on the order of less than 20%, and preferably less than 10% of the total amount of CETP inhibitor.

While the dispersion may have some CETP inhibitor-rich domains, it is preferred that the dispersion itself have a single glass transition temperature ($T_g$) which demonstrates that the dispersion is substantially homogeneous. This contrasts with a simple physical mixture of pure amorphous CETP inhibitor particles and pure amorphous polymer particles which generally display two distinct $T_g$s, one that of the CETP inhibitor and one that of the polymer. $T_g$ as used herein is the characteristic temperature where a glassy material, upon gradual heating, undergoes a relatively rapid (e.g., 10 to 100 seconds) physical change from a glass state to a rubber state. The $T_g$ of an amorphous material such as a polymer, drug or dispersion can be measured by several techniques, including by a dynamic mechanical analyzer (DMA), a dilatometer, dielectric analyzer, and by a differential scanning calorimeter (DSC). The exact values measured by each technique can vary somewhat but usually fall within 10° to 30° C. of each other. Regardless of the technique used, when an amorphous dispersion exhibits a single $T_g$, this indicates that the dispersion is substantially homogenous. Dispersions of the present invention that are substantially homogeneous generally are more physically stable and have improved concentration-enhancing properties and, in turn improved bioavailability, relative to nonhomogeneous dispersions.

The compositions comprising the CETP inhibitor and concentration-enhancing polymer provide enhanced concentration of the dissolved CETP inhibitor in in vitro dissolution tests. It has been determined that enhanced drug concentration in in vitro dissolution tests in Model Fasted Duodenal (MFD) solution or Phosphate Buffered Saline (PBS) is a good indicator of in vivo performance and bioavailability. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate MFD solution is the same PBS solution wherein additionally is present 7.3 mM sodium taurocholic acid and 1.4 mM of 1-palmitoyl-2-oleyl-sn-glycero-3-phosphocholine. In particular, a composition of the present invention can be dissolution-tested by adding it to MFD or PBS solution and agitating to promote dissolution. Generally, the amount of composition added to the solution in such a test is an amount that, if all the drug in the composition dissolved, would produce a CETP inhibitor concentration that is at least about 10-fold and preferably at least 100-fold the equilibrium solubility of the CETP inhibitor alone in the test solution. To demonstrate even higher levels of dissolved CETP inhibitor concentration, addition of even larger amounts of the composition is desirable.

In one aspect, the compositions of the present invention provide a Maximum Drug Concentration (MDC) that is at least about 10-fold the equilibrium concentration of a control composition comprising an equivalent quantity of CETP inhibitor but free from the polymer. In other words, if the equilibrium concentration provided by the control composition is 1 μg/mL, then a composition of the present invention provides an MDC of at least about 10 μg/mL. The control composition is conventionally the undispersed CETP inhibitor alone (e.g., typically, the crystalline CETP inhibitor alone in its most thermodynamically stable crystalline form, or in cases where a crystalline form of the CETP inhibitor is unknown, the control may be the amorphous CETP inhibitor alone) or the CETP inhibitor plus a weight of inert diluent equivalent to the weight of polymer in the test composition. It is to be understood that the control composition is free from solubilizers or other components which would materially affect the solubility of the CETP inhibitor, and that the CETP inhibitor is in solid form in the control composition. Preferably, the MDC of CETP inhibitor achieved with the compositions of the present invention is at least about 50-fold, more preferably at least about 200-fold and even more preferably at least about 500-fold, the equilibrium concentration of the control composition. Surprisingly, the present invention may achieve extremely large enhancements in aqueous concentration. In some cases, the MDC of CETP inhibitor provided by the compositions of the present invention are 200-fold to more than 1000-fold the equilibrium concentration of the control composition. For some CETP inhibitors, due to their extremely low aqueous solubilites, such large enhancements are required in order for the inhibitors to be sufficiently bioavailable when orally dosed.

Alternatively, the compositions of the present invention provide an MDC that is greater than the MDC of the control composition. The MDC provided by the composition comprising a CETP inhibitor and a concentration-enhancing polymer polymer may be 10-, 50-, 200- or 500-fold the MDC provided by a control composition.

Alternatively, the compositions of the present invention provide in an aqueous use environment a concentration versus time Area Under The Curve (AUC), for any period of at least 90 minutes between the time of introduction into the use environment and about 270 minutes following introduction to the use environment, that is at least 5-fold that of a control composition comprising an equivalent quantity of undispersed CETP inhibitor. Preferably, the compositions of the present invention provide in an aqueous use environment a concentration versus time AUC, for any period of at least 90 minutes between the time of introduction into the use environment and about 270 minutes following introduction to the use environment, that is at least about 25-fold, more preferably at least about 100-fold and even more preferably at least about 250-fold that of a control composition as described above. Such large enhancements in aqueous concentration versus time AUC values are surprising given the extremely low aqueous solubility and hydrophobicity of most CETP inhibitors.

A typical in vitro test to evaluate enhanced drug concentration in aqueous solution can be conducted by (1) adding with agitation a sufficient quantity of control composition, typically the CETP inhibitor alone, to the in vitro test medium, typically MFD or PBS solution, to achieve equilibrium concentration of the CETP inhibitor; (2) adding with agitation a sufficient quantity of test composition (e.g., the CETP inhibitor and polymer) in an equivalent test medium, such that if all the CETP inhibitor dissolved, the theoretical concentration of CETP inhibitor would exceed the equilibrium concentration of the CETP inhibitor by a factor of at least 10, and preferably a factor of at least 100; and (3) comparing the measured MDC and/or aqueous concentration versus time AUC of the test composition in the test medium with the equilibrium concentration, and/or the aqueous concentration versus time AUC of the control composition. In conducting such a dissolution test, the amount of test composition or control composition used is an amount such that if all of the CETP inhibitor dissolved the CETP inhibitor concentration would be at least 10-fold and preferably at least 100-fold that of the equilibrium concentration. Indeed, for some extremely insoluble CETP inhibitors, in order to identify the MDC achieved it may be necessary to use an amount of test composition such that if all of the CETP inhibitor dissolved, the CETP inhibitor concentration would be 10,000-fold or even more, that of the equilibrium concentration of the CETP inhibitor.

The concentration of dissolved CETP inhibitor is typically measured as a function of time by sampling the test medium and plotting CETP inhibitor concentration in the test medium vs. time so that the MDC can be ascertained. The MDC is taken to be the maximum value of dissolved CETP inhibitor measured over the duration of the test. The aqueous concentration of the CETP inhibitor versus time AUC is calculated by integrating the concentration versus time curve over any 90-minute time period between the time of introduction of the composition into the aqueous use environment (time equals zero) and 270 minutes following introduction to the use environment (time equals 270 minutes). Typically, when the composition reaches its MDC rapidly, less than about 30 minutes, the time interval used to calculate AUC is from time equals zero to time equals 90 minutes. However, if the AUC over any 90-minute time period described above of a composition meets the criterion of this invention, then the composition is a part of this invention.

To avoid large CETP inhibitor particulates which would give an erroneous determination, the test solution is either filtered or centrifuged. "Dissolved CETP inhibitor" is typically taken as that material that either passes a 0.45 μm syringe filter or, alternatively, the material that remains in the supernatant following centrifugation. Filtration can be conducted using a 13 mm, 0.45 μm polyvinylidine difluoride syringe filter sold by Scientific Resources under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10-40%) than that obtained with the filter specified above but will still allow identification of preferred dispersions. It is recognized that this definition of "dissolved CETP inhibitor" encompasses not only monomeric solvated CETP inhibitor molecules but also a wide range of species such as polymer/CETP inhibitor assemblies that have submicron dimensions such as CETP inhibitor aggregates, aggregates of mixtures of polymer and CETP inhibitor, micelles, polymeric micelles, colloidal particles or nanocrystals, polymer/CETP inhibitor-complexes, and other such CETP inhibitor-containing species that are present in the filtrate or supernatant in the specified dissolution test.

Alternatively, the compositions of the present invention, when dosed orally to a human or other animal, provide an AUC in CETP inhibitor concentration in the blood that is at least about 4-fold that observed when a control composition comprising an equivalent quantity of undispersed drug is dosed. It is noted that such compositions can also be said to have a relative bioavailability of about 4. Preferably, the compositions of the present invention, when dosed orally to a human or other animal, provide an AUC in CETP inhibitor concentration in the blood that is at least about 6-fold, more preferably at least about 10-fold, and even more preferably at least about 20-fold that observed when a control composition comprising an equivalent quantity of undispersed drug is dosed. It is to be understood that when dosed in vivo, the dosing vehicle does not contain any solubilizer or other components which would materially affect the solubility of the CETP inhibitor, and that the CETP inhibitor is in solid form in the control composition. An exemplary dosing vehicle would be a suspension solution of water containing 0.5 wt % hydroxypropyl cellulose (such as METHOCEL) and 0.16 wt % of the surfactant polyoxyethylene 20 sorbitan monooleate (such as TWEEN 80). Thus, the compositions of the present invention can be evaluated in either in vitro or in vivo tests, or both.

Relative bioavailability of CETP inhibitors in the dispersions of the present invention can be tested in vivo in animals or humans using conventional methods for making such a determination. An in vivo test, such as a crossover study, may be used to determine whether a composition of CETP inhibitor and concentration-enhancing polymer provides an enhanced relative bioavailability compared with a control composition comprised of a CETP inhibitor but no polymer as described above. In an in vivo crossover study a "test composition" of CETP inhibitor and polymer is dosed to half a group of test subjects and, after an appropriate washout period (e.g., one week) the same subjects are dosed with a "control composition" that comprises an equivalent quantity of CETP inhibitor as the "test composition" (but with no polymer present). The other half of the group is dosed with the control composition first, followed by the test composition. The relative bioavailability is measured as the concentration in the blood (serum or plasma) versus time area under the curve (AUC) determined for the test group divided by the AUC in the blood provided by the control composition. Preferably, this test/control ratio is determined for each subject, and then the ratios are averaged over all subjects in the study. In vivo determinations of AUC can be made by plotting the serum or plasma concentration of drug along the ordinate (y-axis) against time along the abscissa (x-axis). It is to be understood by those skilled in the art that such in vivo tests are conventionally carried out under fasted conditions.

Thus, as noted above, one embodiment of the present invention is one in which the relative bioavailability of the test composition is at least about 4 relative to a control composition comprised of a CETP inhibitor but with no polymer as described above. (That is, the in vivo AUC provided by the test composition is at least about 4-fold the in vivo AUC provided by the control composition.) A preferred embodiment of the invention is one in which the relative bioavailability of the test composition is at least about 6, and even more preferably at least about 10 relative to a control composition composed of the CETP inhibitor but with no polymer present, as described above. The determination of AUCs is a well-known procedure and is described, for example, in Welling, "Pharmacokinetics Processes and Mathematics," ACS Monograph 185 (1986).

The compositions of the present invention have particular utility when the "absolute bioavailability" of the CETP inhibitor is less than about 5%, and even greater utility when the absolute bioavailability is less than about 1%. By "absolute bioavailability" is meant the ratio of the area under the blood plasma or serum drug concentration versus time curve for oral dosing of a test composition to that obtained by intravenous dosing of a solution of the CETP inhibitor. Care must be taken when determining the absolute bioavailability of CETP inhibitors because their low solubility can result in precipitation of the crystalline form when dosed intravenously, leading to an inaccurate calculation of absolute bioavailability. For CETP inhibitors with such absolute bioavailabilities less than about 5%, the compositions of the present invention preferably provide a relative bioavailability that is at least about 6-fold relative to a control composition comprised of the CETP inhibitor but with no polymer present, as described above. More preferably, when the absolute bioavailability of the CETP inhibitor is less than about 1%, the compositions of the present invention provide relative bioavailability that is at least about 10-fold, and even more preferably at least about 20-fold relative to a control composition, as described above.

Cholesteryl Ester Transfer Protein Inhibitors

The invention is useful for CETP inhibitors which have sufficiently low aqueous solubility, low bioavailability or slow rate of absorption such that it is desirable to increase their concentration in an aqueous environment of use. Therefore, anytime one finds it desirable to raise the aqueous concentration of the CETP inhibitor in a use environment, the invention will find utility. The CETP inhibitor is "substantially water-insoluble" which means that the CETP inhibitor has a minimum aqueous solubility of less than about 0.01 mg/mL (or 10 µg/ml) at any physiologically relevant pH (e.g., pH 1-8) and at about 22° C. (Unless otherwise specified, reference to aqueous solubility herein and in the claims is determined at about 22° C.) Compositions of the present invention find greater utility as the solubility of the CETP inhibitors decreases, and thus are preferred for CETP inhibitors with solubilities less than about 2 µg/mL, and even more preferred for CETP inhibitors with solubilities less than about 0.5 µg/mL. Many CETP inhibitors have even lower solubilities (some even less than 0.1 µg/mL), and require dramatic concentration enhancement to be sufficiently bioavailable upon oral dosing for effective plasma concentrations to be reached at practical doses.

In general, it may be said that the CETP inhibitor has a dose-to-aqueous solubility ratio greater than about 100 mL, where the solubility (mg/mL) is the minimum value observed in any physiologically relevant aqueous solution (e.g., those with pH values from 1 to 8) including USP simulated gastric and intestinal buffers, and dose is in mg. Compositions of the present invention, as mentioned above, find greater utility as the solubility of the CETP inhibitor decreases and the dose increases. Thus, the compositions are preferred as the dose-to-solubility ratio increases, and thus are preferred for dose-to-solubility ratios greater than 1000 mL, and more preferred for dose-to-solubility ratios greater than about 5000 ml. The dose-to-solubility ratio may be determined by dividing the dose (in mg) by the aqueous solubility (in mg/ml).

Oral delivery of many CETP inhibitors is particularly difficult because their aqueous solubility is usually extremely low, typically being less than 2 µg/ml, often being less than 0.1 µg/ml. Such low solubilities are a direct consequence of the particular structural characteristics of species that bind to CETP and thus act as CETP inhibitors. This low solubility is primarily due to the hydrophobic nature of CETP inhibitors. Clog P, defined as the base 10 logarithm of the ratio of the drug solubility in octanol to the drug solubility in water, is a widely accepted measure of hydrophobicity. In general, Clog P values for CETP inhibitors are greater than 4 and are often greater than 5 to 7. Thus, the hydrophobic and insoluble nature of CETP inhibitors as a class pose a particular challenge for oral delivery. Achieving therapeutic drug levels in the blood by oral dosing of practical quantities of drug generally requires a large enhancement in drug concentrations in the gastrointestinal fluid and a resulting large enhancement in bioavailability. Such enhancements in drug concentration in gastrointestinal fluid typically need to be at least about 10-fold and often at least about 50-fold or even at least about 200-fold to achieve desired blood levels. Surprisingly, the dispersions of the present invention have proven to have the required large enhancements in drug concentration and bioavailability.

In contrast to conventional wisdom, the relative degree of enhancement in aqueous concentration and bioavailability generally improves for CETP inhibitors as solubility decreases and hydrophobicity increases. In fact, the inventors have recognized a subclass of these CETP inhibitors that are essentially aqueous insoluble, highly hydrophobic, and are characterized by a set of physical properties. This subclass exhibits dramatic enhancements in aqueous concentration and bioavailability when formulated using the compositions of the present invention.

The first property of this subclass of essentially insoluble, hydrophobic CETP inhibitors is extremely low aqueous solubility. By extremely low aqueous solubility is meant that the minimum aqueous solubility at physiologically relevant pH (pH of 1 to 8) is less than about 10 μg/ml and preferably less than about 1 μg/ml.

A second property is a very high does-to-solubility ratio. Extremely low solubility often leads to poor or slow absorption of the drug from the fluid of the gastrointestinal tract, when the drug is dosed orally in a conventional manner. For extremely low solubility drugs, poor absorption generally becomes progressively more difficult as the dose (mass of drug given orally) increases. Thus, a second property of this subclass of essentially insoluble, hydrophobic CETP inhibitors is a very high dose (in mg) to solubility (in mg/ml) ratio (ml). By "very high dose-to-solubility ratio" is meant that the dose-to-solubility ratio has a value of at least 1000 ml, and preferably at least 5,000 ml, and more preferably at least 10,000 ml.

A third property of this subclass of essentially insoluble, hydrophobic CETP inhibitors is that they are extremely hydrophobic. By extremely hydrophobic is meant that the Clog P value of the drug, has a value of at least 4.0, preferably a value of at least 5.0, and more preferably a value of at least 5.5.

A fourth property of this subclass of essentially insoluble CETP inhibitors is that they have a low melting point. Generally, drugs of this subclass will have a melting point of about 150° C. or less, and preferably about 140° C. or less.

Primarily, as a consequence of some or all of these four properties, CETP inhibitors of this subclass typically have very low absolute bioavailabilities. Specifically, the absolute bioavailability of drugs in this subclass when dosed orally in their undispersed state is less than about 10% and more often less than about 5%.

For this subclass of CETP inhibitors, the CETP inhibitor, when dispersed in the dispersion, should be at least substantially amorphous, and more preferably is almost completely amorphous. In addition, the dispersion should be substantially homogeneous. As discussed below, such dispersions may be made by mechanical processes, such as milling and extrusion; melt processes, such as fusion, melt-extrusion, and melt-congealing; and solvent processes, such as non-solvent precipitation, spray coating, and spray-drying. When prepared in this fashion, this class of essentially insoluble, hydrophobic CETP inhibitors often exhibits dramatic enhancements in aqueous concentration in the use environment and in bioavailability when dosed orally. While the degree of enhancement will depend on the particular concentration-enhancing polymer, when preferred concentration-enhancing polymers are used (as discussed below), such compositions may provide a MDC in an aqueous use environment that is at least about 50-fold, and preferably at least about 200-fold, the equilibrium concentration of a control composition comprising an equivalent quantity of the essentially insoluble, hydrophobic CETP inhibitor but free from the concentration-enhancing polymer. Likewise, the compositions also display in an aqueous use environment an AUC, for any period of at least 90 minutes between the time of introduction into the use environment and about 270 minutes following introduction into the use environment that is at least about 25-fold, and preferably at least about 100-fold, that of the control composition comprising an equivalent quantity of drug but free from the concentration-enhancing polymer.

Turning now to the chemical structures of specific CETP inhibitors, one class of CETP inhibitors that finds utility with the present invention consists of oxy substituted 4-carboxyamino-2-methyl-1,2,3,4-tetrahydroquinolines having the Formula I

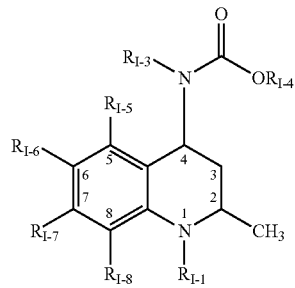

Formula I

And pharmaceutically acceptable forms thereof;

wherein $R_{I-1}$ is hydrogen, $Y_I$, $W_I$—$X_I$, $W_I$—$Y_I$;

wherein $W_I$ is a carbonyl, thiocarbonyl, sulfinyl or sulfonyl;

$X_I$ is —O—$Y_I$, —S—$Y_I$, —N(H)—$Y_I$ or —N—$(Y_I)_2$;

wherein $Y_I$ for each occurrence is independently $Z_I$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_I$;

wherein $Z_I$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_I$ substituent is optionally mono-, di- or tri-substituted independently with halo, $(C_2$-$C_6)$alkenyl, $(C_1$-$C_6)$ alkyl, hydroxy, $(C_1$-$C_6)$alkoxy, $(C_1$-$C_4)$alkylthio, amino, nitro, cyano, oxo, carboxyl, $(C_1$-$C_6)$alkyloxycarbonyl, mono-N— or di-N,N—$(C_1$-$C_6)$alkylamino wherein said $(C_1$-$C_6)$ alkyl substituent is optionally mono-, di- or tri-substituted independently with halo, hydroxy, $(C_1$-$C_6)$alkoxy, $(C_1$-$C_4)$ alkylthio, amino, nitro, cyano, oxo, carboxyl, $(C_1$-$C_6)$alkyloxycarbonyl, mono-N— or di-N,N—$(C_1$-$C_6)$alkylamino, said $(C_1$-$C_6)$alkyl substituent is also optionally substituted with from one to nine fluorines;

$R_{I-1}$ is hydrogen or $Q_I$;

wherein $Q_I$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_I$;

wherein $V_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_I$ substituent is optionally mono-, di-, tri-, or tetra-substituted independently with halo, $(C_1$-$C_6)$alkyl, $(C_2$-$C_6)$alkenyl, hydroxy, $(C_1$-$C_6)$alkoxy, $(C_1$-$C_4)$alkylthio, amino, nitro, cyano, oxo, carbamoyl, mono-N— or di-N,N—$(C_1$-$C_6)$ alkylcarbamoyl, carboxyl, $(C_1$-$C_6)$ alkyloxycarbonyl, mono-N— or di-N,N—$(C_1$-$C_6)$alkylamino wherein said $(C_1$-$C_6)$alkyl or $(C_2$-$C_6)$alkenyl substituent is optionally mono-, di- or tri-substituted independently with hydroxy, $(C_1$-$C_6)$alkoxy, $(C_1$-$C_4)$alkylthio, amino, nitro, cyano, oxo, carboxyl, $(C_1$-$C_6)$alkyloxycarbonyl, mono-N— or di-N,N—$(C_1$-$C_6)$alkylamino, said $(C_1$-$C_6)$alkyl or $(C_2$-$C_6)$alkenyl substituents are also optionally substituted with from one to nine fluorines;

$R_{I-4}$ is $Q_{I-1}$ or $V_{I-1}$ wherein $Q_{I-1}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{I-1}$;

wherein $V_{I-1}$ is a partially saturated, fully saturated or fully unsaturated three to six membered ring optionally having one to two heteroatoms selected independently from oxygen, sulfur and nitrogen;

wherein said $V_{I-1}$ substituent is optionally mono-, di-, tri-, or tetra-substituted independently with halo, $(C_1$-$C_6)$alkyl, $(C_1$-$C_6)$alkoxy, amino, nitro, cyano, $(C_1$-$C_6)$alkyloxycarbonyl, mono-N— or di-N,N—$(C_1$-$C_6)$alkylamino wherein said $(C_1$-$C_6)$alkyl substituent is optionally mono-substituted with oxo, said $(C_1$-$C_6)$alkyl substituent is also optionally substituted with from one to nine fluorines;

wherein either $R_{I-3}$ must contain $V_I$ or $R_{I-4}$ must contain $V_{I-1}$; and $R_{I-5}$, $R_{I-6}$, $R_{I-7}$ and $R_{I-8}$ are each independently hydrogen, hydroxy or oxy wherein said oxy is substituted with $T_I$ or a partially saturated, fully saturated or fully unsaturated one to twelve membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_I$;

wherein $T_I$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $T_I$ substituent is optionally mono-, di- or tri-substituted independently with halo, $(C_1$-$C_6)$alkyl, $(C_2$-$C_6)$alkenyl, hydroxy, $(C_1$-$C_6)$alkoxy, $(C_1$-$C_4)$alkylthio, amino, nitro, cyano, oxo, carboxy, $(C_1$-$C_6)$alkyloxycarbonyl, mono-N— or di-N,N—$(C_1$-$C_6)$alkylamino wherein said $(C_1$-$C_6)$alkyl substituent is optionally mono-, di- or tri-substituted independently with hydroxy, $(C_1$-$C_6)$alkoxy, $(C_1$-$C_4)$alkylthio, amino, nitro, cyano, oxo, carboxy, $(C_1$-$C_6)$alkyloxycarbonyl, mono-N— or di-N,N—$(C_1$-$C_6)$alkylamino, said $(C_1$-$C_6)$alkyl substituent is also optionally substituted with from one to nine fluorines.

Compounds of Formula I are disclosed in commonly assigned U.S. Pat. No. 6,140,342, the complete disclosure of which is herein incorporated by reference.

In a preferred embodiment, the CETP inhibitor is selected from one of the following compounds of Formula I:

[2R,4S]4-[(3,5-dichloro-benzyl)-methoxycarbonyl-amino]-6,7-dimethoxy-2-methyl-3,4-dihydro-2H-quinoline-1-carboxylic acid ethyl ester;

[2R,4S]4-[(3,5-dinitro-benzyl)-methoxycarbonyl-amino]-6,7-dimethoxy-2-methyl-3,4-dihydro-2H-quinoline-1-carboxylic acid ethyl ester;

[2R,4S]4-[(2,6-dichloro-pyridin-4-ylmethyl)-methoxycarbonyl-amino]-6,7-dimethoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-6-methoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-7-methoxy-2-methyl-3,4-dihydro-2H-quinoline-1-carboxylic acid ethyl ester,

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid isopropyl ester;

[2R,4S]4-[(3,5-bis-trifluoromethyl-benzyl)-ethoxycarbonyl-amino]-6,7-dimethoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid 2,2,2-trifluoro-ethylester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid propyl ester;

[2R,4S]4-[(3,5-bis-trifluoromethyl-benzyl)-methoxycarbonyl-amino]-6,7-dimethoxy-2-methyl-3,4-dihydro-2H-quinoline-1-carboxylic acid tert-butyl ester;

[2R,4S]4-[(3,5-bis-trifluoromethyl-benzyl)-methoxycarbonyl-amino]-2-methyl-6-trifluoromethoxy-3,4-dihydro-2H-quinoline-1-carboxylic acid ethyl ester,

[2R,4S](3,5-bis-trifluoromethyl-benzyl)-(1-butyryl-6,7-dimethoxy-2-methyl-1,2,3,4-tetrahydro-quinolin-4-yl)-carbamic acid methyl ester;

[2R,4S](3,5-bis-trifluoromethyl-benzyl)-(1-butyl-6,7-dimethoxy-2-methyl-1,2,3,4-tetrahydro-quinolin-4-yl)-carbamic acid methyl ester;

[2R,4S](3,5-bis-trifluoromethyl-benzyl)-[1-(2-ethyl-butyl)-6,7-dimethoxy-2-methyl-1,2,3,4-tetrahydro-quinolin-4-yl]-carbamic acid methyl ester, hydrochloride Another class of CETP inhibitors that finds utility with the present invention consists of 4-carboxyamino-2-methyl-1,2,3,4,-tetrahydroquinolines, having the Formula II

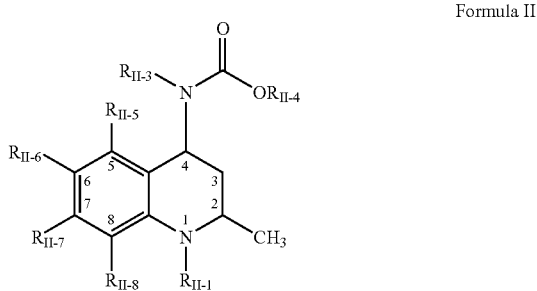

Formula II and pharmaceutically acceptable forms thereof;

wherein $R_{II-1}$ is hydrogen, $Y_{II}$, $W_{II}$—$X_{II}$, $W_{II}$—$Y_{II}$;

wherein $W_{II}$ is a carbonyl, thiocarbonyl, sulfinyl or sulfonyl;

$X_{II}$ is —O—$Y_{II}$, —S—$Y_{II}$, —N(H)—$Y_{II}$ or —N—$(Y_{II})_2$;

wherein $Y_{II}$ for each occurrence is independently $Z_{II}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{II}$;

$Z_{II}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{II}$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl is also optionally substituted with from one to nine fluorines;

$R_{II-3}$ is hydrogen or $Q_{II}$;

wherein $Q_{II}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II}$;

wherein $V_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{II}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$ alkylcarboxamoyl, carboxy, $(C_1-C_6)$ alkyloxycarbonyl, mono-N— or di-N,N—$(C_1-C_6)$alkylamino wherein said $(C_1-C_6)$alkyl or $(C_2-C_6)$-alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino or said $(C_1-C_6)$alkyl or $(C_1-C_6)$alkenyl substituents are optionally substituted with from one to nine fluorines;

$R_{II-4}$ is $Q_{II-1}$ or $V_{II-1}$ wherein $Q_{II-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{II-1}$;

wherein $V_{II-1}$ is a partially saturated, fully saturated or fully unsaturated three to six membered ring optionally having one to two heteroatoms selected independently from oxygen, sulfur and nitrogen;

wherein said $V_{II-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is optionally substituted with from one to nine fluorines;

wherein either $R_{II-3}$ must contain $V_{II}$ or $R_{II-4}$ must contain $V_{II-1}$; and $R_{II-5}$, $R_{II-6}$, $R_{II-7}$ and $R_{II-8}$ are each independently hydrogen, a bond, nitro or halo wherein said bond is substituted with $T_{II}$ or a partially saturated, fully saturated or fully unsaturated $(C_1-C_{12})$ straight or branched carbon chain wherein carbon may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{II}$;

wherein $T_{II}$ is a partially saturated, fully saturated or fully unsaturated three to twelve membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{II}$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; provided that at least one of substituents $R_{II-5}$, $R_{II-6}$, $R_{II-7}$ and $R_{II-8}$ is not hydrogen and is not linked to the quinoline moiety through oxy.

Compounds of Formula II are disclosed in commonly assigned U.S. Pat. No. 6,147,090, the complete disclosure of which is herein incorporated by reference.

In a preferred embodiment, the CETP inhibitor is selected from one of the following compounds of Formula II:

[2R,4S]4-[(3,5-Bis-trifluoromethyl-benzyl)-methoxycarbonyl-amino]-2-methyl-7-trifluoromethyl-3,4-dihydro-2H-quinoline-1-carboxylic acid ethyl ester;

[2R,4S]4-[(3,5-Bis-trifluoromethyl-benzyl)-methoxycarbonyl-amino]-7-chloro-2-methyl-3,4-dihydro-2H-quinoline-1-carboxylic acid ethyl ester;

[2R,4S]4-[(3,5-Bis-trifluoromethyl-benzyl)-methoxycarbonyl-amino]-6-chloro-2-methyl-3,4-dihydro-2H-quinoline-1-carboxylic acid ethyl ester;

[2R,4S]4-[(3,5-Bis-trifluoromethyl-benzyl)-methoxycarbonyl-amino]-2,6,7-trimethyl-3,4-dihydro-2H-quinoline-1-carboxylic acid ethyl ester

[2R,4S]4-[(3,5-Bis-trifluoromethyl-benzyl)-methoxycarbonyl-amino]-6,7-diethyl-2-methyl-3,4-dihydro-2H-quinoline-1-carboxylic acid ethyl ester;

[2R,4S]4-[(3,5-Bis-trifluoromethyl-benzyl)-methoxycarbonyl-amino]-6-ethyl-2-methyl-3,4-dihydro-2H-quinoline-1-carboxylic acid ethyl ester;

[2R,4S]4-[(3,5-Bis-trifluoromethyl-benzyl)-methoxycarbonyl-amino]-2-methyl-6-trifluoromethyl-3,4-dihydro-2H-quinoline-1-carboxylic acid ethyl ester.

[2R,4S]4-[(3,5-bis-trifluoromethyl-benzyl)-methoxycarbonyl-amino]-2-methyl-6-trifluoromethyl-3,4-dihydro-2H-quinoline-1-carboxylic acid isopropyl ester.

Another class of CETP inhibitors that finds utility with the present invention consists of annulated 4-carboxyamino-2-methyl-1,2,3,4,-tetrahydroquinolines, having the Formula III

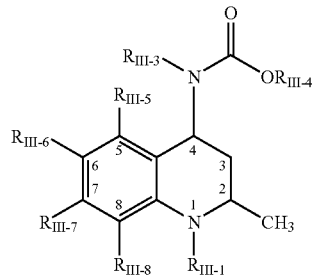

Formula III and pharmaceutically acceptable forms thereof;

wherein $R_{III-1}$ is hydrogen, $Y_{III}$, $W_{III}$—$X_{III}$, $W_{III}$—$Y_{III}$;

wherein $W_{III}$ is a carbonyl, thiocarbonyl, sulfinyl or sulfonyl;

$X_{III}$ is —O—$Y_{III}$, —S—$Y_{III}$, —N(H)—$Y_{III}$ or —N—$(Y_{III})_2$;

$Y_{III}$ for each occurrence is independently $Z_{III}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{III}$;

wherein $Z_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{III}$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl optionally substituted with from one to nine fluorines;

$R_{III-3}$ is hydrogen or $Q_{III}$;

wherein $Q_{III}$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{III}$;

wherein $V_{III}$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{III}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N, N—$(C_1-C_6)$ alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino or said $(C_1-C_6)$alkyl or $(C_2-C_6)$alkenyl are optionally substituted with from one to nine fluorines;

$R_{III-4}$ is $Q_{III-1}$ or $V_{III-1}$;

wherein $Q_{III-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{III-1}$;

wherein $V_{III-1}$ is a partially saturated, fully saturated or fully unsaturated three to six membered ring optionally having one to two heteroatoms selected independently from oxygen, sulfur and nitrogen;

wherein said $V_{III-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent optionally having from one to nine fluorines;

wherein either $R_{III-3}$ must contain $V_{III}$ or $R_{III-4}$ must contain $V_{III-1}$; and $R_{III-5}$ and $R_{III-6}$, or $R_{III-6}$ and $R_{III-7}$, and/or $R_{III-7}$ and $R_{III-8}$ are taken together and form at least one four to eight membered ring that is partially saturated or fully unsaturated optionally having one to three heteroatoms independently selected from nitrogen, sulfur and oxygen;

wherein said ring or rings formed by $R_{III-5}$ and $R_{III-6}$, or $R_{III-6}$ and $R_{III-7}$, and/or $R_{III-7}$ and $R_{III-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally, mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent optionally having from one to nine fluorines;

provided that the $R_{III-5}$, $R_{III-6}$, $R_{III-7}$ and/or $R_{III-8}$, as the case may be, that do not form at least one ring are each independently hydrogen, halo, $(C_1-C_6)$alkoxy or $(C_1-C_6)$alkyl, said $(C_1-C_6)$alkyl optionally having from one to nine fluorines.

Compounds of Formula III are disclosed in commonly assigned pending U.S. Pat. No. 6,147,089, the complete disclosure of which is herein incorporated by reference.

In a preferred embodiment, the CETP inhibitor is selected from one of the following compounds of Formula III:

[2R,4S]4-[(3,5-bis-trifluoromethyl-benzyl)-methoxycarbonyl-amino]-2-methyl-2,3,4,6,7,8-hexahydro-cyclopenta[g]quinoline-1-carboxylic acid ethyl ester;

[6R,8S]8-[(3,5-bis-trifluoromethyl-benzyl)-methoxycarbonyl-amino]-6-methyl-3,6,7,8-tetrahydro-1H-2-thia-5-aza-cyclopenta[b]naphthalene-5-carboxylic acid ethylester;

[6R,8S]8-[(3,5-bis-trifluoromethyl-benzyl)-methoxycarbonyl-amino]-6-methyl-3,6,7,8-tetrahydro-2H-furo[2,3-g]quinoline-5-carboxylic acid ethyl ester;

[2R,4S]4-[(3,5-bis-trifluoromethyl-benzyl)-methoxycarbonyl-amino]-2-methyl-3,4,6,8-tetrahydro-2H-furo[3,4-g]quinoline-1-carboxylic acid ethyl ester;

[2R,4S]4-[(3,5-bis-trifluoromethyl-benzyl)-methoxycarbonyl-amino]-2-methyl-3,4,6,7,8,9-hexahydro-2H-benzo[g]quinoline-1-carboxylic acid propyl ester;

[7R,9S]9-[(3,5-bis-trifluoromethyl-benzyl)-methoxycarbonyl-amino]-7-methyl-1,2,3,7,8,9-hexahydro-6-aza-cyclopenta[a]naphthalene-6-carboxylic acid ethyl ester; and

[6S,8R]6-[(3,5-bis-trifluoromethyl-benzyl)-methoxycarbonyl-amino]-8-methyl-1,2,3,6,7,8-hexahydro-9-aza-cyclopenta[a]naphthalene-9-carboxylic acid ethyl ester.

Another class of CETP inhibitors that finds utility with the present invention consists of 4-carboxyamino-2-substituted-1,2,3,4,-tetrahydroquinolines, having the Formula IV

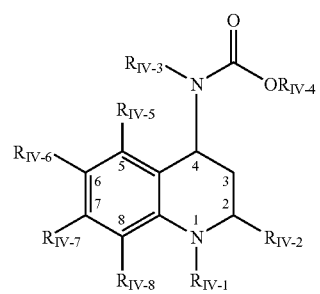

Formula IV and pharmaceutically acceptable forms thereof;

wherein $R_{IV-1}$ is hydrogen, $Y_{IV}$, $W_{IV}$—$X_{IV}$ or $W_{IV}$—$Y_{IV}$;

wherein $W_{IV}$ is a carbonyl, thiocarbonyl, sulfinyl or sulfonyl;

$X_{IV}$ is —O—$Y_{IV}$, —S—$Y_{IV}$, —N(H)—$Y_{IV}$ or —N—$(Y_{IV})_2$;

wherein $Y_{IV}$ for each occurrence is independently $Z_{IV}$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_{IV}$;

wherein $Z_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_{IV}$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines;

$R_{IV-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{IV-2}$ is a partially saturated, fully saturated or fully unsaturated three to seven membered ring optionally having one to two heteroatoms selected independently from oxygen, sulfur and nitrogen, wherein said $R_{IV-2}$ ring is optionally attached through $(C_1-C_4)$ alkyl;

wherein said $R_{IV-2}$ ring is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$ alkylthio, oxo or $(C_1-C_6)$ alkyloxycarbonyl;

with the proviso that $R_{IV-2}$ is not methyl;

$R_{IV-3}$ is hydrogen or $Q_{IV}$;

wherein $Q_{IV}$ is a fully saturated, partially unsaturated or fully unsaturated one to six membered straight or branched carbon chain wherein the carbons other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV}$;

wherein $V_{IV}$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_{IV}$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$ alkylcarboxamoyl, carboxy, $(C_1-C_6)$alkyloxycarbonyl, mono-N— or di-N,N—$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl or $(C_2-C_6)$ alkenyl substituents are also optionally substituted with from one to nine fluorines;

$R_{IV-4}$ is $Q_{IV-1}$ or $V_{IV-1}$, wherein $Q_{IV-1}$ a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V_{IV-1}$;

wherein $V_{IV-1}$ is a partially saturated, fully saturated or fully unsaturated three to six membered ring optionally having one to two heteroatoms selected independently from oxygen, sulfur and nitrogen;

wherein said $V_{IV-1}$ substituent is optionally mono-, di-, tri-, or tetra-substituted independently with halo, $(C_1-C_6)$alkyl, $(C_1-C_6)$alkoxy, amino, nitro, cyano, $(C_1-C_6)$ alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein either $R_{IV-3}$ must contain $V_{IV}$ or $R_{IV-4}$ must contain $V_{IV-1}$;

$R_{IV-5}$, $R_{IV-6}$, $R_{IV-7}$ and $R_{IV-8}$ are each independently hydrogen, a bond, nitro or halo wherein said bond is substituted with $T_{IV}$ or a partially saturated, fully saturated or fully unsaturated $(C_1-C_{12})$ straight or branched carbon chain wherein carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon is optionally mono-substituted with $T_{IV}$;

wherein $T_{IV}$ is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said $T_{IV}$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; and wherein $R_{IV-5}$ and $R_{IV-6}$, or $R_{IV-6}$ and $R_{IV-7}$, and/or $R_{IV-7}$ and $R_{IV-8}$ may also be taken together and can form at least one four to eight membered ring that is partially saturated or fully unsaturated optionally having one to three heteroatoms independently selected from nitrogen, sulfur and oxygen;

wherein said ring or rings formed by $R_{IV-5}$ and $R_{IV-6}$, or $R_{IV-6}$ and $R_{IV-7}$, and/or $R_{IV-7}$ and $R_{IV-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines; with the proviso that when $R_{IV-2}$ is carboxyl or $(C_1-C_4)$alkylcarboxyl, then $R_{IV-1}$ is not hydrogen.

Compounds of Formula IV are disclosed in commonly assigned U.S. Pat. No. 6,197,786, the complete disclosure of which is herein incorporated by reference.

In a preferred embodiment, the CETP inhibitor is selected from one of the following compounds of Formula IV:

[2S,4S]4-[(3,5-bis-trifluoromethyl-benzyl)-methoxycarbonyl-amino]-2-isopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-6-chloro-2-cyclopropyl-3,4-dihydro-2H-quinoline-1-carboxylic acid isopropyl ester;

[2S,4S]2-cyclopropyl-4-[(3,5-dichloro-benzyl)-methoxycarbonyl-amino]-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid tert-butyl ester;

[2R,4R]4-[(3,5-bis-trifluoromethyl-benzyl)-methoxycarbonyl-amino]-2-cyclopropyl-6-trifluoromethyl-3,4-dihydro-2H-quinaline-1-carboxylic acid isopropyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-cyclobutyl-6-trifluoromethyl-3,4-dihydro-2H-quinoline-1-carboxylic acid isopropyl ester,

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester;

[2S,4S]4-[(3,5-bis-trifluoromethyl-benzyl)-methoxycarbonyl-amino]-2-methoxymethyl-6-trifluoromethyl-3,4-dihydro-2H-quinoline-1-carboxylic acid isopropyl ester;

[2R,4S]4-[((3,5-bis-trifluoromethyl-benzyl)-methoxycarbonyl-amino]-2-ethyl-6-trifluoromethyl-3,4-dihydro-2H-quinoline-1-carboxylic acid 2-hydroxy-ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

[2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid propyl ester; and

[2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid propyl ester.

Another class of CETP inhibitors that finds utility with the present invention consists of 4-amino substituted-2-substituted-1,2,3,4,-tetrahydroquinolines, having the Formula V

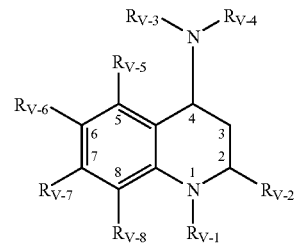

Formula V and pharmaceutically acceptable forms thereof;

wherein $R_{V-1}$ is $Y_V$, $W_V$—$X_V$ or $W_V$—$Y_V$;

wherein $W_V$ is a carbonyl, thiocarbonyl, sulfinyl or sulfonyl;

$X_V$ is —O—$Y_V$, —S—$Y_V$, —N(H)—$Y_V$ or —N—$(Y_V)_2$;

wherein $Y_V$ for each occurrence is independently $Z_V$ or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $Z_V$;

wherein $Z_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $Z_V$ substituent is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent is also optionally substituted with from one to nine fluorines;

$R_{V-2}$ is a partially saturated, fully saturated or fully unsaturated one to six membered straight or branched carbon chain wherein the carbons, other than the connecting carbon, may optionally be replaced with one or two heteroatoms selected independently from oxygen, sulfur and nitrogen wherein said carbon atoms are optionally mono-, di- or tri-substituted independently with halo, said carbon is optionally mono-substituted with oxo, said carbon is optionally mono-substituted with hydroxy, said sulfur is optionally mono- or di-substituted with oxo, said nitrogen is optionally mono- or di-substituted with oxo; or said $R_{V-2}$ is a partially saturated, fully saturated or fully unsaturated three to seven membered ring optionally having one to two heteroatoms selected independently from oxygen, sulfur and nitrogen, wherein said $R_{V-1}$ ring is optionally attached through $(C_1-C_4)$alkyl;

wherein said $R_{V-2}$ ring is optionally mono-, di- or tri-substituted independently with halo, $(C_2-C_6)$alkenyl, $(C_1-C_6)$ alkyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$alkylthio, oxo or $(C_1-C_6)$ alkyloxycarbonyl;

$R_{V-3}$ is hydrogen or $Q_V$;

wherein $Q_V$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_V$;

wherein $V_V$ is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_V$ substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxamoyl, mono-N— or di-N,N—$(C_1-C_6)$ alkylcarboxamoyl, carboxy, $(C_1-C_6)$ alkyloxycarbonyl, mono-N— or di-N,N—$(C_1-C_6)$ alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl or $(C_2-C_6)$ alkenyl substituents are also optionally substituted with from one to nine fluorines;

$R_{V-4}$ is cyano, formyl, $W_{V-1}Q_{V-1}$, $W_{V-1}Y_{V-1}$, $(C_1-C_4)$alkyleneV$_{V-1}$, or V$_{V-2}$;

wherein $W_{V-1}$ is carbonyl, thiocarbonyl, SO or $SO_2$;

wherein $Q_{V-1}$ a fully saturated, partially unsaturated or fully unsaturated one to six membered straight or branched carbon chain wherein the carbons may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V_{V-1}$;

wherein $V_{V-1}$ is a partially saturated, fully saturated or fully unsaturated three to six membered ring optionally having one to two heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said $V_V$ substituent is optionally mono-, di-, tri-, or tetra-substituted independently with halo, $(C_1-C_6)$alkyl, $(C_1-C_6)$alkoxy, hydroxy, oxo, amino, nitro, cyano, $(C_1-C_6)$ alkyloxycarbonyl, mono-N— or di-N,N—$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein $V_{V-2}$ is a partially saturated, fully saturated or fully unsaturated five to seven membered ring containing one to four heteroatoms selected independently from oxygen, sulfur and nitrogen;

wherein said $V_{V-2}$ substituent is optionally mono-, di- or tri-substituted independently with halo, $(C_1-C_2)$alkyl, $(C_1-C_2)$alkoxy, hydroxy, or oxo wherein said $(C_1-C_2)$alkyl optionally has from one to five fluorines; and wherein $R_{V-4}$ does not include oxycarbonyl linked directly to the $C_4$ nitrogen;

wherein either $R_{V-3}$ must contain $V_V$ or $R_{V-4}$ must contain $V_{V-1}$;

$R_{V-5}$, $R_{V-6}$, $R_{V-7}$ and $R_{V-8}$ are independently hydrogen, a bond, nitro or halo wherein said bond is substituted with $T_V$ or a partially saturated, fully saturated or fully unsaturated $(C_1-C_{12})$ straight or branched carbon chain wherein carbon may optionally be replaced with one or two heteroatoms selected independently from oxygen, sulfur and nitrogen, wherein said carbon atoms are optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $T_V$;

wherein $T_V$ is a partially saturated, fully saturated or fully unsaturated three to twelve membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms-selected independently from nitrogen, sulfur and oxygen;

wherein said $T_V$ substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent also optionally has from one to nine fluorines;

wherein $R_{V-5}$ and $R_{V-6}$, or $R_{V-6}$ and $R_{V-7}$, and/or $R_{V-7}$ and $R_{V-8}$ may also be taken together and can form at least one ring that is a partially saturated or fully unsaturated four to eight membered ring optionally having one to three heteroatoms independently selected from nitrogen, sulfur and oxygen;

wherein said rings formed by $R_{V-5}$ and $R_{V-6}$, or $R_{V-6}$ and $R_{V-7}$, and/or $R_{V-7}$ and $R_{V-8}$ are optionally mono-, di- or tri-substituted independently with halo, $(C_1-C_6)$alkyl, $(C_1-C_4)$alkylsulfonyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$ alkyloxycarbonyl, mono-N— or di-N,N—$(C_1-C_6)$ alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N— or di-N,N—$(C_1-C_6)$alkylamino, said $(C_1-C_6)$alkyl substituent also optionally has from one to nine fluorines.

Compounds of Formula V are disclosed in commonly assigned U.S. Pat. No. 6,140,343, the complete disclosure of which is herein incorporated by reference.

In a preferred embodiment, the CETP inhibitor is selected from one of the following compounds of Formula V:

[2S,4S]4-[(3,5-bis-trifluoromethyl-benzyl)-formyl-amino]-2-cyclopropyl-6-trifluoromethyl-3,4-dihydro-2H-quinoline-1-carboxylic acid isopropyl ester;

[2S,4S]4-[(3,5-bis-trifluoromethyl-benzyl)-formyl-amino]-2-cyclopropyl-6-trifluoromethyl-3,4-dihydro-2H-quinoline-1-carboxylic acid propyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid tert-butyl ester;

[2R,4S]4-[acetyl-(3,5-bis-trifluoromethyl-benzyl)-amino]-2-ethyl-6-trifluoromethyl-3,4-dihydro-2H-quinoline-1-carboxylic acid isopropyl ester;

[2R,4S]4-[acetyl-(3,5-bis-trifluoromethyl-benzyl)-amino]-2-methyl-6-trifluoromethyl-3,4-dihydro-2H-quinoline-1-carboxylic acid ethyl ester,

[2S,4S]4-[1-(3,5-bis-trifluoromethyl-benzyl)-ureido]-2-cyclopropyl-6-trifluoromethyl-3,4-dihydro-2H-quinoline-1-carboxylic acid isopropyl ester;

[2R,4S]4-[acetyl-(3,5-bis-trifluoromethyl-benzyl)-amino]-2-ethyl-6-trifluoromethyl-3,4-dihydro-2H-quinoline-1-carboxylic acid ethyl ester;

[2S,4S]4-[acetyl-(3,5-bis-trifluoromethyl-benzyl)-amino]-2-methoxymethyl-6-trifluoromethyl-3,4-dihydro-2H-quinoline-1-carboxylic acid isopropyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid propyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-formyl-amino]-2-ethyl-6-trifluoromethyl-3,4-dihydro-2H-quinoline-1-carboxylic acid isopropyl ester;

[2R,4S]4-[(3,5-bis-trifluoromethyl-benzyl)-formyl-amino]-2-methyl-6-trifluoromethyl-3,4-dihydro-2H-quinoline-1-carboxylic acid ethyl ester;

[2S,4S]4-[acetyl-(3,5-bis-trifluoromethyl-benzyl)-amino]-2-cyclopropyl-6-trifluoromethyl-3,4-dihydro-2H-quinoline-1-carboxylic acid isopropyl ester;

[2R,4S]4-[(3,5-bis-trifluoromethyl-benzyl)-formyl-amino]-2-ethyl-6-trifluoromethyl-3,4-dihydro-2H-quinoline-1-carboxylic acid ethyl ester;

[2S,4S]4-[(3,5-bis-trifluoromethyl-benzyl)-formyl-amino]-2-cyclopropyl-6-trifluoromethyl-3,4-dihydro-2H-quinoline-1-carboxylic acid ethyl ester;

[2R,4S]4-[(3,5-bis-trifluoromethyl-benzyl)-formyl-amino]-2-methyl-6-trifluoromethyl-3,4-dihydro-2H-quinoline-1-carboxylic acid isopropyl ester; and

[2R,4S]4-[acetyl-(3,5-bis-trifluoromethyl-benzyl)-amino]-2-methyl-6-trifluoromethyl-3,4-dihydro-2H-quinoline-1-carboxylic acid isopropyl ester.

Another class of CETP inhibitors that finds utility with the present invention consists of cycloalkano-pyridines having the Formula VI

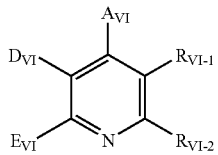

Formula VI and pharmaceutically acceptable forms thereof;

in which $A_{VI}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula —$NR_{VI-3}R_{VI-4}$, wherein $R_{VI-3}$ and $R_{VI-4}$ are identical or different and denote a hydrogen, phenyl or a straight-chain or branched alkyl containing up to 6 carbon atoms, $D_{VI}$ denotes an aryl containing 6 to 10 carbon atoms, which is optionally substituted with a phenyl, nitro, halogen, trifluoromethyl or trifluoromethoxy, or a radical according to the formula $R_{VI-5}$-$L_{VI}$,

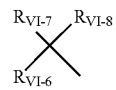

or $R_{VI-9}$-$T_{VI}$$V_{VI}$—$X_{VI}$, wherein $R_{VI-5}$, $R_{VI-6}$ and $R_{VI-9}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O, wherein the rings are optionally substituted, in the case of the nitrogen-containing rings also via the N function, with up to five identical or different substituents in the form of a halogen, trifluoromethyl, nitro, hydroxyl, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed, aromatic 5- to 7-membered heterocycle containing up to 3 heteroatoms from the series of S, N and/or O, and/or in the form of a group according to the formula —$OR_{VI-10}$, —$SR_{VI-11}$, —$SO_2R_{VI-12}$ or —$NR_{VI-13}R_{VI-14}$, wherein $R_{VI-10}$, $R_{VI-11}$ and $R_{VI-12}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms, $R_{VI-13}$ and $R_{VI-14}$ are identical or different and have the meaning of $R_{VI-3}$ and $R_{VI-4}$ given above, or $R_{VI-5}$ and/or $R_{VI-6}$ denote a radical according to the formula

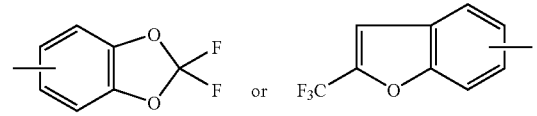

$R_{VI-7}$ denotes a hydrogen or halogen, and $R_{VI-8}$ denotes a hydrogen, halogen, azido, trifluoromethyl, hydroxyl, trifluoromethoxy, a straight-chain or branched alkoxy or alkyl containing up to 6 carbon atoms each, or a radical according to the formula

—$NR_{VI-15}R_{VI-16}$ wherein $R_{VI-15}$ and $R_{VI-16}$ are identical or different and have the meaning of —$R_{VI-3}$ and $R_{VI-4}$ given above, or $R_{VI-7}$ and $R_{VI-8}$ together form a radical according to the formula =O or =$NR_{VI-17}$, wherein $R_{VI-17}$ denotes a hydrogen or a straight-chain or branched alkyl, alkoxy or acyl containing up to 6 carbon atoms each, $L_{VI}$ denotes a straight-chain or branched alkylene or alkenylene chain containing up to 8 carbon atoms each, which 4 are optionally substituted with up to two hydroxyl groups, $T_{VI}$ and $X_{VI}$ are identical or different and denote a straight-chain or branched alkylene chain containing up to 8 carbon atoms, or $T_{VI}$ or $X_{VI}$ denotes a bond, $V_{VI}$ denotes an oxygen or sulfur atom or an —$NR_{VI-18}$ group, wherein $R_{VI-18}$ denotes a hydrogen or a straight-chain or branched alkyl containing up to 6 carbon atoms or a phenyl, $E_{VI}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl, $R_{VI-1}$ and $R_{VI-2}$ together form a straight-chain or branched alkylene chain containing up to 7 carbon atoms, which must be substituted with a carbonyl group and/or a radical according to the formula

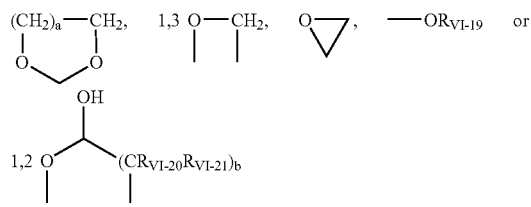

wherein a and b are identical or different and denote a number equaling 1, 2 or 3, $R_{VI-19}$ denotes a hydrogen atom, a cycloalkyl containing 3 to 7 carbon atoms, a straight-chain or branched silylalkyl containing up to 8 carbon atoms, or a straight-chain or branched alkyl containing up to 8 carbon atoms, which is optionally substituted with a hydroxyl, a straight-chain or a branched alkoxy containing up to 6 carbon atoms or a phenyl, which may in turn be substituted with a halogen, nitro, trifluoromethyl, trifluoromethoxy or phenyl or tetrazole-substituted phenyl, and an alkyl that is optionally substituted with a group according to the formula —$OR_{VI-22}$, wherein $R_{VI-22}$ denotes a straight-chain or branched acyl containing up to 4 carbon atoms or benzyl, or $R_{VI-19}$ denotes a straight-chain or branched acyl containing up to 20 carbon atoms or benzoyl, which is optionally substituted with a halogen, trifluoromethyl, nitro or trifluoromethoxy, or a straight-chain or branched fluoroacyl containing up to 8 carbon atoms, $R_{VI-20}$ and $R_{VI-21}$ are identical or different and denote a p hydrogen, phenyl or a straight-chain or branched alkyl containing up to 6 carbon atoms, or $R_{VI-20}$ and $R_{VI-21}$ together form a 3- to 6-membered carbocyclic ring, and a the carbocyclic rings formed are optionally substituted, optionally also geminally, with up to six identical or different substituents in the form of trifluoromethyl, hydroxyl, nitrile, halogen, carboxyl, nitro, azido, cyano, cycloalkyl or cycloalkyloxy containing 3 to 7 carbon atoms each, a straight-chain or branched alkoxycarbonyl, alkoxy or alkylthio containing up to 6 carbon atoms each, or a straight-chain or branched alkyl containing up to 6 carbon atoms, which is in turn substituted with up to two identical or different substituents in the form of a hydroxyl, benzyloxy, trifluoromethyl, benzoyl, a straight-chain or branched alkoxy, oxyacyl or carboxyl containing up to 4 carbon atoms each and/or a phenyl, which may in turn be substituted with a halogen, trifluoromethyl or trifluoromethoxy, and/or the carbocyclic rings formed are optionally substituted, also geminally, with up to five identical or different substituents in the form of a phenyl, benzoyl, thiophenyl or sulfonylbenzyl, which in turn are optionally substituted with a halogen, trifluoromethyl, trifluoromethoxy or nitro, and/or optionally in the form of a radical according to the formula

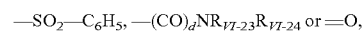

wherein c is a number equaling 1, 2, 3 or 4, d is a number equaling 0 or 1, $R_{VI-23}$ and $R_{VI-24}$ are identical or different and denote a hydrogen, cycloalkyl containing 3 to 6 carbon atoms, a straight-chain or branched alkyl containing up to 6 carbon atoms, benzyl or phenyl, which is optionally substituted with up to two identical or different substituents in the form of halogen, trifluoromethyl, cyano, phenyl or nitro, and/or the carbocyclic rings formed are optionally substituted with a spiro-linked radical according to the formula

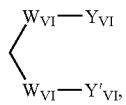 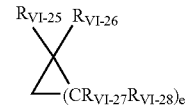

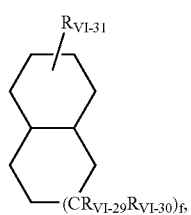 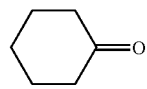

wherein $W_{VI}$ denotes either an oxygen atom or a sulfur atom, $Y_{VI}$ and $Y'_{VI}$ together form a 2- to 6-membered straight-chain or branched alkylene chain, e is a number equaling 1, 2, 3, 4, 5, 6 or 7, f is a number equaling 1 or 2, $R_{VI-25}$, $R_{VI-26}$, $R_{VI-27}$, $R_{VI-28}$, $R_{VI-29}$, $R_{VI-30}$ and $R_{VI-31}$ are identical or different and denote a hydrogen, trifluoromethyl, phenyl, halogen or a straight-chain or branched alkyl or alkoxy containing up to 6 carbon atoms each, or $R_{VI-25}$ and $R_{VI-26}$ or $R_{VI-27}$ and $R_{VI-28}$ each together denote a straight-chain or branched alkyl chain containing up to 6 carbon atoms or $R_{VI-25}$ and $R_{VI-26}$ or $R_{VI-27}$ and $R_{VI-28}$ each together form a radical according to the formula

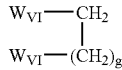

wherein $W_{VI}$ has the meaning given above, g is a number equaling 1, 2, 3, 4, 5, 6 or 7, $R_{VI-32}$ and $R_{VI-33}$ together form a 3- to 7-membered heterocycle, which contains an oxygen or sulfur atom or a group according to the formula SO, $SO_2$ or $-NR_{VI-34}$, wherein $R_{VI-34}$ denotes a hydrogen atom, a phenyl, benzyl, or a straight-chain or branched alkyl containing up to 4 carbon atoms, and salts and N oxides thereof, with the exception of 5(6H)-quinolones, 3-benzoyl-7,8-dihydro-2,7,7-trimethyl-4-phenyl.

Compounds of Formula VI are disclosed in European Patent Application No. EP 818448 A1, the complete disclosure of which is herein incorporated by reference.

In a preferred embodiment, the CETP inhibitor is selected from one of the following compounds of Formula VI:

2-cyclopentyl-4-(4-fluorophenyl)-7,7-dimethyl-3-(4-trifluoromethylbenzoyl)-4,6,7,8-tetrahydro-1H-quinolin-5-one;

2-cyclopentyl-4-(4-fluorophenyl)-7,7-dimethyl-3-(4-trifluoromethylbenzoyl)-7,8-dihydro-6H-quinolin-5-one;

[2-cyclopentyl-4-(4-fluorophenyl)-5-hydroxy-7,7-dimethyl-5,6,7,8-tetrahydroquinolin-3-yl]-(4-trifluoromethylphenyl)-methanone;

[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanone;

[5-(t-butyldimethylsilanyloxy)-2-cyclopentyl-4-(4-fluorophenyl)-7,7-dimethyl-5,6,7,8-tetrahydroquinolin-3-yl]-(4-trifluoromethylphenyl)-methanol;

5-(t-butyldimethylsilanyloxy)-2-cyclopentyl-4-(4-fluorophenyl)-3-[fluoro-(4-trifluoromethylphenyl)-methyl]-7,7-dimethyl-5,6,7,8-tetrahydroquinoline;

2-cyclopentyl-4-(4-fluorophenyl)-3-[fluoro-(4-trifluoromethylphenyl)-methyl]-7,7-dimethyl-5,6,7,8-tetrahydroquinolin-5-ol.

Another class of CETP inhibitors that finds utility with the present invention consists of substituted-pyridines having the Formula VII

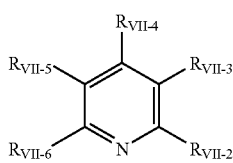

Formula VII and pharmaceutically acceptable forms thereof, wherein $R_{VII-2}$ and $R_{VII-6}$ are independently selected from the group consisting of hydrogen, hydroxy, alkyl, fluorinated alkyl, fluorinated aralkyl, chlorofluorinated alkyl, cycloalkyl, heterocyclyl, aryl, heteroaryl, alkoxy, alkoxyalkyl, and alkoxycarbonyl; provided that at least one of $R_{VII-2}$ and $R_{VII-6}$ is fluorinated alkyl, chlorofluorinated alkyl or alkoxyalkyl;

$R_{VII-3}$ is selected from the group consisting of hydroxy, amido, arylcarbonyl, heteroarylcarbonyl, hydroxymethyl —CHO, $-CO_2R_{VII-7}$, wherein $R_{VII-7}$ is selected from the group consisting of hydrogen, alkyl and cyanoalkyl; and

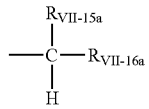

wherein $R_{VII-15a}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy and heterocyclyloxy, and $R_{VII-16a}$ is selected from the group consisting of alkyl, haloalkyl, alkenyl, haloalkenyl, alkynyl, haloalkynyl, aryl, heteroaryl, and heterocyclyl, arylalkoxy, trialkylsilyloxy;

$R_{VII-4}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkoxy, alkenoxy, alkynoxy, aryloxy, heteroaryloxy, heterocyclyloxy, alkanoyloxy, alkenoyloxy, alkynoyloxy, aryloyloxy, heteroaroyloxy, heterocyclyloyloxy, alkoxycarbonyl, alkenoxycarbonyl, alkynoxycarbonyl, aryloxycarbonyl, heteroaryloxycarbonyl, heterocyclyloxycarbonyl, thio, alkylthio, alkenylthio, alkynylthio, arylthio, heteroarylthio, heterocyclylthio, cycloalkylthio, cycloalkenylthio, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclythioalkenyl, alkylamino, alkenylamino, alkynylamino, arylamino, heteroarylamino, heterocyclylamino, aryldialkylamino, diarylamino, diheteroarylamino, alkylarylamino, alkylheteroarylamino, arylheteroarylamino, trialkylsilyl, trialkenylsilyl, triarylsilyl, $-CO(O)N(R_{VII-8a}R_{VII-8b})$, wherein $R_{VII-8a}$ and $R_{VII-8b}$ are independently selected from the group consisting of alkyl, alkenyl, alkynyl, aryl, heteroaryl and heterocyclyl, $-SO_2R_{VII-9}$, wherein $R_{VII-9}$ is selected from the group consisting of hydroxy, alkyl, alkenyl, alkynyl, aryl, heteroaryl and heterocyclyl, $-OP(O)(OR_{VII-10a})(OR_{VII-10b})$, wherein $R_{VII-10a}$ and $R_{VII-10b}$ are independently selected from the group consisting of hydrogen, hydroxy, alkyl, alkenyl, alkynyl, aryl, heteroaryl and heterocyclyl, and $-OP(S)$ $(OR_{VII-11a})(OR_{VII-11b})$ wherein $R_{VII-11a}$ and $R_{VII-11b}$ are independently selected from the group consisting of alkyl, alkenyl, alkynyl, aryl, heteroaryl and heterocyclyl;

$R_{VII-5}$ is selected from the group consisting of hydrogen, hydroxy, halogen, alkyl, alkenyl, alkynyl, cycloalkyl, cycloalkenyl, haloalkyl, haloalkenyl, haloalkynyl, aryl, heteroaryl, heterocyclyl, alkoxy, alkenoxy, alkynoxy, aryloxy, heteroaryloxy, heterocyclyloxy, alkylcarbonyloxyalkyl, alkenylcarbonyloxyalkyl, alkynylcarbonyloxyalkyl, arylcarbonyloxyalkyl, heteroarylcarbonyloxyalkyl, heterocyclylcarbonyloxyalkyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, cycloalkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, alkoxyalkyl, alkenoxyalkyl, alkynoxylalkyl, aryloxyalkyl, heteroaryloxyalkyl, heterocyclyloxyalkyl, alkoxyalkenyl, alkenoxyalkenyl, alkynoxyalkenyl, aryloxyalkenyl, heteroaryloxyalkenyl, heterocyclyloxyalkenyl, cyano, hydroxymethyl, —CO$_2$R$_{VII-14}$, wherein R$_{VII-14}$ is selected from the group consisting of alkyl, alkenyl, alkynyl, aryl, heteroaryl and heterocyclyl;

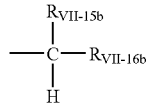

wherein R$_{VII-15b}$ is selected from the group consisting of hydroxy, hydrogen, halogen, alkylthio, alkenylthio, alkynylthio, arylthio, heteroarylthio, heterocyclylthio, alkoxy, alkenoxy, alkynoxy, aryloxy, heteroaryloxy, heterocyclyloxy, aroyloxy, and alkylsulfonyloxy, and R$_{VII-16b}$ is selected form the group consisting of alkyl, alkenyl, alkynyl, aryl, heteroaryl, heterocyclyl, arylalkoxy, and trialkylsilyloxy;

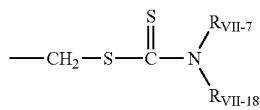

wherein R$_{VII-17}$ and R$_{VII-18}$ are independently selected from the group consisting of alkyl, cycloalkyl, alkenyl, alkynyl, aryl, heteroaryl and heterocyclyl;

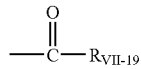

wherein R$_{VII-19}$ is selected from the group consisting of alkyl, cycloalkyl, alkenyl, alkynyl, aryl, heteroaryl, heterocyclyl, —SR$_{VII-20}$, —OR$_{VII-21}$, and —R$_{VII-22}$CO$_2$R$_{VII-23}$, wherein R$_{VII-20}$ is selected from the group consisting of alkyl, alkenyl, alkynyl, aryl, heteroaryl, heterocyclyl, aminoalkyl, aminoalkenyl, aminoalkynyl, aminoaryl, aminoheteroaryl, aminoheterocyclyl, alkylheteroarylamino, arylheteroarylamino, R$_{VII-21}$ is selected from the group consisting of alkyl, alkenyl, alkynyl, aryl, heteroaryl, and heterocyclyl, R$_{VII-22}$ is selected from the group consisting of alkylene or arylene, and R$_{VII-23}$ is selected from the group consisting of alkyl, alkenyl, alkynyl, aryl, heteroaryl, and heterocyclyl;

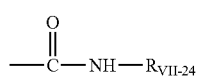

wherein R$_{VII-24}$ is selected from the group consisting of hydrogen, alkyl, cycloalkyl, alkenyl, alkynyl, aryl, heteroaryl, heterocyclyl, aralkyl, aralkenyl, and aralkynyl;

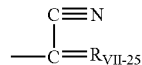

wherein R$_{VII-25}$ is heterocyclylidenyl;

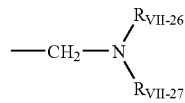

wherein R$_{VII-26}$ and R$_{VII-27}$ are independently selected from the group consisting of hydrogen, alkyl, cycloalkyl, alkenyl, alkynyl, aryl, heteroaryl, and heterocyclyl;

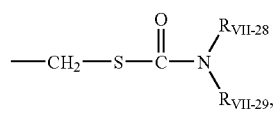

wherein R$_{VII-28}$ and R$_{VII-29}$ are independently selected from the group consisting of hydrogen, alkyl, cycloalkyl, alkenyl, alkynyl, aryl, heteroaryl, and heterocyclyl;

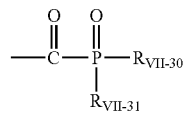

wherein R$_{VII-30}$ and R$_{VII-31}$ are independently alkoxy, alkenoxy, alkynoxy, aryloxy, heteroaryloxy, and heterocyclyloxy; and

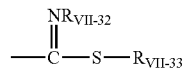

wherein R$_{VII-32}$ and R$_{VII-33}$ are independently selected from the group consisting of hydrogen, alkyl, cycloalkyl, alkenyl, alkynyl, aryl, heteroaryl, and heterocyclyl;

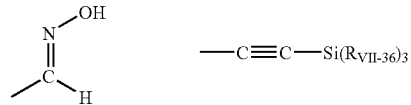

wherein $R_{VII-36}$ is selected from the group consisting of alkyl, alkenyl, aryl, heteroaryl and heterocyclyl;

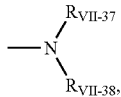

wherein $R_{VII-37}$ and $R_{VII-38}$ are independently selected from the group consisting of hydrogen, alkyl, cycloalkyl, alkenyl, alkynyl, aryl, heteroaryl, and heterocyclyl;

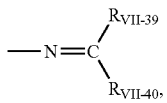

wherein $R_{VII-39}$ is selected from the group consisting of hydrogen, alkoxy, alkenoxy, alkynoxy, aryloxy, heteroaryloxy, heterocyclyloxy, alkylthio, alkenylthio, alkynylthio, arylthio, heteroarylthio and heterocyclylthio, and $R_{VII-40}$ is selected from the group consisting of haloalkyl, haloalkenyl, haloalkynyl, haloaryl, haloheteroaryl, haloheterocyclyl, cycloalkyl, cycloalkenyl, heterocyclylalkoxy, heterocyclylalkenoxy, heterocyclylalkynoxy, alkylthio, alkenylthio, alkynylthio, arylthio, heteroarylthio and heterocyclylthio;

—N=$R_{VII-41}$, wherein $R_{VII-41}$ is heterocyclylidenyl;

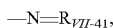
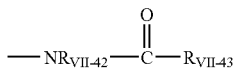

wherein $R_{VII-42}$ is selected from the group consisting of hydrogen, alkyl, alkenyl, alkynyl, aryl, heteroaryl, and heterocyclyl, and $R_{VII-43}$ is selected from the group consisting of hydrogen, alkyl, alkenyl, alkynyl, aryl, heteroaryl, heterocyclyl, cycloalkyl, cycloalkenyl, haloalkyl, haloalkenyl, haloalkynyl, haloaryl, haloheteroaryl, and haloheterocyclyl;

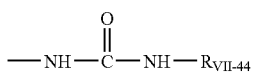

wherein $R_{VII-44}$ is selected from the group consisting of hydrogen, alkyl, cycloalkyl, alkenyl, alkynyl, aryl, heteroaryl and heterocyclyl;

—N=S=O;

—N=C=S;

—N=C=O;

—N$_3$;

—S$R_{VII-45}$ wherein $R_{VII-45}$ is selected from the group consisting of hydrogen, alkyl, alkenyl, alkynyl, aryl, heteroaryl, heterocyclyl, haloalkyl, haloalkenyl, haloalkynyl, haloaryl, haloheteroaryl, haloheterocyclyl, heterocyclyl, cycloalkylalkyl, cycloalkenylalkyl, aralkyl, heteroarylalkyl, heterocyclylalkyl, cycloalkylalkenyl, cycloalkenylalkenyl, aralkenyl, heteroarylalkenyl, heterocyclylalkenyl, alkylthioalkyl, alkenylthioalkyl, alkynylthioalkyl, arylthioalkyl, heteroarylthioalkyl, heterocyclylthioalkyl, alkylthioalkenyl, alkenylthioalkenyl, alkynylthioalkenyl, arylthioalkenyl, heteroarylthioalkenyl, heterocyclylthioalkenyl, aminocarbonylalkyl, aminocarbonylalkenyl, aminocarbonylalkynyl, aminocarbonylaryl, aminocarbonylheteroaryl, and aminocarbonylheterocyclyl, —S$R_{VII-46}$, and —CH$_2$$R_{VII-47}$, wherein $R_{VII-46}$ is selected from the group consisting of alkyl, alkenyl, alkynyl, aryl, heteroaryl and heterocyclyl, and $R_{VII-47}$ is selected from the group consisting of hydrogen, alkyl, alkenyl, alkynyl, aryl, heteroaryl and heterocyclyl; and

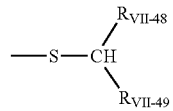

wherein $R_{VII-49}$ is selected from the group consisting of hydrogen, alkyl, cycloalkyl, alkenyl, alkynyl, aryl, heteroaryl and heterocyclyl, and $R_{VII-49}$ is selected from the group consisting of alkoxy, alkenoxy, alkynoxy, aryloxy, heteroaryloxy, heterocyclyloxy, haloalkyl, haloalkenyl, haloalkynyl, haloaryl, haloheteroaryl and haloheterocyclyl;

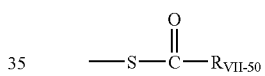

wherein $R_{VII-50}$ is selected from the group consisting of hydrogen, alkyl, cycloalkyl, alkenyl, alkynyl, aryl, heteroaryl, heterocyclyl, alkoxy, alkenoxy, alkynoxy, aryloxy, heteroaryloxy and heterocyclyloxy;

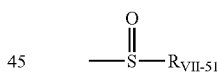

wherein $R_{VII-51}$ is selected from the group consisting of alkyl, alkenyl, alkynyl, aryl, heteroaryl, heterocyclyl, haloalkyl, haloalkenyl, haloalkynyl, haloaryl, haloheteroaryl and haloheterocyclyl; and

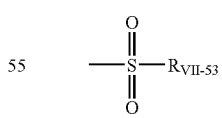

wherein $R_{VII-53}$ is selected from the group consisting of alkyl, alkenyl, alkynyl, aryl, heteroaryl and heterocyclyl;

provided that when $R_{VII-5}$ is selected from the group consisting of heterocyclylalkyl and heterocyclylalkenyl, the heterocyclyl radical of the corresponding heterocyclylalkyl or heterocyclylalkenyl is other than δ-lactone; and provided that when $R_{VII-4}$ is aryl, heteroaryl or heterocyclyl, and one of $R_{VII-2}$ and $R_{VII-6}$ is trifluoromethyl, then the other of $R_{VII-2}$ and $R_{VII-6}$ is difluoromethyl.

Compounds of Formula VII are disclosed in WO 9941237-A1, the complete disclosure of which is incorporated by reference.

In a preferred embodiment, the CETP inhibitor is selected from the following compounds of Formula VII:

Dimethyl 5,5'-dithiobis[2-difluoromethyl-4-(2-methylpropyl)-6-(trifluoromethyl)-3-pyridine-carboxylate].

Another class of CETP inhibitors that finds utility with the present invention consists of substituted pyridines and biphenyls having the Formula VIII

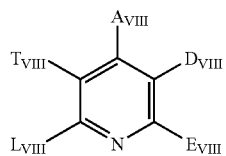

Formula VIII and pharmaceutically acceptable forms thereof, in which $A_{VIII}$ stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-1}R_{VIII-2}$, wherein $R_{VIII-1}$ and $R_{VIII-2}$ are identical or different and denote hydrogen, phenyl, or straight-chain or branched alkyl with up to 6 carbon atoms, $D_{VIII}$ stands for straight-chain or branched alkyl with up to 8 carbon atoms, which is substituted by hydroxy, $E_{VIII}$ and $L_{VIII}$ are either identical or different and stand for straight-chain or branched alkyl with up to 8 carbon atoms, which is optionally substituted by cycloalkyl with 3 to 8 carbon atoms, or stands for cycloalkyl with 3 to 8 carbon atoms, or $E_{VIII}$ has the above-mentioned meaning and $L_{VIII}$ in this case stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-3}R_{VIII-4}$, wherein $R_{VIII-3}$ and $R_{VIII-4}$ are identical or different and have the meaning given above for $R_{VIII-1}$ and $R_{VIII-2}$, or $E_{VIII}$ stands for straight-chain or branched alkyl with up to 8 carbon atoms, or stands for aryl with 6 to 10 carbon atoms, which is optionally substituted up to 3 times in an identical manner or differently by halogen, hydroxy, trifluoromethyl, trifluoromethoxy, or by straight-chain or branched alkyl, acyl, or alkoxy with up to 7 carbon atoms each, or by a group of the formula —$NR_{VIII-5}R_{VIII-6}$, wherein $R_{VIII-5}$ and $R_{VIII-6}$ are identical or different and have the meaning given above for $R_{VIII-1}$ and $R_{VIII-2}$, and $L_{VIII}$ in this case stands for straight-chain or branched alkoxy with up to 8 carbon atoms or for cycloalkyloxy with 3 to 8 carbon atoms, $T_{VIII}$ stands for a radical of the formula

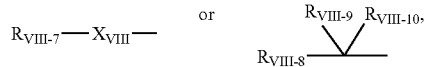

wherein $R_{VIII-7}$ and $R_{VIII-8}$ are identical or different and denote cycloalkyl with 3 to 8 carbon atoms, or aryl with 6 to 10 carbon atoms, or denote a 5- to 7-member aromatic, optionally benzo-condensed, heterocyclic compound with up to 3 heteroatoms from the series S, N and/or O, which are optionally substituted up to 3 times in an identical manner or differently by trifluoromethyl, trifluoromethoxy, halogen, hydroxy, carboxyl, by straight-chain or branched alkyl, acyl, alkoxy, or alkoxycarbonyl with up to 6 carbon atoms each, or by phenyl, phenoxy, or thiophenyl, which can in turn be substituted by halogen, trifluoromethyl, or trifluoromethoxy, and/or the rings are substituted by a group of the formula —$NR_{VIII-11}R_{VIII-12}$, wherein $R_{VIII-11}$ and $R_{VIII-12}$ are identical or different and have the meaning given above for $R_{VIII-1}$ and $R_{VIII-2}$, $X_{VIII}$ denotes a straight or branched alkyl chain or alkenyl chain with 2 to 10 carbon atoms each, which are optionally substituted up to 2 times by hydroxy, $R_{VIII-9}$ denotes hydrogen, and $R_{VIII-10}$ denotes hydrogen, halogen, azido, trifluoromethyl, hydroxy, mercapto, trifluoromethoxy, straight-chain or branched alkoxy with up to 5 carbon atoms, or a radical of the formula —$NR_{VIII-13}R_{VIII-14}$, wherein $R_{VIII-13}$ and $R_{VIII-14}$ are identical or different and have the meaning given above for $R_{VIII-1}$ and $R_{VIII-2}$, or $R_{VIII-9}$ and $R_{VIII-10}$ form a carbonyl group together with the carbon atom.

Compounds of Formula $V_{III}$ are disclosed in WO 9804528, the complete disclosure of which is incorporated by reference.

Another class of CETP inhibitors that finds utility with the present invention consists of substituted 1,2,4-triazoles having the Formula IX

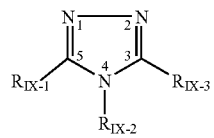

Formula IX and pharmaceutically acceptable forms thereof;

wherein $R_{IX-1}$ is selected from higher alkyl, higher alkenyl, higher alkynyl, aryl, aralkyl, aryloxyalkyl, alkoxyalkyl, alkylthioalkyl, arylthioalkyl, and cycloalkylalkyl;

wherein $R_{IX-2}$ is selected from aryl, heteroaryl, cycloalkyl, and cycloalkenyl, wherein $R_{IX-2}$ is optionally substituted at a substitutable position with one or more radicals independently selected from alkyl, haloalkyl, alkylthio, alkylsulfinyl, alkylsulfonyl, alkoxy, halo, aryloxy, aralkyloxy, aryl, aralkyl, aminosulfonyl, amino, monoalkylamino and dialkylamino; and wherein $R_{IX-3}$ is selected from hydrido, —SH and halo; provided $R_{IX-2}$ cannot be phenyl or 4-methylphenyl when $R_{IX-1}$ is higher alkyl and when $R_{IX-3}$ is —SH.

Compounds of Formula IX are disclosed in WO 9914204, the complete disclosure of which is incorporated by reference.

In a preferred embodiment, the CETP inhibitor is selected from the following compounds of Formula IX:
2,4-dihydro-4-(3-methoxyphenyl)-5-tridecyl-3H-1,2,4-triazole-3-thione;
2,4-dihydro-4-(2-fluorophenyl)-5-tridecyl-3H-1,2,4-triazole-3-thione;
2,4-dihydro-4-(2-methylphenyl)-5-tridecyl-3H-1,2,4-triazole-3-thione;
2,4-dihydro-4-(3-chlorophenyl)-5-tridecyl-3H-1,2,4-triazole-3-thione;
2,4-dihydro-4-(2-methoxyphenyl)-5-tridecyl-3H-1,2,4-triazole-3-thione;
2,4-dihydro-4-(3-methylphenyl)-5-tridecyl-3H-1,2,4-triazole-3-thione;
4-cyclohexyl-2,4-dihydro-5-tridecyl-3H-1,2,4-triazole-3-thione;
2,4-dihydro-4-(3-pyridyl)-5-tridecyl-3H-1,2,4-triazole-3-thione;
2,4-dihydro-4-(2-ethoxyphenyl)-5-tridecyl-3H-1,2,4-triazole-3-thione;
2,4-dihydro-4-(2,6-dimethylphenyl)-5-tridecyl-3H-1,2,4-triazole-3-thione;
2,4-dihydro-4-(4-phenoxyphenyl)-5-tridecyl-3H-1,2,4-triazole-3-thione;
4-(1,3-benzodioxol-5-yl)-2,4-dihydro-5-tridecyl-3H-1,2,4-triazole-3-thione;
4-(2-chlorophenyl)-2,4-dihydro-5-tridecyl-3H-1,2,4-triazole-3-thione;
2,4-dihydro-4-(4-methoxyphenyl)-5-tridecyl-3H-1,2,4-triazole-3-thione;
2,4-dihydro-5-tridecyl-4-(3-trifluoromethylphenyl)-3H-1,2,4-triazole-3-thione;
2,4-dihydro-5-tridecyl-4-(3-fluorophenyl)-3H-1,2,4-triazole-3-thione;
4-(3-chloro-4-methylphenyl)-2,4-dihydro-5-tridecyl-3H-1,2,4-triazole-3-thione;
2,4-dihydro-4-(2-methylthiophenyl)-5-tridecyl-3H-1,2,4-triazole-3-thione;
4-(4-benzyloxyphenyl)-2,4-dihydro-5-tridecyl-3H-1,2,4-triazole-3-thione;
2,4-dihydro-4-(2-naphthyl)-5-tridecyl-3H-1,2,4-triazole-3-thione;
2,4-dihydro-5-tridecyl-4-(4-trifluoromethylphenyl)-3H-1,2,4-triazole-3-thione;
2,4-dihydro-4-(1-naphthyl)-5-tridecyl-3H-1,2,4-triazole-3-thione;
2,4-dihydro-4-(3-methylthiophenyl)-5-tridecyl-3H-1,2,4-triazole-3-thione;
2,4-dihydro-4-(4-methylthiophenyl)-5-tridecyl-3H-1,2,4-triazole-3-thione;
2,4-dihydro-4-(3,4-dimethoxyphenyl)-5-tridecyl-3H-1,2,4-triazole-3-thione;
2,4-dihydro-4-(2,5-dimethoxyphenyl)-5-tridecyl-3H-1,2,4-triazole-3-thione;
2,4-dihydro-4-(2-methoxy-5-chlorophenyl)-5-tridecyl-3H-1,2,4-triazole-3-thione;
4-(4-aminosulfonylphenyl)-2,4-dihydro-5-tridecyl-3H-1,2,4-triazole-3-thione;
2,4-dihydro-5-dodecyl-4-(3-methoxyphenyl)-3H-1,2,4-triazole-3-thione;
2,4-dihydro-4-(3-methoxyphenyl)-5-tetradecyl-3H-1,2,4-triazole-3-thione;
2,4-dihydro-4-(3-methoxyphenyl)-5-undecyl-3H-1,2,4-triazole-3-thione; and
2,4-dihydro-(4-methoxyphenyl)-5-pentadecyl-3H-1,2,4-triazole-3-thione.

Another class of CETP inhibitors that finds utility with the present invention consists of hetero-tetrahydroquinolines having the Formula X

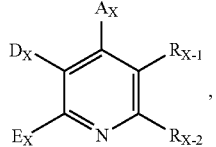

Formula X

N-oxides of said compounds, and pharmaceutically acceptable forms thereof;
in which $A_X$ represents cycloalkyl with 3 to 8 carbon atoms or a 5- to 7-membered, saturated, partially saturated or unsaturated, optionally benzo-condensed heterocyclic ring containing up to 3 heteroatoms from the series comprising S, N and/or O, that in case of a saturated heterocyclic ring is bonded to a nitrogen function, optionally bridged over it, and in which the aromatic systems mentioned above are optionally substituted up to 5-times in an identical or different substituents in the form of halogen, nitro, hydroxy, trifluoromethyl, trifluoromethoxy or by a straight-chain or branched alkyl, acyl, hydroxyalkyl or alkoxy each having up to 7 carbon atoms or by a group of the formula —$NR_{X-3}R_{X-4}$, in which $R_{X-3}$ and $R_{X-4}$ are identical or different and denote hydrogen, phenyl or straight-chain or branched alkyl having up to 6 carbon atoms, or $A_X$ represents a radical of the formula

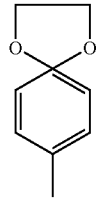

$D_X$ represents an aryl having 6 to 10 carbon atoms, that is optionally substituted by phenyl, nitro, halogen, trifluormethyl or trifluoromethoxy, or it represents a radical of the formula

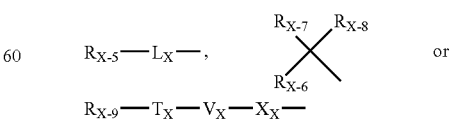

in which $R_{X-5}$, $R_{X-6}$ and $R_{X-9}$ independently of one another denote cycloalkyl having 3 to 6 carbon atoms, or an aryl having 6 to 10 carbon atoms or a 5- to 7-membered aromatic, optionally benzo-condensed saturated or unsaturated, mono-, bi-, or tricyclic heterocyclic ring from the series consisting of S, N and/or O, in which the rings are substituted, optionally, in case of the nitrogen containing aromatic rings via the N function, with up to 5 identical or different substituents in the form of halogen, trifluoromethyl, nitro, hydroxy, cyano, carbonyl, trifluoromethoxy, straight straight-chain or branched acyl, alkyl, alkylthio, alkylalkoxy, alkoxy, or alkoxycarbonyl each having up to 6 carbon atoms, by aryl or trifluoromethyl-substituted aryl each having 6 to 10 carbon atoms or by an, optionally benzo-condensed, aromatic 5- to 7-membered heterocyclic ring having up to 3 heteroatoms from the series consisting of S, N, and/or o, and/or substituted by a group of the formula —$OR_{X-10}$, —$SR_{X-11}$, $SO_2R_{X-12}$ or —$NR_{X-13}R_{X-14}$, in which $R_{X-10}$, $R_{X-11}$ and $R_{X-12}$ independently from each other denote aryl having 6 to 10 carbon atoms, which is in turn substituted with up to 2 identical or different substituents in the form of phenyl, halogen or a straight-chain or branched alkyl having up to 6 carbon atoms, $R_{X-13}$ and $R_{X-14}$ are identical or different and have the meaning of $R_{X-3}$ and $R_{X-4}$ indicated above, or $R_{X-5}$ and/or $R_{X-6}$ denote a radical of the formula

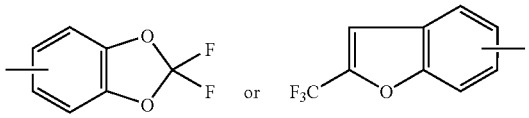

$R_{X-7}$ denotes hydrogen or halogen, and $R_{X-8}$ denotes hydrogen, halogen, azido, trifluoromethyl, hydroxy, trifluoromethoxy, straight-chain or branched alkoxy or alkyl having up to 6 carbon atoms or a radical of the formula

—$NR_{X-15}R_{X-16}$ in which $R_{X-15}$ and $R_{X-16}$ are identical or different and have the meaning of $R_{X-3}$ and $R_{X-4}$ indicated above, or $R_{X-7}$ and $R_{X-8}$ together form a radical of the formula =O or =$NR_{X-17}$, in which $R_{X-17}$ denotes hydrogen or straight chain or branched alkyl, alkoxy or acyl having up to 6 carbon atoms, $L_X$ denotes a straight chain or branched alkylene or alkenylene chain having up to 8 carbon atoms, that are optionally substituted with up to 2 hydroxy groups, $T_X$ and $X_X$ are identical or different and denote a straight chain or branched alkylene chain with up to 8 carbon atoms or $T_X$ or $X_X$ denotes a bond, $V_X$ represents an oxygen or sulfur atom or an —$NR_{X-18}$- group, in which $R_{X-18}$ denotes hydrogen or straight chain or branched alkyl with up to 6 carbon atoms or phenyl, $E_X$ represents cycloalkyl with 3 to 8 carbon atoms, or straight chain or branched alkyl with up to 8 carbon atoms, that is optionally substituted by cycloalkyl with 3 to 8 carbon atoms or hydroxy, or represents a phenyl, that is optionally substituted by halogen or trifluoromethyl, $R_{X-1}$ and $R_{X-2}$ together form a straight-chain or branched alkylene chain with up to 7 carbon atoms, that must be substituted by carbonyl group and/or by a radical with the formula

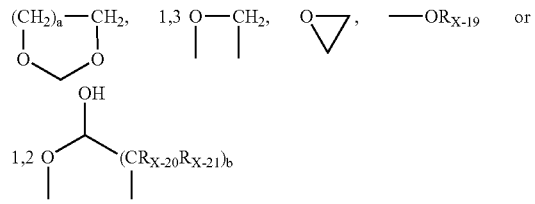

in which a and b are identical or different and denote a number equaling 1, 2, or 3, $R_{X-19}$ denotes hydrogen, cycloalkyl with 3 up to 7 carbon atoms, straight chain or branched silylalkyl with up to 8 carbon atoms or straight chain or branched alkyl with up to 8 carbon atoms, that are optionally substituted by hydroxyl, straight chain or branched alkoxy with up to 6 carbon atoms or by phenyl, which in turn might be substituted by halogen, nitro, trifluormethyl, trifluoromethoxy or by phenyl or by tetrazole-substituted phenyl, and alkyl, optionally be substituted by a group with the formula —$OR_{X-22}$, in which $R_{X-22}$ denotes a straight chain or branched acyl with up to 4 carbon atoms or benzyl, or $R_{X-19}$ denotes straight chain or branched acyl with up to 20 carbon atoms or benzoyl, that is optionally substituted by halogen, trifluoromethyl, nitro or trifluoromethoxy, or it denotes straight chain or branched fluoroacyl with up to 8 carbon atoms and 9 fluorine atoms, $R_{X-20}$ and $R_{X-21}$ are identical or different and denote hydrogen, phenyl or straight chain or branched alkyl with up to 6 carbon atoms, or $R_{X-20}$ and $R_{X-21}$ together form a 3- to 6-membered carbocyclic ring, and the carbocyclic rings formed are optionally substituted, optionally also geminally, with up to six identical or different substituents in the form of trifluoromethyl, hydroxy, nitrile, halogen, carboxyl, nitro, azido, cyano, cycloalkyl or cycloalkyloxy with 3 to 7 carbon atoms each, by straight chain or branched alkoxycarbonyl, alkoxy or alkylthio with up to 6 carbon atoms each or by straight chain or branched alkyl with up to 6 carbon atoms, which in turn is substituted with up to 2 identically or differently by hydroxyl, benzyloxy, trifluoromethyl, benzoyl, straight chain or branched alkoxy, oxyacyl or carbonyl with up to 4 carbon atoms each and/or phenyl, which may in turn be substituted with a halogen, trifluoromethyl or trifluoromethoxy, and/or the formed carbocyclic rings are optionally substituted, also geminally, with up to 5 identical or different substituents in the form of phenyl, benzoyl, thiophenyl or sulfonylbenzyl, which in turn are optionally substituted by halogen, trifluoromethyl, trifluoromethoxy or nitro, and/or optionally are substituted by a radical with the formula

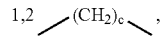

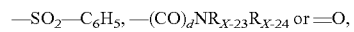

in which
c denotes a number equaling 1, 2, 3, or 4,
d denotes a number equaling 0 or 1,
$R_{X-23}$ and $R_{X-24}$ are identical or different and denote hydrogen, cycloalkyl with 3 to 6 carbon atoms, straight chain or branched alkyl with up to 6 carbon atoms, benzyl or phenyl, that is optionally substituted with up to 2 identically or differently by halogen, trifluoromethyl, cyano, phenyl or nitro, and/or the formed carbocyclic rings are substituted optionally by a spiro-linked radical with the formula

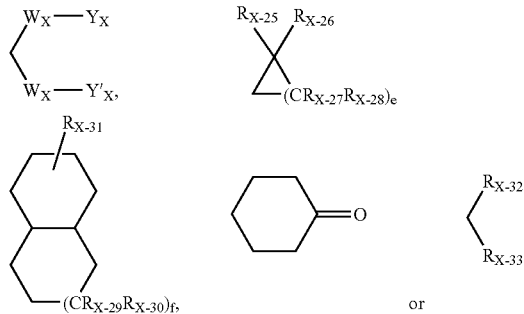

in which
$W_X$ denotes either an oxygen or a sulfur atom
$Y_X$ and $Y'_X$ together form a 2 to 6 membered straight chain or branched alkylene chain,
e denotes a number equaling 1, 2, 3, 4, 5, 6, or 7,
f denotes a number equaling 1 or 2,
$R_{X-25}$, $R_{X-26}$, $R_{X-27}$, $R_{X-28}$, $R_{X-29}$, $R_{X-30}$ and $R_{X-31}$ are identical or different and denote hydrogen, trifluoromethyl, phenyl, halogen or straight chain or branched alkyl or alkoxy with up to 6 carbon atoms each,
or
$R_{X-25}$ and $R_{X-26}$ or $R_{X-27}$ and $R_{X-28}$ respectively form together a straight chain or branched alkyl chain with up to 6 carbon atoms,
or
$R_{X-25}$ and $R_{X-26}$ or $R_{X-27}$ and $R_{X-28}$ each together form a radical with the formula

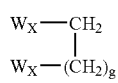

in which
$W_X$ has the meaning given above,
g denotes a number equaling 1, 2, 3, 4, 5, 6, or 7,
$R_{X-32}$ and $R_{X-33}$ form together a 3- to 7-membered heterocycle, which contains an oxygen or sulfur atom or a group with the formula SO, $SO_2$ or $\pi$-$NR_{X-34}$,
in which
$R_{X-34}$ denotes hydrogen, phenyl, benzyl or straight or branched alkyl with up to 4 carbon atoms.
Compounds of Formula X are disclosed in WO 9914215, the complete disclosure of which is incorporated by reference.
In a preferred embodiment, the CETP inhibitor is selected from the following compounds of Formula X:
2-cyclopentyl-5-hydroxy-7,7-dimethyl-4-(3-thienyl)-3-(4-trifluoromethylbenxoyl)-5,6,7,8-tetrahydroquinoline;
2-cyclopentyl-3-[fluoro-(4-trifluoromethylphenyl)methyl]-5-hydroxy-7,7-dimethyl-4-(3-thienyl)-5,6,7,8-tetrahydroquinoline; and
2-cyclopentyl-5-hydroxy-7,7-dimethyl-4-(3-thienyl)-3-(trifluoromethylbenxyl)-5,6,7,8-tetrahydroquinoline.

Another class of CETP inhibitors that finds utility with the present invention consists of substituted tetrahydro naphthalines and analogous compounds having the Formula XI

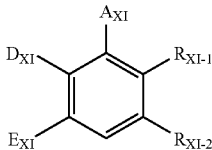

Formula XI and pharmaceutically acceptable forms thereof, in which
$A_{XI}$ stands for cycloalkyl with 3 to 8 carbon atoms, or stands for aryl with 6 to 10 carbon atoms, or stands for a 5- to 7-membered, saturated, partially unsaturated or unsaturated, possibly benzocondensated, heterocycle with up to 4 heteroatoms from the series S, N and/or O, where aryl and the heterocyclic ring systems mentioned above are substituted up to 5-fold, identical or different, by cyano, halogen, nitro, carboxyl, hydroxy, trifluoromethyl, trifluoro-methoxy, or by straight-chain or branched alkyl, acyl, hydroxyalkyl, alkylthio, alkoxycarbonyl, oxyalkoxycarbonyl or alkoxy each with up to 7 carbon atoms, or by a group of the formula

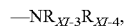

—$NR_{XI-3}R_{XI-4}$, in which
$R_{XI-3}$ and $R_{XI-4}$ are identical or different and denote hydrogen, phenyl, or straight-chain or branched alkyl with up to 6 carbon atoms
$D_{XI}$ stands for a radical of the formula

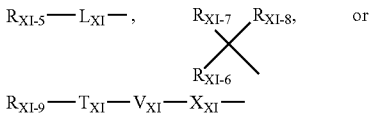

in which
$R_{XI-5}$, $R_{XI-6}$ and $R_{XI-9}$, independent of each other, denote cycloalkyl with 3 to 6 carbon atoms, or denote aryl with 6 to 10 carbon atoms, or denote a 5- to 7-membered, possibly benzocondensated, saturated or unsaturated, mono-, bi- or tricyclic heterocycle with up to 4 heteroatoms of the series S, N and/or O, where the cycles are possibly substituted—in the case of the nitrogen-containing rings also via the N-function-up to 5-fold, identical or different, by halogen, trifluoromethyl, nitro, hydroxy, cyano, carboxyl, trifluoromethoxy, straight-chain or branched acyl, alkyl, alkylthio, alkylalkoxy, alkoxy or alkoxycarbonyl with up to 6 carbon atoms each by aryl or trifluoromethyl substituted aryl with 6 to 10 carbon atoms each, or by a possibly benzocondensated aromatic 5- to 7-membered heterocycle with up to 3 heteroatoms of the series S, N and/or O, and/or are substituted by a group of the formula

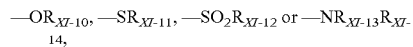

—$OR_{XI-10}$, —$SR_{XI-11}$, —$SO_2R_{XI-12}$ or —$NR_{XI-13}R_{XI-14}$, in which
$R_{XI-10}$, $R_{XI-11}$ and $R_{XI-12}$, independent of each other, denote aryl with 6 to 10 carbon atoms, which itself is substituted up to 2-fold, identical or different, by phenyl, halogen. or by straight-chain or branched alkyl with up to 6 carbon atoms, $R_{XI-13}$ and $R_{XI-14}$ are identical or different and have the meaning given above for $R_{XI-3}$ and $R_{XI-4}$, or $R_{XI-5}$ and/or $R_{XI-6}$ denote a radical of the formula

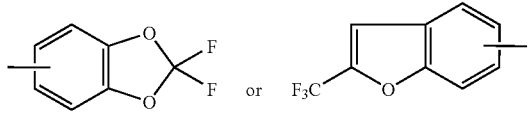

$R_{XI-7}$ denotes hydrogen, halogen or methyl, and $R_{XI-8}$ denotes hydrogen, halogen, azido, trifluoromethyl, hydroxy, trifluoromethoxy, straight-chain or branched alkoxy or alkyl with up to 6 carbon atoms each, or a radical of the formula —$NR_{XI-15}R_{XI-16}$, in which $R_{XI-15}$ and $R_{XI-16}$ are identical or different and have the meaning given above for $R_{XI-3}$ and $R_{XI-4}$, or $R_{XI-7}$ and $R_{XV-8}$ together form a radical of the formula $=O$ or $=NR_{XI-17}$, in which $R_{XI-17}$ denotes hydrogen or straight-chain or branched alkyl, alkoxy or acyl with up to 6 carbon atoms each, $L_{XI}$ denotes a straight-chain or branched alkylene- or alkenylene chain with up to 8 carbon atoms each, which is possibly substituted up to 2-fold by hydroxy, $T_{XI}$ and $X_{XI}$ are identical or different and denote a straight-chain or branched alkylene chain with up to 8 carbon atoms, or $T_{XI}$ and $X_{XI}$ denotes a bond, $V_{XI}$ stands for an oxygen- or sulfur atom or for an —$NR_{XI-18}$ group, in which $R_{XI-18}$ denotes hydrogen or straight-chain or branched alkyl with up to 6 carbon atoms, or phenyl, $E_{XI}$ stands for cycloalkyl with 3 to 8 carbon atoms, or stands for straight-chain or branched alkyl with up to 8 carbon atoms, which is possibly substituted by cycloalkyl with 3 to 8 carbon atoms or hydroxy, or stands for phenyl, which is possibly substituted by halogen or trifluoromethyl, $R_{XI-1}$ and $R_{XI-2}$ together form a straight-chain or branched alkylene chain with up to 7 carbon atoms, which must be substituted by a carbonyl group and/or by a radical of the formula

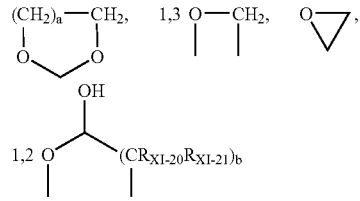

in which a and b are identical or different and denote a number 1, 2 or 3

$R_{XI-19}$ denotes hydrogen, cycloalkyl with 3 to 7 carbon atoms, straight-chain or branched silylalkyl with up to 8 carbon atoms, or straight-chain or branched alkyl with up to 8 carbon atoms, which is possibly substituted by hydroxy, straight-chain or branched alkoxy with up to 6 carbon atoms, or by phenyl, which itself can be substituted by halogen, nitro, trifluoromethyl, trifluoromethoxy or by phenyl substituted by phenyl or tetrazol, and alkyl is possibly substituted by a group of the formula —$OR_{XI-22}$, in which $R_{XI-22}$ denotes straight-chain or branched acyl with up to 4 carbon atoms, or benzyl, or $R_{XI-19}$ denotes straight-chain or branched acyl with up to 20 carbon atoms or benzoyl, which is possibly substituted by halogen, trifluoromethyl, nitro or trifluoromethoxy, or denotes straight-chain or branched fluoroacyl with up to 8 carbon atoms and 9 fluorine atoms, $R_{XI-20}$ and $R_{XI-21}$ are identical or different, denoting hydrogen, phenyl or straight-chain or branched alkyl with up to 6 carbon atoms, or $R_{XI-20}$ and $R_{XI-21}$ together form a 3- to 6-membered carbocycle, and, possibly also geminally, the alkylene chain formed by $R_{XI-1}$ and $R_{XI-2}$, is possibly substituted up to 6-fold, identical or different, by trifluoromethyl, hydroxy, nitrile, halogen, carboxyl, nitro, azido, cyano, cycloalkyl or cycloalkyloxy with 3 to 7 carbon atoms each, by straight-chain or branched alkoxycarbonyl, alkoxy or alkoxythio with up to 6 carbon atoms each, or by straight-chain or branched alkyl with up to 6 carbon atoms, which itself is substituted up to 2-fold, identical or different, by hydroxyl, benzyloxy, trifluoromethyl, benzoyl, straight-chain or branched alkoxy, oxyacyl or carboxyl with up to 4 carbon atoms each, and/or phenyl—which itself can be substituted by halogen, trifluoromethyl or trifluoromethoxy, and/or the alkylene chain formed by $R_{XI-1}$ and $R_{XI-2}$ is substituted, also geminally, possibly up to 5-fold, identical or different, by phenyl, benzoyl, thiophenyl or sulfobenzyl which themselves are possibly substituted by halogen, trifluoromethyl, trifluoromethoxy or nitro, and/or the alkylene chain formed by $R_{XI-1}$ and $R_{XI-2}$ is possibly substituted by a radical of the formula

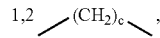

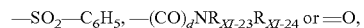

in which c denotes a number 1, 2, 3 or 4, d denotes a number 0 or 1, $R_{XI-23}$ and $R_{XI-24}$ are identical or different and denote hydrogen, cycloalkyl with 3 to 6 carbon atoms, straight-chain or branched alkyl with up to 6 carbon atoms, benzyl or phenyl, which is possibly substituted up to 2-fold. identical or different, by halogen, trifluoromethyl, cyano, phenyl or nitro, and/or the alkylene chain formed by $R_{XI-1}$ and $R_{XI-2}$ is possibly substituted by a spiro-jointed radical of the formula

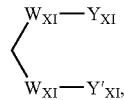  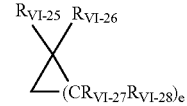

-continued

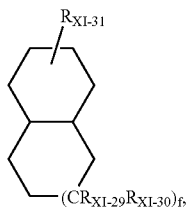 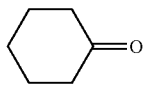 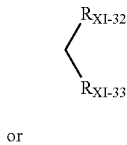

in which

W$_{XI}$ denotes either an oxygen or a sulfur atom,

Y$_{XI}$ and Y'$_{XI}$ together form a 2- to 6-membered straight-chain or branched alkylene chain, e is a number 1, 2, 3, 4, 5, 6 or 7, f denotes a number 1 or 2, R$_{XI-25}$, R$_{XI-26}$, R$_{XI-27}$, R$_{XI-28}$, R$_{XI-29}$, R$_{XI-30}$ and R$_{XI-31}$ are identical or different and denote hydrogen, trifluoromethyl, phenyl, halogen, or straight-chain or branched alkyl or alkoxy with up to 6 carbon atoms each, or R$_{XI-25}$ and R$_{XI-26}$ or R$_{XI-27}$ and R$_{XI-28}$ together form a straight-chain or branched alkyl chain with up to 6 carbon atoms, or R$_{XI-25}$ and R$_{XI-26}$ or R$_{XI-27}$ and R$_{XI-28}$ together form a radical of the formula

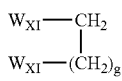

in which

W$_{XI}$ has the meaning given above, g is a number 1, 2, 3, 4, 5, 6 or 7,

R$_{XI-32}$ and R$_{XI-33}$ together form a 3- to 7-membered heterocycle that contains an oxygen- or sulfur atom or a group of the formula SO, SO$_2$ or —NR$_{XI-34}$, in which R$_{XI-34}$ denotes hydrogen, phenyl, benzyl, or straight-chain or branched alkyl with up to 4 carbon atoms.

Compounds of Formula XI are disclosed in WO 9914174, the complete disclosure of which is incorporated by reference.

Another class of CETP inhibitors that finds utility with the present invention consists of 2-aryl-substituted pyridines having the Formula XII Formula XII

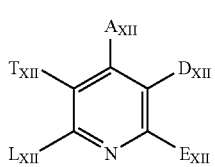

and pharmaceutically acceptable forms thereof, in which

A$_{XII}$ and E$_{XII}$ are identical or different and stand for aryl with 6 to 10 carbon atoms which is possibly substituted, up to 5-fold identical or different, by halogen, hydroxy, trifluoromethyl, trifluoromethoxy, nitro or by straight-chain or branched alkyl, acyl, hydroxy alkyl or alkoxy with up to 7 carbon atoms each, or by a group of the formula —NR$_{XII-1}$R$_{XII-2}$, where R$_{XII-1}$ and R$_{XII-2}$ are identical or different and are meant to be hydrogen, phenyl or straight-chain or branched alkyl with up to 6 carbon atoms, D$_{XII}$ stands for straight-chain or branched alkyl with up to 8 carbon atoms, which is substituted by hydroxy, L$_{XII}$ stands for cycloalkyl with 3 to 8 carbon atoms or for straight-chain or branched alkyl with up to 8 carbon atoms, which is possibly substituted by cycloalkyl with 3 to 8 carbon atoms, or by hydroxy, T$_{XII}$ stands for a radical of the formula R$_{XII-3}$—X$_{XII}$— or

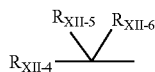

where

R$_{XII-3}$ and R$_{XII-4}$ are identical or different and are meant to be cycloalkyl with 3 to 8 carbon atoms, or aryl with 6 to 10 carbon atoms, or a 5- to 7-membered aromatic, possibly benzocondensated heterocycle with up to 3 heteroatoms from the series S, N and/or O, which are possibly substituted up to 3-fold identical or different, by trifluoromethyl, trifluoromethoxy, halogen, hydroxy, carboxyl, nitro, by straight-chain or branched alkyl, acyl, alkoxy or alkoxycarbonyl with up to 6 carbon atoms each or by phenyl, phenoxy or phenylthio which in turn can be substituted by halogen trifluoromethyl or trifluoromethoxy, and/or where the cycles are possibly substituted by a group of the formula —NR$_{XII-7}$R$_{XII-8}$, where R$_{XII-7}$ and R$_{XII-8}$ are identical or different and have the meaning of R$_{XII-1}$ and R$_{XII-2}$ given above, X$_{XII}$ is a straight-chain or branched alkyl or alkenyl with 2 to 10 carbon atoms each, possibly substituted up to 2-fold by hydroxy or halogen, R$_{XII-5}$ stands for hydrogen, and R$_{XII-6}$ means to be hydrogen, halogen, mercapto, azido, trifluoromethyl, hydroxy, trifluoromethoxy, straight-chain or branched alkoxy with up to 5 carbon atoms, or a radical of the formula —NR$_{XII-9}$R$_{XII-10}$, where R$_{XII-9}$ and R$_{XII-10}$ are identical or different and have the meaning of R$_{XII-1}$ and R$_{XII-2}$ given above, or R$_{XII-5}$ and R$_{XII-6}$, together with the carbon atom, form a carbonyl group.

Compounds of Formula XII are disclosed in EP 796846-A1, the complete disclosure of which is incorporated by reference.

In a preferred embodiment, the CETP inhibitor is selected from the following compounds of Formula XII:

4,6-bis-(p-fluorophenyl)-2-isopropyl-3-[(p-trifluoromethylphenyl)-(fluoro)-methyl]-5-(1-hydroxyethyl)pyridine;

2,4-bis-(4-fluorophenyl)-6-isopropyl-5-[4-(trifluoromethylphenyl)-fluoromethyl]-3-hydroxymethyl)pyridine; and 2,4-bis-(4-fluorophenyl)-6-isopropyl-5-[2-(3-trifluoromethylphenyl)vinyl]-3-hydroxymethyl)pyridine.

Another class of CETP inhibitors that finds utility with the present invention consists of compounds having the Formula XIII

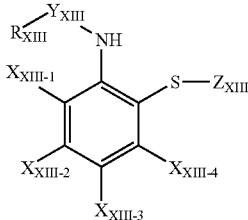

Formula XIII and pharmaceutically acceptable forms thereof, in which $R_{XIII}$ is a straight chain or branched $C_{1-10}$ alkyl; straight chain or branched $C_{2-10}$ alkenyl; halogenated $C_{1-4}$ lower alkyl; $C_{3-10}$ cycloalkyl that may be substituted; $C_{5-8}$ cycloalkenyl that may be substituted; $C_{3-10}$ cycloalkyl $C_{1-10}$ alkyl that may be substituted; aryl that may be substituted; aralkyl that may be substituted; or a 5- or 6-membered heterocyclic group having 1 to 3 nitrogen atoms, oxygen atoms or sulfur atoms that may be substituted, $X_{XIII-1}, X_{XIII-2}, X_{XIII-3}, X_{XIII-4}$ may be the same or different and are a hydrogen atom; halogen atom; $C_{1-4}$ lower alkyl; halogenated $C_{1-4}$ lower alkyl; $C_{1-4}$ lower alkoxy; cyano group; nitro group; acyl; or aryl, respectively;

$Y_{XIII}$ is —CO—; or —SO$_2$—; and $Z_{XIII}$ is a hydrogen atom; or mercapto protective group.

Compounds of Formula XIII are disclosed in WO 98/35937, the complete disclosure of which is incorporated by reference.

In a preferred embodiment, the CETP inhibitor is selected from the following compounds of Formula XIII:

N,N'-(dithiodi-2,1-phenylene)bis[2,2-dimethyl-propanamide];

N,N'-(dithiodi-2,1-phenylene)bis[1-methyl-cyclohexanecarboxamide];

N,N'-(dithiodi-2,1-phenylene)bis[1-(3-methylbutyl)-cyclopentanecarboxamide];

N,N'-(dithiodi-2,1-phenylene)bis[1-(3-methylbutyl)-cyclohexanecarboxamide];

N,N'-(dithiodi-2,1-phenylene)bis[1-(2-ethylbutyl)-cyclohexanecarboxamide];

N,N'-(dithiodi-2,1-phenylene)bis-tricyclo[3.3.1.1$^{3,7}$]decane-1-carboxamide;

propanethioic acid, 2-methyl-,S-[2[[[1-(2-ethylbutyl)cyclohexyl]carbonyl]amino]phenyl]ester;

propanethioic acid, 2,2-dimethyl-,S-[2-[[[1-(2-ethylbutyl) cyclohexyl]carbonyl]amino]phenyl]ester; and ethanethioic acid, S-[2-[[[1-(2-ethylbutyl)cyclohexyl]carbonyl]amino]phenyl]ester.

Another class of CETP inhibitors that finds utility with the present invention consists of polycyclic aryl and heteroaryl tertiary-heteroalkylamines having the Formula XIV

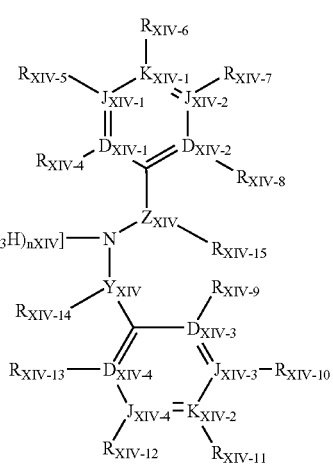

Formula XIV and pharmaceutically acceptable forms thereof, wherein:

$n_{XIV}$ is an integer selected from 0 through 5;

$R_{XIV-1}$ is selected from the group consisting of haloalkyl, haloalkenyl, haloalkoxyalkyl, and haloalkenyloxyalkyl;

$X_{XIV}$ is selected from the group consisting of O, H, F, S, S(O), NH, N(OH), N(alkyl), and N(alkoxy);

$R_{XIV-16}$ is selected from the group consisting of hydrido, alkyl, alkenyl, alkynyl, aryl, aralkyl, aryloxyalkyl, alkoxyalkyl, alkenyloxyalkyl, alkylthioalkyl, arylthioalkyl, aralkoxyalkyl, heteroaralkoxyalkyl, alkylsulfinylalkyl, alkylsulfonylalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxyalkyl, haloalkenyloxyalkyl, halocycloalkoxyalkyl, halocycloalkenyloxyalkyl, perhaloaryl, perhaloaralkyl, perhaloaryloxyalkyl, heteroaryl, heteroarylalkyl, monocarboalkoxyalkyl, monocarboalkoxy, dicarboalkoxyalkyl, monocarboxamido, monocyanoalkyl, dicyanoalkyl, carboalkoxycyanoalkyl, acyl, aroyl, heteroaroyl, heteroaryloxyalkyl, dialkoxyphosphonoalkyl, trialkylsilyl, and a spacer selected from the group consisting of a covalent single bond and a linear spacer moiety having from 1 through 4 contiguous atoms linked to the point of bonding of an aromatic substituent selected from the group consisting of $R_{XIV-4}$, $R_{XIV-8}$, $R_{XIV-9}$, and $R_{XIV-13}$ to form a heterocyclyl ring having from 5 through 10 contiguous members with the provisos that said spacer moiety is other than a covalent single bond when $R_{XIV-2}$ is alkyl and there is no $R_{XIV-16}$ wherein X is H or F;

$D_{XIV-1}$, $D_{XIV-2}$, $J_{XIV-1}$, $J_{XIV-2}$ and $K_{XIV-1}$ are independently selected from the group consisting of C, N, O, S and a covalent bond with the provisos that no more than one of $D_{XIV-1}$, $D_{XIV-2}$, $J_{XIV-1}$, $J_{XIV-2}$ and $K_{XIV-1}$ is a covalent bond, no more than one of $D_{XIV-1}$, $D_{XIV-2}$, $J_{XIV-1}$, $J_{XIV-2}$ and $K_{XIV-1}$ is O, no more than one of $D_{XIV-1}$, $D_{XIV-2}$, $J_{XIV-1}$, $J_{XIV-2}$ and $K_{XIV-1}$ is S, one of $D_{XIV-1}$, $D_{XIV-2}$, $J_{XIV-1}$, $J_{XIV-2}$ and $K_{XIV-1}$ must be a covalent bond when two of $D_{XIV-1}$, $D_{XIV-2}$, $J_{XIV-1}$, $J_{XIV-2}$ and $K_{XIV-1}$ are O and S, and no more than four of $D_{XIV-1}$, $D_{XIV-2}$, $J_{XIV-1}$, $J_{XIV-2}$ and $K_{XIV-1}$ are N;

$D_{XIV-3}$, $D_{XIV-4}$, $J_{XIV-3}$, $J_{XIV-4}$ and $K_{XIV-2}$ are independently selected from the group consisting of C, N, O, S and a covalent bond 9 with the provisos that no more than one of $D_{XIV-3}$, $D_{XIV-4}$, $J_{XIV-3}$, $J_{XIV-4}$ and $K_{XIV-2}$ is a covalent bond, no more than one of $D_{XIV-3}$, $D_{XIV-4}$, $J_{XIV-3}$, $J_{XIV-4}$ and $K_{XIV-2}$ is O, no more than one of $D_{XIV-3}$, $D_{XIV-4}$, $J_{XIV-3}$, $J_{XIV-4}$ and $K_{XIV-2}$ is S, one of $D_{XIV-3}$, $D_{XIV-4}$, $J_{XIV-3}$, $J_{XIV-4}$ and $K_{XIV-2}$ must be a covalent bond when two of $D_{XIV-3}$, $D_{XIV-4}$, $J_{XIV-3}$, $J_{XIV-4}$ and $K_{XIV-2}$ are O and S, and no more than four of $D_{XIV-3}$, $D_{XIV-4}$, $J_{XIV-3}$, $J_{XIV-4}$ and $K_{XIV-2}$ and $K_{XIV-2}$ are N;

$R_{XIV-2}$ is independently selected from the group consisting of hydrido, hydroxy, hydroxyalkyl, amino, aminoalkyl, alkylamino, dialkylamino, alkyl, alkenyl, alkynyl, aryl, aralkyl, aralkoxyalkyl, aryloxyalkyl, alkoxyalkyl, heteroaryloxyalkyl, alkenyloxyalkyl, alkylthioalkyl, aralkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, alkylsulfinylalkyl, alkylsulfonylalkyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

$R_{XIV-2}$ and $R_{XIV-3}$ are taken together to form a linear spacer moiety selected from the group consisting of a covalent single bond and a moiety having from 1 through 6 contiguous atoms to form a ring selected from the group consisting of a cycloalkyl having from 3 through 8 contiguous members, a cycloalkenyl having from 5 through 8 contiguous members, and a heterocyclyl having from 4 through 8 contiguous members;

$R_{XIV-3}$ is selected from the group consisting of hydrido, hydroxy, halo, cyano, aryloxy, hydroxyalkyl, amino, alkylamino, dialkylamino, acyl, sulfhydryl, acylamido, alkoxy, alkylthio, arylthio, alkyl, alkenyl, alkynyl, aryl, aralkyl, aryloxyalkyl, alkoxyalkyl, heteroarylthio, aralkylthio, aralkoxyalkyl, alkylsulfinylalkyl, alkylsulfonylalkyl, aroyl, heteroaroyl, aralkylthioalkyl, heteroaralkylthioalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, and diaralkoxyphosphonoalkyl;

$Y_{XIV}$ is selected from a group consisting of a covalent single bond, $(C(R_{XIV-14})_2)_{qXIV}$ wherein $_{qXIV}$ is an integer selected from 1 and 2 and $(CH(R_{XIV-14}))_{gXIV}$—$W_{XIV}$—$(CH(R_{XIV-14}))_{pXIV}$ wherein $_{gXIV}$ and $_{pXIV}$ are integers independently selected from 0 and 1;

$R_{XIV-14}$ is independently selected from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkylalkoxy, alkylsulfinylalkyl, alkylsulfonylalkyl, aralkylthioalkyl, heteroaralkoxythioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_{XIV-9}$ and $R_{XIV-13}$ to form a ring selected from the group consisting of a cycloalkenyl ring having from 5 through 8 contiguous members and a heterocyclyl ring having from 5 through 8 contiguous members and a spacer selected from a moiety having a chain length of 2 to 5 atoms connected to the point of bonding selected from the group consisting of $R_{XIV-4}$ and $R_{XIV-8}$ to form a heterocyclyl having from 5 through 8 contiguous members with the proviso that, when $Y_{XIV}$ is a covalent bond, an $R_{XIV-14}$ substituent is not attached to $Y_{XIV}$;

$R_{XIV-14}$ and $R_{XIV-14}$, when bonded to the different atoms, are taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{XIV-14}$ and $R_{XIV-14}$, when bonded to the same atom are taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$W_{XIV}$ is selected from the group consisting of O, C(O), C(S), C(O)N($R_{XIV-14}$), C(S)N($R_{XIV-14}$), ($R_{XIV-14}$)NC(O), ($R_{XIV-14}$)NC(S), S, S(O), S(O)$_2$, S(O)$_2$N($R_{XIV-14}$), ($R_{XIV-14}$)NS(O)$_2$, and N($R_{XIV-14}$) with the proviso that $R_{XIV-14}$ is selected from other than halo and cyano;

$Z_{XIV}$ is independently selected from a group consisting of a covalent single bond, $(C(R_{XIV-15})_2)_{qXIV-2}$ wherein $_{qXIV-2}$ is an integer selected from 1 and 2, $(CH(R_{XIV-15}))_{jXIV}$—$W$—$(CH(R_{XIV-15}))_{kXIV}$ wherein $_{jXIV}$ and $_{kXIV}$ are integers independently selected from 0 and 1 with the proviso that, when $Z_{XIV}$ is a covalent single bond, an $R_{XIV-15}$ substituent is not attached to $Z_{XIV}$;

$R_{XIV-15}$ is independently selected, when $Z_{XIV}$ is $(C(R_{XIV-15})_2)_{qXIV}$ wherein $_{qXIV}$ is an integer selected from 1 and 2, from the group consisting of hydrido, hydroxy, halo, cyano, aryloxy, amino, alkylamino, dialkylamino, hydroxyalkyl, acyl, aroyl, heteroaroyl, heteroaryloxyalkyl, sulfhydryl, acylamido, alkoxy, alkylthio, arylthio, alkyl, alkenyl, alkynyl, aryl, aralkyl, aryloxyalkyl, aralkoxyalkyl, alkylsulfinylalkyl, alkylsulfonylalkyl, aralkylthioalkyl, heteroaralkylthioalkyl, alkoxyalkyl, heteroaryloxyalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxy, carboxyalkyl, carboalkoxy, carboxamide, carboxamidoalkyl, carboaralkoxy, dialkoxyphosphono, diaralkoxyphosphono, dialkoxyphosphonoalkyl, diaralkoxyphosphonoalkyl, a spacer selected from a moiety having a chain length of 3 to 6 atoms connected to the point of bonding selected from the group consisting of $R_{XIV-4}$ and $R_{XIV-8}$ to form a ring selected from the group consisting of a cycloalkenyl ring having from 5 through 8 contiguous members and a heterocyclyl ring having from 5 through 8 contiguous members, and a spacer selected from a moiety having a chain length of 2 to 5 atoms connected to the point of bonding selected from the group consisting of $R_{XIV-9}$ and $R_{XIV-13}$ to form a heterocyclyl having from 5 through 8 contiguous members;

$R_{XIV-15}$ and $R_{XIV-15}$, when bonded to the different atoms, are taken together to form a group selected from the group consisting of a covalent bond, alkylene, haloalkylene, and a spacer selected from a group consisting of a moiety having a chain length of 2 to 5 atoms connected to form a ring selected from the group of a saturated cycloalkyl having from 5 through 8 contiguous members, a cycloalkenyl having from 5 through 8 contiguous members, and a heterocyclyl having from 5 through 8 contiguous members;

$R_{XIV-15}$ and $R_{XIV-15}$, when bonded to the same atom are taken together to form a group selected from the group consisting of oxo, thiono, alkylene, haloalkylene, and a spacer selected from the group consisting of a moiety having a chain length of 3 to 7 atoms connected to form a ring selected from the group consisting of a cycloalkyl having from 4 through 8 contiguous members, a cycloalkenyl having from 4 through 8 contiguous members, and a heterocyclyl having from 4 through 8 contiguous members;

$R_{XIV-15}$ is independently selected, when $Z_{XIV}$ is $(CH(R_{XIV-15}))_{jXIV}$—W—$(CH(R_{XIV-15}))_{kXIV}$ wherein $_{jXIV}$ and $_{kXIV}$ are integers independently selected from 0 and 1, from the group consisting of hydrido, halo, cyano, aryloxy, carboxyl, acyl, aroyl, heteroaroyl, hydroxyalkyl, heteroaryloxyalkyl, acylamido, alkoxy, alkylthio, arylthio, alkyl, alkenyl, alkynyl, aryl, aralkyl, aryloxyalkyl, alkoxyalkyl, heteroaryloxyalkyl, aralkoxyalkyl, heteroaralkoxyalkyl, alkylsulfonylalkyl, alkylsulfinylalkyl, alkenyloxyalkyl, alkylthioalkyl, arylthioalkyl, cycloalkyl, cycloalkylalkyl, cycloalkylalkenyl, cycloalkenyl, cycloalkenylalkyl, haloalkyl, haloalkenyl, halocycloalkyl, halocycloalkenyl, haloalkoxy, haloalkoxyalkyl, haloalkenyloxyalkyl, halocycloalkoxy, halocycloalkoxyalkyl, halocycloalkenyloxyalkyl, perhaloaryl, perhaloaralkyl, perhaloaryloxyalkyl, heteroaryl, heteroarylalkyl, heteroarylthioalkyl, heteroaralkylthioalkyl, monocarboalkoxyalkyl, dicarboalkoxyalkyl, monocyanoalkyl, dicyanoalkyl, carboalkoxycyanoalkyl, alkylsulfinyl, alkylsulfonyl, haloalkylsulfinyl, haloalkylsulfonyl, arylsulfinyl, arylsulfinylalkyl, arylsulfonyl, arylsulfonylalkyl, aralkylsulfinyl, aralkylsulfonyl, cycloalkylsulfinyl, cycloalkylsulfonyl, cycloalkylsulfinylalkyl, cycloalkylsulfonylalkyl, heteroarylsulfonylalkyl, heteroarylsulfinyl, heteroarylsulfonyl, heteroarylsulfinylalkyl, aralkylsulfinylalkyl, aralkylsulfonylalkyl, carboxyalkyl, carboalkoxy, carboxamide, carboxamidoalkyl, carboaralkoxy, dialkoxyphosphonoalkyl, diaralkoxyphosphonoalkyl, a spacer selected from a linear moiety having a chain length of 3 to 6 atoms connected to the point of bonding selected from the group consisting of $R_{XIV-4}$ and $R_{XIV-8}$ to form a ring selected from the group consisting of a cycloalkenyl ring having from 5 through 8 contiguous members and a heterocyclyl ring having from 5 through 8 contiguous members, and a spacer selected from a linear moiety having a chain length of 2 to 5 atoms connected to the point of bonding selected from the group consisting of $R_{XIV-9}$ and $R_{XIV-13}$ to form a heterocyclyl ring having from 5 through 8 contiguous members;

$R_{XIV-4}$, $R_{XIV-5}$, $R_{XIV-6}$, $R_{XIV-7}$, $R_{XIV-8}$, $R_{XIV-9}$, $R_{XIV-10}$, $R_{XIV-11}$, $R_{XIV-12}$, and $R_{XIV-13}$ are independently selected from the group consisting of perhaloaryloxy, alkanoylalkyl, alkanoylalkoxy, alkanoyloxy, N-aryl-N-alkylamino, heterocyclylalkoxy, heterocyclylthio, hydroxyalkoxy, carboxamidoalkoxy, alkoxycarbonylalkoxy, alkoxycarbonylalkenyloxy, aralkanoylalkoxy, aralkenoyl, N-alkylcarboxamido, N-haloalkylcarboxamido, N-cycloalkylcarboxamido, N-arylcarboxamidoalkoxy, cycloalkylcarbonyl, cyanoalkoxy, heterocyclylcarbonyl, hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl; haloalkenyl, haloalkoxy, hydroxyhaloalkyl, hydroxyaralkyl, hydroxyalkyl, hydroxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that there are one to five non-hydrido ring substituents $R_{XIV-4}$, $R_{XIV-5}$, $R_{XIV-6}$, $R_{XIV-7}$ and $R_{XIV-8}$ present, that there are one to five non-hydrido ring substituents $R_{XIV-9}$, $R_{XIV-10}$, $R_{XIV-11}$, $R_{XIV-12}$, and $R_{XIV-13}$ present, and $R_{XIV-4}$, $R_{XIV-5}$, $R_{XIV-6}$, $R_{XIV-7}$, $R_{XIV-8}$, $R_{XIV-9}$, $R_{XIV-10}$, $R_{XIV-11}$, $R_{XIV-12}$, and $R_{XIV-13}$ are each independently selected to maintain the tetravalent nature of carbon, trivalent nature of nitrogen, the divalent nature of sulfur, and the divalent nature of oxygen;

$R_{XIV-4}$ and $R_{XIV-5}$, $R_{XIV-5}$ and $R_{XIV-6}$, $R_{XIV-6}$ and $R_{XIV-7}$, $R_{XIV-7}$ and $R_{XIV-8}$, $R_{XIV-8}$ and $R_{XIV-9}$, $R_{XIV-9}$ and $R_{XIV-10}$, $R_{XIV-10}$ and $R_{XIV-11}$, $R_{XIV-11}$ and $R_{XIV-12}$, and $R_{XIV-12}$ and $R_{XIV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XIV-4}$ and $R_{XIV-5}$, $R_{XIV-5}$ and $R_{XIV-6}$, $R_{XIV-6}$ and $R_{XIV-7}$, and $R_{XIV-7}$ and $R_{XIV-8}$ are used at the same time and that no more than one of the group consisting of spacer pairs $R_{XIV-9}$ and $R_{XIV-10}$, $R_{XIV-10}$ and $R_{XIV-11}$, $R_{XIV-11}$ and $R_{XIV-12}$, and $R_{XIV-13}$ are used at the same time;

$R_{XIV-4}$ and $R_{XIV-9}$, $R_{XIV-4}$ and $R_{XIV-13}$, $R_{XIV-8}$ and $R_{XIV-9}$, $R_{XIV-8}$ and $R_{XIV-13}$ are independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_{XIV-4}$ and $R_{XIV-9}$, $R_{XIV-4}$ and $R_{XIV-13}$, $R_{XIV-8}$ and $R_{XIV-9}$ and $R_{XIV-8}$ and $R_{XIV-13}$ is used at the same time.

Compounds of Formula XIV are disclosed in WO 00/18721, the entire disclosure of which is incorporated by reference.

In a preferred embodiment, the CETP inhibitor is selected from the following compounds of Formula XIV:

3-[[3-(3-trifluoromethoxyphenoxy)phenyl][[3-(1,1,2,2-tetrafluoroethoxy)-phenyl]methyl]amino]-1,1,1-trifluoro-2-propanol;

3-[[3-(3-isopropylphenoxy)phenyl][[3-(1,1,2,2-tetrafluoroethoxy)phenyl]-methyl]amino]-1,1,1-trifluoro-2-propanol;

3-[[3-(3-cyclopropylphenoxy)phenyl][[3-(1,1,2,2-tetrafluoroethoxy)phenyl]-methyl]amino]-1,1,1-trifluoro-2-propanol;

3-[[3-(3-(2-furyl)phenoxy)phenyl][[3-(1,1,2,2-tetrafluoroethoxy)phenyl]-methyl]amino]-1,1,1-trifluoro-2-propanol;

3-[[3-(2,3-dichlorophenoxy)phenyl][[3-(1,1,2,2-tetrafluoroethoxy)phenyl]-methyl]amino]-1,1,1-trifluoro-2-propanol;

3-[[3-(4-fluorophenoxy)phenyl][[3-(1,1,2,2-tetrafluoroethoxy)phenyl]-methyl]amino]-1,1,1-trifluoro-2-propanol;

3-[[3-(4-methylphenoxy)phenyl][[3-(1,1,2,2-tetrafluoroethoxy)phenyl]-methyl]amino]-1,1,1-trifluoro-2-propanol;

3-[[3-(2-fluoro-5-bromophenoxy)phenyl][[3-(1,1,2,2-tetrafluoroethoxy)phenyl]-methyl]amino]-1,1,1-trifluoro-2-propanol;

3-[[3-(4-chloro-3-ethylphenoxy)phenyl][[3-(1,1,2,2-tetrafluoroethoxy)phenyl]-methyl]amino]-1,1,1-trifluoro-2-propanol;

3-[[3-[3-(1,1,2,2-tetrafluoroethoxy)phenoxy]phenyl][[3-(1,1,2,2-tetrafluoro-ethoxy)phenyl]methyl]amino]-1,1,1-trifluoro-2-propanol;

3-[[3-[3-(pentafluoroethyl)phenoxy]phenyl][[3-(1,1,2,2-tetrafluoroethoxy)-phenyl]methyl]amino]-1,1,1-trifluoro-2-propanol;

3-[[3-(3,5-dimethylphenoxy)phenyl][[3-(1,1,2,2-tetrafluoroethoxy)phenyl]-methyl]amino]-1,1,1-trifluoro-2-propanol;

3-[[3-(3-ethylphenoxy)phenyl][[3-(1,1,2,2-tetrafluoroethoxy)phenyl]-methyl]amino]-1,1,1-trifluoro-2-propanol;

3-[[3-(3-t-butylphenoxy)phenyl][[3-(1,1,2,2-tetrafluoroethoxy)phenyl]-methyl]amino]1,1,1-trifluoro-2-propanol;

3-[[3-(3-methylphenoxy)phenyl][[3-(1,1,2,2-tetrafluoroethoxy)phenyl]-methyl]amino]-1,1,1-trifluoro-2-propanol;

3-[[3-(5,6,7,8-tetrahydro-2-naphthoxy)phenyl][[3-(1,1,2,2-tetrafluoroethoxy)phenyl]methyl]amino]-1,1,1-trifluoro-2-propanol;

3-[[3-(phenoxy)phenyl][[3-(1,1,2,2-tetrafluoroethoxy)phenyl]methyl]amino]-1,1,1-trifluoro-2-propanol;

3-[[3-[3-(N,N-dimethylamino)phenoxy]phenyl][[3-(1,1,2,2-tetrafluoroethoxy)phenyl]methyl]amino]-1,1,1-trifluoro-2-propanol;

3-[[[3-(1,1,2,2-tetrafluoroethoxy)phenyl]methyl][3-[[3-(trifluoromethoxy)-phenyl]methoxy]phenyl]amino]-1,1,1-trifluoro-2-propanol;

3-[[[3-(1,1,2,2-tetrafluoroethoxy)phenyl]methyl][3-[[3-(trifluoromethyl)-phenyl]methoxy]phenyl]amino]-1,1,1-trifluoro-2-propanol;

3-[[[3-(1,1,2,2-tetrafluoroethoxy)phenyl]methyl][3-[[3,5-dimethylphenyl]-methoxy]phenyl]amino]-1,1,1-trifluoro-2-propanol;

3-[[[3-(1,1,2,2-tetrafluoroethoxy)phenyl]methyl][3-[[3-(trifluoromethylthio)-phenyl]methoxy]phenyl]amino]-1,1,1,-trifluoro-2-propanol;

3-[[[3-(1,1,2,2-tetrafluoroethoxy)phenyl]methyl][3-[[3,5-difluorophenyl]-methoxy]phenyl]amino]-1,1,1-trifluoro-2-propanol;

3-[[[3-(1,1,2,2-tetrafluoroethoxy)phenyl]methyl][3-[cyclohexylmethoxy]-phenyl]amino]-1,1,1-trifluoro-2-propanol;

3-[[3-(2-difluoromethoxy-4-pyridyloxy)phenyl][[3-(1,1,2,2-tetrafluoroethoxy)-phenyl]methyl]amino]-1,1,1-trifluoro-2-propanol;

3-[[3-(2-trifluoromethyl-4-pyridyloxy)phenyl][[3-(1,1,2,2-tetrafluoroethoxy)-phenyl]methyl]amino]-1,1,1-trifluoro-2-propanol;

3-[[3-(3-difluoromethoxyphenoxy)phenyl][[3-(1,1,2,2-tetrafluoroethoxy)-phenyl]methyl]amino]-1,1,1-trifluoro-2-propanol;

3-[[[3-(3-trifluoromethylthio)phenoxy]phenyl][[3-(1,1,2,2-tetrafluoroethoxy)-phenyl]methyl]amino]-1,1,1-trifluoro-2-propanol;

3-[[3-(4-chloro-3-trifluoromethylphenoxy)phenyl][[3-(1,1,2,2-tetrafluoroethoxy)-phenyl]methyl]amino]-1,1,1,-trifluoro-2-propanol;

3-[[3-(3-trifluoromethoxyphenoxy)phenyl][[3-(pentafluoroethylmethyl]amino]-1,1,1-trifluoro-2-propanol;
3-[[3-(3-isopropylphenoxy)phenyl][[3-(pentafluoroethyl)phenyl]methyl-amino]-1,1,1-trifluoro-2-propanol;
3-[[3-(3-cyclopropylphenoxy)phenyl][[3-(pentafluoroethyl)phenyl]methyl]-amino]-1,1,1-trifluoro-2-propanol;
3-[[3-(3-(2-furyl)phenoxy)phenyl][[3-(pentafluoroethyl)phenyl]methyl]-amino]-1,1,1-trifluoro-2-propanol;
3-[[3-(2,3-dichlorophenoxy)phenyl][[3-(pentafluoroethyl)phenyl]methyl]-amino]-1,1,1-trifluoro-2-propanol;
3-[[3-(4-fluorophenoxy)phenyl][[3-(pentafluoroethyl)phenyl]methyl]amino]-1,1,1-trifluoro-2-propanol;
3-[[3-(4-methylphenoxy)phenyl][[3-(pentafluoroethyl)phenyl]methyl]amino]-1,1,1-trifluoro-2-propanol;
3-[[3-(2-fluoro-5-bromophenoxy)phenyl][[3-(pentafluoroethyl)phenyl]methyl]-amino]-1,1,1-trifluoro-2-propanol;
3-[[3-(4-chloro-3-ethylphenoxy)phenyl][[3-(pentafluoroethyl)phenyl]methyl]-amino]-1,1,1-trifluoro-2-propanol;
3-[[3-[3-(1,1,2,2-tetrafluoroethoxy)phenoxy]phenyl][[3-(pentafluoroethyl)-phenyl]methyl]amino]-1,1,1-trifluoro-2-propanol;
3-[[3-[3-(pentafluoroethyl)phenoxy]phenyl][[3-(pentafluoroethyl)phenyl]-methyl]amino]-1,1,1-trifluoro-2-propanol;
3-[[3-(3,5-dimethylphenoxy)phenyl][[3-(pentafluoroethyl)phenyl]methyl-amino]-1,1,1-trifluoro-2-propanol;
3-[[3-(3-ethylphenoxy)phenyl][[3-(pentafluoroethyl)phenyl]methyl]amino]-1,1,1-trifluoro-2-propanol;
3-[[3-(3-t-butylphenoxy)phenyl][[3-(pentafluoroethyl)phenyl]methyl]amino]-1,1,1-trifluoro-2-propanol;
3-[[3-(3-methylphenoxy)phenyl][[3-pentafluoroethyl)phenyl]methyl]amino]-1,1,1-trifluoro-2-propanol;
3-[[3-(5,6,7,8-tetrahydro-2-naphthoxy)phenyl][[3-(pentafluoroethyl)phenyl]-methyl]amino]-1,1,1-trifluoro-2-propanol;
3-[[3-(phenoxy)phenyl][[3-(pentafluoroethyl)phenyl]methyl]amino]-1,1,1-trifluoro-2-propanol;
3-[[3-[3-(N,N-dimethylamino)phenoxy]phenyl][[3-(pentafluoroethyl)phenyl]-methyl]amino]-1,1,1-trifluoro-2-propanol;
3-[[[3-(pentafluoroethyl)phenyl]methyl][3-[[3-(trifluoromethoxy)phenyl]-methoxy]phenyl]amino]-1,1,1-trifluoro-2-propanol;
3-[[[3-(pentafluoroethyl)phenyl]methyl][3-[[3-(trifluoromethyl)phenyl]-methoxy]phenyl]amino]-1,1,1-trifluoro-2-propanol;
3-[[[3-(pentafluoroethyl)phenyl]methyl][3-[[3,5-dimethylphenyl]methoxy]-phenyl]amino]-1,1,1-trifluoro-2-propanol;
3-[[[3-(pentafluoroethyl)phenyl]methyl][3-[[3-(trifluoromethylthio)phenyl]-methoxy]phenyl]amino]-1,1,1-trifluoro-2-propanol;
3-[[[3-(pentafluoroethyl)phenyl]methyl][3-[[3,5-difluorophenyl]methoxy]-phenyl]amino]-1,1,1-trifluoro-2-propanol;
3-[[[3-(pentafluoroethyl)phenyl]methyl][3-[cyclohexylmethoxy]phenyl]-amino]-1,1,1-trifluoro-2-propanol;
3-[[3-(2-difluoromethoxy-4-pyridyloxy)phenyl][[3-(pentafluoroethyl)phenyl]-methyl]amino]-1,1,1-trifluoro-2-propanol;
3-[[3-(2-trifluoromethyl-4-pyridyloxy)phenyl][[3-(pentafluoroethyl)phenyl]-methyl]amino]-1,1,1-trifluoro-2-propanol;
3-[[3-(3-difluoromethoxyphenoxy)phenyl][[3-(pentafluoroethyl)phenyl]-methyl]amino]-1,1,1-trifluoro-2-propanol;
3-[[[3-(3-trifluoromethylthio)phenoxy]phenyl][[3-(pentafluoroethyl)phenyl]-methyl]amino]-1,1,1-trifluoro-2-propanol;
3-[[3-(4-chloro-3-trifluoromethylphenoxy)phenyl][[3-(pentafluoroethyl)-phenyl]methyl]amino]-1,1,1-trifluoro-2-propanol;
3-[[3-(3-trifluoromethoxyphenoxy)phenyl][[3-(heptafluoropropyl)phenyl]-methyl]amino]-1,1,1-trifluoro-2-propanol;
3-[[3-(3-isopropylphenoxy)phenyl][[3-(heptafluoropropyl)phenyl]methyl-amino]-1,1,1-trifluoro-2-propanol;
3-[[3-(3-cyclopropylphenoxy)phenyl][[3-(heptafluoropropyl)phenyl]methyl]-amino]-1,1,1-trifluoro-2-propanol;
3-[[3-(3-(2-furyl)phenoxy)phenyl][[3-(heptafluoropropyl)phenyl]methyl]-amino]-1,1,1-trifluoro-2-propanol;
3-[[3-(2,3-dichlorophenoxy)phenyl][[3-(heptafluoropropyl)phenyl]methyl]-amino]-1,1,1-trifluoro-2-propanol;
3-[[3-(4-fluorophenoxy)phenyl][[3-(heptafluoropropyl)phenyl]methyl]amino]-1,1,1-trifluoro-2-propanol;
3-[[3-(4-methylphenoxy)phenyl][[3-(heptafluoropropyl)phenyl]methyl]amino]-1,1,1-trifluoro-2-propanol;
3-[[3-(2-fluoro-5-bromophenoxy)phenyl][[3-(heptafluoropropyl)phenyl]methyl]-amino]-1,1,1-trifluoro-2-propanol;
3-[[3-(4-chloro-3-ethylphenoxy)phenyl][[3-(heptafluoropropyl)phenyl]methyl]-amino]-1,1,1-trifluoro-2-propanol;
3-[[3-[3-(1,1,2,2-tetrafluoroethoxy)phenoxy]phenyl][[3-(heptafluoropropyl)-phenyl]methyl]amino]-1,1,1-trifluoro-2-propanol;
3-[[3-[3-(pentafluoroethyl)phenoxy]phenyl][[3-(heptafluoropropyl)phenyl]-methyl]amino]-1,1,1-trifluoro-2-propanol;
3-[[3-(3,5-dimethylphenoxy)phenyl][[3-(heptafluoropropyl)phenyl]methyl]-amino]-1,1,1-trifluoro-2-propanol;
3-[[3-(3-ethylphenoxy)phenyl][[3-(heptafluoropropyl)phenyl]methyl]amino]-1,1,1-trifluoro-2-propanol;
3-[[3-(3-t-butylphenoxy)phenyl][[3-(heptafluoropropyl)phenyl]methyl]amino]-1,1,1-trifluoro-2-propanol;
3-[[3-(3-methylphenoxy)phenyl][[3-(heptafluoropropyl)phenyl]methyl]amino]-1,1,1-trifluoro-2-propanol;
3-[[3-(5,6,7,8-tetrahydro-2-naphthoxy)-phenyl][[3-(heptafluoropropyl)phenyl]methyl]amino]-1,1,1-trifluoro-2-propanol;
3-[[3-(phenoxy)phenyl][[3-(heptafluoropropyl)phenyl]methyl]amino]-1,1,1-trifluoro-2-propanol;
3-[[3-[3-(N,N-dimethylamino)phenoxy]phenyl][[3-(heptafluoropropyl)phenyl]-methyl]amino]-1,1,1-trifluoro-2-propanol;
3-[[[3-(heptafluoropropyl)phenyl]methyl][3-[[3-(trifluoromethoxy)phenyl]-methoxy]phenyl]amino]-1,1,1-trifluoro-2-propanol;
3-[[[3-(heptafluoropropyl)phenyl]methyl][3-[[3-(trifluoromethyl)phenyl]-methoxy]phenyl]amino]-1,1,1-trifluoro-2-propanol;
3-[[[3-(heptafluoropropyl)phenyl]methyl][3-[[3,5-dimethylphenyl]methoxy]-phenyl]amino]-1,1,1-trifluoro-2-propanol;
3-[[[3-(heptafluoropropyl)phenyl]methyl][3-[[3-(trifluoromethylthio)phenyl]-methoxy]phenyl]amino]-1,1,1-trifluoro-2-propanol;
3-[[[3-(heptafluoropropyl)phenyl]methyl][3-[[3,5-difluorophenyl]methoxy]-phenyl]amino]-1,1,1-trifluoro-2-propanol;
3-[[[3-(heptafluoropropyl)phenyl]methyl][3-[cyclohexylmethoxy]phenyl]-amino]-1,1,1-trifluoro-2-propanol;

3-[[3-(2-difluoromethoxy-4-pyridyloxy)phenyl][[3-(heptafluoropropyl)phenyl]-methyl]amino]-1,1,1-trifluoro-2-propanol;

3-[[3-(2-trifluoromethyl-4-pyridyloxy)phenyl][[3-(heptafluoropropyl)phenyl]-methyl]amino]-1,1,1-trifluoro-2-propanol;

3-[[3-(3-difluoromethoxyphenoxy)phenyl][[3-(heptafluoropropyl)phenyl]-methyl]amino]-1,1,1-trifluoro-2-propanol;

3-[[[3-(3-trifluoromethylthio)phenoxy]phenyl][[3-(heptafluoropropyl)phenyl]-methyl]-amino]-1,1,1-trifluoro-2-propanol;

3-[[3-(4-chloro-3-trifluoromethylphenoxy)phenyl][[3-(heptafluoropropyl)-phenyl]-methyl]amino]-1,1,1-trifluoro-2-propanol;

3-[[3-(3-trifluoromethoxyphenoxy)phenyl][[2-fluoro-5-(trifluoromethyl)-phenyl]-methyl]amino]-1,1,1-trifluoro-2-propanol;

3-[[3-(3-isopropylphenoxy)phenyl][[2-fluoro-5-(trifluoromethyl)phenyl]-methyl]amino]-1,1,1-trifluoro-2-propanol;

3-[[3-(3-cyclopropylphenoxy)phenyl][[2-fluoro-5-(trifluoromethyl)phenyl]-methyl]amino]-1,1,1-trifluoro-2-propanol;

3-[[3-(3-(2-furyl)phenoxy)phenyl][[2-fluoro-5-(trifluoromethyl)phenyl]-methyl]amino]-1,1,1-trifluoro-2-propanol;

3-[[3-(2,3-dichlorophenoxy)phenyl][[2-fluoro-5-(trifluoromethyl)phenyl]-methyl]amino]-1,1,1-trifluoro-2-propanol;

3-[[3-(4-fluorophenoxy)phenyl][[2-fluoro-5-(trifluoromethyl)phenyl]-methyl]amino]-1,1,1-trifluoro-2-propanol;

3-[[3-(4-methylphenoxy)phenyl][[2-fluoro-5-(trifluoromethyl)phenyl]-methyl]amino]-1,1,1-trifluoro-2-propanol;

3-[[3-(2-fluoro-5-bromophenoxy)phenyl][[2-fluoro-5-(trifluoromethyl)-phenyl]methyl]amino]-1,1,1-trifluoro-2-propanol;

3-[[3-(4-chloro-3-ethylphenoxy)phenyl][[2-fluoro-5-(trifluoromethyl)-phenyl]methyl]amino]-1,1,1-trifluoro-2-propanol;

3-[[3-[3-(1,1,2,2-tetrafluoroethoxy)phenoxy]phenyl][[2-fluoro-5-(trifluoro-methyl)phenyl]methyl]amino]-1,1,1-trifluoro-2-propanol;

3-[[3-[3-(pentafluoroethyl)phenoxy]phenyl][[2-fluoro-5-(trifluoromethyl)-phenyl]-methyl]amino]-1,1,1-trifluoro-2-propanol;

3-[[3-(3,5-dimethylphenoxy)phenyl][[2-fluoro-5-(trifluoromethyl)phenyl]-methyl]amino]-1,1,1-trifluoro-2-propanol;

3-[[3-(3-ethylphenoxy)phenyl][[2-fluoro-5-(trifluoromethyl)phenyl]methyl]-amino]-1,1,1-trifluoro-2-propanol;

3-[[3-(3-t-butylphenoxy)phenyl][[2-fluoro-5-(trifluoromethyl)phenyl]methyl]-amino]-1,1,1-trifluoro-2-propanol;

3-[[3-(3-methylphenoxy)phenyl][[2-fluoro-5-(trifluoromethyl)phenyl]methyl]-amino]-1,1,1-trifluoro-2-propanol;

3-[[3-(5,6,7,8-tetrahydro-2-naphthoxy)phenyl][[2-fluoro-5-(trifluoromethyl)-phenyl]methyl]amino]-1,1,1-trifluoro-2-propanol;

3-[[3-(phenoxy)phenyl][[2-fluoro-5-(trifluoromethyl)phenyl]methyl]amino]-1,1,1-trifluoro-2-propanol;

3-[[3-[3-(N,N-dimethylamino)phenoxy]phenyl][[2-fluoro-5-(trifluoromethyl)-phenyl]methyl]amino]-1,1,1-trifluoro-2-propanol;

3-[[[2-fluoro-5-(trifluoromethyl)phenyl]methyl][3-[[3-(trifluoromethoxy)-phenyl]methoxy]phenyl]amino]-1,1,1-trifluoro-2-propanol;

3-[[[2-fluoro-5-(trifluoromethyl)phenyl]methyl][3-[[3-(trifluoromethyl)-phenyl]methoxy]phenyl]amino]-1,1,1-trifluoro-2-propanol;

3-[[[2-fluoro-5-(trifluoromethyl)phenyl]methyl][3-[[3,5-dimethylphenyl]-methoxy]phenyl]amino]-1,1,1-trifluoro-2-propanol;

3-[[[2-fluoro-5-(trifluoromethyl)phenyl]methyl][3-[[3-(trifluoromethylthio)-phenyl]methoxy]phenyl]amino]-1,1,1-trifluoro-2-propanol;

3-[[[2-fluoro-5-(trifluoromethyl)phenyl]methyl][3-[[3,5-difluorophenyl]-methoxy]phenyl]amino]-1,1,1-trifluoro-2-propanol;

3-[[[2-fluoro-5-(trifluoromethyl)phenyl]methyl][3-[cyclohexylmethoxy]-phenyl]amino]-1,1,1-trifluoro-2-propanol;

3-[[3-(2-difluoromethoxy-4-pyridyloxy)phenyl][[2-fluoro-5-(trifluoromethyl)-phenyl]methyl]amino]-1,1,1-trifluoro-2-propanol;

3-[[3-(2-trifluoromethyl-4-pyridyloxy)phenyl][[2-fluoro-5-(trifluoromethyl)-phenyl]methyl]amino]-1,1,1-trifluoro-2-propanol;

3-[[3-(3-difluoromethoxyphenoxy)phenyl][[2-fluoro-5-(trifluoromethyl)-phenyl]methyl]amino]-1,1,1-trifluoro-2-propanol;

3-[[[3-(3-trifluoromethylthio)phenoxy]phenyl][[2-fluoro-5-(trifluoromethyl)-phenyl)methyl]amino]-1,1,1-trifluoro-2-propanol;

3-[[3-(4-chloro-3-trifluoromethylphenoxy)phenyl][[2-fluoro-5-(trifluoromethyl)phenyl]methyl]amino]-1,1,1-trifluoro-2-propanol;

3-[[3-(3-trifluoromethoxyphenoxy)phenyl][[2-fluoro-4-(trifluoromethyl)-phenyl]methyl]amino]-1,1,1-trifluoro-2-propanol;

3-[[3-(3-isopropylphenoxy)phenyl][[2-fluoro-4-(trifluoromethyl)phenyl]-methyl]amino]-1,1,1-trifluoro-2-propanol;

3-[[3-(3-cyclopropylphenoxy)phenyl][[2-fluoro-4-(trifluoromethyl)phenyl]-methyl]amino]-1,1,1-trifluoro-2-propanol;

3-[[3-(3-(2-furyl)phenoxy)phenyl][[2-fluoro-4-(trifluoromethyl)phenyl]-methyl]amino]-1,1,1-trifluoro-2-propanol;

3-[[3-(2,3-dichlorophenoxy)phenyl][[2-fluoro-4-(trifluoromethyl)phenyl]-methyl]amino]-1,1,1-trifluoro-2-propanol;

3-[[3-(4-fluorophenoxy)phenyl][[2-fluoro-4-(trifluoromethyl)phenyl]-methyl]amino]-1,1,1-trifluoro-2-propanol;

3-[[3-(4-methylphenoxy)phenyl][[2-fluoro-4-(trifluoromethyl)phenyl]-methyl]amino]-1,1,1-trifluoro-2-propanol;

3-[[3-(2-fluoro-5-bromophenoxy)phenyl][[2-fluoro-4-(trifluoromethyl)-phenyl]methyl]amino]-1,1,1-trifluoro-2-propanol;

3-[[3-(4-chloro-3-ethylphenoxy)phenyl][[2-fluoro-4-(trifluoromethyl)-phenyl]methyl]amino]-1,1,1-trifluoro-2-propanol;

3-[[3-[3-(1,1,2,2-tetrafluoroethoxy)phenoxy]phenyl][[2-fluoro-4-(trifluoro-methyl)phenyl]methyl]amino]-1,1,1-trifluoro-2-propanol;

3-[[3-[3-(pentafluoroethyl)phenoxy]phenyl][[2-fluoro-4-(trifluoromethyl)-phenyl]methyl]amino]-1,1,1-trifluoro-2-propanol;

3-[[3-(3,5-dimethylphenoxy)phenyl][[2-fluoro-4-(trifluoromethyl)phenyl]-methyl]amino]-1,1,1-trifluoro-2-propanol;

3-[[3-(3-ethylphenoxy)phenyl][[2-fluoro-4-(trifluoromethyl)phenyl]methyl]-amino]-1,1,1-trifluoro-2-propanol;

3-[[3-(3-t-butylphenoxy)phenyl][[2-fluoro-4-(trifluoromethyl)phenyl]methyl]-amino]-1,1,1-trifluoro-2-propanol;

3-[[3-(3-methylphenoxy)phenyl][[2-fluoro-4-(trifluoromethyl)phenyl]methyl]-amino]-1,1,1-trifluoro-2-propanol;

3-[[3-(5,6,7,8-tetrahydro-2-naphthoxy)phenyl][[2-fluoro-4-(trifluoromethyl)-phenyl]methyl]amino]-1,1,1-trifluoro-2-propanol;

3-[[3-(phenoxy)phenyl][[2-fluoro-4-(trifluoromethyl)phenyl]methyl]amino]-1,1,1-trifluoro-2-propanol;

3-[[3-[3-(N,N-dimethylamino)phenoxy]phenyl][[2-fluoro-4-(trifluoromethyl)-phenyl]methyl]amino]-1,1,1-trifluoro-2-propanol;

3-[[[2-fluoro-4-(trifluoromethyl)phenyl]methyl][3-[[3-(trifluoromethoxy)-phenyl]methoxy]phenyl]amino]-1,1,1-trifluoro-2-propanol;

3-[[[2-fluoro-4-(trifluoromethyl)phenyl]methyl][3-[[3-(trifluoromethyl)-phenyl]methoxy]phenyl]amino]-1,1,1-trifluoro-2-propanol;

3-[[[2-fluoro-4-(trifluoromethyl)phenyl]methyl][3-[[3,5-dimethylphenyl]-methoxy]phenyl]amino]-1,1,1-trifluoro-2-propanol;

3-[[[2-fluoro-4-(trifluoromethyl)phenyl]methyl][3-[[3-(trifluoromethylthio)-phenyl]methoxy]phenyl]amino]-1,1,1-trifluoro-2-propanol;

3-[[[2-fluoro-4-(trifluoromethyl)phenyl]methyl][3-[[3,5-difluorophenyl]-methoxy]phenyl]amino]-1,1,1-trifluoro-2-propanol;

3-[[[2-fluoro-4-(trifluoromethyl)phenyl]methyl][3-[cyclohexylmethoxy]-phenyl]amino]-1,1,1-trifluoro-2-propanol;

3-[[3-(2-difluoromethoxy-4-pyridyloxy)phenyl][[2-fluoro-4-(trifluoromethyl)-phenyl]methyl]amino]-1,1,1-trifluoro-2-propanol;

3-[[3-(2-trifluoromethyl-4-pyridyloxy)phenyl][[2-fluoro-4-(trifluoromethyl)-phenyl]methyl]amino]-1,1,1-trifluoro-2-propanol;

3-[[3-(3-difluoromethoxyphenoxy)phenyl][[2-fluoro-4-(trifluoromethyl)-phenyl]methyl]amino]-1,1,1-trifluoro-2-propanol;

3-[[[3-(3-trifluoromethylthio)phenoxy]phenyl][[2-fluoro-4-(trifluoromethyl)-phenyl]methyl]amino]-1,1,1-trifluoro-2-propanol; and 3-[[3-(4-chloro-3-trifluoromethylphenoxy)phenyl][[2-fluoro-4-(trifluoro-methyl)phenyl]methyl]amino]-1,1,1-trifluoro-2-propanol.

Another class of CETP inhibitors that finds utility with the present invention consists of substituted N-Aliphatic-N-Aromatic tertiary-Heteroalkylamines having the Formula XV

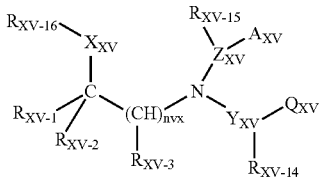

Formula XV and pharmaceutically acceptable forms thereof, wherein:

$n_{XV}$ is an integer selected from 1 through 2;

$A_{XV}$ and $Q_{XV}$ are independently selected from the group consisting of $-CH_2(CR_{XV-37}R_{XV-38})_{vXV}-(CR_{XV-33}R_{XV-34})_{uXV}-T_{XV}-(CR_{XV-35}R_{XV-36})_{wXV}H$,

 AQ-1

AQ-2 with the provisos that one of $A_{XV}$ and $Q_{XV}$ must be AQ-1 and that one of $A_{XV}$ and $Q_{XV}$ must be selected from the group consisting of AQ-2 and $-CH_2(CR_{XV-37}R_{XV-38})_{vXV}-(CR_{XV-33}R_{XV-34})_{uXV}-T_{XV}-(CR_{XV-35}R_{XV-36})_{wXV}-H$;

$T_{XV}$ is selected from the group consisting of a single covalent bond, O, S, S(O), S(O)$_2$, C(R$_{XV-33}$)=C(R$_{XV-35}$), and C≡C;

$_{vXV}$ is an integer selected from 0 through 1 with the proviso that $_{vXV}$ is 1 when any one of R$_{XV-33}$, R$_{XV-34}$, R$_{XV-35}$, and R$_{XV-36}$ is aryl or heteroaryl;

$_{uXV}$ and $_{wXV}$ are integers independently selected from 0 through 6;

$A_{XV-1}$ is C(R$_{XV-30}$);

$D_{XV-1}$, $D_{XV-2}$, $J_{XV-1}$, $J_{XV-2}$, and $K_{XV-1}$ are independently selected from the group consisting of C, N, O, S and a covalent bond with the provisos that no more than one of $D_{XV-1}$, $D_{XV-2}$, $J_{XV-1}$, $J_{XV-2}$, and $K_{XV-1}$ is a covalent bond, no more than one of $D_{XV-1}$, $D_{XV-2}$, $J_{XV-1}$, $J_{XV-2}$ and $K_{XV-1}$ is O, no more than one of $D_{XV-1}$, $D_{XV-2}$, $J_{XV-1}$, $J_{XV-2}$, and $K_{XV-1}$ is S, one of $D_{XV-1}$, $D_{XV-2}$, $J_{XV-1}$, $J_{XV-2}$, and $K_{XV-1}$ must be a covalent bond when two of $D_{XV-1}$, $D_{XV-2}$, $J_{XV-1}$, $J_{XV-2}$, and $K_{XV-1}$ are O and S, and no more than four of $D_{XV-1}$, $D_{XV-2}$, $J_{XV-1}$, $J_{XV-2}$ and $K_{XV-1}$ are N;

$B_{XV-1}$, $B_{XV-2}$, $D_{XV-3}$, $D_{XV-4}$, $J_{XV-3}$, $J_{XV-4}$, and $K_{XV-2}$ are independently selected from the group consisting of C, C(R$_{XV-30}$), N, O, S and a covalent bond with the provisos that no more than 5 of $B_{XV-1}$, $B_{XV-2}$, $D_{XV-3}$, $D_{XV-4}$, $J_{XV-3}$, $J_{XV-4}$, and $K_{XV-2}$ are a covalent bond, no more than two of $B_{XV-1}$, $B_{XV-2}$, $D_{XV-3}$, $D_{XV-4}$, $J_{XV-3}$, $J_{XV-4}$ and $K_{XV-2}$ are O, no more than two of $B_{XV-1}$, $B_{XV-2}$, $D_{XV-3}$, $D_{XV-4}$, $J_{XV-3}$, $J_{XV-4}$, and $K_{XV-2}$ are S, no more than two of $B_{XV-1}$, $B_{XV-2}$, $D_{XV-3}$, $D_{XV-4}$, $J_{XV-3}$, $J_{XV-4}$, and $K_{XV-2}$ are simultaneously O and S, and no more than two of $B_{XV-1}$, $B_{XV-2}$, $D_{XV-3}$, $D_{XV-4}$, $J_{XV-3}$, $J_{XV-4}$, and $K_{XV-2}$ are N;

$B_{XV-1}$ and $D_{XV-3}$, $D_{XV-3}$ and $J_{XV-3}$, $J_{XV-3}$ and $K_{XV-2}$, $K_{XV-2}$ and $J_{XV-4}$, $J_{XV-4}$ and $D_{XV-4}$, and $D_{XV-4}$ and $B_{XV-2}$ are independently selected to form an in-ring spacer pair wherein said spacer pair is selected from the group consisting of C(R$_{XV-33}$)=C(R$_{XV-35}$) and N=N with the provisos that AQ-2 must be a ring of at least five contiguous members, that no more than two of the group of said spacer pairs are simultaneously C(R$_{XV-33}$)=C(R$_{XV-35}$) and that no more than one of the group of said spacer pairs can be N=N unless the other spacer pairs are other than C(R$_{XV-33}$)=C(R$_{XV-35}$), O, N, and S;

$R_{XV-1}$ is selected from the group consisting of haloalkyl and haloalkoxymethyl;

$R_{XV-2}$ is selected from the group consisting of hydrido, aryl, alkyl, alkenyl, haloalkyl, haloalkoxy, haloalkoxyalkyl, perhaloaryl, perhaloaralkyl, perhaloaryloxyalkyl and heteroaryl;

$R_{XV-3}$ is selected from the group consisting of hydrido, aryl, alkyl, alkenyl, haloalkyl, and haloalkoxyalkyl;

$Y_{XV}$ is selected from the group consisting of a covalent single bond, $(CH_2)_q$ wherein q is an integer selected from 1 through 2 and $(CH_2)_j$—O—$(CH_2)_k$ wherein j and k are integers independently selected from 0 through 1;

$Z_{XV}$ is selected from the group consisting of covalent single bond, $(CH_2)_q$ wherein q is an integer selected from 1 through 2, and $(CH_2)_j$—O—$(CH_2)_k$ wherein j and k are integers independently selected from 0 through 1;

$R_{XV-4}$, $R_{XV-8}$, $R_{XV-9}$, and $R_{XV-13}$ are independently selected from the group consisting of hydrido, halo, haloalkyl, and alkyl;

$R_{XV-30}$ is selected from the group consisting of hydrido, alkoxy, alkoxyalkyl, halo, haloalkyl, alkylamino, alkylthio, V alkylthioalkyl, alkyl, alkenyl, haloalkoxy, and haloalkoxyalkyl with the proviso that $R_{XV-30}$ is selected to maintain the tetravalent nature of carbon, trivalent nature of nitrogen, the divalent nature of sulfur, and the divalent nature of oxygen;

$R_{XV-30}$, when bonded to $A_{XV-1}$, is taken together to form an intra-ring linear spacer connecting the $A_{XV-1}$-carbon at the point of attachment of $R_{XV-30}$ to the point of bonding of a group selected from the group consisting of $R_{XV-10}$, $R_{XV-11}$, $R_{XV-12}$, $R_{XV-31}$, and $R_{XV-32}$ wherein said intra-ring linear spacer is selected from the group consisting of a covalent single bond and a spacer moiety having from 1 through 6 contiguous atoms to form a ring selected from the group consisting of a cycloalkyl having from 3 through 10 contiguous members, a cycloalkenyl having from 5 through 10 contiguous members, and a heterocyclyl having from 5 through 10 contiguous members;

$R_{XV-30}$, when bonded to $A_{XV-1}$, is taken together to form an intra-ring branched spacer connecting the $A_{XV-1}$-carbon at the point of attachment of $R_{XV-30}$ to the points of bonding of each member of any one of substituent pairs selected from the group consisting of substituent pairs $R_{XV-10}$, and $R_{XV-11}$, $R_{XV-10}$ and $R_{XV-31}$, $R_{XV-10}$ and $R_{XV-32}$, $R_{XV-10}$ and $R_{XV-12}$, and $R_{XV-11}$ and $R_{XV-31}$, $R_{XV-11}$ and $R_{XV-32}$, $R_{XV-11}$ and $R_{XV-12}$, $R_{XV-31}$ and $R_{XV-32}$, $R_{XV-31}$ and $R_{XV-12}$, and $R_{XV-32}$ and $R_{XV-12}$ and wherein said intra-ring branched spacer is selected to form two rings selected from the group consisting of cycloalkyl having from 3 through 10 contiguous members, cycloalkenyl having from 5 through 10 contiguous members, and heterocyclyl having from 5 through 10 contiguous members;

$R_{XV-4}$, $R_{XV-5}$, $R_{XV-6}$, $R_{XV-7}$, $R_{XV-8}$, $R_{XV-9}$, $R_{XV-10}$, $R_{XV-11}$, $R_{XV-12}$, $R_{XV-13}$, $R_{XV-31}$, $R_{XV-32}$, $R_{XV-33}$, $R_{XV-34}$, $R_{XV-35}$, and $R_{XV-36}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroarylaminoalkyl, haloalkylthio, alkanoyloxy, alkoxy, alkoxyalkyl, haloalkoxyalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydroxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, alkylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the provisos that $R_{XV-4}$, $R_{XV-5}$, $R_{XV-6}$, $R_{XV-7}$, $R_{XV-8}$, $R_{XV-9}$, $R_{XV-10}$, $R_{XV-11}$, $R_{XV-12}$, $R_{XV-13}$, $R_{XV-31}$, $R_{XV-32}$, $R_{XV-33}$, $R_{XV-34}$, $R_{XV-35}$, and $R_{XV-36}$ are each independently selected to maintain the tetravalent nature of carbon, trivalent nature of nitrogen, the divalent nature of sulfur, and the divalent nature of oxygen, that no more than three of the $R_{XV-33}$ and $R_{XV-34}$ substituents are simultaneously selected from other than the group consisting of hydrido and halo, and that no more than three of the $R_{XV-35}$ and $R_{XV-36}$ substituents are simultaneously selected from other than the group consisting of hydrido and halo;

$R_{XV-9}$, $R_{XV-10}$, $R_{XV-11}$, $R_{XV-12}$, $R_{XV-13}$, $R_{XV-31}$, and $R_{XV-32}$ are independently selected to be oxo with the provisos that $B_{XV-1}$, $B_{XV-2}$, $D_{XV-3}$, $D_{XV-4}$, $J_{XV-3}$, $J_{XV-4}$, and $K_{XV-2}$ are independently selected from the group consisting of C and S, no more than two of $R_{XV-9}$, $R_{XV-10}$, $R_{XV-11}$, $R_{XV-12}$, $R_{XV-13}$, $R_{XV-31}$, and $R_{XV-32}$ are simultaneously oxo, and that $R_{XV-9}$, $R_{XV-10}$, $R_{XV-11}$, $R_{XV-12}$, $R_{XV-13}$, $R_{XV-31}$, and $R_{XV-32}$ are each independently selected to maintain the tetravalent nature of carbon, trivalent nature of nitrogen, the divalent nature of sulfur, and the divalent nature of oxygen;

$R_{XV-4}$ and $R_{XV-5}$, $R_{XV-5}$ and $R_{XV-6}$, $R_{XV-6}$ and $R_{XV-7}$, $R_{XV-7}$ and $R_{XV-8}$, $R_{XV-9}$ and $R_{XV-10}$, $R_{XV-10}$ and $R_{XV-11}$, $R_{XV-11}$ and $R_{XV-31}$, $R_{XV-31}$ and $R_{XV-32}$, $R_{XV-32}$ and $R_{XV-12}$, and $R_{XV-12}$ and $R_{XV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XV-4}$ and $R_{XV-5}$, $R_{XV-5}$ and $R_{XV-6}$, $R_{XV-6}$ and $R_{XV-7}$, $R_{XV-7}$ and $R_{XV-8}$ is used at the same time and that no more than one of the group consisting of spacer pairs $R_{XV-9}$ and $R_{XV-10}$, $R_{XV-10}$ and $R_{XV-11}$, $R_{XV-11}$ and $R_{XV-31}$, $R_{XV-31}$ and $R_{XV-32}$, $R_{XV-32}$ and $R_{XV-12}$, and $R_{XV-12}$ and $R_{XV-13}$ are used at the same time;

$R_{XV-9}$ and $R_{XV-11}$, $R_{XV-9}$ and $R_{XV-12}$, $R_{XV-9}$ and $R_{XV-13}$ $R_{XV-9}$ and $R_{XV-31}$, $R_{XV-9}$ and $R_{XV-32}$, $R_{XV-10}$ and $R_{XV-12}$, $R_{XV-10}$ and $R_{XV-13}$, $R_{XV-10}$ and $R_{XV-31}$, $R_{XV-10}$ and $R_{XV-32}$, $R_{XV-11}$ and $R_{XV-12}$, $R_{XV-11}$ and $R_{XV-13}$, $R_{XV-11}$ and $R_{XV-32}$, $R_{XV-12}$ and $R_{XV-31}$, $R_{XV-13}$ and $R_{XV-31}$, and $R_{XV-13}$ and $R_{XV-32}$ are independently selected to form a spacer pair wherein said spacer-pair is taken together to form a linear spacer moiety selected from the group consisting of a covalent single bond and a moiety having from 1 through 3 contiguous atoms to form a ring selected from the group consisting of a cycloalkyl having from 3 through 8 contiguous members, a cycloalkenyl having from 5 through 8 contiguous members, a saturated heterocyclyl having from 5 through 8 contiguous members and a partially saturated heterocyclyl having from 5 through 8 contiguous members with the provisos that no more than one of said group of spacer pairs is used at the same time;

$R_{XV-37}$ and $R_{XV-38}$ are independently selected from the group consisting of hydrido, alkoxy, alkoxyalkyl, hydroxy, amino, thio, halo, haloalkyl, alkylamino, alkylthio, alkylthioalkyl, cyano, alkyl, alkenyl, haloalkoxy, and haloalkoxyalkyl.

Compounds of Formula XV are disclosed in WO 00/18723, the entire disclosure of which is incorporated by reference.

In a preferred embodiment, the CETP inhibitor is selected from the following compounds of Formula XV:

3-[[3-(4-chloro-3-ethylphenoxy)phenyl](cyclohexylmethyl)amino]-1,1,1-trifluoro-2-propanol;
3-[[3-(4-chloro-3-ethylphenoxy)phenyl](cyclopentylmethyl)amino]-1,1,1-trifluoro-2-propanol;
3-[[3-(4-chloro-3-ethylphenoxy)phenyl](cyclopropylmethyl)amino]-1,1,1-trifluoro-2-propanol;
3-[[3-(4-chloro-3-ethylphenoxy)phenyl][(3-trifluoromethyl)cyclohexyl-methyl]amino]-1,1,1-trifluoro-2-propanol;
3-[[3-(4-chloro-3-ethylphenoxy)phenyl][(3-pentafluoroethyl)cyclohexyl-methyl]amino]-1,1,1-trifluoro-2-propanol;
3-[[3-(4-chloro-3-ethylphenoxy)phenyl][(3-trifluoromethoxy)cyclohexyl-methyl]amino]-1,1,1-trifluoro-2-propanol;
3-[[3-(4-chloro-3-ethylphenoxy)phenyl][[3-(1,1,2,2-tetrafluoroethoxy)cyclo-hexylmethyl]amino]-1,1,1-trifluoro-2-propanol;
3-[[3-(3-trifluoromethoxyphenoxy)phenyl](cyclohexylmethyl)amino]-1,1,1-trifluoro-2-propanol;
3-[[3-(3-trifluoromethoxyphenoxy)phenyl](cyclopentylmethyl)amino]-1,1,1-trifluoro-2-propanol;
3-[[3-(3-trifluoromethoxyphenoxy)phenyl](cyclopropylmethyl)amino]-1,1,1-trifluoro-2-propanol;
3-[[3-(3-trifluoromethoxyphenoxy)phenyl][(3-trifluoromethyl)cyclohexyl-methyl]amino]-1,1,1-trifluoro-2-propanol;
3-[[3-(3-trifluoromethoxyphenoxy)phenyl]](3-pentafluoroethyl)cyclohexyl-methyl]amino]-1,1,1-trifluoro-2-propanol;
3-[[3-(3-trifluoromethoxyphenoxy)phenyl][(3-trifluoromethoxy)cyclohexyl-methyl]amino]-1,1,1-trifluoro-2-propanol;
3-[[3-(3-trifluoromethoxyphenoxy)phenyl][[3-(1,1,2,2-tetrafluoroethoxy)cyclohexyl-methyl]amino]-1,1,1-trifluoro-2-propanol;
3-[[3-(3-isopropylphenoxy)phenyl](cyclohexylmethyl)amino]-1,1,1-trifluoro-2-propanol;
3-[[3-(3-isopropylphenoxy)phenyl](cyclopentylmethyl)amino]-1,1,1-trifluoro-2-propanol;
3-[[3-(3-isopropylphenoxy)phenyl](cyclopropylmethyl)amino]-1,1,1-trifluoro-2-propanol;
3-[[3-(3-isopropylphenoxy)phenyl][(3-trifluoromethyl)cyclohexyl-methyl]amino]-1,1,1-trifluoro-2-propanol;
3-[[3-(3-isopropylphenoxy)phenyl][(3-pentafluoroethyl)cyclohexyl-methyl]amino]-1,1,1-trifluoro-2-propanol;
3-[[3-(3-isopropylphenoxy)phenyl][(3-trifluoromethoxy)cyclohexyl-methyl]amino]-1,1,1-trifluoro-2-propanol;
3-[[3-(3-isopropylphenoxy)phenyl][3-(1,1,2,2-tetrafluoroethoxy)cyclohexyl-methyl]amino]-1,1,1-trifluoro-2-propanol;
3-[[3-(2,3-dichlorophenoxy)phenyl](cyclohexylmethyl)amino]-1,1,1-trifluoro-2-propanol;
3-[[3-(2,3-dichlorophenoxy)phenyl](cyclopentylmethyl)amino]-1,1,1-trifluoro-2-propanol;
3-[[3-(2,3-dichlorophenoxy)phenyl](cyclopropylmethyl)amino]-1,1,1-trifluoro-2-propanol;
3-([3-(2,3-dichlorophenoxy)phenyl][(3-trifluoromethyl)cyclohexyl-methyl)amino]-1,1,1-trifluoro-2-propanol;
3-[[3-(2,3-dichlorophenoxy)phenyl][(3-pentafluoroethyl)cyclohexyl-methyl]amino]-1,1,1-trifluoro-2-propanol;
3-[[3-(2,3-dichlorophenoxy)phenyl][(3-trifluoromethoxy)cyclohexyl-methyl]amino]-1,1,1-trifluoro-2-propanol;
3-[[3-(2,3-dichlorophenoxy)phenyl][3-(1,1,2,2-tetrafluoroethoxy)cyclo-hexyl-methyl]amino]-1,1,1-trifluoro-2-propanol;
3-[[3-(4'-fluorophenoxy)phenyl](cyclohexylmethyl)amino]-1,1,1-trifluoro-2-propanol;
3-[[3-(4-fluorophenoxy)phenyl](cyclopentylmethyl)amino]-1,1,1-trifluoro-2-propanol;
3-[[3-(4-fluorophenoxy)phenyl](cyclopropylmethyl)amino]-1,1,1-trifluoro-2-propanol;
3-[[3-(4-fluorophenoxy)phenyl][(3-trifluoromethyl)cyclohexyl-methyl]amino]-1,1,1-trifluoro-2-propanol;
3-[[3-(4-fluorophenoxy)phenyl][(3-pentafluoroethyl)cyclohexyl-methyl]amino]-1,1,1-trifluoro-2-propanol;
3-[[3-(4-fluorophenoxy)phenyl][(3-trifluoromethoxy)cyclohexyl-methyl]amino]-1,1,1-trifluoro-2-propanol;
3-[[3-(4-fluorophenoxy)phenyl][[3-(1,1,2,2-tetrafluoroethoxy)cyclohexyl-methyl]amino]-1,1,1-trifluoro-2-propanol;
3-[[3-(3-trifluoromethoxybenzyloxy)phenyl](cyclohexylmethyl)amino]-1,1,1-trifluoro-2-propanol;
3-[[3-(3-trifluoromethoxybenzyloxy)phenyl](cyclopentylmethyl)amino]-1,1,1-trifluoro-2-propanol;
3-[[3-(3-trifluoromethoxybenzyloxy)phenyl](cyclopropylmethyl)amino]-1,1,1-trifluoro-2-propanol;
3-[[3-(3-trifluoromethoxybenzyloxy)phenyl][(3-trifluoromethyl)cyclohexyl-methyl]amino]-1,1,1-trifluoro-2-propanol;
3-[[3-(3-trifluoromethoxybenzyloxy)phenyl][(3-pentafluoroethyl)cyclohexyl-methyl]amino]-1,1,1-trifluoro-2-propanol;
3-[[3-(3-trifluoromethoxybenzyloxy)phenyl][(3-trifluoromethoxy)cyclohexyl-methyl]amino]-1,1,1-trifluoro-2-propanol;
3-[[3-(3-trifluoromethoxybenzyloxy)phenyl][3-(1,1,2,2-tetrafluoroethoxy)-cyclohexylmethyl]amino]-1,1,1-trifluoro-2-propanol;
3-[[3-(3-trifluoromethylbenzyloxy)phenyl](cyclohexylmethyl)amino]-1,1,1-trifluoro-2-propanol;
3-[[3-(3-trifluoromethylbenzyloxy)phenyl](cyclopentylmethyl)amino]-1,1,1-trifluoro-2-propanol;
3-[[3-(3-trifluoromethylbenzyloxy)phenyl](cyclopropylmethyl)amino]-1,1,1-trifluoro-2-propanol;

3-[[3-(3-trifluoromethylbenzyloxy)phenyl][(3-trifluoromethyl)cyclohexyl-methyl]amino]-1,1,1-trifluoro-2-propanol;

3-[[3-(3-trifluoromethylbenzyloxy)phenyl][(3-pentafluoroethyl)cyclohexyl-methyl]amino]-1,1,1-trifluoro-2-propanol;

3-[[3-(3-trifluoromethylbenzyloxy)phenyl][(3-trifluoromethoxy)cyclohexyl-methyl]amino]-1,1,1-trifluoro-2-propanol;

3-[[3-(3-trifluoromethylbenzyloxy)phenyl][3-(1,1,2,2-tetrafluoroethoxy)cyclohexyl-methyl]amino]-1,1,1-trifluoro-2-propanol;

3-[[[(3-trifluoromethyl)phenyl]methyl](cyclohexyl)amino]-1,1,1-trifluoro-2-propanol;

3-[[[(3-pentafluoroethyl)phenyl]methyl](cyclohexyl)amino]-1,1,1-trifluoro-2-propanol;

3-[[[(3-trifluoromethoxy)phenyl]methyl](cyclohexyl)amino]-1,1,1-trifluoro-2-propanol;

3-[[[3-(1,1,2,2-tetrafluoroethoxy)phenyl]methyl](cyclohexyl)amino]-1,1,1-trifluoro-2-propanol;

3-[[[(3-trifluoromethyl)phenyl]methyl](4-methylcyclohexyl)amino]-1,1,1-trifluoro-2-propanol;

3-[[[(3-pentafluoroethyl)phenyl]methyl](4-methylcyclohexyl)amino]-1,1,1-trifluoro-2-propanol;

3-[[[(3-trifluoromethoxy)phenyl]methyl](4-methylcyclohexyl)amino]-1,1,1-trifluoro-2-propanol;

3-[[[3-(1,1,2,2-tetrafluoroethoxy)phenyl]methyl](4-methylcyclohexyl)amino]-1,1,1-trifluoro-2-propanol;

3-[[[(3-trifluoromethyl)phenyl]methyl](3-trifluoromethylcyclohexyl)amino]-1,1,1-trifluoro-2-propanol;

3-[[[(3-pentafluoroethyl)phenyl]methyl](3-trifluoromethylcyclohexyl)amino]-1,1,1-trifluoro-2-propanol;

3-[[[(3-trifluoromethoxy)phenyl]methyl](3-trifluoromethylcyclohexyl)amino]-1,1,1-trifluoro-2-propanol;

3-[[[3-(1,1,2,2-tetrafluoroethoxy)phenyl]methyl](3-trifluoromethylcyclohexyl)amino]-1,1,1-trifluoro-2-propanol;

3-[[[(3-trifluoromethyl)phenyl]methyl][3-(4-chloro-3-ethylphenoxy)cyclo-hexyl]amino]-1,1,1-trifluoro-2-propanol;

3-[[[(3-pentafluoroethyl)phenyl]methyl][3-(4-chloro-3-ethylphenoxy)cyclo-hexyl]amino]-1,1,1-trifluoro-2-propanol;

3-[[[(3-trifluoromethoxy)phenyl]methyl][3-(4-chloro-3-ethylphenoxy)cyclo-hexyl]amino]-1,1,1-trifluoro-2-propanol;

3-[[[3-(1,1,2,2-tetrafluoroethoxy)phenyl]methyl][3-(4-chloro-3-ethylphenoxy)-cyclohexyl]amino]-1,1,1-trifluoro-2-propanol;

3-[[[(3-trifluoromethyl]phenyl]methyl](3-phenoxycyclohexyl)amino]-1,1,1-trifluoro-2-propanol;

3-[[[(3-pentafluoroethyl)phenyl]methyl](3-phenoxycyclohexyl)amino]-1,1,1-trifluoro-2-propanol;

3-[[[(3-trifluoromethoxy)phenyl]methyl](3-phenoxycyclohexyl)amino]-1,1,1-trifluoro-2-propanol;

3-[[[3-(1,1,2,2-tetrafluoroethoxy)phenyl]methyl](3-phenoxycyclohexyl)amino]-1,1,1-trifluoro-2-propanol;

3-[[[(3-trifluoromethyl)phenyl]methyl](3-isopropoxycyclohexyl)amino]-1,1,1-trifluoro-2-propanol;

3-[[[(3-pentafluoroethyl)phenyl]methyl](3-isopropoxycyclohexyl)amino]-1,1,1-trifluoro-2-propanol;

3-[[[(3-trifluoromethoxy)phenyl]methyl](3-isopropoxycyclohexyl)amino]-1,1,1-trifluoro-2-propanol;

3-[[[3-(1,1,2,2-tetrafluoroethoxy)phenyl]methyl](3-isopropoxycyclohexyl)-amino]-1,1,1-trifluoro-2-propanol;

3-[[[(3-trifluoromethyl)phenyl]methyl](3-cyclopentyloxycyclohexyl]amino]-1,1,1-trifluoro-2-propanol;

3-[[[(3-pentafluoroethyl)phenyl]methyl](3-cyclopentyloxycyclohexyl)amino]-1,1,1-trifluoro-2-propanol;

3-[[[(3-trifluoromethoxy)phenyl]methyl](3-cyclopentyloxycyclohexyl)amino]-1,1,1-trifluoro-2-propanol;

3-[[[3-(1,1,2,2-tetrafluoroethoxy)phenyl]methyl](3-cyclopentyloxycyclohexyl)-amino]-1,1,1-trifluoro-2-propanol;

3-[[[(2-trifluoromethyl)pyrid-6-yl]methyl](3-isopropoxycyclohexyl)amino]-1,1,1-trifluoro-2-propanol;

3-[[[(2-trifluoromethyl)pyrid-6-yl]methyl](3-cyclopentyloxycyclohexyl)-amino]-1,1,1-trifluoro-2-propanol;

3-[[[(2-trifluoromethyl)pyrid-6-yl]methyl](3-phenoxycyclohexyl)amino]-1,1,1-trifluoro-2-propanol;

3-[[[(2-trifluoromethyl)pyrid-6-yl]methyl](3-trifluoromethylcyclohexyl)amino]-1,1,1-trifluoro-2-propanol;

3-[[[(2-trifluoromethyl)pyrid-6-yl]methyl][3-(4-chloro-3-ethylphenoxy)cyclo-hexyl]amino]-1,1,1-trifluoro-2-propanol;

3-[[[(2-trifluoromethyl)pyrid-6-yl]methyl][3-(1,1,2,2-tetrafluoroethoxy)cyclo-hexyl]amino]-1,1,1-trifluoro-2-propanol;

3-[[[(2-trifluoromethyl)pyrid-6-yl]methyl](3-pentafluoroethylcyclohexyl)-amino]-1,1,1-trifluoro-2-propanol;

3-[[[(2-trifluoromethyl)pyrid-6-yl]methyl](3-trifluoromethoxycyclohexyl)-amino]-1,1,1-trifluoro-2-propanol;

3-[[[(3-trifluoromethyl)phenyl]methyl][3-(4-chloro-3-ethylphenoxy)propyl]-amino]-1,1,1-trifluoro-2-propanol;

3-[[[(3-pentafluoroethyl)phenyl]methyl][3-(4-chloro-3-ethylphenoxy)propyl]-amino]-1,1,1-trifluoro-2-propanol;

3-[[[(3-trifluoromethoxy)phenyl]methyl][3-(4-chloro-3-ethylphenoxy)propyl]-amino]-1,1,1-trifluoro-2-propanol;

3-[[[3-(1,1,2,2-tetrafluoroethoxy)phenyl]methyl][3-(4-chloro-3-ethylphenoxy)-propyl]amino]-1,1,1-trifluoro-2-propanol;

3-[[[(3-trifluoromethyl)phenyl]methyl][3-(4-chloro-3-ethylphenoxy)-2,2,-di-fluoropropyl]amino]-1,1,1-trifluoro-2-propanol;

3-[[[(3-pentafluoroethyl)phenyl]methyl][3-(4-chloro-3-ethylphenoxy)-2,2-di-fluoropropyl]amino]-1,1,1-trifluoro-2-propanol;

3-[[[(3-trifluoromethoxy)phenyl]methyl][3-(4-chloro-3-ethylphenoxy)-2,2,-di-fluoropropyl]amino]-1,1,1-trifluoro-2-propanol;

3-[[[3-(1,1,2,2-tetrafluoroethoxy)phenyl]methyl][3-(4-chloro-3-ethylphenoxy)-2,2,-difluoropropyl]amino]-1,1,1-trifluoro-2-propanol;

3-[[[(3-trifluoromethyl)phenyl]methyl][3-(isopropoxy)propyl]amino]-1,1,1-trifluoro-2-propanol;

3-[[[(3-pentafluoroethyl)phenyl]methyl][3-(isopropoxy)propyl]amino]-1,1,1-trifluoro-2-propanol;

3-[[[(3-trifluoromethoxy)phenyl]methyl](3-(isopropoxy)propyl]amino]1,1,1-trifluoro-2-propanol;

3-[[[3-(1,1,2,2-tetrafluoroethoxy)phenyl]methyl][3-(isopropoxy)propyl]amino]-1,1,1-trifluoro-2-propanol; and 3-[[[3-(1,1,2,2-tetrafluoroethoxy)phenyl]methyl][3-(phenoxy)propyl]amino]-1,1,1-trifluoro-2-propanol.

Another class of CETP inhibitors that finds utility with the present invention consists of (R)-chiral halogenated 1-substituted amino-(n+1)-alkanols having the Formula XVI Formula XVI

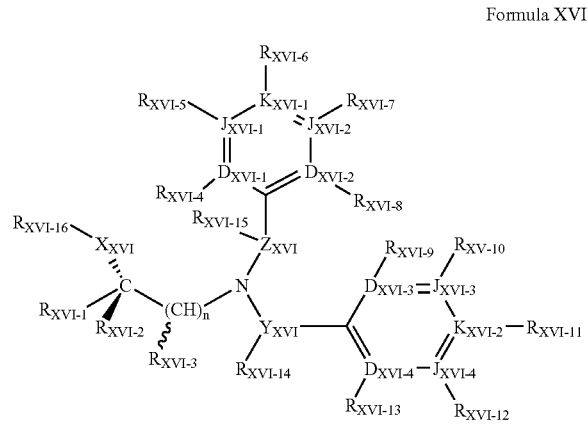

and pharmaceutically acceptable forms thereof, wherein:
$n_{XVI}$ is an integer selected from 1 through 4;
$X_{XVI}$ is oxy;
$R_{XVI-1}$ is selected from the group consisting of haloalkyl, haloalkenyl, haloalkoxymethyl, and haloalkenyloxymethyl with the proviso that $R_{XVI-1}$ has a
higher Cahn-Ingold-Prelog stereochemical system ranking than both $R_{XVI-2}$ and $(CHR_{XVI-3})_n$—$N(A_{XVI})Q_{XVI}$ wherein $A_{XVI}$ is Formula XVI-(II) and Q is Formula XVI-(III);

XVI-II

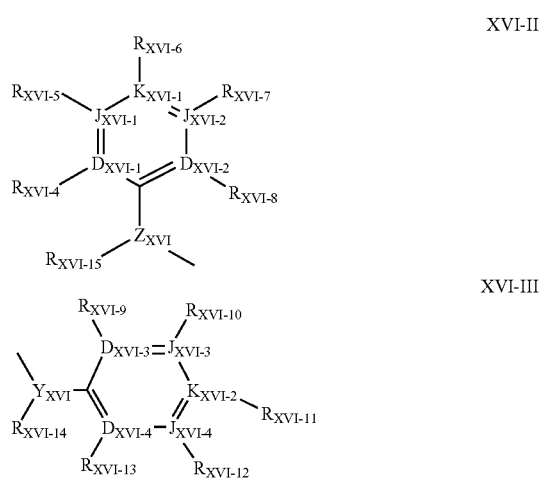

XVI-III $R_{XVI-16}$ is selected from the group consisting of hydrido, alkyl, acyl, aroyl, heteroaroyl, trialkylsilyl, and a spacer selected from the group consisting of a covalent single bond and a linear spacer moiety having a chain length of 1 to 4 atoms linked to the point of bonding of any aromatic substituent selected from the group consisting of $R_{XVI-4}$, $R_{XVI-8}$, $R_{XVI-9}$, and $R_{XVI-13}$ to form a heterocyclyl ring having from 5 through 10 contiguous members;

$D_{XVI-1}$, $D_{XVI-2}$, $J_{XVI-1}$, $J_{XVI-2}$ and $K_{XVI-1}$ are independently selected from the group consisting of C, N, O, S and covalent bond with the provisos that no more than one of $D_{XVI-1}$, $D_{XVI-2}$, $J_{XVI-1}$, $J_{XVI-2}$, and $K_{XVI-1}$ is a covalent bond, no more than one $D_{XVI-1}$, $D_{XVI-2}$, $J_{XVI-1}$, $J_{XVI-2}$ and $K_{XVI-1}$ is be O, no more than one of $D_{XVI-1}$, $D_{XVI-2}$, $J_{XVI-1}$, $J_{XVI-2}$ and $K_{XVI-1}$ is S, one of $D_{XVI-1}$, $D_{XVI-2}$, $J_{XVI-1}$, $J_{XVI-2}$ and $K_{XVI-1}$ must be a covalent bond when two of $D_{XVI-1}$, $D_{XVI-2}$, $J_{XVI-1}$, $J_{XVI-2}$ and $K_{XVI-1}$ are O and S, and no more than four of $D_{XVI-1}$, $D_{XVI-2}$, $J_{XVI-1}$, $J_{XVI-2}$ and $K_{XVI-1}$ is N;

$D_{XVI-3}$, $D_{XVI-4}$, $J_{XVI-3}$, $J_{XVI-4}$ and $K_{XVI-2}$ are independently selected from the group consisting of C, N, O, S and covalent bond with the provisos that no more than one is a covalent bond, no more than one of $D_{XVI-3}$, $D_{XVI-4}$, $J_{XVI-3}$, $J_{XVI-4}$ and $K_{XVI-2}$ is O, no more than one of $D_{XVI-3}$, $D_{XVI-4}$, $J_{XVI-3}$, $J_{XVI-4}$ and $K_{XVI-2}$ is S, no more than two of $D_{XVI-3}$, $D_{XVI-4}$, $J_{XVI-3}$, $J_{XVI-4}$ and $K_{XVI-2}$ is 0 and S, one of $D_{XVI-3}$, $D_{XVI-4}$, $J_{XVI-3}$, $J_{XVI-4}$ and $K_{XV-2}$ must be a covalent bond when two of $D_{XVI-3}$, $D_{XVI-4}$, $J_{XVI-3}$, $J_{XVI-4}$ and $K_{XVI-2}$ are O and S, and no more than four of $D_{XVI-3}$, $D_{XVI-4}$, $J_{XVI-3}$, $J_{XVI-4}$ and $K_{XVI-2}$ are N;

$R_{XVI-2}$ is selected from the group consisting of hydrido, aryl, aralkyl, alkyl, alkenyl, alkenyloxyalkyl, haloalkyl, haloalkenyl, halocycloalkyl, haloalkoxy, haloalkoxyalkyl, haloalkenyloxyalkyl, halocycloalkoxy, halocycloalkoxyalkyl, perhaloaryl, perhaloaralkyl, perhaloaryloxyalkyl, heteroaryl, dicyanoalkyl, and carboalkoxycyanoalkyl, with the proviso that $R_{XVI-2}$ has a lower Cahn-Ingold-Prelog system ranking than both $R_{XVI-1}$ and $(CHR_{XVI-3})_n$—$N(A_{XVI})Q_{XVI}$;

$R_{XVI-3}$ is selected from the group consisting of hydrido, hydroxy, cyano, aryl, aralkyl, acyl, alkoxy, alkyl, alkenyl, alkoxyalkyl, heteroaryl, alkenyloxyalkyl, haloalkyl, haloalkenyl, haloalkoxy, haloalkoxyalkyl, haloalkenyloxyalkyl, monocyanoalkyl, dicyanoalkyl, carboxamide, and carboxamidoalkyl, with the provisos that $(CHR_{XVI-3})_n$—$N(A_{XVI})Q_{XVI}$ has a lower Cahn-Ingold-Prelog stereochemical system ranking than $R_{XVI-1}$ and a higher Cahn-Ingold-Prelog stereochemical system ranking than $R_{XVI-2}$;

$Y_{XVI}$ is selected from a group consisting of a covalent single bond, $(C(R_{XVI-14})_2)_q$ wherein q is an integer selected from 1 and 2 and $(CH(R_{XVI-14}))_g$—$W_{XVI}$—$(CH(R_{XVI-14}))_p$ wherein g and p are integers independently selected from 0 and 1;

$R_{XVI-14}$ is selected from the group consisting of hydrido, hydroxy, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$Z_{XVI}$ is selected from a group consisting of a covalent single bond, $(C(R_{XVI-15})_2)_q$, wherein q is an integer selected from 1 and 2, and $(CH(R_{XVI-15}))_j$—$W_{XVI}$—$(CH(R_{XVI-15}))_k$ wherein j and k are integers independently selected from 0 and 1;

$W_{XVI}$ is selected from the group consisting of O, C(O), C(S), C(O)N($R_{XVI-14}$), C(S)N($R_{XVI-14}$), ($R_{XVI-14}$)NC(O), ($R_{XVI-14}$)NC(S), S, S(O), S(O)$_2$, S(O)$_2$N($R_{XVI-14}$), ($R_{XVI-14}$)NS(O)$_2$, and N($R_{XVI-14}$) with the proviso that $R_{XVI-14}$ is other than cyano;

$R_{XVI-15}$ is selected, from the group consisting of hydrido, cyano, hydroxyalkyl, acyl, alkoxy, alkyl, alkenyl, alkynyl, alkoxyalkyl, haloalkyl, haloalkenyl, haloalkoxy, haloalkoxyalkyl, haloalkenyloxyalkyl, monocarboalkoxyalkyl, monocyanoalkyl, dicyanoalkyl, carboalkoxycyanoalkyl, carboalkoxy, carboxamide, and carboxamidoalkyl;

$R_{XVI-4}$, $R_{XVI-5}$, $R_{XVI-6}$, $R_{XVI-7}$, $R_{XVI-8}$, $R_{XVI-9}$, $R_{XVI-10}$, $R_{XVI-11}$, $R_{XVI-12}$, and $R_{XVI-13}$ are independently selected from the group consisting of hydrido, carboxy, heteroaralkylthio, heteroaralkoxy, cycloalkylamino, acylalkyl, acylalkoxy, aroylalkoxy, heterocyclyloxy, aralkylaryl, aralkyl, aralkenyl, aralkynyl, heterocyclyl, perhaloaralkyl, aralkylsulfonyl, aralkylsulfonylalkyl, aralkylsulfinyl, aralkylsulfinylalkyl, halocycloalkyl, halocycloalkenyl, cycloalkylsulfinyl, cycloalkylsulfinylalkyl, cycloalkylsulfonyl, cycloalkylsulfonylalkyl, heteroarylamino, N-heteroarylamino-N-alkylamino, heteroaralkyl, heteroarylaminoalkyl, haloalkylthio, alkanoyloxy, alkoxy, alkoxyalkyl, haloalkoxylalkyl, heteroaralkoxy, cycloalkoxy, cycloalkenyloxy, cycloalkoxyalkyl, cycloalkylalkoxy, cycloalkenyloxyalkyl, cycloalkylenedioxy, halocycloalkoxy, halocycloalkoxyalkyl, halocycloalkenyloxy, halocycloalkenyloxyalkyl, hydroxy, amino, thio, nitro, lower alkylamino, alkylthio, alkylthioalkyl, arylamino, aralkylamino, arylthio, arylthioalkyl, heteroaralkoxyalkyl, alkylsulfinyl, alkylsulfinylalkyl, arylsulfinylalkyl, arylsulfonylalkyl, heteroarylsulfinylalkyl, heteroarylsulfonylalkyl, alkylsulfonyl, alkylsulfonylalkyl, haloalkylsulfinylalkyl, haloalkylsulfonylalkyl, alkylsulfonamido, alkylaminosulfonyl, amidosulfonyl, monoalkyl amidosulfonyl, dialkyl, amidosulfonyl, monoarylamidosulfonyl, arylsulfonamido, diarylamidosulfonyl, monoalkyl monoaryl amidosulfonyl, arylsulfinyl, arylsulfonyl, heteroarylthio, heteroarylsulfinyl, heteroarylsulfonyl, heterocyclylsulfonyl, heterocyclylthio, alkanoyl, alkenoyl, aroyl, heteroaroyl, aralkanoyl, heteroaralkanoyl, haloalkanoyl, alkyl, alkenyl, alkynyl, alkenyloxy, alkenyloxyalky, alkylenedioxy, haloalkylenedioxy, cycloalkyl, cycloalkylalkanoyl, cycloalkenyl, lower cycloalkylalkyl, lower cycloalkenylalkyl, halo, haloalkyl, haloalkenyl, haloalkoxy, hydroxyhaloalkyl, hydroxyaralkyl, hydroxyalkyl, hydroxyheteroaralkyl, haloalkoxyalkyl, aryl, heteroaralkynyl, aryloxy, aralkoxy, aryloxyalkyl, saturated heterocyclyl, partially saturated heterocyclyl, heteroaryl, heteroaryloxy, heteroaryloxyalkyl, arylalkenyl, heteroarylalkenyl, carboxyalkyl, carboalkoxy, alkoxycarboxamido, alkylamidocarbonylamido, arylamidocarbonylamido, carboalkoxyalkyl, carboalkoxyalkenyl, carboaralkoxy, carboxamido, carboxamidoalkyl, cyano, carbohaloalkoxy, phosphono, phosphonoalkyl, diaralkoxyphosphono, and diaralkoxyphosphonoalkyl with the proviso that $R_{XVI-4}$, $R_{XVI-5}$, $R_{XVI-6}$, $R_{XVI-7}$, $R_{XVI-8}$, $R_{XVI-9}$, $R_{XVI-10}$, $R_{XVI-11}$, $R_{XVI-12}$, and $R_{XVI-13}$ are each independently selected to maintain the tetravalent nature of carbon, trivalent nature of nitrogen, the divalent nature of sulfur, and the divalent nature of oxygen;

$R_{XVI-4}$ and $R_{XVI-5}$, $R_{XVI-5}$ and $R_{XVI-6}$, $R_{XVI-6}$ and $R_{XVI-7}$, $R_{XVI-7}$ and $R_{XVI-8}$, $R_{XVI-9}$ and $R_{XVI-10}$, $R_{XVI-10}$ and $R_{XVI-11}$, $R_{XVI-11}$ and $R_{XVI-12}$, and $R_{XVI-12}$ and $R_{XIV-13}$ are independently selected to form spacer pairs wherein a spacer pair is taken together to form a linear moiety having from 3 through 6 contiguous atoms connecting the points of bonding of said spacer pair members to form a ring selected from the group consisting of a cycloalkenyl ring having 5 through 8 contiguous members, a partially saturated heterocyclyl ring having 5 through 8 contiguous members, a heteroaryl ring having 5 through 6 contiguous members, and an aryl with the provisos that no more than one of the group consisting of spacer pairs $R_{XVI-4}$ and $R_{XVI-5}$, $R_{XVI-5}$ and $R_{XVI-6}$, $R_{XVI-6}$ and $R_{XVI-7}$, and $R_{XVI-7}$ and $R_{XVI-8}$ is used at the same time and that no more than one of the group consisting of spacer pairs $R_{XIV-9}$ and $R_{XVI-10}$, $R_{XVI-10}$ and $R_{XVI-11}$, $R_{XVI-11}$ and $R_{XVI-12}$, and $R_{XVI-12}$ and $R_{XVI-13}$ can be used at the same time;

$R_{XVI-4}$ and $R_{XVI-9}$, $R_{XVI-4}$ and $R_{XVI-13}$, $R_{XVI-8}$ and $R_{XVI-9}$, and $R_{XVI-8}$ and $R_{XVI-13}$ is independently selected to form a spacer pair wherein said spacer pair is taken together to form a linear moiety wherein said linear moiety forms a ring selected from the group consisting of a partially saturated heterocyclyl ring having from 5 through 8 contiguous members and a heteroaryl ring having from 5 through 6 contiguous members with the proviso that no more than one of the group consisting of spacer pairs $R_{XVI-4}$ and $R_{XVI-9}$, $R_{XV-4}$ and $R_{XVI-13}$, $R_{XVI-8}$ and $R_{XVI-9}$, and $R_{XVI-8}$ and $R_{XVI-13}$ is used at the same time.

Compounds of Formula XVI are disclosed in WO 00/18724, the entire disclosure of which is incorporated by reference.

In a preferred embodiment, the CETP inhibitor is selected from the following compounds of Formula XVI:

(2R)-3-[[3-(3-trifluoromethoxyphenoxy)phenyl][[3-(1,1,2,2-tetrafluoroethoxy)phenyl]methyl]amino]-1,1,1-trifluoro-2-propanol;

(2R)-3-[[3-(3-isopropylphenoxy)phenyl][[3-(1,1,2,2-tetrafluoroethoxy)phenyl]-methyl]amino]-1,1,1-trifluoro-2-propanol;

(2R)-3-[[3-(3-cyclopropylphenoxy)phenyl][[3-(1,1,2,2-tetrafluoroethoxy)phenyl]-methyl]amino]-1,1,1-trifluoro-2-propanol;

(2R)-3-[[3-(3-(2-furyl)phenoxy)phenyl][[3-(1,1,2,2-tetrafluoroethoxy)phenyl]-methyl]amino]-1,1,1-trifluoro-2-propanol;

(2R)-3-[[3-(2,3-dichlorophenoxy)phenyl][[3-(1,1,2,2-tetrafluoroethoxy)phenyl]-methyl]amino]-1,1,1-trifluoro-2-propanol;

(2R)-3-[[3-(4-fluorophenoxy)phenyl][[3-(1,1,2,2-tetrafluoroethoxy)phenyl]-methyl]amino]-1,1,1-trifluoro-2-propanol;

(2R)-3-[[3-(4-methylphenoxy)phenyl][[3-(1,1,2,2-tetrafluoroethoxy)phenyl]-methyl]amino]-1,1,1-trifluoro-2-propanol;

(2R)-3-[[3-(2-fluoro-5-bromophenoxy)phenyl][[3-(1,1,2,2-tetrafluoroethoxy)phenyl]-methyl]amino]-1,1,1-trifluoro-2-propanol;

(2R)-3-[[3-(4-chloro-3-ethylphenoxy)phenyl][[3-(1,1,2,2-tetrafluoroethoxy)phenyl]-methyl]amino]-1,1,1-trifluoro-2-propanol;

(2R)-3-[[3-[3-(1,1,2,2-tetrafluoroethoxy)phenoxy]phenyl][[3-(1,1,2,2-tetrafluoro-ethoxy)phenyl]methyl]amino]-1,1,1-trifluoro-2-propanol;

(2R)-3-[[3-[3-(pentafluoroethyl)phenoxy]phenyl][[3-(1,1,2,2-tetrafluoroethoxy)-phenyl]methyl]amino]-1,1,1-trifluoro-2-propanol;

(2R)-3-[[3-(3,5-dimethylphenoxy)phenyl][[3-(1,1,2,2-tetrafluoroethoxy)phenyl]-methyl]amino]-1,1,1-trifluoro-2-propanol;

(2R)-3-[[3-(3-ethylphenoxy)phenyl][[3-(1,1,2,2-tetrafluoroethoxy)phenyl]-methyl]amino]-1,1,1-trifluoro-2-propanol;

(2R)-3-[[3-(3-t-butylphenoxy)phenyl][[3-(1,1,2,2-tetrafluoroethoxy)phenyl]-methyl]amino]-1,1,1-trifluoro-2-propanol;

(2R)-3-[[3-(3-methylphenoxy)phenyl][[3-(1,1,2,2-tetrafluoroethoxy)phenyl]-methyl]amino]-1,1,1-trifluoro-2-propanol;

(2R)-3-[[3-(5,6,7,8-tetrahydro-2-naphthoxy)phenyl][[3-(1,1,2,2-tetrafluoro-ethoxy)phenyl]methyl]amino]-1,1,1-trifluoro-2-propanol;

(2R)-3-[[3-(phenoxy)phenyl][[3-(1,1,2,2-tetrafluoroethoxy)phenyl]methyl]amino]-1,1,1-trifluoro-2-propanol;

(2R)-3-[[3-[3-(N,N-dimethylamino)phenoxy]phenyl][[3-(1,1,2,2-tetrafluoro-ethoxy)phenyl]methyl]amino]-1,1,1-trifluoro-2-propanol;

(2R)-3-[[[3-(1,1,2,2,-tetrafluoroethoxy)phenyl]methyl][3-[[3-(trifluoromethoxy)-phenyl]methoxy]phenyl]amino]-1,1,1-trifluoro-2-propanol;

(2R)-3-[[[3-(1,1,2,2-tetrafluoroethoxy)phenyl]methyl][3-[[3-(trifluoro-methyl)phenyl]methoxy]phenyl]amino]-1,1,1-trifluoro-2-propanol;

(2R)-3-[[[3-(1,1,2,2-tetrafluoroethoxy)phenyl]methyl][3-[[3,5-dimethylphenyl]-methoxy]phenyl]amino]-1,1,1-trifluoro-2-propanol;

(2R)-3-[[[3-(1,1,2,2-tetrafluoroethoxy)phenyl]methyl][3-[[3-(trifluoromethylthio)-phenyl]methoxy]phenyl]amino]-1,1,1-trifluoro-2-propanol;

(2R)-3-[[[3-(1,1,2,2-tetrafluoroethoxy)phenyl]methyl][3-[[3,5-difluorophenyl]-methoxy]phenyl]amino]-1,1,1-trifluoro-2-propanol;

(2R)-3-[[[3-(1,1,2,2-tetrafluoroethoxy)phenyl]methyl][3-[cyclohexylmethoxy]-phenyl]amino]-1,1,1-trifluoro-2-propanol;

(2R)-3-[[3-(2-difluoromethoxy-4-pyridyloxy)phenyl][[3-(1,1,2,2-tetrafluoroethoxy)-phenyl]methyl]amino]-1,1,1-trifluoro-2-propanol;

(2R)-3-[[3-(2-trifluoromethyl-4-pyridyloxy)phenyl][[3-(1,1,2,2-tetrafluoroethoxy)-phenyl]methyl]amino]-1,1,1-trifluoro-2-propanol;

(2R)-3-[[3-(3-difluoromethoxyphenoxy)phenyl][[3-(1,1,2,2-tetrafluoroethoxy)-phenyl]methyl]amino]-1,1,1-trifluoro-2-propanol;

(2R)-3-[[[3-(3-trifluoromethylthio)phenoxy]phenyl][[3-(1,1,2,2-tetrafluoroethoxy)-phenyl]methyl]amino]-1,1,1-trifluoro-2-propanol;

(2R)-3-[[3-(4-chloro-3-trifluoromethylphenoxy)phenyl][[3-(1,1,2,2-tetrafluoroethoxy)-phenyl]methyl]amino]-1,1,1-trifluoro-2-propanol;

(2R)-3-[[3-(3-trifluoromethoxyphenoxy)phenyl][[3-(pentafluoroethyl)phenyl]-methyl]amino]-1,1,1-trifluoro-2-propanol;

(2R)-3-[[3-(3-isopropylphenoxy)phenyl][[3-(pentafluoroethyl)phenyl]methyl]-amino]-1,1,1-trifluoro-2-propanol;

(2R)-3-[[3-(3-cyclopropylphenoxy)phenyl][[3-(pentafluoroethyl)phenyl]methyl]-amino]-1,1,1-trifluoro-2-propanol;

(2R)-3-[[3-(3-(2-furyl)phenoxy)phenyl][[3-(pentafluoroethyl)phenyl]methyl]-amino]-1,1,1-trifluoro-2-propanol;

(2R)-3-[[3-(2,3-dichlorophenoxy)phenyl][[3-(pentafluoroethyl)phenyl]methyl]amino]-1,1,1-trifluoro-2-propanol;

(2R)-3-[[3-(4-fluorophenoxy)phenyl][[3-(pentafluoroethyl)phenyl]methyl]amino]-1,1,1-trifluoro-2-propanol;

(2R)-3-[[3-(4-methylphenoxy)phenyl][[3-(pentafluoroethyl)phenyl]methyl]amino]-1,1,1-trifluoro-2-propanol;

(2R)-3-[[3-(2-fluoro-5-bromophenoxy)phenyl][[3-(pentafluoroethyl)phenyl]methyl]-amino]-1,1,1-trifluoro-2-propanol;

(2R)-3-[[3-(4-chloro-3-ethylphenoxy)phenyl][[3-(pentafluoroethyl)phenyl]methyl]-amino]-1,1,1-trifluoro-2-propanol;

(2R)-3-[[3-[3-(1,1,2,2-tetrafluoroethoxy)phenoxy]phenyl][[3-(pentafluoroethyl)-phenyl]methyl]amino]-1,1,1-trifluoro-2-propanol;

(2R)-3-[[3-[3-(pentafluoroethyl)phenoxy]phenyl][[3-(pentafluoroethyl)phenyl]-methyl]amino]-1,1,1-trifluoro-2-propanol;

(2R)-3-[[3-(3,5-dimethylphenoxy)phenyl][[3-(pentafluoroethyl)phenyl]methyl]-amino]-1,1,1-trifluoro-2-propanol;

(2R)-3-[[3-(3-ethylphenoxy)phenyl][[3-(pentafluoroethyl)phenyl]methyl]amino]-1,1,1-trifluoro-2-propanol;

(2R)-3-[[3-(3-t-butylphenoxy)phenyl][[3-(pentafluoroethyl)phenyl]methyl]amino]-1,1,1-trifluoro-2-propanol;

(2R)-3-[[3-(3-methylphenoxy)phenyl][[3-(pentafluoroethyl)phenyl]methyl]amino]-1,1,1-trifluoro-2-propanol;

(2R)-3-[[3-(5,6,7,8-tetrahydro-2-naphthoxy)phenyl][[3-(pentafluoroethyl)phenyl]methyl]amino]-1,1,1-trifluoro-2-propanol;

(2R)-3-[[3-(phenoxy)phenyl][[3 (pentafluoroethyl)phenyl]methyl]amino]-1,1,1-trifluoro-2-propanol;

(2R)-3-[[3-[3-(N,N-dimethylamino)phenoxy]phenyl][[3-(pentafluoroethyl)phenyl]-methyl]amino]-1,1,1-trifluoro-2-propanol;

(2R)-3-[[[3-(pentafluoroethyl)phenyl]methyl][3-[[3-(trifluoromethoxy)phenyl]-methoxy]phenyl]amino]-1,1,1-trifluoro-2-propanol;

(2R)-3-[[[3-(pentafluoroethyl)phenyl]methyl][3-[[3-(trifluoromethyl)-phenyl]-methoxy]phenyl]amino]-1,1,1-trifluoro-2-propanol;

(2R)-3-[[[3-(pentafluoroethyl)phenyl]methyl][3-[[3,5-dimethylphenyl]methoxy]-phenyl]amino]-1,1,1-trifluoro-2-propanol;

(2R)-3-[[[3-(pentafluoroethyl)phenyl]methyl][3-[[3-(trifluoromethylthio)phenyl]-methoxy]phenyl]amino]-1,1,1-trifluoro-2-propanol;

(2R)-3-[[[3-(pentafluoroethyl)phenyl]methyl][3-[[3,5-difluorophenyl]methoxy]-phenyl]amino]-1,1,1-trifluoro-2-propanol;

(2R)-3-[[[3-(pentafluoroethyl)phenyl]methyl][3-[cyclohexylmethoxy]phenyl]-amino]-1,1,1-trifluoro-2-propanol;

(2R)-3-[[3-(2-difluoromethoxy-4-pyridyloxy)phenyl][[3-(pentafluoroethyl)phenyl]-methyl]amino]-1,1,1-trifluoro-2-propanol;

(2R)-3-[[3-(2-trifluoromethyl-4-pyridyloxy)phenyl][[3-(pentafluoroethyl)phenyl]-methyl]amino]-1,1,1-trifluoro-2-propanol;

(2R)-3-[[3-(3-difluoromethoxyphenoxy)phenyl][[3-(pentafluoroethyl)phenyl]-methyl]amino]-1,1,1-trifluoro-2-propanol;

(2R)-3-[[[3-(3-trifluoromethylthio)phenoxy]phenyl][[3-(pentafluoroethyl)phenyl]-methyl]amino]-1,1,1-trifluoro-2-propanol;

(2R)-3-[[3-(4-chloro-3-trifluoromethylphenoxy)phenyl][[3-(pentafluoroethyl)-phenyl]methyl]amino]-1,1,1-trifluoro-2-propanol;

(2R)-3-[[3-(3-trifluoromethoxyphenoxy)phenyl][[3-(heptafluoropropyl)phenyl]-methyl]amino]-1,1,1-trifluoro-2-propanol;

(2R)-3-[[3-(3-isopropylphenoxy)phenyl][[3-(heptafluoropropyl)phenyl]methyl]-amino]-1,1,1-trifluoro-2-propanol;

(2R)-3-[[3-(3-cyclopropylphenoxy)phenyl][[3-(heptafluoropropyl)phenyl]methyl]-amino]-1,1,1-trifluoro-2-propanol;

(2R)-3-[[3-(3-(2-furyl)phenoxy)phenyl][[3-(heptafluoropropyl)phenyl]methyl]-amino]-1,1,1-trifluoro-2-propanol;

(2R)-3-[[3-(2,3-dichlorophenoxy)phenyl][[3-(heptafluoropropyl)phenyl]methyl]-amino]-1,1,1-trifluoro-2-propanol;

(2R)-3-[[3-(4-fluorophenoxy)phenyl][[3-(heptafluoropropyl)phenyl]methyl]amino]-1,1,1-trifluoro-2-propanol;

(2R)-3-[[3-(4-methylphenoxy)phenyl][[3-(heptafluoropropyl)phenyl]methyl]amino]-1,1,1,-trifluoro-2-propanol;

(2R)-3-[[3-(2-fluoro-5-bromophenoxy)phenyl][[3-(heptafluoropropyl)phenyl]methyl]-amino]-1,1,1-trifluoro-2-propanol;

(2R)-3-[[3-(4-chloro-3-ethylphenoxy)phenyl][[3-(heptafluoropropyl)phenyl]methyl]-amino]-1,1,1-trifluoro-2-propanol;

(2R)-3-[[3-[3-(1,1,2,2-tetrafluoroethoxy)phenoxy]phenyl][[3-(heptafluoropropyl)-phenyl]methyl]amino]-1,1,1-trifluoro-2-propanol;

(2R)-3-[[3-[3-(pentafluoroethyl)phenoxy]phenyl][[3-(heptafluoropropyl)phenyl]-methyl]amino]-1,1,1-trifluoro-2-propanol;

(2R)-3-[[3-(3,5-dimethylphenoxy)phenyl][[3-(heptafluoropropyl)phenyl]methyl]-amino]-1,1,1-trifluoro-2-propanol;
(2R)-3-[[3-(3-ethylphenoxy)phenyl][[3-(heptafluoropropyl)phenyl]methyl]amino]-1,1,1-trifluoro-2-propanol;
(2R)-3-[[3-(3-t-butylphenoxy)phenyl][[3-(heptafluoropropyl)phenyl]methyl]amino]-1,1,1-trifluoro-2-propanol;
(2R)-3-[[3-(3-methylphenoxy)phenyl][[3-(heptafluoropropyl)phenyl]methyl]amino]-1,1,1-trifluoro-2-propanol;
(2R)-3-[[3-(5,6,7,8-tetrahydro-2-naphthoxy)phenyl][[3-(heptafluoropropyl)phenyl]-methyl]amino]-1,1,1-trifluoro-2-propanol;
(2R)-3-[[3-(phenoxy)phenyl][[3-(heptafluoropropyl)phenyl]methyl]amino]-1,1,1-trifluoro-2-propanol;
(2R)-3-[[3-[3-(N,N-dimethylamino)phenoxy]phenyl][[3-(heptafluoropropyl)phenyl]-methyl]amino]-1,1,1-trifluoro-2-propanol;
(2R)-3-[[[3-(heptafluoropropyl)phenyl]methyl][3-[[3-(trifluoromethoxy)phenyl]-methoxy]phenyl]amino]-1,1,1-trifluoro-2-propanol;
(2R)-3-[[[3-(heptafluoropropyl)phenyl]methyl][3-[[3-(trifluoromethyl)phenyl]-methoxy]phenyl]amino]-1,1,1-trifluoro-2-propanol;
(2R)-3-[[[3-(heptafluoropropyl)phenyl]methyl][3-[[3,5-dimethylphenyl]methoxy]-phenyl]amino]-1,1,1-trifluoro-2-propanol;
(2R)-3-[[[3-(heptafluoropropyl)phenyl]methyl][3-[[3-(trifluoromethylthio)phenyl]-methoxy]phenyl]amino]-1,1,1-trifluoro-2-propanol;
(2R)-3-[[[3-(heptafluoropropyl)phenyl]methyl][3-[[3,5-difluorophenyl]methoxy]-phenyl]amino]-1,1,1-trifluoro-2-propanol;
(2R)-3-[[[3-(heptafluoropropyl)phenyl]methyl][3-[cyclohexylmethoxy]phenyl]-amino]-1,1,1-trifluoro-2-propanol;
(2R)-3-[[3-(2-difluoromethoxy-4-pyridyloxy)phenyl][[3-(heptafluoropropyl)phenyl]-methyl]amino]-1,1,1-trifluoro-2-propanol;
(2R)-3-[[3-(2-trifluoromethyl-4-pyridyloxy)phenyl][[3-(heptafluoropropyl)phenyl]-methyl]amino]-1,1,1-trifluoro-2-propanol;
(2R)-3-[[3-(3-difluoromethoxyphenoxy)phenyl][[3-(heptafluoropropyl)phenyl]-methyl]amino]-1,1,1-trifluoro-2-propanol;
(2R)-3-[[[3-(3-trifluoromethylthio)phenoxy]phenyl][[3-(heptafluoropropyl)phenyl]-methyl]amino]-1,1,1-trifluoro-2-propanol;
(2R)-3-[[3-(4-chloro-3-trifluoromethylphenoxy)phenyl][[3-(heptafluoropropyl)-phenyl]methyl]amino]-1,1,1-trifluoro-2-propanol;
(2R)-3-[[3-(3-trifluoromethoxyphenoxy)phenyl][[2-fluoro-5-(trifluoromethyl)-phenyl]methyl]amino]-1,1,1-trifluoro-2-propanol;
(2R)-3-[[3-(3-isopropylphenoxy)phenyl][[2-fluoro-5-(trifluoromethyl)phenyl]-methyl]amino]-1,1,1-trifluoro-2-propanol;
(2R)-3-[[3-(3-cyclopropylphenoxy)phenyl][[2-fluoro-5-(trifluoromethyl)phenyl]-methyl]amino]-1,1,1-trifluoro-2-propanol;
(2R)-3-[[3-(3-(2-furyl)phenoxy)phenyl][[2-fluoro-5-(trifluoromethyl)phenyl]-methyl]amino]-1,1,1-trifluoro-2-propanol;
(2R)-3-[[3-(2,3-dichlorophenoxy)phenyl][[2-fluoro-5-(trifluoromethyl)phenyl]-methyl]amino]-1,1,1-trifluoro-2-propanol;
(2R)-3-[[3-(4-fluorophenoxy)phenyl][[2-fluoro-5-(trifluoromethyl)phenyl]-methyl]amino]-1,1,1-trifluoro-3-propanol;
(2R)-3-[[3-(4-methylphenoxy)phenyl][[2-fluoro-5-(trifluoromethyl)phenyl]-methyl]amino]-1,1,1-trifluoro-2-propanol;
(2R)-3-[[3-(2-fluoro-5-bromophenoxy)phenyl][[2-fluoro-5-(trifluoromethyl)-phenyl]methyl]amino]-1,1,1-trifluoro-2-propanol;
(2R)-3-[[3-(4-chloro-3-ethylphenoxy)phenyl][[2-fluoro-5-(trifluoromethyl)-phenyl]methyl]amino]-1,1,1-trifluoro-2-propanol;
(2R)-3-[[3-[3-(1,1,2,2-tetrafluoroethoxy)phenoxy]phenyl][[2-fluoro-5-(trifluoro-methyl)phenyl]methyl]amino]-1,1,1-trifluoro-2-propanol;
(2R)-3-[[3-(pentafluoroethyl)phenoxy)phenyl][[2-fluoro-5-(trifluoromethyl)-phenyl]methyl]amino]-1,1,1-trifluoro-2-propanol;
(2R)-3-[[3-(3,5-dimethylphenoxy)phenyl][[2-fluoro-5-(trifluoromethyl)phenyl]-methyl]amino]-1,1,1-trifluoro-2-propanol;
(2R)-3-[[3-(3-ethylphenoxy)phenyl][[2-fluoro-5-(trifluoromethyl)phenyl]methyl]-amino]-1,1,1-trifluoro-2-propanol;
(2R)-3-[[3-(3-t-butylphenoxy)phenyl][[2-fluoro-5-(trifluoromethyl)phenyl]methyl]-amino]-1,1,1-trifluoro-2-propanol;
(2R)-3-[[3-(3-methylphenoxy)phenyl][[2-fluoro-5-(trifluoromethyl)phenyl]methyl]-amino]-1,1,1-trifluoro-2-propanol;
(2R)-3-[[3-(5,6,7,8-tetrahydro-2-naphthoxy)phenyl][[2-fluoro-5-(trifluoromethyl)-phenyl]methyl]amino]-1,1,1-trifluoro-2-propanol;
(2R)-3-[[3-(phenoxy)phenyl][[2-fluoro-5-(trifluoromethyl)phenyl]methyl]amino]-1,1,1-trifluoro-2-propanol;
(2R)-3-[[3-[3-(N,N-dimethylamino,phenoxy]phenyl][[2-fluoro-5-(trifluoromethyl)-phenyl]methyl]amino]-1,1,1-trifluoro-2-propanol;
(2R)-3-[[[2-fluoro-5-(trifluoromethyl)phenyl]methyl][3-[[3-(trifluoromethoxy)-phenyl]methoxy]phenyl]amino]-1,1,1-trifluoro-3-propanol;
(2R)-3-[[[2-fluoro-5-(trifluoromethyl)phenyl]methyl][3-[[3-(trifluoromethyl)-phenyl]methoxy]phenyl]amino]-1,1,1-trifluoro-2-propanol;
(2R)-3-[[[2-fluoro-5-(trifluoromethyl)phenyl]methyl][3-[[3,5-dimethylphenyl]-methoxy]phenyl]amino]-1,1,1-trifluoro-2-propanol;
(2R)-3-[[[2-fluoro-5-(trifluoromethyl)phenyl]methyl][3-[[3-(trifluoromethylthio)-phenyl]methoxy]phenyl]amino]-1,1,1-trifluoro-2-propanol;
(2R)-3-[[[2-fluoro-5-(trifluoromethyl)phenyl]methyl][3-[[3,5-difluorophenyl]-methoxy]phenyl]amino]-1,1,1-trifluoro-2-propanol;
(2R)-3-[[[2-fluoro-5-(trifluoromethyl)phenyl]methyl][3-[cyclohexylmethoxy]-phenyl]amino]-1,1,1-trifluoro-2-propanol;
(2R)-3-[[3-(2-difluoromethoxy-4-pyridyloxy)phenyl][[2-fluoro-5-(trifluoromethyl)-phenyl]methyl]amino]-1,1,1-trifluoro-2-propanol;
(2R)-3-[[3-(2-trifluoromethyl-4-pyridyloxy)phenyl][[2-fluoro-5-(trifluoromethyl)-phenyl]methyl]amino]-1,1,1-trifluoro-2-propanol;
(2R)-3-[[3-(3-difluoromethoxyphenoxy)phenyl][[2-fluoro-5-(trifluoromethyl)-phenyl]methyl]amino]-1,1,1-trifluoro-2-propanol;

(2R)-3-[[[3-(3-trifluoromethylthio)phenoxy]phenyl][[2-fluoro-5-(trifluoromethyl)-phenyl]methyl]amino]-1,1,1-trifluoro-2-propanol;
(2R)-3-[[3-(4-chloro-3-trifluoromethylphenoxy)phenyl][[2-fluoro-5-(trifluoro-methyl)phenyl]methyl]amino]-1,1,1-trifluoro-2-propanol;
(2R)-3-[[3-(3-trifluoromethoxyphenoxy)phenyl][[2-fluoro-4-(trifluoromethyl)-phenyl]methyl]amino]-1,1,1-trifluoro-2-propanol;
(2R)-3-[[3-(3-isopropylphenoxy)phenyl][[2-fluoro-4-(trifluoromethyl)phenyl]-methyl]amino]-1,1,1-trifluoro-2-propanol;
(2R)-3-[[3-(3-cyclopropylphenoxy)phenyl][[2-fluoro-4-(trifluoromethyl)phenyl]-methyl]amino]-1,1,1-trifluoro-2-propanol;
(2R)-3-[[3-(3-(2-furyl)phenoxy)phenyl][[2-fluoro-4-(trifluoromethyl)phenyl]-methyl]amino]-1,1,1-trifluoro-2-propanol;
(2R)-3-[[3-(2,3-dichlorophenoxy)phenyl][[2-fluoro-4-(trifluoromethyl)phenyl]-methyl]amino]-1,1,1-trifluoro-2-propanol;
(2R)-3-[[3-(4-fluorophenoxy)phenyl][[2-fluoro-4-(trifluoromethyl)phenyl]-methyl]amino]-1,1,1-trifluoro-2-propanol;
(2R)-3-[[3-(4-methylphenoxy)phenyl][[2-fluoro-4-(trifluoromethyl)phenyl]-methyl]amino]-1,1,1-trifluoro-2-propanol;
(2R)-3-[[3-(2-fluoro-5-bromophenoxy)phenyl][[2-fluoro-4-(trifluoromethyl)-phenyl]methyl]amino]-1,1,1-trifluoro-2-propanol;
(2R)-3-[[3-(4-chloro-3-ethylphenoxy)phenyl][[2-fluoro-4-(trifluoromethyl)-phenyl]methyl]amino]-1,1,1-trifluoro-2-propanol;
(2R)-3-[[3-[3-(1,1,2,2-tetrafluoroethoxy)phenoxy]phenyl][[2-fluoro-4-(trifluoromethyl)phenyl]methyl]amino]-1,1,1-trifluoro-2-propanol;
(2R)-3-[[3-[3-(pentafluoroethyl)phenoxy]phenyl][[2-fluoro-4-(trifluoromethyl)-phenyl]methyl]amino]-1,1,1-trifluoro-2-propanol;
(2R)-3-[[3-(3,5-dimethylphenoxy)phenyl][[2-fluoro-4-(trifluoromethyl)phenyl]-methyl]amino]-1,1,1-trifluoro-2-propanol;
(2R)-3-[[3-(3-ethylphenoxy)phenyl][[2-fluoro-4-(trifluoromethyl)phenyl]methyl]-amino]-1,1,1-trifluoro-2-propanol;
(2R)-3-[[3-(3-t-butylphenoxy)phenyl][[2-fluoro-4-(trifluoromethyl)phenyl]methyl]-amino]-1,1,1-trifluoro-2-propanol;
(2R)-3-[[3-(3-methylphenoxy)phenyl][[2-fluoro-4-(trifluoromethyl)phenyl]methyl]-amino]-1,1,1-trifluoro-2-propanol;
(2R)-3-[[3-(5,6,7,8-tetrahydro-2-naphthoxy)phenyl][[2-fluoro-4-(trifluoromethyl)-phenyl]methyl]amino]-1,1,1-trifluoro-2-propanol;
(2R)-3-[[3-(phenoxy)phenyl][[2-fluoro-4-(trifluoromethyl)phenyl]methyl]amino]-1,1,1-trifluoro-2-propanol;
(2R)-3-[[3-[3-(N,N-dimethylamino)phenoxy]phenyl][[2-fluoro-4-(trifluoromethyl)-phenyl]methyl]amino]-1,1,1-trifluoro-2-propanol;
(2R)-3-[[[2-fluoro-4-(trifluoromethyl)phenyl]methyl][3-[[3-(trifluoromethoxy)phenyl]methoxy]phenyl]amino]-1,1,1-trifluoro-2-propanol;
(3R)-3-[[[2-fluoro-4-(trifluoromethyl)phenyl]methyl][3-[[3-(trifluoromethyl)phenyl]methoxy]phenyl]amino]-1,1,1-trifluoro-2-propanol;

(2R)-3-[[[2-fluoro-4-(trifluoromethyl)phenyl]methyl][3-[[3,5-dimethylphenyl]-methoxy]phenyl]amino]-1,1,1-trifluoro-2-propanol;
(2R)-3-[[[2-fluoro-4-(trifluoromethyl)phenyl]methyl][3-[[3-(trifluoromethylthio)-phenyl]methoxy]phenyl]amino]-1,1,1-trifluoro-2-propanol;
(2R)-3-[[[2-fluoro-4-(trifluoromethyl)phenyl]methyl][3-[[3,5-difluorophenyl]-methoxy]phenyl]amino]-1,1,1-trifluoro-2-propanol;
(2R)-3-[[[2-fluoro-4-(trifluoromethyl)phenyl]methyl][3-[cyclohexylmethoxy]-phenyl]amino]-1,1,1-trifluoro-2-propanol;
(2R)-3-[[3-(2-difluoromethoxy-4-pyridyloxy)phenyl][[2-fluoro-4-(trifluoromethyl)-phenyl]methyl]amino]-1,1,1-trifluoro-2-propanol;
(2R)-3-[[3-(2-trifluoromethyl-4-pyridyloxy)phenyl][[2-fluoro-4-(trifluoromethyl)-phenyl]methyl]amino]-1,1,1-trifluoro-2-propanol;
(2R)-3-[[3-(3-difluoromethoxyphenoxy)phenyl][[2-fluoro-4-(trifluoromethyl)-phenyl]methyl]amino]-1,1,1-trifluoro-2-propanol;
(2R)-3-[[[3-(3-trifluoromethylthio)phenoxy]phenyl][[2-fluoro-4-(trifluoromethyl)-phenyl]methyl]amino]-1,1,1-trifluoro-2-propanol; and
(2R)-3-[[3-(4-chloro-3-trifluoromethylphenoxy)phenyl][[2-fluoro-4-(trifluoromethyl)phenyl]methyl]amino]-1,1,1-trifluoro-2-propanol.

Another class of CETP inhibitors that finds utility with the present invention consists of quinolines of Formula XVII

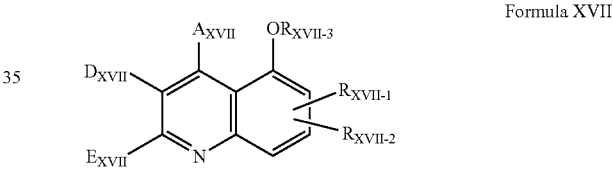

Formula XVII and pharmaceutically acceptable forms thereof, wherein:

$A_{XVII}$ denotes an aryl containing 6 to 10 carbon atoms, which is optionally substituted with up to five identical or different substituents in the form of a halogen, nitro, hydroxyl, trifluoromethyl, trifluoromethoxy or a straight-chain or branched alkyl, acyl, hydroxyalkyl or alkoxy containing up to 7 carbon atoms each, or in the form of a group according to the formula —$NR_{XVII-4}R_{XVII-5}$, wherein $R_{XVII-4}$ and $R_{XVII-5}$ are identical or different and denote a hydrogen, phenyl or a straight-chain or branched alkyl containing up to 6 carbon atoms, $D_{XVII}$ denotes an aryl containing 6 to 10 carbon atoms, which is optionally substituted with a phenyl, nitro, halogen, trifluoromethyl or trifluoromethoxy, or a radical according to the formula

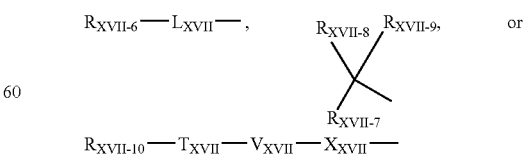

wherein $R_{XVII-6}$, $R_{XVII-7}$, $R_{XVII-10}$ denote, independently from one another, a cycloalkyl containing 3 to 6 carbon atoms, or an aryl containing 6 to 10 carbon atom or a 5- to 7-membered, optionally benzo-condensed, saturated or unsaturated, mono-, bi- or tricyclic heterocycle containing up to 4 heteroatoms from the series of S, N and/or O, wherein the rings are optionally substituted, in the case of the nitrogen-containing rings also via the N function, with up to five identical or different substituents in the form of a halogen, trifluoromethyl, nitro, hydroxyl, cyano, carboxyl, trifluoromethoxy, a straight-chain or branched acyl, alkyl, alkylthio, alkylalkoxy, alkoxy or alkoxycarbonyl containing up to 6 carbon atoms each, an aryl or trifluoromethyl-substituted aryl containing 6 to 10 carbon atoms each, or an optionally benzo-condensed; aromatic 5- to 7-membered heterocycle containing up to 3 heteoatoms from the series of S, N and/or O, and/or in the form of a group according to the formula —$OR_{XVII-11}$, —$SR_{XVII-12}$, —$SO_2R_{XVII-13}$, or —$NR_{XVII-14}R_{XVII-15}$;

$R_{XVI-11}$, $R_{XVII-12}$, and $R_{XVII-13}$ denote, independently from one another, an aryl containing 6 to 10 carbon atoms, which is in turn substituted with up to two identical or different substituents in the form of a phenyl, halogen or a straight-chain or branched alkyl containing up to 6 carbon atoms, $R_{XVII-14}$ and $R_{XVII-15}$ are identical or different and have the meaning of $R_{XVII-4}$ and $R_{XVII-5}$ given above, or $R_{XVII-6}$ and/or $R_{XVII-7}$ denote a radical according to the formula

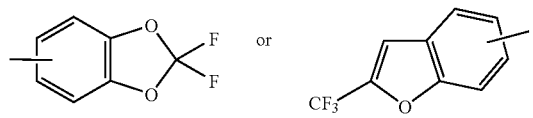

$R_{XVII-8}$ denotes a hydrogen or halogen, and $R_{XVII-9}$ denotes a hydrogen, halogen, azido, trifluoromethyl, hydroxyl, trifluoromethoxy, a straight-chain or branched alkoxy or alkyl containing up to 6 carbon atoms each, or a radical according to the formula $NR_{XVII-16}R_{XVII-17}$;

$R_{XVII-16}$ and $R_{XVII-17}$ are identical or different and have the meaning of $R_{XVII-4}$ and $R_{XVII-5}$ above; or $R_{XVII-8}$ and $R_{XVII-9}$ together form a radical according to the formula =O or =$NR_{XVII-18}$;

$R_{XVII-18}$ denotes a hydrogen or a straight-chain or branched alkyl, alkoxy or acyl containing up to 6 carbon atoms each;

$L_{XVII}$ denotes a straight-chain or branched alkylene or alkenylene chain containing up to 8 carbon atoms each, which are optionally substituted with up to two hydroxyl groups;

$T_{XVII}$ and $X_{XVII}$ are identical or different and denote a straight-chain or branched alkylene chain containing up to 8 carbon atoms; or $T_{XVII}$ and $X_{XVII}$ denotes a bond;

$V_{XVII}$ denotes an oxygen or sulfur atom or —$NR_{XVII-19}$;

$R_{XVII-19}$ denotes a hydrogen or a straight-chain or branched alkyl containing up to 6 carbon atoms or a phenyl;

$E_{XVII}$ denotes a cycloalkyl containing 3 to 8 carbon atoms, or a straight-chain or branched alkyl containing up to 8 carbon atoms, which is optionally substituted with a cycloalkyl containing 3 to 8 carbon atoms or a hydroxyl, or a phenyl, which is optionally substituted with a halogen or trifluoromethyl;

$R_{XVII-1}$ and $R_{XVII-2}$ are identical or different and denote a cycloalkyl containing 3 to 8 carbon atoms, hydrogen, nitro, halogen, trifluoromethyl, trifluoromethoxy, carboxy, hydroxy, cyano, a straight-chain or branched acyl, alkoxycarbonyl or alkoxy with up to 6 carbon atoms, or $NR_{XVII-20}R_{XVII-21}$;

$R_{XVII-20}$ and $R_{XVII-21}$ are identical or different and denote hydrogen, phenyl, or a straight-chain or branched alkyl with up to 6 carbon atoms; and or $R_{XVII-1}$ and/or $R_{XVII-2}$ are straight-chain or branched alkyl with up to 6 carbon atoms, optionally substituted with halogen, trifluoromethoxy, hydroxy, or a straight-chain or branched alkoxy with up to 4 carbon atoms, aryl containing 6-10 carbon atoms optionally substituted with up to five of the same or different substituents selected from halogen, cyano, hydroxy, trifluoromethyl, trifluoromethoxy, nitro, straight-chain or branched alkyl, acyl, hydroxyalkyl, alkoxy with up to 7 carbon atoms and $NR_{XVII-22}R_{XVII-23}$;

$R_{XVII-22}$ and $R_{XVII-23}$ are identical or different and denote hydrogen, phenyl or a straight-chain or branched alkyl up to 6 carbon atoms; and/or $R_{XVII-1}$ and $R_{XVII-2}$ taken together form a straight-chain or branched alkene or alkane with up to 6 carbon atoms optionally substituted with halogen, trifluoromethyl, hydroxy or straight-Chain or branched alkoxy with up to 5 carbon atoms;

$R_{XVII-3}$ denotes hydrogen, a straight-chain or branched acyl with up to 20 carbon atoms, a benzoyl optionally substituted with halogen, trifluoromethyl, nitro or trifluoromethoxy, a straight-chained or branched fluoroacyl with up to 8 carbon atoms and 7 fluoro atoms, a cycloalkyl with 3 to 7 carbon atoms, a straight chained or branched alkyl with up to 8 carbon atoms optionally substituted with hydroxyl, a straight-chained or branched alkoxy with up to 6 carbon atoms optionally substituted with phenyl which may in turn be substituted with halogen, nitro, trifluoromethyl, trifluoromethoxy, or phenyl or a tetrazol substituted phenyl, and/or an alkyl that is optionally substituted with a group according to the formula —$OR_{XVII-24}$;

$R_{XVII-24}$ is a straight-chained or branched acyl with up to 4 carbon atoms or benzyl.

Compounds of Formula XVII are disclosed in WO 98/39299, the entire disclosure is incorporated by reference.

Another class of CETP inhibitors that finds utility with the present invention consists of 4-Phenyltetrahydroquinolines of Formula XVIII

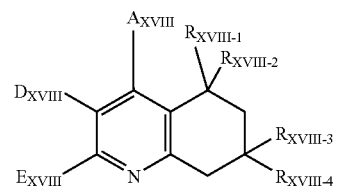

Formula XVIII

N oxides thereof, and pharmaceutically acceptable forms thereof, wherein:

$A_{XVIII}$ denotes a phenyl optionally substituted with up to two identical or different substituents in the form of halogen, trifluoromethyl or a straight-chain or branched alkyl or alkoxy containing up to three carbon atoms;

$D_{XVIII}$ denotes the formula

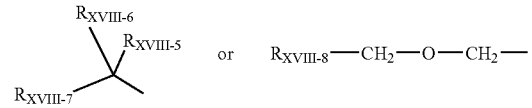

$R_{XVIII-5}$ and $R_{XVIII-6}$ are taken together to form =O; or $R_{XVIII-5}$ denotes hydrogen and $R_{XVIII-6}$ denotes halogen or hydrogen; or $R_{XVIII-5}$ and $R_{XVIII-6}$ denote hydrogen;

$R_{XVIII-7'}$ and $R_{XVIII-8}$ are identical or different and denote phenyl, naphthyl, benzothiazolyl, quinolinyl, pyrimidyl or pyridyl with up to four identical or different substituents in the form of halogen, trifluoromethyl, nitro, cyano, trifluoromethoxy, —$SO_2$, —$CH_3$ or $NR_{XVIII-9}R_{XVIII-10}$;

$R_{XVIII-9}$ and $R_{XVIII-10}$ are identical or different and denote hydrogen or a straight-chained or branched alkyl of up to three carbon atoms;

$E_{XVIII}$ denotes a cycloalkyl of from three to six carbon atoms or a straight-chained or branched alkyl of up to eight carbon atoms;

$R_{XVIII-1}$ denotes hydroxy;

$R_{XVIII-2}$ denotes hydrogen or methyl;

$R_{XVIII-3}$ and $R_{XVIII-4}$ are identical or different and denote straight-chained or branched alkyl of up to three carbon atoms; or $R_{XVIII-3}$ and $R_{XVIII-4}$ taken together form an alkenylene made up of between two and four carbon atoms.

Compounds of Formula XVIII are disclosed in WO 99/15504, the entire disclosure of which is incorporated by reference.

Concentration-Enhancing Polymers

Concentration-enhancing polymers suitable for use in the compositions of the present invention should be inert, in the sense that they do not chemically react with the CETP inhibitor in an adverse manner, are pharmaceutically acceptable, and have at least some solubility in aqueous solution at physiologically relevant pHs (e.g. 1-8). The polymer can be neutral or ionizable, and should have an aqueous-solubility of at least 0.1 mg/mL over at least a portion of the pH range of 1-8.

The polymer is a "concentration-enhancing polymer," meaning that it meets at least one, and more preferably both, of the following conditions. The first condition is that the concentration-enhancing polymer increases the MDC of the CETP inhibitor in the environment of use relative to a control composition consisting of an equivalent amount of the CETP inhibitor but no polymer. That is, once the composition is introduced into an environment of use, the polymer increases the aqueous concentration of CETP inhibitor relative to the control composition. Preferably, the polymer increases the MDC of the CETP inhibitor in aqueous solution by at least 10-fold relative to a control composition, preferably by at least 50-fold, and more preferably by at least 200-fold. Even more preferably, the polymer increases the MDC of the CETP inhibitor in aqueous solution by at least 500-fold, and most preferably by at least 1000-fold. Such large enhancements may be necessary in order for some extremely water insoluble CETP inhibitors to achieve effective blood levels through oral dosing. The second condition is that the concentration-enhancing polymer increases the AUC of the CETP inhibitor in the environment of use relative to a control composition consisting of a CETP inhibitor but no polymer as described above. That is, in the environment of use, the composition comprising the CETP inhibitor and the concentration-enhancing polymer provides an area under the concentration versus time curve (AUC) for any period of 90 minutes between the time of introduction into the use environment and about 270 minutes following introduction to the use environment that is at least 5-fold that of a control composition comprising an equivalent quantity of CETP inhibitor but no polymer. Preferably, the AUC provided by the composition is at least 25-fold, more preferably at least 100-fold, and even more preferably at least 250-fold that of the control composition.

Concentration-enhancing polymers suitable for use with the present invention may be cellulosic or non-cellulosic. The polymers may be neutral or ionizable in aqueous solution. Of these, ionizable and cellulosic polymers are preferred, with ionizable cellulosic polymers being more preferred.

A preferred class of polymers comprises polymers that are "amphiphilic" in nature, meaning that the polymer has hydrophobic and hydrophilic portions. The hydrophobic portion may comprise groups such as aliphatic or aromatic hydrocarbon groups. The hydrophilic portion may comprise either ionizable or non-ionizable groups that are capable of hydrogen bonding such as hydroxyls, carboxylic acids, esters, amines or amides.

Amphiphilic and/or ionizable polymers are preferred because it is believed that such polymers may tend to have relatively strong interactions with the CETP inhibitor and may promote the formation of the various types of polymer/drug assemblies in the use environment as described previously. In addition, the repulsion of the like charges of the ionized groups of such polymers may serve to limit the size of the polymer/drug assemblies to the nanometer or submicron scale. For example, while not wishing to be bound by a particular theory, such polymer/drug assemblies may comprise hydrophobic CETP inhibitor clusters surrounded by the polymer with the polymer's hydrophobic regions turned inward towards the CETP inhibitor and the hydrophilic regions of the polymer turned outward toward the aqueous environment. Alternatively, depending on the specific chemical nature of the CETP inhibitor, the ionized functional groups of the polymer may associate, for example, via ion pairing or hydrogen bonds, with ionic or polar groups of the CETP inhibitor. In the case of ionizable polymers, the hydrophilic regions of the polymer would include the ionized functional groups. Such polymer/drug assemblies in solution may well resemble charged polymeric micellar-like structures. In any case, regardless of the mechanism of action, the inventors have observed that such amphiphilic polymers, particularly ionizable cellulosic polymers, have been shown to improve the MDC and/or AUC of CETP inhibitor in aqueous solution relative to control compositions free from such polymers.

Surprisingly, such amphiphilic polymers can greatly enhance the maximum concentration of CETP inhibitor obtained when CETP inhibitor is dosed to a use environment. In addition, such amphiphilic polymers interact with the CETP inhibitor to prevent the precipitation or crystallization of the CETP inhibitor from solution despite its concentration being substantially above its equilibrium concentration. In particular, when the preferred compositions are solid amorphous dispersions of the CETP inhibitor and the concentration-enhancing polymer, the compositions provide a greatly enhanced drug concentration, particularly when the dispersions are substantially homogeneous. The maximum drug concentration may be 10-fold and often more than 50-fold the equilibrium concentration of the crystalline CETP inhibitor. Indeed, for some extremely water insoluble CETP inhibitors, the maximum drug concentration may be 200-fold to 500-fold and often more than 1000-fold the equilibrium concentration of the crystalline CETP inhibitor. Such enhanced CETP inhibitor concentrations in turn lead to substantially enhanced relative bioavailability for the CETP inhibitor.

One class of polymers suitable for use with the present invention comprises neutral non-cellulosic polymers. Exemplary polymers include: vinyl polymers and copolymers having substituents of hydroxyl, alkylacyloxy, or cyclicamido;

polyvinyl alcohols that have at least a portion of their repeat units in the unhydrolyzed (vinyl acetate) form; polyvinyl alcohol polyvinyl acetate copolymers; polyvinyl pyrrolidone; polyoxyethylene-polyoxypropylene copolymers, also known as poloxamers; and polyethylene polyvinyl alcohol copolymers.

Another class of polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGITS® manufactured by Rohm Tech Inc., of Malden, Mass.; amine-functionalized polyacrylates and polymethacrylates; proteins; and carboxylic acid functionalized starches such as starch glycolate.

Non-cellulosic polymers that are amphiphilic are copolymers of a relatively hydrophilic and a relatively hydrophobic monomer. Examples include acrylate and methacrylate copolymers, and polyoxyethylene-polyoxypropylene copolymers. Exemplary commercial grades of such copolymers include the EUDRAGITS, which are copolymers of methacrylates and acrylates, and the PLURONICS supplied by BASF, which are polyoxyethylene-polyoxypropylene copolymers.

A preferred class of polymers comprises ionizable and neutral cellulosic polymers with at least one ester- and/or ether-linked substituent in which the polymer has a degree of substitution of at least 0.1 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

It should also be noted that a polymer name such as "cellulose acetate phthalate" (CAP) refers to any of the family of cellulosic polymers that have acetate and phthalate groups attached via ester linkages to a significant fraction of the cellulosic polymer's hydroxyl groups. Generally, the degree of substitution of each substituent group can range from 0.1 to 2.9 as long as the other criteria of the polymer are met. "Degree of substitution" refers to the average number of the three hydroxyls per saccharide repeat unit on the cellulose chain that have been substituted. For example, if all of the hydroxyls on the cellulose chain have been phthalate substituted, the phthalate degree of substitution is 3. Also included within each polymer family type are cellulosic polymers that have additional substituents added in relatively small amounts that do not substantially alter the performance of the polymer.

Amphiphilic cellulosics comprise polymers in which the parent cellulosic polymer has been substituted at any or all of the 3 hydroxyl groups present on each saccharide repeat unit with at least one relatively hydrophobic substituent. Hydrophobic substituents may be essentially any substituent that, if substituted to a high enough level or degree of substitution, can render the cellulosic polymer essentially aqueous insoluble. Examples of hydrophobic substitutents include ether-linked alkyl groups such as methyl, ethyl, propyl, butyl, etc.; or ester-linked alkyl groups such as acetate, propionate, butyrate, etc.; and ether- and/or ester-linked aryl groups such as phenyl, benzoate, or phenylate. Hydrophilic regions of the polymer can be either those portions that are relatively unsubstituted, since the unsubstituted hydroxyls are themselves relatively hydrophilic, or those regions that are substituted with hydrophilic substituents. Hydrophilic substituents include ether- or ester-linked nonionizable groups such as the hydroxy alkyl substituents hydroxyethyl, hydroxypropyl, and the alkyl ether groups such as ethoxyethoxy or methoxyethoxy. Particularly preferred hydrophilic substituents are those that are ether- or ester-linked ionizable groups such as carboxylic acids, thiocarboxylic acids, substituted phenoxy groups, amines, phosphates or sulfonates.

One class of cellulosic polymers comprises neutral polymers, meaning that the polymers are substantially non-ionizable in aqueous solution. Such polymers contain non-ionizable substituents, which may be either ether-linked or ester-linked. Exemplary ether-linked non-ionizable substituents include: alkyl groups, such as methyl, ethyl, propyl, butyl, etc.; hydroxy alkyl groups such as hydroxymethyl, hydroxyethyl, hydroxypropyl, etc.; and aryl groups such as phenyl. Exemplary ester-linked non-ionizable substituents include: alkyl groups, such as acetate, propionate, butyrate, etc.; and aryl groups such as phenylate. However, when aryl groups are included, the polymer may need to include a sufficient amount of a hydrophilic substituent so that the polymer has at least some water solubility at any physiologically relevant pH of from 1 to 8.

Exemplary non-ionizable polymers that may be used as the polymer include: hydroxypropyl methyl cellulose acetate, hydroxypropyl methyl cellulose, hydroxypropyl cellulose, methyl cellulose, hydroxyethyl methyl cellulose, hydroxyethyl cellulose acetate, and hydroxyethyl ethyl cellulose.

A preferred set of neutral cellulosic polymers are those that are amphiphilic. Exemplary polymers include hydroxypropyl methyl cellulose and hydroxypropyl cellulose acetate, where cellulosic repeat units that have relatively high numbers of methyl or acetate substituents relative to the unsubstituted hydroxyl or hydroxypropyl substituents constitute hydrophobic regions relative to other repeat units on the polymer.

A preferred class of cellulosic polymers comprises polymers that are at least partially ionizable at physiologically relevant pH and include at least one ionizable substituent, which may be either ether-linked or ester-linked. Exemplary ether-linked ionizable substituents include: carboxylic acids, such as acetic acid, propionic acid, benzoic acid, salicylic acid, alkoxybenzoic acids such as ethoxybenzoic acid or propoxybenzoic acid, the various isomers of alkoxyphthalic acid such as ethoxyphthalic acid and ethoxyisophthalic acid, the various isomers of alkoxynicotinic acid such as ethoxynicotinic acid, and the various isomers of picolinic acid such as ethoxypicolinic acid, etc.; thiocarboxylic acids, such as thioacetic acid; substituted phenoxy groups, such as hydroxyphenoxy, etc.; amines, such as aminoethoxy, diethylaminoethoxy, trimethylaminoethoxy, etc.; phosphates, such as phosphate ethoxy; and sulfonates, such as sulphonate ethoxy. Exemplary ester linked ionizable substituents include: carboxylic acids, such as succinate, citrate, phthalate, terephthalate, isophthalate, trimellitate, and the various isomers of pyridinedicarboxylic acid, etc.; thiocarboxylic acids, such as thiosuccinate; substituted phenoxy groups, such as amino salicylic acid; amines, such as natural or synthetic amino acids, such as alanine or phenylalanine; phosphates, such as acetyl phosphate; and sulfonates, such as acetyl sulfonate. For aromatic-substituted polymers to also have the requisite aqueous solubility, it is also desirable that sufficient hydrophilic groups such as hydroxypropyl or carboxylic acid functional groups be attached to the polymer to render the polymer aqueous soluble at least at pH values where any ionizable groups are ionized. In some cases, the aromatic group may itself be ionizable, such as phthalate or trimellitate substituents.

Exemplary cellulosic polymers that are at least partially ionized at physiologically relevant pHs include: hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, carboxymethylethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Exemplary ionizable cellulosic polymers that meet the definition of amphiphilic, having hydrophilic and hydrophobic regions, include polymers such as cellulose acetate phthalate and cellulose acetate trimellitate where the cellulosic repeat units that have one or more acetate substituents are hydrophobic relative to those that have no acetate substituents or have one or more ionized phthalate or trimellitate substituents.

A particularly desirable subset of cellulosic ionizable polymers are those that possess both a carboxylic acid functional aromatic substituent and an alkylate substituent and thus are amphiphilic. Exemplary polymers include cellulose acetate phthalate, methyl cellulose acetate phthalate, ethyl cellulose acetate phthalate, hydroxypropyl cellulose acetate phthalate, hydroxylpropyl methyl cellulose phthalate, hydroxypropyl methyl cellulose acetate phthalate, hydroxypropyl cellulose acetate phthalate succinate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

Another particularly desirable subset of cellulosic ionizable polymers are those that are amphiphilic and possess a non-aromatic carboxylate substituent. Exemplary polymers include hydroxypropyl methyl cellulose acetate succinate, hydroxypropyl methyl cellulose succinate, hydroxypropyl cellulose acetate succinate, hydroxyethyl methyl cellulose acetate succinate, hydroxyethyl methyl cellulose succinate, hydroxyethyl cellulose acetate succinate, and carboxymethyl ethyl cellulose.

While, as listed above, a wide range of polymers may be used to form dispersions of CETP inhibitors, the inventors have found that relatively hydrophobic polymers have shown the best performance as demonstrated by high MDC and AUC values. In particular, cellulosic polymers that are aqueous insoluble in their nonionized state but are at least sparingly aqueous soluble in their ionized state perform particularly well. A particular subclass of such polymers are the so-called "enteric" polymers which include, for example, certain grades of hydroxypropyl methyl cellulose phthalate and cellulose acetate trimellitate. Dispersions formed from such polymers generally show very large enhancements, on the order of 50-fold to over 1000-fold, in the maximum drug concentration achieved in dissolution tests relative to that for a crystalline drug control. In addition, non-enteric grades of such polymers as well as closely related cellulosic polymers are expected to perform well due to the similarities in physical properties within the CETP inhibitor class.

Thus, especially preferred polymers are hydroxypropyl methyl cellulose acetate succinate (HPMCAS), hydroxypropyl methyl cellulose phthalate (HPMCP), cellulose acetate phthalate (CAP), cellulose acetate trimellitate (CAT), methyl cellulose acetate phthalate, hydroxypropyl cellulose acetate phthalate, cellulose acetate terephthalate cellulose acetate isophthalate, and carboxymethyl ethyl cellulose. The most preferred ionizable cellulosic polymers are hydroxypropyl methyl cellulose acetate succinate, hydroxypropyl methyl cellulose phthalate, cellulose acetate phthalate, cellulose acetate trimellitate, and carboxymethyl ethyl cellulose.

One particularly effective polymer for forming dispersions of the present invention is carboxymethyl ethyl cellulose (CMEC). Dispersions made from CETP inhibitors and CMEC typically have high glass-transition temperatures at high relative humidities, due to the high glass-transition temperature of CMEC. As discussed below, such high $T_g$s result in solid amorphous dispersions with excellent physical stability. In addition, because all of the substituents on CMEC are attached to the cellulose backbone through ether linkages, CMEC has excellent chemical stability. Additionally, commercial grades of CMEC, such as that provided by Freund Industrial Company, Limited (Tokyo, Japan), are amphiphilic, leading to high degrees of concentration enhancement. Finally, hydrophobic CETP inhibitors often have a high solubility in CMEC allowing for formation of physically stable dispersions with high drug loadings.

Another preferred class of polymers consists of neutralized acidic polymers. By "neutralized acidic polymer" is meant any acidic polymer for which a significant fraction of the "acidic moieties" or "acidic substituents" have been "neutralized"; that is, exist in their deprotonated form. By "acidic polymer" is meant any polymer that possesses a significant number of acidic moieties. In general, a significant number of acidic moieties would be greater than or equal to about 0.1 milliequivalents of acidic moieties per gram of polymer. "Acidic moieties" include any functional groups that are sufficiently acidic that, in contact with or dissolved in water, can at least partially donate a hydrogen cation to water and thus increase the hydrogen-ion concentration. This definition includes any functional group or "substituent," as it is termed when the functional group is covalently attached to a polymer, that has a $pK_a$ of less than about 10. Exemplary classes of functional groups that are included in the above description include carboxylic acids, thiocarboxylic acids, phosphates, phenolic groups, and sulfonates. Such functional groups may make up the primary structure of the polymer such as for polyacrylic acid, but more generally are covalently attached to the backbone of the parent polymer and thus are termed "substituents."

The "degree of neutralization," $\alpha$, of a polymer substituted with monoprotic acids (such as carboxylic acids) is defined as the fraction of the acidic moieties on the polymer that have been neutralized; that is, deprotonated by a base. Typically, for an acidic polymer to be considered a "neutralized acidic polymer," $\alpha$ must be at least about 0.001 (or 0.1%), preferably about 0.01 (1%) and more preferably at least about 0.1 (10%). Such small degrees of neutralization may be acceptable because often the effective pH of the polymer changes dramatically with small increases in the degree of neutralization. Nonetheless, even greater degrees of neutralization are even more preferred. Thus, $\alpha$ is preferably at least 0.5 (meaning that at least 50% of the acidic moieties have been neutralized) and $\alpha$ is more preferably at least 0.9 (meaning that at least 90% of the acidic moieties have been neutralized).

Neutralized acidic polymers are described in more detail in commonly assigned pending U.S. provisional patent application Ser. No. 60/300,256 entitled "Pharmaceutical Compositions of Drugs and Neutralized Acidic Polymers" filed Jun. 22, 2001, the relevant disclosure of which is incorporated by reference.

When the neutralized form of the acidic polymer comprises a multivalent cationic species such as $Ca^{2+}$, $Mg^{2+}$, $Al^{3+}$, $Fe^{2+}$, $Fe^{3+}$, or a diamine, such as ethylene diamine, the cationic species may interact with two or more neutralized acidic moieties on more than one polymer chain, resulting in an ionic crosslink between the polymer chains. An acidic polymer may be considered "ionically crosslinked" if the number of milliequivalents of multivalent cationic species per gram of polymer is at least 5%, preferably at least 10% the number of milliequivalents of acidic moieties (of the polymer) per gram of polymer. Alternatively, an acidic polymer may be considered "ionically crosslinked" if sufficient multivalent cationic species are present such that the neutralized acidic polymer has a higher $T_g$ than the same polymer containing essentially no multivalent cationic species. Drug mobility in dispersions formed from such ionically crosslinked polymers is particularly low relative to dispersions formed from the acidic form of the same polymers. Such ionically crosslinked polymers may be formed by neutralization of the acidic polymer using any base where the cationic counterion of the base is divalent. Thus, calcium hydroxide, magnesium acetate or ethylene diamine may be added to an acidic polymer such as cellulosic acetate phthalate or hydroxypropyl methyl cellulose acetate succinate to form a neutralized, ionically crosslinked, acidic cellulosic polymer. Low drug mobility in such polymers may be indicated by high $T_g$ values or, more typically, a decrease in the magnitude of the heat capacity increase in the vicinity of the $T_g$ or, in some cases, the absence of any apparent $T_g$ when the dispersion is subjected to differential thermal analysis. Thus, when the polymer is essentially completely neutralized, no $T_g$ is apparent when the neutralized polymer is subjected to differential thermal analysis. Such ionically cross-linked polymers may provide improved physical stability for the drug in the dispersion relative to non-ionically crosslinked neutralized acidic polymer.

While specific polymers have been discussed as being suitable for use in the compositions of the present invention, blends of such polymers may also be suitable. Thus the term "polymer" is intended to include blends of polymers in addition to a single species of polymer.

To obtain the best performance, particularly upon storage for long times prior to use, it is preferred that the CETP inhibitor remain, to the extent possible, in the amorphous state. The inventors have found that this may best be achieved by two distinct methods. In the first method, the glass-transition temperature, $T_g$, of the amorphous CETP inhibitor material is substantially above the storage temperature of the composition. In particular, it is preferable that the $T_g$ of the amorphous state of the CETP inhibitor be at least 40° C. and preferably at least 60° C. For those aspects of the invention in which the composition is a solid, substantially amorphous dispersion of CETP inhibitor in the concentration-enhancing polymer and in which the CETP inhibitor itself has a relatively low $T_g$ (about 70° C. or less) it is preferred that the concentration-enhancing polymer have a $T_g$ of at least 40° C., preferably at least 70° C. and more preferably greater than 100° C. Exemplary high $T_g$ polymers include HPMCAS, HPMCP, CAP, CAT, CMEC and other cellulosics that have alkylate or aromatic substituents or both alkylate and aromatic substituents.

In a second method, the concentration-enhancing polymer is chosen such that the amorphous CETP inhibitor is highly soluble in the concentration-enhancing polymer. In general, the concentration-enhancing polymer and CETP inhibitor concentration are chosen such that the solubility of the CETP inhibitor is roughly equal to or greater than the concentration of CETP inhibitor in the concentration-enhancing polymer. It is often preferred that the CETP inhibitor composition be chosen such that both methods—high $T_g$ and high solubility—are satisfied.

In addition, the preferred polymers listed above, that is amphiphilic cellulosic polymers, tend to have greater concentration-enhancing properties relative to the other polymers of the present invention. For any particular CETP inhibitor, the amphiphilic cellulosic with the best concentration-enhancing properties may vary. However, the inventors have found that generally those that have ionizable substituents as well as hydrophobic substituents such as methoxy, ethoxy and acetate tend to perform best. In vitro tests of compositions with such polymers tend to have higher MDC and AUC values than compositions with other polymers of the invention.

Preparation of Compositions

Dispersions of the CETP inhibitor and concentration-enhancing polymer may be made according to any known process which results in at least a major portion (at least 60%) of the CETP inhibitor being in the amorphous state. Exemplary mechanical processes include milling and extrusion; melt processes include high temperature fusion, solvent modified fusion and melt-congeal processes; and solvent processes include non-solvent precipitation, spray coating and spray-drying. See, for example, U.S. Pat. No. 5,456,923, U.S. Pat. No. 5,939,099 and U.S. Pat. No. 4,801,460 which describe formation of dispersions via extrusion processes; U.S. Pat. No. 5,340,591 and U.S. Pat. No. 4,673,564 which describe forming dispersions by milling processes; and U.S. Pat. No. 5,684,040, U.S. Pat. No. 4,894,235 and U.S. Pat. No. 5,707,646 which describe the formation of dispersions via melt/congeal processes, the disclosures of which are incorporated by reference. Although the dispersions of the present invention may be made by any of these processes, the dispersions generally have their maximum bioavailability and stability when the CETP inhibitor is dispersed in the polymer such that it is substantially amorphous and substantially homogeneously distributed throughout the polymer.

In general, as the degree of homogeneity of the dispersion increases, the enhancement in the aqueous concentration of the CETP inhibitor and relative bioavailability increases as well. Given the extremely low aqueous solubility and bioavailability of many CETP inhibitors, it is often highly preferred for the dispersions to be as homogeneous as possible to achieve therapeutically effective levels of CETP inhibitors. Thus, most preferred are dispersions having a single glass transition temperature, which indicates a high degree of homogeneity. Dispersions with more than one $T_g$, indicating at least partial amorphous phase separation, may also function well, particularly when neither amorphous phase is comprised only of amorphous drug, but rather also contains a significant amount of concentration-enhancing polymer.

In one embodiment, the solid amorphous dispersion of CETP inhibitor and concentration-enhancing polymer may be formed via a melt-congeal or melt-extrusion process. Such processes are particularly suitable when the CETP inhibitor has a relatively low melting point, typically less than about 200° C. and preferably less than about 150° C. In such processes, a molten mixture comprising the CETP inhibitor and concentration-enhancing polymer is rapidly cooled such that the molten mixture solidifies to form a solid amorphous dispersion. By "molten mixture" is meant that the mixture comprising the CETP inhibitor and concentration-enhancing polymer is heated sufficiently that it becomes sufficiently fluid that the drug substantially disperses in one or more of the concentration-enhancing polymer and other excipients. Generally, this requires that the mixture be heated to about 10° C. or more above the lower of the melting point of the lowest melting point component in the composition and the melting point of the drug. The CETP inhibitor can exist in the molten mixture as a pure phase, as a solution of CETP inhibitor homogeneously distributed throughout the molten mixture, or any combination of these states or those states that lie intermediate between them. The molten mixture is preferably substantially homogeneous so that the CETP inhibitor is dispersed as homogeneously as possible throughout the molten mixture. When the temperature of the molten mixture is below the melting point of both the CETP inhibitor and the concentration-enhancing polymer, the molten excipients, concentration-enhancing polymer, and CETP inhibitor are preferably sufficiently soluble in each other that a substantial portion of the CETP inhibitor disperses in the concentration-enhancing polymer or excipients. It is often preferred that the mixture be heated above the lower of the melting point of the concentration-enhancing polymer and the CETP inhibitor.

Generally, the processing temperature may vary from 50° C. up to about 200° C. or higher, depending on the melting point of the CETP inhibitor and polymer, which is a function of the polymer grade selected. However, the processing temperature should not be so high that an unacceptably high level of degradation of the drug or polymer occurs. In some cases, the molten mixture should be formed under an inert atmosphere to prevent degradation of the drug and/or polymer at the processing temperature. When relatively high temperatures are used, it is often preferable to minimize the time that the mixture is at the elevated temperature to minimize degradation.

The molten mixture may also comprise an excipient that will reduce the melting temperature of the composition (either the drug and/or the polymer), allowing processing at lower temperature. When such excipients have low volatility and substantially remain in the mixture upon solidification, they generally can comprise up to 30 wt % of the molten mixture. For example, a plasticizer may be added to the composition to reduce the melting temperature of the polymer. Examples of plasticizers include water, triethylcitrate, triacetin, and dibutyl sebacate. Volatile agents that dissolve or swell the polymer, such as acetone, water, methanol, and ethyl acetate, may also be added in low quantities to reduce the melting point of the composition. When such volatile excipients are added, at least a portion, up to essentially all, of such excipients may evaporate in the process of or following conversion of the molten mixture to a solid mixture. In such cases, the processing may be considered to be a combination of solvent processing and melt-congealing or melt-extrusion. Removal of such volatile excipients from the molten mixture can be accomplished by breaking up or atomizing the molten mixture into small droplets and contacting the droplets with a fluid such that the droplets both cool and lose all or part of the volatile excipient. Examples of other excipients that can be added to the composition to reduce the processing temperature include low molecular weight polymers or oligomers, such as polyethylene glycol, polyvinylpyrrolidone, and poloxamers; fats and oils, including mono-, di-, and triglycerides; natural and synthetic waxes, such as carnauba wax, beeswax, microcrystalline wax, castor wax, and paraffin wax; long-chain alcohols, such as cetyl alcohol and stearyl alcohol; and long-chain fatty acids, such as stearic acid. As mentioned above, when the excipient added is volatile, it may be removed from the mixture while still molten or following solidification to form the solid amorphous dispersion.

Virtually any process may be used to form the molten mixture. One method involves melting the concentration-enhancing polymer in a vessel and then adding the CETP inhibitor to the molten polymer. Another method involves melting the CETP inhibitor in a vessel and then adding the concentration-enhancing polymer. In yet another method, a solid blend of the CETP inhibitor and concentration-enhancing polymer may be added to a vessel and the blend heated to form the molten mixture.

Once the molten mixture is formed, it may be mixed to ensure the CETP inhibitor is homogeneously distributed throughout the molten mixture. Such mixing may be done using mechanical means, such as overhead mixers, magnetically driven mixers and stir bars, planetary mixers, and homogenizers. Optionally, when the molten mixture is formed in a vessel, the contents of the vessel can be pumped out of the vessel and through an in-line or static mixer and then returned to the vessel. The amount of shear used to mix the molten mixture should be sufficiently high to ensure uniform distribution of the drug in the molten mixture. The molten mixture can be mixed from a few minutes to several hours, the mixing time being dependent on the viscosity of the mixture and the solubility of the drug and any optional excipients in the concentration-enhancing polymer.

An alternative method of preparing the molten mixture is to use two vessels, melting the CETP inhibitor in the first vessel and the concentration-enhancing polymer in a second vessel. The two melts are then pumped through an in-line static mixer or extruder to produce the molten mixture that is then rapidly solidified.

Alternatively, the molten mixture can be generated using an extruder, such as a single-screw or twin-screw extruder, both well known in the art. In such devices, a solid feed of the composition is fed to the extruder whereby the combination of heat and shear forces produce a uniformly mixed molten mixture, which can then be rapidly solidified to form the solid amorphous dispersion. The solid feed can be prepared using methods well known in the art for obtaining solid mixtures with high content uniformity. Alternatively, the extruder may be equipped with two feeders, allowing the CETP inhibitor to be fed to the extruder through one feeder and the polymer through the other. Other excipients to reduce the processing temperature as described above may be included in the solid feed, or in the case of liquid excipients, such as water, may be injected into the extruder using methods well-known in the art.

The extruder should be designed such that it produces a molten mixture with the drug uniformly distributed throughout the composition. The various zones in the extruder should be heated to appropriate temperatures to obtain the desired extrudate temperature as well as the desired degree of mixing or shear, using procedures well known in the art.

When the drug has a high solubility in the concentration-enhancing polymer, a lower amount of mechanical energy will be required to form the dispersion. In such cases, when the melting point of the undispersed CETP inhibitor is greater than the melting point of the undispersed concentration-enhancing polymer, the processing temperature may be below the melting temperature of the undispersed CETP inhibitor but greater than the melting point of the polymer, since the CETP inhibitor will dissolve into the molten polymer. When the melting point of the undispersed CETP inhibitor is less than the melting point of the undispersed concentration-enhancing polymer, the processing temperature may be above the melting point of the undispersed CETP inhibitor but below the melting point of the undispersed concentration-enhancing polymer since the molten CETP inhibitor will dissolve in the polymer or be absorbed into the polymer.

When the CETP inhibitor has a low solubility in the polymer, a higher amount of mechanical energy may be required to form the dispersion. Here, the processing temperature may need to be above the melting point of the CETP inhibitor and the polymer. As mentioned above, alternatively, a liquid or low-melting point excipient may be added that promotes melting or the mutual solubility of the concentration-enhancing polymer and CETP inhibitor. A high amount of mechanical energy may also be needed to mix the CETP inhibitor and the polymer to form a dispersion. Typically, the lowest processing temperature and an extruder design that imparts the lowest amount of mechanical energy (e.g., shear) that produces a satisfactory dispersion (substantially amorphous and substantially homogeneous) is chosen in order to minimize the exposure of the CETP inhibitor to harsh conditions.

Once the molten mixture of CETP inhibitor and concentration-enhancing polymer is formed, the mixture should be rapidly solidified to form the solid amorphous dispersion. By "rapidly solidified" is meant that the molten mixture is solidified sufficiently fast such that substantial phase separation of the drug and polymer does not occur. Typically, this means that the mixture should be solidified in less than about 10 minutes, preferably less than about 5 minutes, more preferably less than about 1 minute. If the mixture is not rapidly solidified, phase separation can occur, resulting in the formation of CETP inhibitor-rich phases and polymer-rich phases. Over time, the drug in the CETP inhibitor-rich phases can crystallize. Such compositions are therefore not substantially amorphous or substantially homogeneous and tend not to perform as well as those compositions that are rapidly solidified and are substantially amorphous and substantially homogeneous. Solidification often takes place primarily by cooling the molten mixture to at least about 10° C. and preferably at least about 30° C. below its melting point. As mentioned above, solidification can be additionally promoted by evaporation of all or part of one or more volatile excipients or solvents. To promote rapid cooling and evaporation of volatile excipients, the molten mixture is often formed into a high surface area shape such as a rod or fiber or droplets. For example, the molten mixture can be forced through one or more small holes to form long thin fibers or rods or may be fed to a device, such as an atomizer such as a rotating disk, that breaks the molten mixture up into droplets from 1 µm to 1 cm in diameter. The droplets are then contacted with a relatively cool fluid such as air or nitrogen to promote cooling and evaporation.

A useful tool for evaluating and selecting conditions for forming substantially homogeneous, substantially amorphous dispersions via a melt-congeal or extrusion process is the differential scanning calorimeter (DSC). While the rate at which samples can be heated and cooled in a DSC is limited, it does allow for precise control of the thermal history of a sample. For example, the CETP inhibitor and concentration-enhancing polymer may be dry blended and then placed into the DSC sample pan. The DSC can then be programmed to heat the sample at the desired rate, hold the sample at the desired temperature for a desired time, and then rapidly cool the sample to ambient or lower temperature. The sample can then be re-analyzed on the DSC to verify the sample was transformed into a substantially homogeneous, substantially amorphous dispersion (e.g., the sample has a single Tg). Using this procedure, the temperature and time required to achieve a substantially homogeneous, substantially amorphous dispersion for a given CETP inhibitor and concentration-enhancing polymer can be determined.

Another method for forming substantially amorphous and substantially homogeneous dispersions is by "solvent processing," which consists of dissolution of the CETP inhibitor and one or more polymers in a common solvent. "Common" here means that the solvent, which can be a mixture of compounds, will simultaneously dissolve the drug and the polymer(s). After both the CETP inhibitor and the polymer have been dissolved, the solvent is rapidly removed by evaporation or by mixing with a non-solvent. Exemplary processes are spray-drying, spray-coating (pan-coating, fluidized bed coating, etc.), and precipitation by rapid mixing of the polymer and drug solution with $CO_2$, water, or some other non-solvent. Preferably, removal of the solvent results in a solid dispersion which is substantially homogeneous. As described previously, in such substantially homogeneous dispersions, the CETP inhibitor is dispersed as homogeneously as possible throughout the polymer and can be thought of as a solid solution of CETP inhibitor dispersed in the polymer(s). When the resulting dispersion constitutes a solid solution of CETP inhibitor in polymer, the dispersion may be thermodynamically stable, meaning that the concentration of CETP inhibitor in the polymer is at or below its equilibrium value, or it may be considered a supersaturated solid solution where the CETP inhibitor concentration in the dispersion polymer(s) is above its equilibrium value.

The solvent may be removed through the process of spray-drying. The term spray-drying is used conventionally and broadly refers to processes involving breaking up liquid mixtures into small droplets (atomization) and rapidly removing solvent from the mixture in a container (spray-drying apparatus) where there is a strong driving force for evaporation of solvent from the droplets. The strong driving force for solvent evaporation is generally provided by maintaining the partial pressure of solvent in the spray-drying apparatus well below the vapor pressure of the solvent at the temperature of the drying droplets. This is accomplished by either (1) maintaining the pressure in the spray-drying apparatus at a partial vacuum (e.g., 0.01 to 0.50 atm); (2) mixing the liquid droplets with a warm drying gas; or (3) both. In addition, at least a portion of the heat required for evaporation of solvent may be provided by heating the spray solution.

Solvents suitable for spray-drying can be any organic compound in which the CETP inhibitor and polymer are mutually soluble. Preferably, the solvent is also volatile with a boiling point of 150° C. or less. In addition, the solvent should have relatively low toxicity and be removed from the dispersion to a level that is acceptable according to The International Committee on Harmonization (ICH) guidelines. Removal of solvent to this level may require a processing step such as tray-drying subsequent to the spray-drying or spray-coating process. Preferred solvents include alcohols such as methanol, ethanol, n-propanol, iso-propanol, and butanol; ketones such as acetone, methyl ethyl ketone and methyl iso-butyl ketone; esters such as ethyl acetate and propylacetate; and various other solvents such as acetonitrile, methylene chloride, toluene, and 1,1,1-trichloroethane. Lower volatility solvents such as dimethyl acetamide or dimethylsulfoxide can also be used. Mixtures of solvents, such as 50% methanol and 50% acetone, can also be used, as can mixtures with water as long as the polymer and CETP inhibitor are sufficiently soluble to make the spray-drying process practicable. Generally, due to the hydrophobic nature of CETP inhibitors, non-aqueous solvents are preferred meaning that the solvent comprises less than about 10 wt % water, and preferably less than 1 wt % water.

Generally, the temperature and flow rate of the drying gas is chosen so that the polymer/drug-solution droplets are dry enough by the time they reach the wall of the apparatus that they are essentially solid, and so that they form a fine powder and do not stick to the apparatus wall. The actual length of time to achieve this level of dryness depends on the size of the droplets. Droplet sizes generally range from 1 μm to 500 μm in diameter, with 5 μm to 100 μm being more typical. The large surface-to-volume ratio of the droplets and the large driving force for evaporation of solvent leads to actual drying times of a few seconds or less, and more typically less than 0.1 second. This rapid drying is often critical to the particles maintaining a uniform, homogeneous dispersion instead of separating into drug-rich and polymer-rich phases. As above, to get large enhancements in concentration and bioavailability it is often necessary to obtain as homogeneous of a dispersion as possible. Solidification times should be less than 100 seconds, preferably less than a few seconds, and more preferably less than 1 second. In general, to achieve this rapid solidification of the CETP inhibitor/polymer solution, it is preferred that the size of droplets formed during the spray-drying process are less than about 100 μm in diameter. The resultant solid particles thus formed are generally less than about 100 μm in diameter.

Following solidification, the solid powder typically stays in the spray-drying chamber for about 5 to 60 seconds, further evaporating solvent from the solid powder. The final solvent content of the solid dispersion as it exits the dryer should be low, since this reduces the mobility of CETP inhibitor molecules in the dispersion, thereby improving its stability. Generally, the solvent content of the dispersion as it leaves the spray-drying chamber should be less than 10 wt % and preferably less than 2 wt %. In some cases, it may be preferable to spray a solvent or a solution of a polymer or other excipient into the spray-drying chamber to form granules, so long as the dispersion is not adversely affected.

Spray-drying processes and spray-drying equipment are described generally in Perry's *Chemical Engineers' Handbook*, Sixth Edition (R. H. Perry, D. W. Green, J. O. Maloney, eds.) McGraw-Hill Book Co. 1984, pages 20-54 to 20-57. More details on spray-drying processes and equipment are reviewed by Marshall "Atomization and Spray-Drying," 501 *Chem. Eng. Prog. Monogr. Series* 2 (1954).

The amount of concentration-enhancing polymer relative to the amount of CETP inhibitor present in the dispersions of the present invention depends on the CETP inhibitor and polymer and may vary widely from a CETP inhibitor-to-polymer weight ratio of from 0.01 to about 4 (e.g., 1 wt % CETP inhibitor to 80 wt % CETP inhibitor). However, in most cases it is preferred that the CETP inhibitor-to-polymer ratio is greater than about 0.05 (4.8 wt % CETP inhibitor) and less than about 2.5 (71 wt % CETP inhibitor). Often the enhancement in CETP inhibitor concentration or relative bioavailability that is observed increases as the CETP inhibitor-to-polymer ratio decreases from a value of about 1 (50 wt % CETP inhibitor) to a value of about 0.11 (10 wt % CETP inhibitor). In some cases it has been found that the bioavailability of dispersions with a CETP-inhibitor-to-polymer ratio of about 0.33 (25 wt % CETP inhibitor) have higher bioavailability when dosed orally than dispersions with a CETP-inhibitor-to-polymer ratio of 0.11 (10 wt % CETP inhibitor). The CETP inhibitor:polymer ratio that yields optimum results varies from CETP inhibitor to CETP inhibitor and is best determined in in vitro dissolution tests and/or in vivo bioavailability tests.

In addition, the amount of concentration-enhancing polymer that can be used in a dosage form is often limited by the total mass requirements of the dosage form. For example, when oral dosing to a human is desired, at low CETP inhibitor-to-polymer ratios the total mass of drug and polymer may be unacceptably large for delivery of the desired dose in a single tablet or capsule. Thus, it is often necessary to use CETP inhibitor-to-polymer ratios that are less than optimum in specific dosage forms to provide a sufficient CETP inhibitor dose in a dosage form that is small enough to be easily delivered to a use environment.

Excipients and Dosage Forms

Although the key ingredients present in the compositions of the present invention are simply the CETP inhibitor to be delivered and the concentration-enhancing polymer(s), the inclusion of other excipients in the composition may be useful. These excipients may be utilized with the CETP inhibitor and polymer composition in order to formulate the composition into tablets, capsules, suspensions, powders for suspension, creams, transdermal patches, depots, and the like. The composition of CETP inhibitor and polymer can be added to other dosage form ingredients in essentially any manner that does not substantially alter the CETP inhibitor. The excipients may be either physically mixed with the dispersion and/or included within the dispersion.

One very useful class of excipients is surfactants. Suitable surfactants include fatty acid and alkyl sulfonates; commercial surfactants such as benzalkonium chloride (HYAMINE® 1622, available from Lonza, Inc., Fairlawn, N.J.); dioctyl sodium sulfosuccinate, DOCUSATE SODIUM® (available from Mallinckrodt Spec. Chem., St. Louis, Mo.); polyoxyethylene sorbitan fatty acid esters (TWEEN®, available from ICI Americas Inc., Wilmington, Del.; LIPOSORB® P-20 available from Lipochem Inc., Patterson N.J.; CAPMUL® POE-0 available from Abitec Corp., Janesville, Wis.), and natural surfactants such as sodium taurocholic acid, 1-palmitoyl-2-oleoyl-sn-glycero-3-phosphocholine, lecithin, and other phospholipids and mono- and diglycerides. Such materials can advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, formation of micelles or adsorbing to the surface of solid drug, crystalline or amorphous. These surfactants may comprise up to 5 wt % of the composition.

The addition of pH modifiers such as acids, bases, or buffers may also be beneficial, retarding the dissolution of the composition (e.g., acids such as citric acid or succinic acid when the concentration-enhancing polymer is anionic) or, alternatively, enhancing the rate of dissolution of the composition (e.g., bases such as sodium acetate or amines when the polymer is anionic).

Conventional matrix materials, complexing agents, solubilizers, fillers, disintegrating agents (disintegrants), or binders may also be added as part of the composition itself or added by granulation via wet or mechanical or other means. These materials may comprise up to 90 wt % of the composition.

Examples of matrix materials, fillers, or diluents include lactose, mannitol, xylitol, microcrystalline cellulose, calcium diphosphate, and starch.

Examples of disintegrants include sodium starch glycolate, sodium alginate, carboxy methyl cellulose sodium, methyl cellulose, and croscarmellose sodium.

Examples of binders include methyl cellulose, microcrystalline cellulose, starch, and gums such as guar gum, and tragacanth.

Examples of lubricants include magnesium stearate and calcium stearate.

Other conventional excipients may be employed in the compositions of this invention, including those excipients well-known in the art. Generally, excipients such as pigments, lubricants, flavorants, and so forth may be used for customary purposes and in typical amounts without adversely affecting the properties of the compositions. These excipients may be utilized in order to formulate the composition into tablets, capsules, suspensions, powders for suspension, creams, transdermal patches, and the like.

The compositions of the present invention may be delivered by a wide variety of routes, including, but not limited to, oral, nasal, rectal, and pulmonary. Generally, the oral route is preferred.

Compositions of this invention may also be used in a wide variety of dosage forms for administration of CETP inhibitors. Exemplary dosage forms are powders or granules that may be taken orally either dry or reconstituted by addition of water or other liquids to form a paste, slurry, suspension or solution; tablets; capsules; multiparticulates; and pills. Various additives may be mixed, ground, or granulated with the compositions of this invention to form a material suitable for the above dosage forms.

The compositions of the present invention may be formulated in various forms such that they are delivered as a suspension of particles in a liquid vehicle. Such suspensions may be formulated as a liquid or paste at the time of manufacture, or they may be formulated as a dry powder with a liquid, typically water, added at a later time but prior to oral administration. Such powders that are constituted into a suspension are often termed sachets or oral powder for constitution (OPC) formulations. Such dosage forms can be formulated and reconstituted via any known procedure. The simplest approach is to formulate the dosage form as a dry powder that is reconstituted by simply adding water and agitating. Alternatively, the dosage form may be formulated as a liquid and a dry powder that are combined and agitated to form the oral suspension. In yet another embodiment, the dosage form can be formulated as two powders which are reconstituted by first adding water to one powder to form a solution to which the second powder is combined with agitation to form the suspension.

Generally, it is preferred that the dispersion of CETP inhibitor be formulated for long-term storage in the dry state as this promotes the chemical and physical stability of the CETP inhibitor. Various excipients and additives are combined with the compositions of the present invention to form the dosage form. For example, it may be desirable to add some or all of the following: preservatives such as sulfites (an antioxidant), benzalkonium chloride, methyl paraben, propyl paraben, benzyl alcohol or sodium benzoate; suspending agents or thickeners such as xanthan gum, starch, guar gum, sodium alginate, carboxymethyl cellulose, sodium carboxymethyl cellulose, methyl cellulose, hydroxypropyl methyl cellulose, polyacrylic acid, silica gel, aluminum silicate, magnesium silicate, or titanium dioxide; anticaking agents or fillers such as silicon oxide, or lactose; flavorants such as natural or artificial flavors; sweeteners such as sugars such as sucrose, lactose, or sorbitol as well as artificial sweeteners such as aspartame or saccharin; wetting agents or surfactants such as various grades of polysorbate, docusate sodium, or sodium lauryl sulfate; solubilizers such as ethanol propylene glycol or polyethylene glycol; coloring agents such as FD and C Red No. 3 or FD and C Blue No. 1; and pH modifiers or buffers such as carboxylic acids (including citric acid, ascorbic acid, lactic acid, and succinic acid), various salts of carboxylic acids, amino acids such as glycine or alanine, various phosphate, sulfate and carbonate salts such as trisodium phosphate, sodium bicarbonate or potassium bisulfate, and bases such as amino glucose or triethanol amine.

A preferred additive to such formulations is additional concentration-enhancing polymer which may act as a thickener or suspending agent as well as to enhance the concentration of CETP inhibitor in the environment of use and may also act to prevent or retard precipitation or crystallization of CETP inhibitor from solution. Such preferred additives are hydroxyethyl cellulose, hydroxypropyl cellulose, and hydroxypropyl methyl cellulose. In particular, the salts of carboxylic acid functional polymers such as cellulose acetate phthalate, hydroxypropyl methyl cellulose acetate succinate, and carboxymethyl cellulose are useful in this regard. Such polymers may be added in their salt forms or the salt form may be formed in situ during reconstitution by adding a base such as trisodium phosphate and the acid form of such polymers.

In some cases, the overall dosage form or particles, granules or beads that make up the dosage form may have superior performance if coated with an enteric polymer to prevent or retard dissolution until the dosage form leaves the stomach. Exemplary enteric coating materials include hydroxypropyl methyl cellulose acetate succinate, hydroxypropyl methyl cellulose phthalate, cellulose acetate phthalate, cellulose acetate trimellitate, carboxylic acid-functionalized polymethacrylates, and carboxylic acid-functionalized polyacrylate.

Compositions of this invention may be administered in a controlled release dosage form. In one such dosage form, the composition of the CETP inhibitor and polymer is incorporated into an erodible polymeric matrix device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or "matrix" that entraps the dispersion of CETP inhibitor and polymer. The aqueous-swollen matrix gradually erodes, swells, disintegrates or dissolves in the environment of use, thereby controlling the release of the dispersion to the environment of use. Examples of such dosage forms are disclosed more fully in commonly assigned pending U.S. patent application Ser. No. 09/495,059 filed Jan. 31, 2000 which claimed the benefit of priority of provisional patent application Ser. No. 60/119,400 filed Feb. 10, 1999, the relevant disclosure of which is herein incorporated by reference.

Alternatively, the compositions of the present invention may be administered by or incorporated into a non-erodible matrix device.

Alternatively, the compositions of the invention may be delivered using a coated osmotic controlled release dosage form. This dosage form has two components: (a) the core which contains an osmotic agent and the dispersion of CETP inhibitor and concentration-enhancing polymer; and (b) a non-dissolving and non-eroding coating surrounding the core, the coating controlling the influx of water to the core from an aqueous environment of use so as to cause drug release by extrusion of some or all of the core to the environment of use. The osmotic agent contained in the core of this device may be an aqueous-swellable hydrophilic polymer, osmogen, or osmagent. The coating is preferably polymeric, aqueous-permeable, and has at least one delivery port. Examples of such dosage forms are disclosed more fully in commonly assigned pending U.S. patent application Ser. No. 09/495,061 filed Jan. 31, 2000 which claimed the benefit of priority of provisional Patent Application Ser. No. 60/119, 406 filed Feb. 10, 1999, the relevant disclosure of which is herein incorporated by reference.

Alternatively, the compositions may be delivered via a coated hydrogel controlled release form having at least two components: (a) a core comprising the dispersion of the present invention and a hydrogel, and (b) a coating through which the dispersion has passage when the dosage form is exposed to a use environment. Examples of such dosage forms are more fully disclosed in commonly assigned European Patent EP0378404, the relevant disclosure of which is herein incorporated by reference.

Alternatively, the drug mixture of the invention may be delivered via a coated hydrogel controlled release dosage form having at least three components: (a) a composition if containing the dispersion, (b) a water-swellable composition wherein the water-swellable composition is in a separate region within a core formed by the drug-containing composition and the water-swellable composition, and (c) a coating around the core that is water-permeable, water-insoluble, and has at least one delivery port therethrough. In use, the core imbibes water through the coating, swelling the water-swellable composition and increasing the pressure within the core, and fluidizing the dispersion-containing composition. Because the coating remains intact, the dispersion-containing composition is extruded out of the delivery port into an environment of use. Examples of such dosage forms are more fully disclosed in commonly assigned pending U.S. patent application Ser. No. 09/745,095, filed Dec. 20, 2000, which claims priority to Provisional Application Ser. No. 60/171, 968 filed Dec. 23, 1999, the relevant disclosure of which is herein incorporated by reference.

Alternatively, the compositions may be administered as multiparticulates. Multiparticulates generally refer to dosage forms that comprise a multiplicity of particles that may range in size from about 10 µm to about 2 mm, more typically about 100 µm to 1 mm in diameter. Such multiparticulates may be packaged, for example, in a capsule such as a gelatin capsule or a capsule formed from an aqueous-soluble polymer such as HPMCAS, HPMC or starch or they may be dosed as a suspension or slurry in a liquid.

Such multiparticulates may be made by any known process, such as wet- and dry-granulation processes, extrusion/ spheronization, roller-compaction, or by spray-coating seed cores. For example, in wet- and dry-granulation processes, the composition of CETP inhibitor and concentration-enhancing polymer is prepared as described above. This composition is then granulated to form multiparticulates of the desired size. Other excipients, such as a binder (e.g., microcrystalline cellulose), may be blended with the composition to aid in processing and forming the multiparticulates. In the case of wet granulation, a binder such as microcrystalline cellulose may be included in the granulation fluid to aid in forming a suitable multiparticulate.

In any case, the resulting particles may themselves constitute the multiparticulate dosage form or they may be coated by various film-forming materials such as enteric polymers or water-swellable or water-soluble polymers, or they may be combined with other excipients or vehicles to aid in dosing to patients.

Compositions of the present invention may be used to treat any condition which is subject to treatment by administering a CETP inhibitor.

One aspect of this invention is directed to a method for treating atherosclerosis in a mammal (including a human being) by administering to a mammal in need of such treatment an atherosclerotic treating amount of a composition of the present invention.

Yet another aspect of this invention is directed to a method for treating peripheral vascular disease in a mammal (including a human being) by administering to a mammal in need of such treatment a peripheral vascular disease treating amount of a composition of the present invention.

Yet another aspect of this invention is directed to a method for treating dyslipidemia in a mammal (including a human being) by administering to a mammal in need of such treatment a dyslipidemia treating amount of a composition of the present invention.

Yet another aspect of this invention is directed to a method for treating hyperbetalipoproteinemia in a mammal (including a human being) by administering to a mammal in need of such treatment a hyperbetalipoproteinemia treating amount of a composition of the present invention.

Yet another aspect of this invention is directed to a method for treating hypoalphalipoproteinemia in a mammal (including a human being) by administering to a mammal in need of such treatment a hypoalphalipoproteinemia treating amount of a composition of the present invention.

Yet another aspect of this invention is directed to a method for treating hypercholesterolemia in a mammal (including a human being) by administering to a mammal in need of such treatment a hypercholesterolemia treating amount of a composition of the present invention.

Yet another aspect of this invention is directed to a method for treating hypertriglyceridemia in a mammal (including a human being) by administering to a mammal in need of such treatment a hypertriglyceridemia treating amount of a composition of the present invention.

Yet another aspect of this invention is directed to a method for treating familial-hypercholesterolemia in a mammal (including a human being) by administering to a mammal in need of such treatment a familial-hypercholesterolemia treating amount of a composition of the present invention.

Yet another aspect of this invention is directed to a method for treating cardiovascular disorders in a mammal (including a human being) by administering to a mammal in need of such treatment a cardiovascular disorder treating amount of a composition of the present invention.

Yet another aspect of this invention is directed to a method for treating angina in a mammal (including a human being) by administering to a mammal in need of such treatment an angina treating amount of a composition of the present invention.

Yet another aspect of this invention is directed to a method for treating ischemia in a mammal (including a human being) by administering to a mammal in need of such treatment an ischemic disease treating amount of a composition of the present invention.

Yet another aspect of this invention is directed to a method for treating cardiac ischemia in a mammal (including a human being) by administering to a mammal in need of such treatment a cardiac ischemic treating amount of a composition of the present invention.

Yet another aspect of this invention is directed to a method for treating stroke in a mammal (including a human being) by administering to a mammal in need of such treatment a stroke treating amount of a composition of the present invention.

Yet another aspect of this invention is directed to a method for treating a myocardial infarction in a mammal (including a human being) by administering to a mammal in need of such treatment a myocardial infarction treating amount of a composition of the present invention.

Yet another aspect of this invention is directed to a method for treating reperfusion injury in a mammal (including a human being) by administering to a mammal in need of such treatment a reperfusion injury treating amount of a composition of the present invention.

Yet another aspect of this invention is directed to a method for treating angioplastic restenosis in a mammal (including a human being) by administering to a mammal in need of such treatment an angioplastic restenosis treating amount of a composition of the present invention.

Yet another aspect of this invention is directed to a method for treating hypertension in a mammal (including a human being) by administering to a mammal in need of such treatment a hypertension treating amount of a composition of the present invention.

Yet another aspect of this invention is directed to a method for treating the vascular complications of diabetes in a mammal (including a human being) by administering to a mammal in need of such treatment a vascular complications of diabetes treating amount of a composition of the present invention.

Yet another aspect of this invention is directed to a method for treating obesity in a mammal (including a human being) by administering to a mammal in need of such treatment an obesity treating amount of a composition of the present invention.

Yet another aspect of this invention is directed to a method for treating endotoxemia in a mammal (including a human being) by administering to a mammal in need of such treatment an endotoxemia treating amount of a composition of the present invention.

Other features and embodiments of the invention will become apparent from the following examples which are given for illustration of the invention rather than for limiting its intended scope.

EXAMPLES

Example 1

This example discloses preparation of an amorphous solid dispersion of [2R,4R]4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester ("Drug 1"), which has a solubility in water of less than 1 μg/mL and a Clog P value of 7.6. A dispersion of 10 wt % Drug 1 and 90 wt % polymer was made by mixing Drug 1 in the solvent acetone together with a "medium fine" (AQUOT-MF) grade of the cellulosic ester polymer HPMCAS (manufactured by Shin Etsu) to form a solution. The solution comprised 0.053 wt % Drug 1, 0.477 wt % HPMCAS, and 99.47 wt % acetone. The spray-dried dispersion ("SDD") was prepared using a "mini" spray-dryer, which consisted of an atomizer in the top cap of a vertically oriented stainless steel pipe. The atomizer was a two-fluid nozzle (Spraying Systems Co. 1650 fluid cap and 64 air cap), where the atomizing gas was nitrogen delivered to the nozzle at 100° C. and a flow rate of 15 gm/min, and the solution to be spray dried was delivered to the nozzle at room temperature and a flow rate of 1.3 mL/min using a syringe pump. Filter paper with a supporting screen was clamped to the bottom end of the pipe to collect the solid spray-dried material and allow the nitrogen and evaporated solvent to escape. These SDD preparation parameters are summarized in Table 1.

Control 1

Comparative composition Control 1 was simply 0.18 mg crystalline Drug 1.

Examples 2-3

Spray-dried dispersions were prepared using the procedure described in Example 1 except that the concentration-enhancing polymer was varied as noted in Table 1.

Example 4

A spray-dried dispersion was prepared using the procedure described in Example 1 except that the ratio of Drug 1 to HPMCAS-MF was 1:1 (50 wt % Drug 1), as shown in Table 1.

TABLE 1

| Example | Drug 1 Mass (mg) | Concentration-enhancing Polymer* | Polymer Mass (mg) | Solvent | Solvent Mass (g) | Spray Apparatus |
|---|---|---|---|---|---|---|
| 1 | 9 | HPMCAS-MF | 81 | acetone | 17 | Mini |
| 2 | 3.8 | HPMCP | 33.7 | acetone | 6 | Mini |
| 3 | 3.5 | PVP | 31.5 | Acetone/MeOH | 6 0.12 | Mini |
| 4 | 25 | HPMCAS-MF | 25 | acetone | 12 | Mini |

*Polymer designations: HPMCAS = hydroxypropyl methyl cellulose acetate succinate; HPMCP = hydroxypropyl methyl cellulose phthalate; PVP = polyvinylpyrrolidone.

Example 5

The spray-dried dispersions of Examples 1 to 4 were evaluated in in vitro dissolution tests using a microcentrifuge method. In this method, 1 mg of the spray-dried dispersions was added to a 1.5-mL microcentrifuge tube. The tube was placed in a 37° C. sonicating bath, and 1 mL of a model-fasted duodenal solution (MFDS) (comprising sodium taurocholate/1-palmitoyl-2-oleoyl-sn-glycero-3-phosphocholine (NaTC-POPC) in phosphate-buffered saline (PBS) at pH 6.5 and 290 mOsm/kg) was added. The samples were quickly mixed using a combination of vortex mixer and sonication for about 90 seconds. The theoretical maximum concentration ("$TC_{max}$") of drug for Examples 1-3 if all the drug dissolved was 100 µg/mL, while for Example 4 the $TC_{max}$ was 500 µg/mL. The samples were centrifuged at 13,000 G at 37° C. for 1 minute. The resulting supernatant solution was then sampled (100 µL) and diluted with 200 µL methanol and then analyzed by HPLC. The tubes were then mixed on the vortex mixer and allowed to stand undisturbed at 37° C. until the next sample. Samples were collected at 3, 10, 30, 60, and 90 minutes and for Examples 1 and 2 at 1200 minutes. Data for Examples 1 to 4 are shown in Table 2.

For Control 1, an in vitro test was performed using the procedure described above, except that 0.18 mg of crystalline Drug 1 was placed in a microcentrifuge tube and mixed with 1.8 mL of MFDS. The test results are included in Table 2.

TABLE 2

| Example | Time (min) | Concentration (µg/mL) | AUC (min-µg/mL) |
|---|---|---|---|
| 1 | 0 | 0 | 0 |
|  | 3 | 83 | 120 |
|  | 10 | 79 | 690 |
|  | 30 | 85 | 2,300 |
|  | 60 | 84 | 4,900 |
|  | 90 | 77 | 7,300 |
|  | 1200 | 26 | 64,400 |
| 2 | 0 | 0 | 0 |
|  | 3 | 81 | 122 |
|  | 10 | 75 | 670 |
|  | 30 | 75 | 2,200 |
|  | 60 | 64 | 4,200 |
|  | 90 | 74 | 6,300 |
|  | 1200 | 21 | 58,700 |
| 3 | 0 | 0 | 0 |
|  | 3 | 35 | 53 |
|  | 10 | 33 | 290 |
|  | 30 | 30 | 900 |
|  | 60 | 28 | 1,800 |
|  | 90 | 28 | 2,600 |
| 4 | 0 | 0 | 0 |
|  | 3 | 62 | 94 |
|  | 10 | 63 | 530 |
|  | 30 | 54 | 1,700 |
|  | 60 | 52 | 3,300 |
|  | 90 | 40 | 4,700 |
| Control 1 | 0 | 0 | 0 |
|  | 4 | <0.1 | <0.1 |
|  | 10 | 0.3 | 1 |
|  | 20 | 0.3 | 4 |
|  | 40 | 0.9 | 16 |
|  | 90 | 0.8 | 57 |

TABLE 3

| Example | Concentration-enhancing Polymer* | Concentration of Drug in In the Dispersion (wt %) | $TC_{max}$ (µg/mL) | $C_{max,90}$ (µg/mL) | $AUC_{90}$ (min-µg/mL) |
|---|---|---|---|---|---|
| 1 | HPMCAS-MF | 10 | 100 | 85 | 7300 |
| 2 | HPMCP | 10 | 100 | 81 | 6300 |
| 3 | PVP | 10 | 100 | 35 | 2600 |
| 4 | HPMCAS-MF | 50 | 500 | 63 | 4700 |
| Control 1 | None | — | 100 | 0.9 | 57 |

*Polymer designations: HPMCAS = hydroxypropyl methyl cellulose acetate succinate; HPMCP = hydroxypropyl methyl cellulose phthalate, PVP = polyvinylpyrrolidone.

The results of the in vitro dissolution tests are summarized in Table 3, which shows the maximum concentration of Drug 1 in solution during the 90-minute test ($C_{max,90}$), and the area under the aqueous concentration versus time curve during the 90-minute test ($AUC_{90}$). The results show that the performance of the spray-dried dispersions of Examples 1 to 4 was much better than that of the crystalline drug alone (Control 1), with $C_{max,90}$ values ranging from 39- to 94-fold that of the crystalline drug, Control 1, and $AUC_{90}$ values ranging from 45- to 128-fold that of the crystalline drug, Control 1.

Examples 6-7

Examples 6-7 demonstrates the utility of the amorphous dispersions of the present invention with another CETP inhibitor, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester ("Drug 2"), which has a solubility in water of <1 µg/ml, and a Clog P value of 7.5. To prepare Example 6, an amorphous solid dispersion of 25 wt % Drug 2 and 75 wt % polymer was made by mixing Drug 2 in the solvent acetone together with a "medium fine" (AQUOT-MF) grade of the cellulosic ester polymer HPMCAS (manufactured by Shin Etsu) to form a solution. The solution comprised 2.5 wt % Drug 2, 7.5 wt % HPMCAS, and 90 wt % acetone. This solution was then spray-dried by directing an atomizing spray using a two-fluid external-mix spray nozzle at 2.7 bar (37 psig) at a feed rate of 150 g/min into the stainless-steel chamber of a Niro PSD1 spray-dryer, maintained at a temperature of 155° C. at the inlet and 70° C. at the outlet. The preparation parameters are summarized in Table 4. The resulting amorphous solid spray-dried dispersion was collected via a cyclone and then dried in a Gruenberg solvent tray-dryer by spreading the spray-dried particles onto polyethylene-lined trays to a depth of not more than 1 cm and then drying them at 40° C. for 24 hours.

Example 7 was prepared following the general procedure described in Example 6 except that the dispersion contained 10 wt % Drug 2 and the spray solution comprised 1.0 wt % Drug 2, 9.0 wt % HPMCAS-MF, and 90 wt % acetone. The preparation parameters are summarized in Table 4.

TABLE 4

| Example | Drug 2 Mass (g) | Concentration-enhancing Polymer | Polymer Mass (g) | Solvent | Solvent Mass (g) | Spray Apparatus |
|---|---|---|---|---|---|---|
| 6 | 100 | HPMCAS-MF | 300 | acetone | 3600 | PSD-1 |
| 7 | 100 | HPMCAS-MF | 900 | acetone | 9000 | PSD-1 |
| Control 2 | 0.0018 | none | — | — | — | — |

Comparative composition Control 2 consisted of 1.8 mg of the crystalline form of Drug 2 alone.

Example 8

The spray-dried dispersions of Examples 6 and 7 were evaluated in an in vitro dissolution test using a microcentrifuge method. In this test, the spray-dried dispersion was added to a microcentrifuge tube for a Drug 2 dose of about 1000 μg/mL (7.2 mg for Example 6, 18 mg for Example 7). The tube was placed in a 37° C. sonicating bath, and 1.8 mL phosphate buffered saline (PBS) at pH 6.5 and 290 mOsm/kg was added. The samples were quickly mixed using a vortex mixer for about 60 seconds. The samples were centrifuged at 13,000 G at 37° C. for 1 minute. The resulting supernatant solution was then sampled and diluted 1:6 (by volume) with methanol and then analyzed by high-performance liquid chromatography (HPLC). The contents of the tubes were mixed on the vortex mixer and allowed to stand undisturbed at 37° C. until the next sample was taken. Samples were collected at 4, 10, 20, 40, 90, and 1200 minutes. The concentrations of drug obtained in these samples are shown in Table 5.

For Control 2, an in vitro dissolution test was performed using the procedures described above except that 1.8 mg of crystalline Drug 2 was used. The concentrations of drug obtained in in vitro dissolution tests are shown in Table 5.

TABLE 5

| Example | Time (mins) | Drug 2 Concentration (μg/mL) | AUC (min-μg/mL) |
|---|---|---|---|
| 6 | 0 | 0 | 0 |
|   | 4 | 328 | 660 |
|   | 10 | 701 | 3,700 |
|   | 20 | 781 | 11,200 |
|   | 40 | 805 | 27,000 |
|   | 90 | 780 | 66,600 |
|   | 1200 | 439 | 743,200 |
| 7 | 0 | 0 | 0 |
|   | 4 | 925 | 1,900 |
|   | 10 | 923 | 7,400 |
|   | 20 | 910 | 16,600 |
|   | 40 | 890 | 34,600 |
|   | 90 | 858 | 78,300 |
|   | 1200 | 623 | 900,200 |
| Control 2 | 0 | 0 | 0 |
|   | 4 | <1 | <2 |
|   | 10 | <1 | <8 |
|   | 20 | <1 | <18 |
|   | 40 | <1 | <38 |
|   | 90 | <1 | <88 |
|   | 1200 | <1 | <1,200 |

The results of dissolution tests for Examples 6 and 7, and Control 2 are summarized in Table 6, which shows the maximum concentration of Drug 2 in solution during the first 90 minutes of the test ($C_{max,90}$), the area under the aqueous concentration versus time curve after 90 minutes ($AUC_{90}$), and the concentration at 1200 minutes ($C_{1200}$).

TABLE 6

| Example | Concentration-enhancing Polymer | Drug 2 Conc. in the Dispersion (wt %) | Receptor Solution | $TC_{max}$ (μg/mL) | $C_{max,90}$ (μg/mL) | $AUC_{90}$ (min-μg/mL) | $C_{1200}$ (μg/mL) |
|---|---|---|---|---|---|---|---|
| 6 | HPMCAS-MF | 25 | PBS | 994 | 805 | 66,600 | 439 |
| 7 | HPMCAS-MF | 10 | PBS | 988 | 925 | 78,300 | 623 |
| Control 2 | None (crystalline drug) | NA | PBS | 1000 | <1 | <88 | <1 |

The results summarized in Table 6 above show that the dissolution results for the compositions of Examples 6 and 7 were much better than that of the crystalline drug alone, providing $C_{max,90}$ values that were greater than 805-fold and 925-fold that of the crystalline drug (Control 2), respectively, and $AUC_{90}$ values that were greater than 756-fold and 889-fold that of the crystalline drug (Control 2), respectively. Accurate measurements of the solubility of crystalline Drug 2 yield a value of about 0.01 μg/ml. Thus, the actual $C_{max,90}$ for Drug 2 in Control 2 is believed to be about 0.01 μg/ml. Using this value, the compositions of Examples 6 and 7 provided $C_{max,90}$ values that were about 80,000-fold to 92,500-fold that of the crystalline drug, and $AUC_{90}$ values that were about 70,000- to 80,000-fold that of the crystalline drug, respectively.

Examples 9-16

Spray-dried dispersions for Examples 9-16 were prepared using the procedure described in Example 1 (using a "mini" spray-dryer apparatus) except that Drug 2 was used instead of Drug 1. Other variables are summarized in Table 7.
Comparative composition Control 3 consisted of 0.72 mg of the crystalline form of Drug 2 alone.

TABLE 7

| Example | Drug 2 Mass (mg) | Concentration-enhancing Polymer* | Polymer Mass (mg) | Solvent | Solvent Mass (g) | Spray Apparatus |
|---|---|---|---|---|---|---|
| 9 | 70 | HPMCAS-MF | 630 | acetone | 14 | mini |
| 10 | 70 | CAT | 630 | acetone | 14 | mini |
| 11 | 70 | CAP | 630 | acetone | 14 | mini |
| 12 | 250 | HPMCAS-MF | 750 | acetone | 75 | mini |
| 13 | 25 | CAP | 75 | acetone | 5 | mini |
| 14 | 3 | HPMC | 27 | Acetone/Methanol (1:1) | 10 | mini |
| 15 | 3 | HPMCP | 27 | Acetone | 10 | mini |
| 16 | 3 | PVP | 27 | Acetone/Methanol (9:1) | 10 | mini |

*Polymer designations: HPMCAS = hydroxypropyl methyl cellulose acetate succinate; CAT = cellulose acetate trimellitate, CAP = cellulose acetate phthalate, HPMC = hydroxypropyl methyl cellulose, HPMCP = hydroxypropyl methyl cellulose phthalate, PVP = polyvinylpyrrolidone.

Example 17

The dispersions of Examples 9-11 and 14 were evaluated in an in vitro dissolution test using receptor solutions of PBS using the procedures outlined in Example 8 except the $TC_{max}$ was either 400 µg/ml or 10 µg/ml as indicated in Table 9, depending on the amount of SDD added to the receptor solution. The data are presented in Table 8.

The dispersions of Examples 9-16 were also evaluated in an in vitro dissolution test using receptor solutions of MFDS using the procedures outlined in Example 8. The data are also presented in Table 8.

For Control 3, an in vitro dissolution test was performed using the procedure described above except that 0.72 mg of crystalline Drug 2 was used. The results are shown in Table 8.

TABLE 8

| Example | Receptor | Time (min) | Concentration (µg/ml) | AUC (min-µg/ml) |
|---|---|---|---|---|
| 9 | PBS | 0 | 0 | 0 |
| | | 4 | 370 | 740 |
| | | 10 | 364 | 2,940 |
| | | 20 | 356 | 6,500 |
| | | 40 | 336 | 13,500 |
| | | 90 | 318 | 29,800 |
| | | 1200 | 131 | 279,200 |
| 9 | MFDS | 0 | 0 | 0 |
| | | 4 | 391 | 780 |
| | | 10 | 388 | 3,120 |
| | | 20 | 384 | 7,000 |
| | | 40 | 372 | 14,500 |
| | | 90 | 340 | 32,300 |
| | | 1200 | 110 | 282,300 |
| 10 | PBS | 0 | 0 | 0 |
| | | 4 | 375 | 750 |
| | | 10 | 366 | 2,970 |
| | | 20 | 360 | 6,600 |
| | | 40 | 321 | 13,400 |
| | | 90 | 300 | 28,900 |
| | | 1200 | 54 | 225,900 |
| 10 | MFDS | 0 | 0 | 0 |
| | | 4 | 395 | 789 |
| | | 10 | 386 | 3,130 |
| | | 20 | 368 | 6,900 |
| | | 40 | 349 | 14,100 |
| | | 90 | 298 | 30,200 |
| | | 1200 | 92 | 246,400 |
| 11 | PBS | 0 | 0 | 0 |
| | | 4 | 383 | 764 |
| | | 10 | 381 | 3,050 |
| | | 20 | 360 | 6,800 |
| | | 40 | 338 | 13,800 |
| | | 90 | 302 | 29,600 |
| | | 1200 | 56 | 228,600 |
| 11 | MFDS | 0 | 0 | 0 |
| | | 4 | 409 | 818 |
| | | 10 | 380 | 3,190 |
| | | 20 | 374 | 7,000 |
| | | 40 | 357 | 14,300 |
| | | 90 | 326 | 31,300 |
| | | 1200 | 102 | 268,700 |
| 12 | MFDS | 0 | 0 | 0 |
| | | 4 | 136 | 272 |
| | | 10 | 168 | 1,180 |
| | | 20 | 161 | 2,800 |
| | | 40 | 145 | 5,900 |
| | | 90 | 122 | 12,600 |
| | | 1200 | 0 | 80,500 |
| 13 | MFDS | 0 | 0 | 0 |
| | | 4 | 285 | 571 |
| | | 10 | 277 | 2,260 |
| | | 20 | 245 | 4,900 |
| | | 40 | 218 | 9,500 |
| | | 90 | 176 | 19,400 |
| | | 1200 | 57 | 149,000 |
| 14 | PBS | 0 | 0 | 0 |
| | | 3 | 70 | 106 |
| | | 10 | 64 | 580 |
| | | 20 | 59 | 1,200 |
| | | 40 | 50 | 2,300 |
| | | 90 | 42 | 4,600 |
| | | 1200 | 18 | 37,900 |
| 14 | MFDS | 0 | 0 | 0 |
| | | 3 | 94 | 142 |
| | | 10 | 94 | 800 |
| | | 20 | 85 | 1,700 |
| | | 40 | 80 | 3,300 |
| | | 90 | 74 | 7,200 |
| | | 1200 | 28 | 63,700 |
| 15 | MFDS | 0 | 0 | 0 |
| | | 3 | 98 | 147 |
| | | 10 | 83 | 780 |
| | | 20 | 67 | 1,500 |
| | | 40 | 56 | 2,800 |
| | | 90 | 46 | 5,300 |
| | | 1200 | 25 | 44,500 |
| 16 | MFDS | 0 | 0 | 0 |
| | | 3 | 19 | 28 |
| | | 10 | 16 | 150 |
| | | 20 | 13 | 300 |
| | | 40 | 13 | 600 |
| | | 90 | 12 | 1,200 |

TABLE 8-continued

| Example | Receptor | Time (min) | Concentration (μg/ml) | AUC (min-μg/ml) |
|---|---|---|---|---|
|  |  | 1200 | 15 | 16,100 |
| Control 3 | MFDS | 0 | 0 | 0 |
|  |  | 4 | <1 | <4 |
|  |  | 10 | <1 | <10 |
|  |  | 20 | <1 | <20 |
|  |  | 40 | <1 | <40 |
|  |  | 90 | <1 | <90 |

The results summarized in Table 9 show that the dissolution results for the compositions of Examples 9-16 were much better than that of the crystalline drug alone, providing $C_{max,90}$ values that were greater than 19- to 409-fold that of the crystalline drug (Control 3), when tested in MFDS, and $AUC_{90}$ values that were greater than 13- to 359-fold that of the crystalline drug (Control 3), when tested in MFDS.

TABLE 9

| Example | Concentration-enhancing Polymer* | Conc. of Drug in the Dispersion (wt %) | Receptor Solution | $TC_{max}$ (μg/mL) | $C_{max,90}$ (μg/mL) | $AUC_{90}$ (min-μg/mL) |
|---|---|---|---|---|---|---|
| 9 | HPMCAS-MF | 10 | PBS | 400 | 370 | 29,800 |
| 9 | HPMCAS-MF | 10 | MFDS | 400 | 391 | 32,300 |
| 10 | CAT | 10 | PBS | 400 | 375 | 28,900 |
| 10 | CAT | 10 | MFDS | 400 | 395 | 30,200 |
| 11 | CAP | 10 | PBS | 400 | 383 | 29,800 |
| 11 | CAP | 10 | MFDS | 400 | 409 | 31,300 |
| 12 | HPMCAS-MF | 25 | MFDS | 400 | 168 | 12,600 |
| 13 | CAP | 25 | MFDS | 400 | 285 | 19,400 |
| 14 | HPMC | 10 | PBS | 100 | 70 | 4,600 |
| 14 | HPMC | 10 | MFDS | 100 | 94 | 7,200 |
| 15 | HPMCP | 10 | MFDS | 100 | 98 | 5,300 |
| 16 | PVP | 10 | MFDS | 100 | 19 | 1,200 |
| Control 3 | None (crystalline drug) | NA | MFDS | 400 | <1 | <90 |

*Polymer designations: HPMCAS = hydroxypropyl methyl cellulose acetate succinate; CAT = cellulose acetate trimellitate, CAP = cellulose acetate phthalate, HPMC = hydroxypropyl methyl cellulose, HPMCP = hydroxypropyl methyl cellulose phthalate, PVP = polyvinylpyrrolidone.

Examples 18-20

These examples demonstrate that the technology of this invention, when orally dosed to beagle dogs, gives a high systemic compound exposure ($C_{max}$ and AUC). Spray-dried dispersions were made using the procedures outlined in Examples 6, 7 and 11, and were used as an oral powder for constitution (OPC) by suspending 360 mg of the composition of Example 6 in about 15 mL of a solution of 3 wt % polyethylglycol (PEG) with a molecular weight of 3,350 daltons, 0.5 wt % methylcellulose, and 0.15 wt % Polysorbate 80 in sterile water (Example 18), suspending 900 mg of the composition of Example 7 in about 15 mL of a solution of 3 wt % PEG with a molecular weight of 3,350 daltons, 0.5 wt % methylcellulose, and 0.15 wt % Polysorbate 80 in sterile water (Example 19), and by suspending 900 mg of the composition of Example 11 in about 15 mL of a solution of 3 wt % PEG with a molecular weight of 3,350 daltons, 0.5 wt % methylcellulose, and 0.15 wt % Polysorbate 80 in sterile water (Example 20). A control OPC containing 90 mg of crystalline drug was also prepared by suspending 90 mg of crystalline drug in about 15 ml of a solution of 3 wt % PEG with a molecular weight of 3,350 daltons, 0.5 wt % methyl cellulose, and 0.15 wt % polysorbate 80 in sterile water (Control 4). Dogs that had fasted overnight were dosed with the OPC. Blood was collected from the jugular vein of the dogs before dosing and at various time points after dosing. To 100 μL of each plasma sample, 5 mL of methyl-tert-butyl ether (MTBE) and 1 mL of 500 mM sodium carbonate buffer (pH 9) were added; the sample was vortexed for 1 minute and then centrifuged for 5 minutes. The aqueous portion of the sample was frozen in a dry-ice/acetone bath, and the MTBE layer was decanted and evaporated in a vortex evaporator. Dried samples were reconstituted in 100 μL of mobile phase (33% acetonitrile and 67% of 0.1% formic acid in water). Analysis was carried out by HPLC.

The results of these tests are shown in Table 10, where $C_{max,24}$ is the maximum concentration in the blood plasma during the first 24 hours, $T_{max}$ is the time to achieve the maximum concentration in the blood plasma and $AUC_{0-24}$ is the concentration in the blood plasma area under the curve in the first 24 hours. The results show that the $C_{max,24}$ and $AUC_{0-24}$ in the blood were much higher for the compositions of the present invention than the controls, with $C_{max,24}$ values that are 21.5- to 40-fold that of the crystalline drug (Control 4), and $AUC_{0-24}$ values that are 21.7- to 55.6-fold that of the crystalline drug (Control 4).

TABLE 10

| Example | Formulation | Dose (mg) | $C_{max,24}$ (μg/mL) | $T_{max}$ (hr) | $AUC_{0-24}$ (μg-hr/mL) |
|---|---|---|---|---|---|
| 18 | 25% Drug 2: HPMCAS OPC | 90 | 1.60 ± 0.60 | 1.10 ± 0.50 | 7.88 ± 2.95 |
| 19 | 10% Drug 2: HPMCAS OPC | 90 | 0.86 ± 1.75 | 2.17 ± 1.94 | 3.47 ± 1.71 |
| 20 | 10% Drug 2: CAP OPC | 90 | 1.51 ± 0.50 | 1.58 ± 1.28 | 8.89 ± 1.75 |
| Control 4 | Crystalline Drug 2 suspension | 90 | 0.04 ± 0.01 | 1.33 ± 0.52 | 0.16 ± 0.14 |

Examples 21-28

Example 21 demonstrates the utility of the amorphous dispersions of the present invention with another CETP inhibitor, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid propyl ester ("Drug 3"), which has a solubility in water of less than 0.1 μg/ml, and a Clog P value of 8.0. To prepare Example 21, an amorphous solid dispersion of a CETP inhibitor comprising 10 wt % Drug 3 and 90 wt % polymer was made by mixing Drug 3 in the solvent acetone together with HPMCAS-MF to form a solution. The solution comprised 0.1 wt % Drug 3, 0.9 wt % HPMCAS, and 99 wt % acetone. This solution was pumped into a "mini" spray-dryer apparatus via a syringe pump at a rate of 1.3 mL/min. The polymer solution was atomized through a spray nozzle using a heated stream of nitrogen. The resulting solid spray-dried dispersion was collected on a filter paper at a yield of about 50%. The preparation parameters are summarized in Table 11.

Spray-dried dispersions were prepared using the procedure described to prepare Example 21 except that the aqueous-soluble polymer and sometimes the solvent was varied as noted in Table 11.

Comparative composition Control 5 consisted of 0.72 mg of the crystalline form of Drug 3 alone.

TABLE 11

| Example | Drug 3 Mass (mg) | Concentration-enhancing Polymer* | Polymer Mass (mg) | Solvent | Solvent Mass (g) | Spray Apparatus |
|---|---|---|---|---|---|---|
| 21 | 20 | HPMCAS-MF | 180 | Acetone | 20 | mini |
| 22 | 10 | HPMCP | 90 | Acetone | 10 | mini |
| 23 | 10 | CAP | 90 | Acetone | 10 | mini |
| 24 | 10 | CAT | 90 | Acetone | 10 | mini |
| 25 | 10 | PVP | 90 | Acetone Methanol | 9 1 | mini |
| 26 | 10 | HPMC | 90 | Methanol | 10 | mini |
| 27 | 10 | HPMCAS-LF | 90 | Acetone | 10 | mini |
| 28 | 10 | HPMCAS-HF | 90 | Acetone | 10 | mini |

*Polymer designations: HPMCAS = hydroxypropyl methyl cellulose acetate succinate; HPMCP = hydroxypropyl methyl cellulose phthalate, CAP = cellulose acetate phthalate, CAT = cellulose acetate trimellitate, PVP = polyvinylpyrrolidone, HPMC = hydroxypropyl methyl cellulose.

Example 29

The spray-dried dispersions of Examples 21-28 were evaluated in an in vitro dissolution test using a microcentrifuge method. In this method, 7.2 mg of each spray-dried dispersion was added to a 2-mL microcentrifuge tube. The tube was placed in a 37° C. sonicating bath, and 1.8 mL of a phosphate-buffered saline (PBS) solution at pH 6.5 and 290 mOsm/kg was added, resulting in a $TC_{max}$ of 400 μg/mL. The samples were quickly mixed using a combination of vortex mixer and sonication for about 90 seconds. The samples were centrifuged at 13,000 G at 37° C. for 1 minute. The resulting supernatant solution was then sampled and diluted 1:6 (by volume) with methanol and then analyzed by HPLC. The tubes were then mixed on the vortex mixer and allowed to stand undisturbed at 37° C. until the next sample. Samples were collected at 4, 10, 20, 40, 90 and 1200 minutes. Data are included in Table 12.

For Control 5, an in vitro dissolution test was performed using the procedure described above, except that 0.72 mg of non-crystalline Drug 3 was placed in a microcentrifuge tube and mixed with 1.8 mL of PBS. The test results are included in Table 12.

TABLE 12

| Example | Time (min) | Concentration (μg/mL) | AUC (min-μg/mL) |
|---|---|---|---|
| 21 | 0 | 0 | 0 |
|  | 4 | 347 | 694 |
|  | 10 | 361 | 2,800 |
|  | 20 | 370 | 6,500 |
|  | 60 | 396 | 14,000 |
|  | 90 | 364 | 33,100 |
|  | 1200 | 291 | 396,500 |
| 22 | 0 | 0 | 0 |
|  | 4 | 373 | 685 |
|  | 10 | 296 | 2,600 |
|  | 20 | 264 | 5,400 |
|  | 40 | 231 | 10,400 |
|  | 90 | 174 | 20,500 |
|  | 1200 | 33 | 135,000 |
| 23 | 0 | 0 | 0 |
|  | 4 | 384 | 769 |
|  | 10 | 368 | 3,000 |
|  | 20 | 376 | 6,700 |
|  | 40 | 356 | 14,100 |
|  | 90 | 371 | 32,200 |
|  | 1200 | 237 | 369,700 |
| 24 | 0 | 0 | 0 |
|  | 4 | 390 | 780 |
|  | 10 | 390 | 3,100 |
|  | 20 | 386 | 7,000 |
|  | 40 | 387 | 14,700 |
|  | 90 | 379 | 33,900 |
|  | 1200 | 231 | 372,400 |
| 25 | 0 | 0 | 0 |
|  | 4 | 196 | 392 |
|  | 10 | 158 | 1,500 |
|  | 20 | 145 | 3,000 |
|  | 40 | 134 | 5,800 |
|  | 90 | 127 | 12,300 |
|  | 1200 | 84 | 129,400 |
| 26 | 0 | 0 | 0 |
|  | 4 | 346 | 693 |
|  | 10 | 349 | 2,800 |
|  | 20 | 343 | 6,200 |
|  | 40 | 323 | 12,900 |
|  | 90 | 296 | 28,400 |
|  | 1200 | 209 | 308,700 |
| 27 | 0 | 0 | 0 |
|  | 4 | 373 | 746 |
|  | 10 | 348 | 2,900 |
|  | 20 | 335 | 6,300 |
|  | 40 | 315 | 12,800 |

TABLE 12-continued

| Example | Time (min) | Concentration (μg/mL) | AUC (min-μg/mL) |
|---|---|---|---|
|  | 90 | 292 | 28,000 |
|  | 1200 | 195 | 298,300 |
| 28 | 0 | 0 | 0 |
|  | 4 | 72 | 144 |
|  | 10 | 172 | 876 |
|  | 20 | 316 | 3,300 |
|  | 40 | 370 | 10,200 |
|  | 90 | 405 | 29,600 |
|  | 1200 | 355 | 451,400 |
| Control 5 | 0 | 0 | 0 |
|  | 4 | <0.1 | <0.4 |
|  | 10 | <0.1 | <1.0 |
|  | 20 | <0.1 | <2.0 |
|  | 40 | <0.1 | <4.0 |
|  | 90 | <0.1 | <9.0 |

The results, summarized in Table 13, show that the dissolution results for the compositions of Examples 21 through 28 were much better than that of the crystalline drug alone, providing $C_{max,90}$ values that were greater than 1,900- to 4,050-fold that of the crystalline drug (Control 5), and $AUC_{90}$ values that were greater than 1,370- to 3,770-fold that of the crystalline drug (Control 5).

TABLE 13

| Example | Concentration-enhancing Polymer* | Concentration of Drug 3 in Polymer (wt %) | $C_{max,90}$ (μg/mL) | $AUC_{90}$ (min-μg/mL) |
|---|---|---|---|---|
| 21 | HPMCAS-MF | 10 | 396 | 33,100 |
| 22 | HPMCP | 10 | 343 | 20,500 |
| 23 | CAP | 10 | 384 | 32,200 |
| 24 | CAT | 10 | 390 | 33,900 |
| 25 | PVP | 10 | 196 | 12,300 |
| 26 | HPMC | 10 | 349 | 28,400 |
| 27 | HPMCAS-LF | 10 | 373 | 28,000 |
| 28 | HPMCAS-HF | 10 | 405 | 29,600 |
| Control 5 | None | — | <0.1 | <9.0 |

*Polymer designations: HPMCAS = hydroxypropyl methyl cellulose acetate succinate; HPMCP = hydroxypropyl methyl cellulose phthalate, CAP = cellulose acetate phthalate, CAT = celluloseacetate trimellitate, PVP = polyvinylpyrrolidone, HPMC = hydroxypropyl methyl cellulose.

Examples 30-41

Examples 30 through 41 demonstrate the utility of the amorphous dispersions of the present invention with a variety of CETP inhibitors. The following drugs were all incorporated into solid amorphous dispersions: [2R,4S]4-[(3,5-bis-trifluoromethyl-benzyl)-methoxycarbonyl-amino]-6,7-dimethoxy-2-methyl-3,4-dihydro-2H-quinoline-1-carboxylic acid ethyl ester ("Drug 4"); [2R,4S]4-[(3,5-bis-trifluoromethyl-benzyl)-methoxycarbonyl-amino]-6,7-diethyl-2-methyl-3,4-dihydro-2H-quinoline-1-carboxylic acid ethyl ester ("Drug 5"); [2R,4S]4-[(3,5-bis-trifluoromethyl-benzyl)-methoxycarbonyl-amino]-2-methyl-2,3,4,6,7,8-hexahydro-cyclopenta[g]quinoline-1-carboxylic acid ethyl ester ("Drug 6"); [2R,4S]-4-[acetyl-(3,5-bis-trifluoromethyl-benzyl)-amino]-2-ethyl-6-trifluoromethyl-3,4-dihydro-2H-quinoline-1-carboxylic acid isopropyl ester ("Drug 7"); [2S,4S]4-[(3,5-bis-trifluoromethyl-benzyl)-methoxycarbonyl-amino]-2-cyclopropyl-6-trifluoromethyl-3,4-dihydro-2H-quinoline-1-carboxylic acid isopropyl ester ("Drug 8"); [3S,5S]2-cyclopentyl-4-(4-fluoro-phenyl)-3-[fluoro-(4-trifluoromethyl-phenyl)-methyl]-7,7-dimethyl-5,6,7,8-tetrahydro-quinolin-5-ol ("Drug 9"). All of these compounds have a solubility in water of less than 1 μg/ml, with Clog P values ranging from 5.5 to 8.3. To prepare Examples 30-41, dispersions comprising 10 wt % drug and 90 wt % polymer were made by mixing each drug in the solvent acetone together with polymer to form a solution. Dispersions with HPMCAS-MF and CAP were prepared for each drug. The solutions comprised 0.05 wt % drug, 0.45 wt % polymer, and 99.5 wt % acetone. Each solution was pumped into a "mini" spray-dryer apparatus via a syringe pump at a rate of 1.3 mL/min. The polymer solution was atomized through a spray nozzle using a heated stream of nitrogen. The resulting solid spray-dried dispersion was collected on a filter paper at a yield of about 65%. The preparation parameters are summarized in Table 14.

Controls 6-11

The comparative compositions of Controls 6-11 consisted of 1.5 mg of the crystalline form of each of Drug 4-9 alone.

TABLE 14

| Example | Drug No. | Drug Mass (mg) | Concentration-enhancing Polymer* | Polymer Mass (mg) | Solvent | Solvent Mass (g) | Spray Apparatus |
|---|---|---|---|---|---|---|---|
| 30 | 4 | 5 | HPMCAS-MF | 45 | acetone | 10 | mini |
| 31 | 4 | 5 | CAP | 45 | acetone | 10 | mini |
| 32 | 5 | 5 | HPMCAS-MF | 45 | acetone | 10 | mini |
| 23 | 5 | 5 | CAP | 45 | acetone | 10 | mini |
| 34 | 6 | 5 | HPMCAS-MF | 45 | acetone | 10 | mini |
| 35 | 6 | 5 | CAP | 45 | acetone | 10 | mini |
| 36 | 7 | 5 | HPMCAS-MF | 45 | acetone | 10 | mini |
| 37 | 7 | 5 | CAP | 45 | acetone | 10 | mini |
| 38 | 8 | 5 | HPMCAS-MF | 45 | acetone | 10 | mini |
| 39 | 8 | 5 | CAP | 45 | acetone | 10 | mini |
| 40 | 9 | 5 | HPMCAS-MF | 45 | acetone | 10 | mini |
| 41 | 9 | 5 | CAP | 45 | acetone | 10 | mini |

*Polymer designations: HPMCAS = hydroxypropyl methyl cellulose acetate succinate, CAP = cellulose acetate phthalate.

Example 42

The spray-dried dispersions of Examples 30-41 were evaluated in an in vitro dissolution test using a microcentrifuge method. In this method, 15 mg of each SDD was added to a 2-mL microcentrifuge tube. The tube was placed in a 37° C. sonicating bath, and 1.5 mL of a phosphate-buffered saline (PBS) solution at pH 6.5 and 290 mOsm/kg) was added, resulting in a $TC_{max}$ of 1000 µg/mL. The samples were quickly mixed using a combination of vortex mixer and sonication for about 90 seconds. The samples were centrifuged at 13,000 G at 37° C. for 1 minute. The resulting supernatant solution was then sampled and diluted 1:6 (by volume) with methanol and then analyzed by HPLC. The tubes were then mixed on the vortex mixer and allowed to stand undisturbed at 37° C. until the next sample. Samples were collected at 4, 10, 20, 40, and 90 minutes. Data are included in Table 15.

For Controls 6-11, an in vitro dissolution test was performed using the procedure described above, except that 1.5 mg of non-crystalline drug was placed in a microcentrifuge tube and mixed with 1.5 mL of PBS. The test results are included in Table 15.

TABLE 15

| Example | Time (min) | Concentration (µg/mL) | AUC (min-µg/mL) |
|---|---|---|---|
| 30 | 0 | 0 | 0 |
|  | 4 | 999 | 2,000 |
|  | 10 | 836 | 7,500 |
|  | 20 | 729 | 15,300 |
|  | 60 | 571 | 28,300 |
|  | 90 | 471 | 54,400 |
| 31 | 0 | 0 | 0 |
|  | 4 | 591 | 1,200 |
|  | 10 | 599 | 4,800 |
|  | 20 | 557 | 10,500 |
|  | 40 | 500 | 21,100 |
|  | 90 | 427 | 44,300 |
| 32 | 0 | 0 | 0 |
|  | 4 | 1091 | 2,200 |
|  | 10 | 1079 | 8,700 |
|  | 20 | 1061 | 19,400 |
|  | 40 | 1033 | 40,300 |
|  | 90 | 985 | 90,800 |
| 33 | 0 | 0 | 0 |
|  | 4 | 836 | 1,700 |
|  | 10 | 965 | 7,100 |
|  | 20 | 971 | 16,800 |
|  | 40 | 973 | 36,200 |
|  | 90 | 943 | 84,100 |
| 34 | 0 | 0 | 0 |
|  | 4 | 852 | 1,700 |
|  | 10 | 890 | 6,900 |
|  | 20 | 896 | 15,900 |
|  | 40 | 852 | 33,300 |
|  | 90 | 781 | 74,200 |
| 35 | 0 | 0 | 0 |
|  | 4 | 536 | 1,100 |
|  | 10 | 623 | 4,600 |
|  | 20 | 650 | 10,900 |
|  | 40 | 713 | 24,500 |
|  | 90 | 610 | 57,600 |
| 36 | 4 | 0 | 0 |
|  | 10 | 947 | 1,900 |
|  | 20 | 912 | 7,500 |
|  | 40 | 876 | 16,400 |
|  | 90 | 832 | 33,500 |
|  | 1200 | 783 | 73,900 |
| 37 | 0 | 0 | 0 |
|  | 4 | 262 | 500 |
|  | 10 | 559 | 3,000 |
|  | 20 | 638 | 9,000 |
|  | 40 | 643 | 21,800 |
|  | 90 | 590 | 52,600 |
| 38 | 0 | 0 | 0 |
|  | 4 | 974 | 1,900 |
|  | 10 | 965 | 7,800 |
|  | 20 | 933 | 17,300 |
|  | 40 | 935 | 35,900 |
|  | 90 | 969 | 83,500 |
| 39 | 0 | 0 | 0 |
|  | 4 | 705 | 1,400 |
|  | 10 | 811 | 6,000 |
|  | 20 | 860 | 14,300 |
|  | 40 | 952 | 32,400 |
|  | 90 | 1003 | 81,300 |
| 40 | 0 | 0 | 0 |
|  | 4 | 224 | 400 |
|  | 10 | 503 | 2,600 |
|  | 20 | 633 | 8,300 |
|  | 40 | 699 | 21,600 |
|  | 90 | 785 | 58,700 |
| 41 | 0 | 0 | 0 |
|  | 4 | 196 | 400 |
|  | 10 | 342 | 2,000 |
|  | 20 | 527 | 6,400 |
|  | 40 | 520 | 16,800 |
|  | 90 | 596 | 44,700 |
| Control 6 | 0 | 0 | 0 |
|  | 4 | <1 | <4 |
|  | 10 | <1 | <10 |
|  | 20 | <1 | <20 |
|  | 40 | <1 | <40 |
|  | 90 | <1 | <90 |
| Control 7 | 0 | 0 | 0 |
|  | 4 | <1 | <4 |
|  | 10 | <1 | <10 |
|  | 20 | <1 | <20 |
|  | 40 | <1 | <40 |
|  | 90 | <1 | <90 |
| Control 8 | 4 | <1 | <4 |
|  | 10 | <1 | <10 |
|  | 20 | <1 | <20 |
|  | 40 | <1 | <40 |
|  | 90 | <1 | <90 |
| Control 9 | 0 | 0 | 0 |
|  | 4 | <1 | <4 |
|  | 10 | <1 | <10 |
|  | 20 | <1 | <20 |
|  | 40 | <1 | <40 |
|  | 90 | — | — |
| Control 10 | 0 | 0 | 0 |
|  | 4 | <1 | <4 |
|  | 10 | <1 | <10 |
|  | 20 | <1 | <20 |
|  | 40 | <1 | <40 |
|  | 90 | <1 | <90 |
| Control 11 | 0 | 0 | 0 |
|  | 4 | <1 | <4 |
|  | 10 | <1 | <10 |
|  | 20 | <1 | <20 |
|  | 40 | <1 | <40 |
|  | 90 | <1 | <90 |

The results, summarized in Table 16, show that the dissolution results for the compositions of Examples 30 through 41 were much better than that of each crystalline drug alone, providing $C_{max,90}$ values that were greater than 596- to 1091-fold that of each respective crystalline drug (Controls 6-11), and $AUC_{90}$ values that were greater than 490- to 1,000-fold that of each respective crystalline drug.

TABLE 16

| Example | Drug No. | Concentration-enhancing Polymer* | Conc. of Drug in Polymer (wt %) | $C_{max,90}$ (µg/mL) | $AUC_{90}$ (min-µg/mL) |
|---|---|---|---|---|---|
| 30 | 4 | HPMCAS-MF | 10 | 999 | 54,400 |
| 31 | 4 | CAP | 10 | 599 | 44,300 |
| 32 | 5 | HPMCAS-MF | 10 | 1091 | 90,800 |
| 33 | 5 | CAP | 10 | 973 | 84,100 |
| 34 | 6 | HPMCAS-MF | 10 | 896 | 74,200 |
| 35 | 6 | CAP | 10 | 713 | 57,600 |
| 36 | 7 | HPMCAS-MF | 10 | 947 | 73,900 |
| 37 | 7 | CAP | 10 | 643 | 52,600 |
| 38 | 8 | HPMCAS-MF | 10 | 974 | 83,500 |
| 39 | 8 | CAP | 10 | 1003 | 81,300 |
| 40 | 9 | HPMCAS-MF | 10 | 785 | 58,700 |
| 41 | 9 | CAP | 10 | 596 | 44,700 |
| Control 6 | 4 | None | — | <1 | <90 |
| Control 7 | 5 | None | — | <1 | <90 |
| Control 8 | 6 | None | — | <1 | <90 |
| Control 9 | 7 | None | — | <1 | <90 |
| Control 10 | 8 | None | — | <1 | <90 |
| Control 11 | 9 | None | — | <1 | <90 |

*Polymer designations: HPMCAS = hydroxypropyl methyl cellulose acetate succinate, CAP = cellulose acetate phthalate.

Examples 43-46

Examples 43 through 46 demonstrate the utility of the amorphous dispersions of the present invention with two additional CETP inhibitors. The following drugs were incorporated into solid amorphous dispersions: (4'S)-5-(4-fluorophenyl)-6'-[(S)-fluoro[4-(trifluoromethyl)phenyl]methyl]-3',4'-dihydro-7'-(1-methylethyl)-spiro[cyclobutane-1,2'(1'H)-naphthalen]-4'-ol ("Drug 10"), and (2R)-3-[[3-(4-chloro-3-ethylphenoxy)phenyl][[3-(1,1,2,2-tetrafluoroethoxy)phenyl]methyl]amino]-1,1,1-trifluoro-2-propanol ("Drug 11"). These compounds have a solubility in water of less than 1 µg/mL, with Clog P values of 8.9 and 9.8, respectively. To prepare Examples 43 through 46, dispersions comprising 10 wt % drug and 90 wt % polymer were made by first mixing each drug in the solvent acetone together with polymer to form a solution. Dispersions with HPMCAS-MF and CAP were prepared for each drug. The solutions comprised 0.05 wt % drug, 0.45 wt % polymer, and 99.5 wt % acetone. Each solution was pumped into a "mini" spray-dryer apparatus via a syringe pump at a rate of 1.3 mL/min. The polymer solution was atomized through a spray nozzle using a heated stream of nitrogen. The resulting solid spray-dried dispersion was collected on a filter paper at a yield of about 40%. The preparation parameters are summarized in Table 17.

TABLE 17

| Example | Drug No. | Drug Mass (mg) | Concentration-enhancing Polymer* | Polymer Mass (mg) | Solvent | Solvent Mass (g) | Spray Apparatus |
|---|---|---|---|---|---|---|---|
| 43 | 10 | 5 | HPMCAS-MF | 45 | Acetone | 10 | mini |
| 44 | 10 | 5 | CAP | 45 | Acetone | 10 | mini |
| 45 | 11 | 5 | HPMCAS-MF | 45 | Acetone | 10 | mini |
| 46 | 11 | 5 | CAP | 45 | Acetone | 10 | mini |

*Polymer designations: HPMCAS = hydroxypropyl methyl cellulose acetate succinate, CAP = cellulose acetate phthalate.

Controls 12-13

The comparative compositions of Controls 12 and 13 consisted of 1.0 mg of the undispersed amorphous form of each of Drugs 10 and 11 alone.

Example 47

The spray-dried dispersions of Examples 43 to 46 were evaluated in an in vitro dissolution test using a microcentrifuge method. In this method, 10 mg of each SDD was added to a 2-mL microcentrifuge tube. The tube was placed in a 37° C. sonicating bath, and 1.0 mL of a phosphate-buffered saline (PBS) solution at pH 6.5 and 290 mOsm/kg was added, resulting in a $TC_{max}$ of 1000 µg/mL. The samples were quickly mixed using a combination of vortex mixer and sonication for about 90 seconds. The samples were centrifuged at 13,000 G at 37° C. for 1 minute. The resulting supernatant solution was then sampled and diluted 1:6 (by volume) with methanol and then analyzed by HPLC. The tubes were then mixed on the vortex mixer and allowed to stand undisturbed at 37° C. until the next sample. Samples were collected at 4, 10, 20, 40, 90, and 1200 minutes. Data are included in Table 19.

For Controls 12 and 13, an in vitro dissolution test was performed using the procedure described above, except that 1.0 mg of undispersed amorphous drug was placed in a microcentrifuge tube and mixed with 1.0 mL of PBS. The test results are included in Table 18.

TABLE 18

| Example | Time (min) | Concentration (µg/mL) | AUC (min-µg/mL) |
|---|---|---|---|
| 43 (Drug 10) | 0 | 0 | 0 |
| | 4 | 540 | 1,100 |
| | 10 | 680 | 4,700 |
| | 30 | 780 | 12,000 |
| | 60 | 880 | 28,600 |
| | 90 | 880 | 72,700 |
| | 1200 | 900 | 1,064,000 |
| 44 (Drug 10) | 0 | 0 | 0 |
| | 4 | 470 | 900 |
| | 10 | 540 | 4,000 |
| | 20 | 650 | 9,900 |
| | 40 | 730 | 23,700 |
| | 90 | 810 | 62,200 |
| | 1200 | 840 | 979,900 |
| 45 (Drug 11) | 0 | 0 | 0 |
| | 4 | 700 | 1,400 |
| | 10 | 890 | 6,200 |
| | 20 | 980 | 15,500 |
| | 40 | 970 | 35,000 |

TABLE 18-continued

| Example | Time (min) | Concentration (μg/mL) | AUC (min-μg/mL) |
|---|---|---|---|
| | 90 | 1040 | 85,100 |
| | 1200 | 1140 | 1,296,100 |
| 46 (Drug 11) | 0 | 0 | 0 |
| | 4 | 920 | 1,800 |
| | 10 | 1110 | 8,000 |
| | 20 | 1120 | 19,200 |
| | 40 | 1030 | 40,700 |
| | 90 | 1030 | 92,300 |
| | 1200 | 920 | 1,177,400 |
| Control 12 (Drug 10) | 0 | 0 | 0 |
| | 4 | 0 | 0 |
| | 10 | 1 | 0 |
| | 20 | 3 | 0 |
| | 40 | 6 | 100 |
| | 90 | 1 | 300 |
| | 1200 | 0 | 1,100 |
| Control 13 (Drug 11) | 0 | 0 | 0 |
| | 4 | 1 | 0 |
| | 10 | 1 | 0 |
| | 20 | 1 | 0 |
| | 40 | 1 | 0 |
| | 90 | 1 | 100 |
| | 1200 | 0 | 600 |

The results, summarized in Table 19, show that the dissolution results for the compositions of Examples 43 through 46 were much better than that of each drug alone, providing $C_{max,90}$ values that were 135- to 1120-fold that of each respective undispersed amorphous drug (Controls 12 and 13), and $AUC_{90}$ values that were 207- to 1,150-fold that of each respective drug alone.

TABLE 19

| Example | Drug No. | Concentration-enhancing Polymer* | Concentration of Drug in Polymer (wt %) | $C_{max,90}$ (μg/mL) | $AUC_{90}$ (min-μg/mL) |
|---|---|---|---|---|---|
| 43 | 10 | HPMCAS-MF | 10 | 880 | 72,700 |
| 44 | 10 | CAP | 10 | 810 | 62,200 |
| 45 | 11 | HPMCAS-MF | 10 | 1040 | 85,100 |
| 46 | 11 | CAP | 10 | 1120 | 92,300 |
| Control 12 | 10 | None | — | 6 | 300 |
| Control 13 | 11 | None | — | 1 | 80 |

*Polymer designations: HPMCAS = hydroxypropyl methyl cellulose acetate succinate, CAP = cellulose acetate phthalate.

Examples 48-53

The suitability of forming solid amorphous dispersions comprising Drug 2 and HPMCAS-MF via a melt-congeal or melt-extrusion process was evaluated using a differential scanning calorimeter (DSC). In this technique, a dry blend of the desired mount of Drug 2 and HPMCAS-MF was formed by adding the ingredients to a container and mixing with a spatula. About 10 mg of this dry blend was then placed in a DSC sample pan and hermetically sealed. The sample pan was then placed into a Perkin-Elmer Pyris-1 DSC and the sample heated to the desired hold temperature at a rate of about 50° C./min and held at this temperature for 1 hour. The sample was then cooled to ambient temperature at a rate of about 50° C./min. The glass-transition temperature of the heated sample was then determined by scanning the sample on the DSC at a constant temperature rate of 10° C./min. Table 20 gives the compositions evaluated and the hold temperatures evaluated as well as the results of the DSC scans after holding at the final temperature for 1 hour.

TABLE 20

| Example | Drug 2 Concentration (wt %) | Hold Temperature (° C.) | Results of DSC Evaluation After Holding at the Hold Temperature for 1 Hour (Tg in ° C.) |
|---|---|---|---|
| 48 | 10 | 100 | Two $T_g$s seen (~35, ~120) |
| 49 | 10 | 125 | Single $T_g$ (~100) |
| 50 | 10 | 150 | Single $T_g$ (~100) |
| 51 | 25 | 100 | Two $T_g$s Seen (~35, ~120) |
| 52 | 25 | 125 | Two $T_g$s seen (small peak at ~35, large at 100 C.) |
| 53 | 25 | 150 | Single $T_g$ (~90 C.) |

These data show that at a Drug 2 concentration of 10 wt %, a solid-amorphous dispersion could be formed by holding the materials at 125° C. for 1 hour. The resulting material had a single $T_g$ at about 100° C.—between the $T_g$ assigned to amorphous Drug 2 (~35° C.) and the $T_g$ of HPMCAS-MF (~120° C.). The data indicate that heating a mixture of 10 wt % Drug 2 and HPMCAS-MF to 125° C. or higher and holding it at that temperature for 1 hour will result in a homogeneous, solid amorphous dispersion.

The data also show that at a Drug 2 concentration of 25 wt %, holding the material at 125° C. resulted in a material with two $T_g$s. The small peak at about 35° C. suggests that the sample contained a small amount of amorphous drug and was therefore not a homogeneous dispersion, but likely a mixture of amorphous Drug 2 and a Drug 2:HPMCAS-MF amorphous dispersion. However, heating to 150° C. for 1 hour (Example 53) did result in a homogeneous, amorphous dispersion, as evidenced by the single $T_g$. Note that the $T_g$ for the homogeneous, amorphous dispersion containing 25 wt %. Drug 2 (Example 53) was somewhat lower than the $T_g$ of the homogeneous, amorphous dispersion containing 10 wt % Drug 2 (Example 50). This was as expected since the dispersion of Example 53 contained a larger fraction of Drug 2, which has a $T_g$ that is lower than that of HPMCAS.

Examples 54-55

A solid amorphous dispersion of Drug 2 and HPMCAS-MF was prepared by melt-extrusion using the following procedure. For Example 54, a blend of 25 wt % Drug 2 and 75 wt % HPMCAS-MF was formed by mixing 3.75 gm of Drug 2 and 11.25 gm of HPMCAS-MF in a Turbula mixer for 10 minutes. For Example 55, a blend of 25 wt % Drug 2 and 75 wt % HPMCAS-MF was formed by mixing 12.5 gm of Drug 2 and 37.5 gm of HPMCAS-MF in a Turbula mixer for 10 minutes. These pre-blended feeds were fed to a DACA Micro-Compounder (Goleta, Calif.) equipped with conical co-rotating screws. For Example 54, the extruder was set at a temperature of 150° C. and the screw speed was set at 40 RPM. For Example 55, the extruder was set at a temperature of 140° C. and the screw speed was set at 120 RPM. In both cases, the extrudate exited the extruder in the form of cylindrical rods with a diameter of about 3 mm. The molten extrudate was transparent with a slight yellow color. The extrudate was cooled with ambient air, with the outside surface of the rod becoming solid within a few seconds after exiting the extruder. After solidification, the solid amorphous dispersion was transparent with a slight yellow color and was very brittle.

The extrudate was collected and milled in a SPEX 6800 cryogenic freezer mill (SPEX CertiPrep, Metuchen, N.J.) set at 10 impacts/sec, 1 cycle, with a 2-minute pre-cool, followed by 5 minutes of milling.

Example 56

The solid amorphous dispersions of Example 54 to 55 were evaluated in an in vitro dissolution test using the procedures described in Example 8 except that a MFD solution was used as the receptor solution. The results of these tests are presented in Table 21.

TABLE 21

| Example | Time (min) | Drug 2 Concentration (μg/mL) | AUC (min-μg/mL) |
|---|---|---|---|
| 54 | 0 | 0 | 0 |
|  | 4 | 53 | 110 |
|  | 10 | 189 | 830 |
|  | 20 | 293 | 3,200 |
|  | 40 | 443 | 10,600 |
|  | 90 | 516 | 34,600 |
|  | 1200 | 265 | 467,700 |
| 55 | 0 | 0 | 0 |
|  | 4 | 175 | 350 |
|  | 10 | 267 | 1,700 |
|  | 20 | 363 | 4,800 |
|  | 40 | 452 | 13,000 |
|  | 90 | 452 | 35,600 |
|  | 1200 | 117 | 351,400 |

The results are also summarized in Table 22, which also includes the data for Control 3 which was tested under the same conditions. These data show that the dispersions made by extrusion provided $C_{max,90}$ values that were greater than 452- to 516-fold that of the crystalline control (Control 3) and $AUC_{90}$ values that were greater than 384- to 396-fold that of the crystalline control.

TABLE 22

| Example | Concentration-enhancing Polymer* | Concentration of Drug in Polymer (wt %) | $C_{max,90}$ (μg/mL) | $AUC_{90}$ (min-μg/mL) |
|---|---|---|---|---|
| 54 | HPMCAS-MF | 25 | 516 | 34,600 |
| 55 | HPMCAS-MF | 25 | 452 | 35,600 |
| Control 3 | None | — | <1 | <90 |

*Polymer designation: HPMCAS = hydroxypropyl methyl cellulose acetate succinate

Examples 57-64

Solid amorphous dispersions of Drug 2 and the poloxamers Pluronic F-127 and Pluronic F-108 (both supplied by BASF) were prepared by a melt-congeal process using the following procedure. For each example, the amount of Drug 2 and poloxamer given in Table 23 were accurately weighed and placed into a container. The container was then placed in a hot oil bath maintained at 105° C. After about 15 minutes, the mixture had melted, and was stirred using a magnetic stirrer for about 15 minutes. The molten mixture was transparent, with no apparent color. Next, the container containing the molten mixture was removed from the hot oil bath and placed into liquid nitrogen, resulting in solidification of the molten mixture within a few seconds. The container was removed from the liquid nitrogen after about 60 seconds and allowed to warm to ambient temperature. The resulting opaque solid amorphous dispersion was then removed from the container using a spatula and broken into small pieces about 1 mm thick. The pieces were then placed into a mortar with some liquid nitrogen and ground into a white powder using a pestle.

TABLE 23

| Example | Concentration of Drug in Polymer (wt %) | Drug Mass (gm) | Aqueous-Soluble Polymer | Polymer Mass (gm) |
|---|---|---|---|---|
| 57 | 10 | 0.1003 | Pluronic F-127 | 0.8999 |
| 58 | 25 | 0.2499 | Pluronic F-127 | 0.7502 |
| 59 | 40 | 0.4020 | Pluronic F-127 | 0.6002 |
| 60 | 50 | 0.5024 | Pluronic F-127 | 0.4992 |
| 61 | 60 | 1.2005 | Pluronic F-127 | 0.8024 |
| 62 | 70 | 0.3517 | Pluronic F-127 | 0.1502 |
| 63 | 80 | 0.8007 | Pluronic F-127 | 0.2004 |
| 64 | 25 | 0.2494 | Pluronic F-108 | 0.7494 |

Example 65

The solid amorphous dispersions of Example 57 to 64 were evaluated in an in vitro dissolution test using the procedures described in Example 8. The amount of each dispersion added to the microcentrifuge tube was adjusted such that the concentration of Drug 2 in solution if all of the drug had dissolved was 1000 μg/ml. The results of these tests are presented in Table 24.

TABLE 24

| Example | Time (min) | Drug 2 Concentration (μg/mL) | AUC (min-μg/mL) |
|---|---|---|---|
| 57 | 0 | 0 | 0 |
|  | 4 | 930 | 1,900 |
|  | 10 | 899 | 7,300 |
|  | 20 | 856 | 16,100 |
|  | 40 | 806 | 32,800 |
|  | 90 | 715 | 70,800 |
|  | 1200 | 385 | 681,700 |
| 58 | 0 | 0 | 0 |
|  | 4 | 699 | 1,400 |
|  | 10 | 653 | 5,500 |
|  | 20 | 594 | 11,700 |
|  | 40 | 551 | 23,100 |
|  | 90 | 438 | 47,900 |
|  | 1200 | 184 | 392,800 |
| 59 | 0 | 0 | 0 |
|  | 4 | 264 | 500 |
|  | 10 | 253 | 2,100 |
|  | 20 | 224 | 4,500 |
|  | 40 | 229 | 9,000 |
|  | 90 | 180 | 19,200 |
|  | 1200 | 90 | 169,100 |
| 60 | 0 | 0 | 0 |
|  | 4 | 305 | 600 |
|  | 10 | 272 | 2,300 |
|  | 20 | 250 | 4,900 |
|  | 40 | 233 | 9,800 |
|  | 90 | 193 | 20,400 |
|  | 1200 | 76 | 169,300 |
| 61 | 0 | 0 | 0 |
|  | 4 | 119 | 200 |
|  | 10 | 122 | 1,000 |
|  | 20 | 108 | 2,100 |
|  | 40 | 114 | 4,300 |
|  | 90 | 97 | 9,600 |
|  | 1200 | 51 | 90,000 |
| 62 | 0 | 0 | 0 |
|  | 4 | 43 | 90 |
|  | 10 | 48 | 400 |
|  | 20 | 58 | 900 |
|  | 40 | 56 | 2,000 |
|  | 90 | 56 | 4,900 |
|  | 1200 | 34 | 54,900 |
| 63 | 0 | 0 | 0 |
|  | 4 | 14 | 30 |
|  | 10 | 17 | 100 |
|  | 20 | 19 | 300 |

TABLE 24-continued

| Example | Time (min) | Drug 2 Concentration (μg/mL) | AUC (min-μg/mL) |
|---|---|---|---|
|  | 40 | 18 | 700 |
|  | 90 | 17 | 1,500 |
|  | 1200 | 10 | 16,800 |
| 64 | 0 | 0 | 0 |
|  | 4 | 542 | 1,100 |
|  | 10 | 496 | 4,200 |
|  | 20 | 459 | 9,000 |
|  | 40 | 397 | 17,500 |
|  | 90 | 318 | 35,400 |
|  | 1200 | 66 | 248,800 |

The results are summarized in Table 25, which also includes the data for Control 2, which was tested under the same conditions. The results show that the dissolution results for the compositions of Examples 57 through 64 were much better than that of the crystalline drug alone (Control 2), providing $C_{max,90}$ values that were greater than 19-fold to 930-fold that of the crystalline drug alone, and $AUC_{90}$ values that were greater than 17-fold to 804-fold that of the crystalline drug alone.

TABLE 25

| Example | Concentration-enhancing Polymer | Concentration of Drug in Polymer (wt %) | $C_{max,90}$ (μg/mL) | $AUC_{90}$ (min-g/mL) |
|---|---|---|---|---|
| 57 | Pluronic F-127 | 10 | 930 | 70,800 |
| 58 | Pluronic F-127 | 25 | 699 | 47,900 |
| 59 | Pluronic F-127 | 40 | 264 | 19,200 |
| 60 | Pluronic F-127 | 50 | 305 | 20,400 |
| 61 | Pluronic F-127 | 60 | 122 | 9,600 |
| 62 | Pluronic F-127 | 70 | 58 | 4,900 |
| 63 | Pluronic F-127 | 80 | 19 | 1,500 |
| 64 | Pluronic F-108 | 25 | 542 | 35,400 |
| Control 2 | None | — | <1 | <88 |

Examples 66-68

Spray-dried solid amorphous dispersions of Drug 2 and the poloxamers Pluronic F-127 and Pluronic F-108 were prepared following the procedures outlined in Examples 43 through 46. Table 26 summarizes the preparation parameters.

TABLE 26

| Ex. | Drug No. | Drug Mass (g) | Concentration-enhancing Polymer | Polymer Mass (g) | Solvent | Solvent Mass (g) | Spray Apparatus |
|---|---|---|---|---|---|---|---|
| 66 | 2 | 0.2502 | Pluronic F-127 | 0.7501 | Acetone | 116 | mini |
| 67 | 2 | 0.2154 | Pluronic F-127 | 0.2163 | Acetone | 54.5 | mini |
| 68 | 2 | 0.0728 | Pluronic F-108 | 0.2199 | Acetone | 44.15 | mini |

Example 69

The spray-dried dispersions of Examples 66 to 68 were evaluated in an in vitro dissolution test using the procedures described in Example 8. The amount of each dispersion added to the microcentrifuge tube was adjusted such that the concentration of Drug 2 in solution if all of the drug had dissolved was 1000 μg/ml. The results of these tests are presented in Table 27.

TABLE 27

| Example | Time (min) | Drug 2 Concentration (μg/mL) | AUC (min-μg/mL) |
|---|---|---|---|
| 66 | 0 | 0 | 0 |
|  | 4 | 508 | 1,000 |
|  | 10 | 449 | 3,900 |
|  | 30 | 420 | 8,200 |
|  | 60 | 371 | 16,100 |
|  | 90 | 272 | 32,200 |
|  | 1200 | 125 | 253,000 |
| 67 | 0 | 0 | 0 |
|  | 4 | 126 | 300 |
|  | 10 | 150 | 1,100 |
|  | 20 | 164 | 2,600 |
|  | 40 | 151 | 5,800 |
|  | 90 | 148 | 13,300 |
|  | 1200 | 62 | 129,600 |
| 68 | 0 | 0 | 0 |
|  | 4 | 267 | 500 |
|  | 10 | 239 | 2,100 |
|  | 20 | 221 | 4,400 |
|  | 40 | 196 | 8,500 |
|  | 90 | 143 | 17,000 |
|  | 1200 | 36 | 116,200 |

The results are summarized in Table 28, which also includes the data for Control 2, which was tested under the same conditions. The results show that the dissolution results for the compositions of Examples 66 through 68 were much better than that of the crystalline drug alone (Control 2), providing $C_{max,90}$ values that were greater than 164-fold to 508-fold that of the crystalline drug alone, and $AUC_{90}$ values that were greater than 151-fold to 365-fold that of the crystalline drug alone.

TABLE 28

| Example | Concentration-enhancing Polymer | Concentration of Drug in the Dispersion (wt %) | $C_{max,90}$ (μg/mL) | $AUC_{90}$ (min-μg/mL) |
|---|---|---|---|---|
| 66 | Pluronic F-127 | 25 | 508 | 32,200 |
| 67 | Pluronic F-127 | 50 | 164 | 13,300 |
| 68 | Pluronic F-108 | 25 | 267 | 17,000 |
| Control 2 | None | — | <1 | <88 |

Examples 70-72

Spray-dried solid amorphous dispersions of Drug 7 and CMEC (carboxy methyl ethyl cellulose, Freund Industrial Co. Ltd., Tokyo, Japan) were prepared following the procedures outlined in Examples 43 through 46. Table 29 summarizes the preparation parameters. Example 70 comprised 25 wt % Drug 7, Example 71 comprised 35 wt % Drug 7, and Example 72 comprised 50 wt % Drug 7.

TABLE 29

| Ex. | Drug No. | Drug Mass (g) | Concentration-enhancing Polymer* | Polymer Mass (g) | Solvent | Solvent Mass (g) | Spray Apparatus |
|---|---|---|---|---|---|---|---|
| 70 | 7 | 0.0626 | CMEC | 0.1875 | 1:1 Ethanol:Ethylacetate | 12.8 | mini |
| 71 | 7 | 0.2100 | CMEC | 0.3901 | 1:1 Ethanol:Ethylacetate | 30.0 | mini |
| 72 | 7 | 0.1250 | CMEC | 0.1251 | 1:1 Ethanol:Ethylacetate | 12.8 | mini |

*Polymer designation: CMEC = carboxymethyl ethyl cellulose

Example 73

The spray-dried dispersions of Examples 70 to 72 were evaluated in an in vitro dissolution test using the procedures described in Example 8. The amount of each dispersion added to the microcentrifuge tube was adjusted such that the concentration of Drug 7 in solution if all of the drug had dissolved was 1000 µg/ml. The results of these tests are presented in Table 30.

TABLE 30

| Example | Time (min) | Drug 7 Concentration (µg/mL) | AUC (min-µg/mL) |
|---|---|---|---|
| 70 | 0 | 0 | 0 |
|  | 4 | 892 | 1,800 |
|  | 10 | 897 | 7,200 |
|  | 30 | 888 | 16,100 |
|  | 60 | 812 | 33,076 |
|  | 90 | 622 | 68,900 |
|  | 1200 | 90 | 464,100 |
| 71 | 0 | 0 | 0 |
|  | 4 | 521 | 1,000 |
|  | 10 | 538 | 4,200 |
|  | 20 | 482 | 9,300 |
|  | 40 | 382 | 18,000 |
|  | 90 | 323 | 35,600 |
|  | 1200 | 111 | 276,500 |
| 72 | 0 | 0 | 0 |
|  | 4 | 82 | 200 |
|  | 10 | 153 | 900 |
|  | 20 | 167 | 2,500 |
|  | 40 | 163 | 5,800 |
|  | 90 | 151 | 13,600 |
|  | 1200 | 83 | 143,500 |

The results are summarized in Table 31, which also includes the data for Control 9 (Drug 7 alone), which was tested under the same conditions. The results show that the dissolution results for the compositions of Examples 70 through 72 were much better than that of the crystalline drug alone (Control 9), providing $C_{max,90}$ values that were greater than 167-fold to 897-fold that of the crystalline drug alone, and $AUC_{90}$ values that were greater than 155-fold to 783-fold that of the crystalline drug alone.

TABLE 31

| Example | Concentration-enhancing Polymer | Concentration of Drug in the Dispersion (wt %) | $C_{max,90}$ (µg/mL) | $AUC_{90}$ (min-µg/mL) |
|---|---|---|---|---|
| 70 | CMEC | 25 | 897 | 68,900 |
| 71 | CMEC | 35 | 538 | 35,600 |
| 72 | CMEC | 50 | 167 | 13,600 |
| Control 9 | None | — | <1 | <88 |

Example 74

Example 74 demonstrates the utility of the amorphous dispersion of the present invention with an additional CETP inhibitor. The following drug was incorporated into an amorphous solid dispersion: [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester ("Drug 12"). This compound has a solubility in water of less than 1 µg/mL, with a Clog P value of 7.8. A spray-dried solid amorphous dispersion of Drug 12 and HPMCAS-MF was prepared following the procedures outlined in Examples 43 through 46. Table 32 summarizes the preparation parameters. Example 74 comprised 25 wt % Drug 12.

TABLE 32

| Ex. No. | Drug No. | Drug Mass (g) | Concentration-enhancing Polymer | Polymer Mass (g) | Solvent | Solvent Mass (g) | Spray Apparatus |
|---|---|---|---|---|---|---|---|
| 74 | 12 | .020 | HPMCAS-MF | 0.060 | acetone | 25.0 | mini |

Control 14

The comparative composition of Control 14 consisted of 1.8 mg of the crystalline form of Drug 12 alone.

Example 75

The spray-dried dispersion of Example 74 was evaluated in an in vitro dissolution test using the procedures described in Example 8. The amount of the dispersion added to the microcentrifuge tube was 7.2 mg, resulting in 1000 µg/ml Drug 12 in solution if all of the drug had dissolved. The results of this test are presented in Table 33.

For Control 14, an in vitro dissolution test was performed using the procedure described in Example 8, except that 1.8 mg of crystalline drug was placed in a microcentrifuge tube and mixed with 1.8 mL of PBS. The test results are included in Table 33.

TABLE 33

| Example | Time (min) | Drug 12 Concentration (µg/mL) | AUC (min-µg/mL) |
|---|---|---|---|
| 74 | 0 | 0 | 0 |
|  | 4 | 479 | 1,000 |
|  | 10 | 448 | 3,700 |
|  | 30 | 434 | 8,100 |
|  | 60 | 399 | 16,500 |
|  | 90 | 361 | 35,500 |
|  | 1200 | 157 | 323,000 |
| C14 | 0 | 0 | 0 |
|  | 4 | <1 | <2 |
|  | 10 | <1 | <8 |

TABLE 33-continued

| Example | Time (min) | Drug 12 Concentration (μg/mL) | AUC (min-μg/mL) |
|---|---|---|---|
| | 20 | <1 | <18 |
| | 40 | <1 | <38 |
| | 90 | <1 | <88 |
| | 1200 | <1 | <1,200 |

The results are summarized in Table 34. The composition of Example 74 provided greater concentration-enhancement than that of the crystalline drug alone (Control 14), providing a $C_{max,90}$ value that was at least 479-fold that of the crystalline drug alone, and an $AUC_{90}$ value that was at least 403-fold that of the crystalline drug alone.

TABLE 34

| Example | Concentration-enhancing Polymer | Concentration of Drug in the Dispersion (wt %) | $C_{max,90}$ (μg/mL) | $AUC_{90}$ (min-μg/mL) |
|---|---|---|---|---|
| 74 | HPMCAS-MF | 25 | 479 | 35,500 |
| Control 14 | None | — | <1 | <88 |

Examples 76 and 77

Spray-dried solid amorphous dispersions of Drug 2 and carboxymethyl ethyl cellulose from Freund Industrial Co. of Tokyo, Japan, were prepared following the procedures outlined in Examples 43 through 46. Table 35 summarizes the preparation parameters. Example 76 comprised 25 wt % Drug 2, while Example 77 comprised 40 wt % Drug 2.

TABLE 35

| Ex. | Drug No. | Drug Mass (g) | Concentration-enhancing Polymer* | Polymer Mass (g) | Solvent | Solvent Mass (g) | Spray Apparatus |
|---|---|---|---|---|---|---|---|
| 76 | 2 | 0.2007 | CMEC | 0.5995 | 1:1 Ethanol:ethylacetate | 30.0 | mini |
| 77 | 2 | 0.2992 | CMEC | 0.4493 | 1:1 Ethanol:ethylacetate | 30.0 | mini |

*Polymer designation: CMEC = carboxymethyl ethyl cellulose

Example 78

The spray-dried dispersions of Examples 76 and 77 were evaluated in an in vitro dissolution test using the procedures described in Example 8. The amount of each dispersion added to the microcentrifuge tube was adjusted such that the concentration of Drug 2 in solution if all of the drug had dissolved was 1000 μg/ml. The results of these tests are presented in Table 36.

TABLE 36

| Example | Time (min) | Drug 2 Concentration (μg/mL) | AUC (min-μg/mL) |
|---|---|---|---|
| 76 | 0 | 0 | 0 |
| | 4 | 783 | 1,600 |
| | 10 | 922 | 6,700 |
| | 30 | 898 | 15,800 |
| | 60 | 889 | 33,700 |
| | 90 | 828 | 76,600 |
| | 1200 | 339 | 724,300 |

TABLE 36-continued

| Example | Time (min) | Drug 2 Concentration (μg/mL) | AUC (min-μg/mL) |
|---|---|---|---|
| 77 | 0 | 0 | 0 |
| | 4 | 192 | 400 |
| | 10 | 401 | 2,200 |
| | 20 | 501 | 6,700 |
| | 40 | 535 | 17,000 |
| | 90 | 464 | 42,000 |
| | 1200 | 188 | 403,900 |

The results are summarized in Table 37, which also includes the data for Control 2 (Drug 2 alone), which was tested under the same conditions. The results show that the dissolution results for the compositions of Examples 76 and 77 were much better than that of the crystalline drug alone (Control 2), providing $C_{max,90}$ values that were at least 922-fold and 535-fold that of the crystalline drug alone, and $AUC_{90}$ values that were at least 870-fold and 477-fold that of the crystalline drug alone, respectively.

TABLE 37

| Example | Concentration-enhancing Polymer | Concentration of Drug in the Dispersion (wt %) | $C_{max,90}$ (μg/mL) | $AUC_{90}$ (min-μg/mL) |
|---|---|---|---|---|
| 76 | CMEC | 25 | 922 | 76,600 |
| 77 | CMEC | 40 | 535 | 42,000 |
| Control 2 | None | — | <1 | <88 |

Example 79

The following process was used to form a spray-dried dispersion containing 25 wt % Drug 2 and 75 wt % HPMCAS-HG. First, a 10,000 g spray solution was formed containing 2.5 wt % Drug 2, 7.5 wt % HPMCAS-MG, and 90% acetone as follows. The HPMCAS-HG and acetone were combined in a container and mixed for at least 2 hours, allowing the HPMCAS to dissolve. The resulting mixture had a slight haze after the entire amount of polymer had been added. Next, Drug 2 was added directly to this mixture, and the mixture stirred for an additional 2 hours. This mixture was then filtered by passing it through a filter with a screen size of 250 μm to remove any large insoluble material from the mixture, thus forming the spray solution.

The spray-dried dispersion was then formed using the following procedure. The spray solution was pumped using a high-pressure pump (a Zenith Z-Drive 2000 High-Pressure Gear Pump), to a spray drier (a Niro type XP Portable Spray-Dryer with a Liquid-Feed Process Vessel) ("PSD-1"), equipped with a pressure nozzle (Spraying Systems Pressure Nozzle and Body) (SK 71-16). The PSD-1 was equipped with a 9-inch chamber extension. The 9-inch chamber extension was added to the spray dryer to increase the vertical length of the dryer. The added length increased the residence time within the dryer, which allowed the product to dry before reaching the angled section of the spray dryer. The spray drier was also equipped with a gas-dispersing means for introduction of the drying gas to the spray drying chamber. The gas-dispersing means consisted of a plate coextensive with the interior of the drying chamber (about 0.8 m diameter) and bearing a multiplicity of 1.7 mm perforations occupying about 1% of the surface area of the plate. The perforations were uniformly distributed across the plate, except that the density of perforations at the center 0.2 m of the diffuser plate was about 25% of the density of perforations in the outer part of the gas dispersing means. The use of the diffuser plate resulted in organized plug flow of drying gas through the drying chamber and dramatically decreased product recirculation within the spray dryer. The nozzle sat flush with the diffuser plate during operation. The spray solution was pumped to the spray drier at about 195 gm/min at a pressure of about 100 psig. Drying gas (e.g., nitrogen) was circulated through the diffuser plate at an inlet temperature of about 106° C. The evaporated solvent and wet drying gas exited the spray drier at a temperature of 45±4° C. The spray-dried dispersion formed by this process was collected in a cyclone, and had have a bulk specific volume of about 5 cm$^3$/gm, with a mean particle size of about 80 μm.

The dispersion formed using the above procedure was post-dried using a Gruenberg single-pass convection tray dryer operating at 40° C. for 25 hours. Following drying, the dispersion was equilibrated with ambient air and humidity (e.g., 20° C./50% RH).

Typical properties of the dispersion after secondary drying were as follows:

TABLE 38

| Bulk Properties (After Secondary Drying) | Tray Dried @ 40° C. |
|---|---|
| Bulk Specific Volume (cc/g) | 5.0 |
| Tapped Specific Volume (cc/g) | 3.2 |
| Hausner Ratio | 1.56 |
| Mean Particle Diameter (μm) | 80 |
| $D_{10}$, $D_{50}$, $D_{90}$* (μm) | 25, 73, 143 |
| Span ($D_{90}$ – $D_{10}$)/$D_{50}$ | 1.60 |
| Residual Acetone (Before Secondary Drying) | 3.0% |

*10 vol % of the particles had a diameter that was smaller than $D_{10}$; 50 vol % of the particles had a diameter that was smaller than $D_{50}$, and 90 vol % of the particles had a diameter that was smaller than $D_{90}$.

Example 80

A solid amorphous dispersion comprising 25 wt % Drug 2 in the polyoxyethylene-polyoxypropylene copolymer PLURONIC F127 was prepared via a melt-congeal process following the procedures outlined in Example 58, with the exceptions noted in Table 39.

TABLE 39

| Example | Concentration of Drug in Polymer (wt %) | Drug Mass (gm) | Concentration-enhancing Polymer | Polymer Mass (gm) |
|---|---|---|---|---|
| 80 | 25 | 1.9997 | Pluronic F-127 | 6.0012 |

This dispersion was evaluated in an in vitro dissolution test using the procedures outlined in Example 65. The results of these tests are presented in Table 40.

TABLE 40

| Example | Time (min) | Drug 2 Concentration (μg/mL) | AUC (min-μg/mL) |
|---|---|---|---|
| 80 | 0 | 0 | 0 |
|  | 4 | 729 | 1,500 |
|  | 10 | 789 | 6,000 |
|  | 20 | 721 | 13,600 |
|  | 40 | 692 | 27,700 |
|  | 90 | 544 | 58,600 |
|  | 1200 | 124 | 429,500 |

The results are summarized in Table 41, which also includes the data for Control 2, which was tested under the same conditions. The results show that the dissolution results for the composition of Example 80 was much better than that of the crystalline drug alone (Control 2), providing a $C_{max,90}$ value that was greater than 789-fold that of the crystalline drug alone, and an $AUC_{90}$ value that was greater than 665-fold that of the crystalline drug alone.

TABLE 41

| Example | Concentration-enhancing Polymer | Concentration of Drug in Polymer | $C_{max,90}$ (μg/mL) | $AUC_{90}$ (min-μg/mL) |
|---|---|---|---|---|
| 80 | Pluronic F-127 | 25 | 789 | 58,600 |
| Control 2 | None | — | <1 | <88 |

Examples 81-82

Solid amorphous dispersions comprising 25 wt % Drug 2 and carboxymethylethyl cellulose (CMEC) (Example 81) and 35 wt % Drug 2 and CMEC (Example 82) were prepared via a spray drying process following the procedures outlined in Example 79, with the exceptions noted in Table 42. The solid amorphous dispersions were dried overnight in a tray drier at 40° C.

TABLE 42

| Ex. | Drug 2 Mass (gm) | Concentration-enhancing Polymer | Polymer Mass (gm) | Solvent | Solvent Mass (gm) | Spray Rate (gm/min) | Atomization Presssure (psig) | Inlet Temp. (C.) | Outlet Temp. (C.) |
|---|---|---|---|---|---|---|---|---|---|
| 81 | 2.5 | CMEC | 7.5 | Acetone | 90 | 190 | 200 | 110 | 40 |
| 82 | 4.2 | CMEC | 7.8 | Acetone | 138 | 200 | 100 | 110 | 45 |

The dispersions were evaluated in an in vitro dissolution test using the procedures outlined in Example 8. The results of these tests are presented in Table 43.

TABLE 43

| Example | Time (min) | Drug 2 Concentration (μg/mL) | AUC (min-μg/mL) |
|---|---|---|---|
| 81 | 0 | 0 | 0 |
| | 4 | 537 | 1,100 |
| | 10 | 772 | 5,000 |
| | 20 | 814 | 12,900 |
| | 40 | 818 | 29,300 |
| | 90 | 814 | 70,000 |
| | 1200 | 408 | 748,100 |
| 82 | 0 | 0 | 0 |
| | 4 | 321 | 600 |
| | 10 | 567 | 3,300 |
| | 20 | 642 | 9,300 |
| | 40 | 637 | 22,100 |
| | 90 | 629 | 53,800 |
| | 1200 | 247 | 541,100 |

The results are summarized in Table 44, which also includes the data for Control 2, which was tested under the same conditions. The results show that the dissolution results for the compositions of Examples 81 and 82 were much better than that of the crystalline drug alone (Control 2), providing $C_{max,90}$ values that were greater than 818-fold and 642-fold that of the crystalline drug alone, and $AUC_{90}$ values that were greater than 795-fold and 611-fold that of the crystalline drug alone, respectively.

TABLE 44

| Example | Concentration-enhancing Polymer | Concentration of Drug in Polymer (wt %) | $C_{max,90}$ (μg/mL) | $AUC_{90}$ (min-μg/mL) |
|---|---|---|---|---|
| 81 | CMEC | 25 | 818 | 70,000 |
| 82 | CMEC | 35 | 642 | 53,800 |
| Control 2 | None | — | <1 | <88 |

Example 83

The compositions of Examples 80, 81, and 82 were used as oral powders for constitution (OPC) for evaluating the performance of the compositions in in vivo tests using male beagle dogs. The OPC was dosed as a suspension in a solution containing 0.5 wt % hydroxypropyl cellulose METHOCEL® (from Dow Chemical Co.), and was prepared as follows. First, 7.5 g of METHOCEL® was weighed out and added slowly to approximately 490 ml of water at 90-100° C. to form a METHOCEL® suspension. After all the METHOCEL® was added, 1000 mL of cool/room temperature water was added to the suspension, which was then placed in an ice water bath. When all of the METHOCEL® had dissolved, 2.55 g of polyoxyethylene 20 sorbitan monooleate (TWEEN 80) were added and the mixture stirred until the TWEEN 80 had dissolved, thus forming a stock suspension solution.

To form the OPC, sufficient quantity of the test composition to result in a 90 mgA amount of Drug 2 was accurately weighed and placed into a mortar. ("mgA" refers to mg of active drug.) A 20 mL quantity of the stock suspension solution was added to the mortar and the test composition was mixed with a pestle. Additional METHOCEL® suspension was added gradually with mixing until a total of 400 mL of the stock suspension solution had been added to the mortar. The suspension was then transferred to a flask, thus forming the OPC. This process was repeated for each of the compositions of Examples 74, 75, and 76. In addition, an OPC containing 90 mgA of amorphous Drug 2 (Control 15) was prepared using the same procedure.

Six male beagle dogs were each dosed with the OPC. On the day of the study, the dogs in a fasted state were dosed with the OPC using a gavage tube and a syringe. Whole blood samples were taken from the jugular vein and analyzed for the concentration of Drug 2 using the procedures outlined in Examples 18-20. The results of these tests are presented in Table 45 and show that the compositions of the present invention provided enhanced drug concentration and relative bioavailability relative to the amorphous Drug 2 control (Control 15).

TABLE 45

| Composition | $C_{max}$ (μg/ml) | $AUC_{(0-24)}$ (μg/ml * hr) |
|---|---|---|
| Example 80 (25 wt % Drug 2 in Pluronic F127) | 544 | 2.1 |
| Example 81 (25 wt % Drug 2 in CMEC) | 691 | 1.7 |
| Example 82 (35 wt % Drug 2 in CMEC) | 375 | 1.2 |
| Control 15 (amorphous Drug 2) | <0.1 | <0.2 |

The composition of Example 80 provided a $C_{max}$ that was more than 5440-fold that of the amorphous control, and a relative bioavailability that was greater than 10. The composition of Example 81 provided a $C_{max}$ that was more than 6910-fold that of the amorphous control, and a relative bioavailability that was greater than 8. The composition of Example 82 provided a $C_{max}$ that was more than 3750-fold that of the amorphous control, and a relative bioavailability that was greater than 6.

Examples 84-86

Solid amorphous dispersions comprising 25 wt % Drug 2 and HPMCAS-MG were prepared via a spray drying process using the procedures outlined in Example 79, except that a 5 feet, nine inches (175 cm) extension on the dryer was used and the pressure nozzle was a Spraying Systems model SK80-16. Other exceptions are noted in Table 46. The spray solutions to form the dispersions contained 16 wt % solids (Example 84), 18 wt % solids (Example 85), and 20 wt % solids (Example 86). After forming the dispersion, the solid amorphous dispersions were dried overnight in a tray drier at 40° C.

TABLE 46

| Ex. | Drug 2 Mass (gm) | Aqueous-Soluble Polymer | Polymer Mass (gm) | Solvent | Solvent Mass (gm) | Spray Rate (gm/min) | Atomization Press. (psig) | Inlet Temp. (° C.) | Outlet Temp. (° C.) |
|---|---|---|---|---|---|---|---|---|---|
| 84 | 75 | HPMCAS-MG | 225 | acetone | 1575 | 300 | 675 | 132 | 46 |
| 85 | 100 | HPMCAS-MG | 300 | acetone | 1822 | 300 | 750 | 145 | 40 |
| 86 | 125 | HPMCAS-MG | 375 | acetone | 2000 | 420 | 750 | 142 | 35 |

The dispersions were evaluated in an in vitro dissolution test using the procedures outlined in Example 8. The results of these tests are presented in Table 47.

TABLE 47

| Example | Time (min) | Drug 2 Concentration (µg/ml) | AUC (min-µg/ml) |
|---|---|---|---|
| 84 | 0 | 0 | 0 |
|  | 4 | 358 | 700 |
|  | 10 | 737 | 4,000 |
|  | 20 | 730 | 11,300 |
|  | 40 | 679 | 25,400 |
|  | 90 | 612 | 57,700 |
|  | 1200 | 231 | 525,500 |
| 85 | 0 | 0 | 0 |
|  | 4 | 360 | 700 |
|  | 10 | 766 | 4,100 |
|  | 20 | 789 | 11,900 |
|  | 40 | 752 | 27,300 |
|  | 90 | 723 | 64,200 |
|  | 1200 | 293 | 628,100 |
| 86 | 0 | 0 | 0 |
|  | 4 | 354 | 700 |
|  | 10 | 776 | 4,100 |
|  | 20 | 847 | 12,200 |
|  | 40 | 816 | 28,800 |
|  | 90 | 766 | 68,400 |
|  | 1200 | 342 | 682,900 |

The results are summarized in Table 48, which also includes the data for Control 2, which was tested under the same conditions. The results show that the compositions of Examples 84, 85 and 86 provided $C_{max,90}$ values that were greater than 737-, 789-, and 847-fold that of the crystalline drug alone (Control 2), and $AUC_{90}$ values that were greater than 656-, 730-, and 777-fold that of the crystalline drug alone, respectively.

TABLE 48

| Example | Concentration-Enhancing Polymer | Concentration of Drug in Polymer (wt %) | $C_{max,90}$ (µg/ml) | $AUC_{90}$ (min-µg/ml) |
|---|---|---|---|---|
| 84 | HPMCAS-MG | 25 | 737 | 57,700 |
| 85 | HPMCAS-MG | 25 | 789 | 64,200 |
| 86 | HPMCAS-MG | 25 | 847 | 68,400 |
| Control 2 | None | — | <1 | <88 |

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A method for forming a pharmaceutical composition, comprising:
(a) forming a molten mixture comprising a cholesteryl ester transfer protein inhibitor and a concentration-enhancing polymer;
(b) cooling said mixture to form a solid amorphous dispersion comprising said cholesteryl ester transfer protein inhibitor and said concentration-enhancing polymer; and
(c) providing a sufficient-amount of said concentration-enhancing polymer in said mixture so that said solid amorphous dispersion provides a maximum concentration of said cholesteryl ester transfer protein inhibitor in a use environment that is at least 10-fold the equilibrium concentration provided by a control composition consisting essentially of an equivalent amount of said cholesteryl ester transfer protein inhibitor but with no concentration-enhancing polymer,
wherein said cholesteryl ester transfer protein inhibitor has a Clog P greater than 4 and a solubility in aqueous solution in the absence of said concentration-enhancing polymer of less than 10 µg/ml at any pH of from 1 to 8, at about 22° C.,
and wherein said concentration-enhancing polymer is selected from vinyl polymers and copolymers having substituents of hydroxyl, alkylacyloxy, or cyclicamido; polyvinyl alcohols that have at least a portion of their repeat units in the unhydrolyzed (vinyl acetate) form; polyvinyl alcohol polyvinyl acetate copolymers; polyvinyl pyrrolidone; poloxamers; polyethylene polyvinyl alcohol copolymers, carboxylic acid functionalized polymethacrylates and carboxylic acid functionalized polyacrylates; amine-functionalized polyacrylates and polymethacrylates; proteins; and carboxylic acid functionalized starches, hydroxypropyl methyl cellulose acetate, hydroxypropyl methyl cellulose, hydroxypropyl cellulose, methyl cellulose, hydroxyethyl methyl cellulose, hydroxyethyl cellulose acetate, hydroxyethyl ethyl cellulose, hydroxypropyl methyl cellulose acetate succinate, hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate, hydroxyethyl methyl cellulose acetate succinate, hydroxyethyl methyl cellulose acetate phthalate, carboxyethyl cellulose, carboxymethyl cellulose, carboxymethylethyl cellulose, cellulose acetate phthalate, methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate, methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate.

2. The method of claim 1, further comprising the step of adding an excipient to reduce the temperature required to form said molten mixture.

3. The method of claim 1, further comprising the step of mixing said molten mixture so that said molten mixture is substantially homogeneous.

4. The method of claim 1 wherein said molten mixture is formed by melting said concentration-enhancing polymer and adding said cholesteryl ester transfer protein inhibitor to said concentration-enhancing polymer.

5. The method of claim 1 wherein said molten mixture is formed by melting said cholesteryl ester transfer protein inhibitor and adding said concentration-enhancing polymer to said cholesteryl ester transfer protein inhibitor.

6. The method of claim 1 wherein said molten mixture is formed by mixing said cholesteryl ester transfer protein inhibitor and said concentration-enhancing polymer together to form a solid blend and heating said solid blend.

7. The method of claim 6 wherein said solid blend is heated in an extruder.

8. The method of claim 1 wherein said cholesteryl ester transfer protein inhibitor is substantially amorphous and said dispersion is substantially homogeneous.

9. The product produced by the method of any one of claims 1-6.

10. The product of claim 9 wherein said dispersion has a single glass transition temperature.

11. The product of claim 9 which provides in a use environment an area under the concentration versus time curve for any period of at least 90 minutes between the time of introduction into the use environment and about 270 minutes following introduction to the use environment that is at least about 5-fold that of a control composition.

12. The product of claim 9 which provides a relative bioavailability that is at least 4-fold relative to said control composition.

13. The product of claim 9 wherein the cholesteryl ester transfer protein inhibitor has a dose-to-aqueous-solubility ratio of at least 1,000 ml.

14. The method of claim 1 wherein said cholesteryl ester transfer protein inhibitor is 3-[[3-(4-chloro-3-ethylphenoxy)phenyl][[3-(1,1,2,2-tetrafluoroethoxy)phenyl]-methyl]amino]-1,1,1-trifluoro-2-propanol.

15. The method of claim 1 wherein said molten mixture of step (a) is formed in an extruder.

16. The method of claim 1 wherein said cholesteryl ester transfer protein inhibitor is propanethioic acid, 2-methyl-S-[2[[[1-(2-ethylbutyl)cyclohexyl]carbonyl]amino]phenyl]ester.

* * * * *